US010450263B2

(12) United States Patent
Pathak et al.

(10) Patent No.: US 10,450,263 B2
(45) Date of Patent: Oct. 22, 2019

(54) BENZO ANNULENES AS ANTIVIRAL AGENTS

(71) Applicant: Southern Research Institute, Birmingham, AL (US)

(72) Inventors: Ashish Kumar Pathak, Birmingham, AL (US); Syed Kaleem Ahmed, Hoover, AL (US); Corinne E. Augelli-Szafran, Homewood, AL (US); Joseph A. Maddry, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 15/892,302

(22) Filed: Feb. 8, 2018

(65) Prior Publication Data

US 2018/0230084 A1   Aug. 16, 2018

Related U.S. Application Data

(60) Provisional application No. 62/457,653, filed on Feb. 10, 2017.

(51) Int. Cl.
| | |
|---|---|
| *C07C 233/64* | (2006.01) |
| *C07C 233/67* | (2006.01) |
| *C07C 233/75* | (2006.01) |
| *C07D 231/12* | (2006.01) |
| *C07D 233/58* | (2006.01) |
| *C07D 261/08* | (2006.01) |
| *C07D 277/22* | (2006.01) |
| *C07D 333/10* | (2006.01) |
| *C07D 307/36* | (2006.01) |
| *C07D 213/16* | (2006.01) |
| *C07D 223/04* | (2006.01) |
| *C07D 241/12* | (2006.01) |
| *C07D 271/12* | (2006.01) |
| *C07D 233/90* | (2006.01) |
| *C07D 277/56* | (2006.01) |
| *C07D 261/18* | (2006.01) |
| *C07D 307/68* | (2006.01) |
| *C07D 333/38* | (2006.01) |
| *C07D 241/24* | (2006.01) |
| *C07D 239/28* | (2006.01) |
| *C07C 255/41* | (2006.01) |
| *C07D 213/56* | (2006.01) |
| *C07D 213/81* | (2006.01) |
| *C07D 307/85* | (2006.01) |
| *C07D 309/08* | (2006.01) |
| *C07D 213/30* | (2006.01) |
| *C07D 209/46* | (2006.01) |
| *C07D 223/16* | (2006.01) |
| *A61P 31/12* | (2006.01) |
| *C07D 231/14* | (2006.01) |
| *C07C 255/58* | (2006.01) |
| *C07C 311/21* | (2006.01) |
| *C07C 233/29* | (2006.01) |

(Continued)

(52) U.S. Cl.
CPC ............ *C07C 233/75* (2013.01); *A61P 31/12* (2018.01); *C07C 233/29* (2013.01); *C07C 233/60* (2013.01); *C07C 233/65* (2013.01); *C07C 235/48* (2013.01); *C07C 255/33* (2013.01); *C07C 255/41* (2013.01); *C07C 255/58* (2013.01); *C07C 311/21* (2013.01); *C07D 209/46* (2013.01); *C07D 213/30* (2013.01); *C07D 213/56* (2013.01); *C07D 213/81* (2013.01); *C07D 223/16* (2013.01); *C07D 231/14* (2013.01); *C07D 233/90* (2013.01); *C07D 239/28* (2013.01); *C07D 241/24* (2013.01); *C07D 261/18* (2013.01); *C07D 271/12* (2013.01); *C07D 277/56* (2013.01); *C07D 307/68* (2013.01); *C07D 307/85* (2013.01); *C07D 309/08* (2013.01); *C07D 333/38* (2013.01); *C07C 2601/02* (2017.05); *C07C 2601/04* (2017.05); *C07C 2602/12* (2017.05); *C07C 2603/74* (2017.05)

(58) Field of Classification Search
CPC ... C07C 233/64; C07C 233/67; C07C 233/75; C07D 231/12; C07D 233/58; C07D 261/08; C07D 277/22; C07D 333/10; C07D 307/36; C07D 213/16; C07D 223/04; C07D 241/12; C07D 271/12
See application file for complete search history.

(56) References Cited

U.S. PATENT DOCUMENTS

| 9,427,440 B2 | 8/2016 | Vendeville et al. |
| 2016/0289216 A1 | 10/2016 | Jones et al. |
| 2018/0230084 A1 | 8/2018 | Pathak et al. |

FOREIGN PATENT DOCUMENTS

| WO | WO-2000/041531 A2 | 7/2000 |
| WO | WO-2016/097761 A1 | 6/2016 |

OTHER PUBLICATIONS

Alexander, J. et al., (Acyloxy)alkyl Carbamates as Novel Bioreversible Prodrugs for Amines: Increased Permeation Through Bilogical Membranes. J Med Chem. 1988; 31(2):318-22.

(Continued)

*Primary Examiner* — Bruce Kifle
(74) *Attorney, Agent, or Firm* — Ballard Spahr LLP

(57) ABSTRACT

The present disclosure is concerned with benzo annulene compounds that are capable of inhibiting a viral infection and methods of treating viral infections such as, for example, chikungunya, Venezuelan equine encephalitis, dengue, influenza, and zika, using these compounds. This abstract is intended as a scanning tool for purposes of searching in the particular art and is not intended to be limiting of the present invention.

19 Claims, No Drawings

(51) Int. Cl.
      *C07C 233/60*    (2006.01)
      *C07C 233/65*    (2006.01)
      *C07C 235/48*    (2006.01)
      *C07C 255/33*    (2006.01)

(56) References Cited

OTHER PUBLICATIONS

Almarasson, Ö. et al., Crystal Engineering of the Composition of Pharmaceutical Phases. Do Pharmaceutical Co-crystals Represent a New Path to Improved Medicines? Chem Commun. 2004; 1889-96.
International Search Report and Written Opinion dated Apr. 23, 2019 by the International Searching Authority for International Application No. PCT/US2018/067454, filed Dec. 24, 2018 (Applicant-Southern Research Institute) (13 Pages).

BENZO ANNULENES AS ANTIVIRAL AGENTS

CROSS-REFERENCE TO RELATED APPLICATIONS

This application claims priority to U.S. Provisional Application No. 62/457,653 filed Feb. 10, 2017, which application is hereby incorporated herein by reference in its' entirety.

STATEMENT REGARDING FEDERALLY SPONSORED RESEARCH

This invention was made with government support under Grant No. 1U19AI109680-01 awarded by the National Institute of Health (NIH). The government has certain rights in the invention.

BACKGROUND

Arthropod borne viruses have developed a complex life cycle adapted to alternate between insect and vertebrate hosts. These arthropod-borne viruses belong mainly to the families Togaviridae, Flaviviridae, and Bunyaviridae. *Flavivirus* is a genus of the family Flaviviridae. This genus includes such viral infections as West Nile virus, dengue virus (DENV), Tick-borne Encephalitis virus, yellow fever virus, and zika virus (ZIKV) that may cause encephalitis. *Alphavirus* is a genus of the family Togaviridae. This genus includes such viral infections as chikungunya virus (CHIKV), Venezuelan Equine Encephalitis virus (VEEZ), and Eastern Equine Encephalitis virus.

Zika virus (ZIKV) is a single stranded RNA virus transmitted to humans primarily via *Aedes aegypti* mosquitos and other mosquitos of the *Stegomyia* subgenus. ZIKV can also be transmitted through sexual intercourse, a blood transfusion, or from a pregnant woman to her fetus. Infection during pregnancy can result in microcephaly and other severe fetal brain defects. Additional problems detected among fetuses and infants infected with ZIKV before birth include as defects of the eye, hearing deficits, and impaired growth. Increased reports of Guillain-Barre syndrome have also been observed in areas affected by Zika. Until recently, only sporadic human ZIKV infections had been reported. Since 2007, ZIKV has expanded from Asia and Africa to include both North and South America.

DENV is a mosquito-borne virus estimated to cause 50-100 million infections each year. DENV infections can result in serious diseases including dengue fever, dengue hemorrhagic fever, and dengue shock syndrome, and may even result in death. This virus is considered by the World Health Organization to be the most important mosquito-borne viral disease worldwide.

Originally isolated in Tanzania, sporadic outbreaks of CHIKV have continued to plague Asia and Africa. In 2007, the first outbreak in Europe was documented with over 200 confirmed cases. To date, CHIKV has been identified in over 40 countries including the United States of America. The symptoms of CHIKV, which include fever, rash, and severe joint pain, are commonly indistinguishable from ZIKV and DENV. While most patients usually recover after days to weeks, some may develop chronic arthritis. Additionally, death related to Chikungunya infection has been reported in older patients or patients with weakened immune systems.

Currently, there are no approved treatments for ZIKV, DENV, or CHIKV. Despite the widespread distribution and severity of the effects of these viral infections, a treatment for ZIKV, DENV, and CHIKV has remained elusive. Thus, there remains a need for antiviral agents capable of targeting these viruses and methods of making and using same.

SUMMARY

In accordance with the purpose(s) of the invention, as embodied and broadly described herein, the invention, in one aspect, relates to benzoannulene compounds useful in the treatment of viral infections including, but not limited to, chikungunya, Venezuelan equine encephalitis, dengue, influenza, and zika.

The present disclosure relates to compounds having a structure represented by a formula selected from:

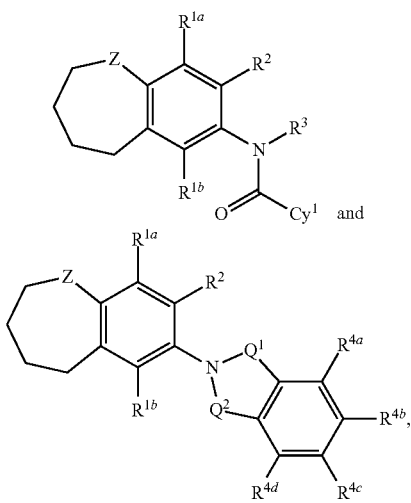

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_n OR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy², provided that when Cy¹ is unsubstituted phenyl, then at least one of $R^{1a}$, $R^{1b}$, and $R^2$ is not hydrogen, or a pharmaceutically acceptable salt thereof.

Also disclosed are pharmaceutical compositions comprising a therapeutically effective amount of at least one compound having a structure represented by a formula selected from:

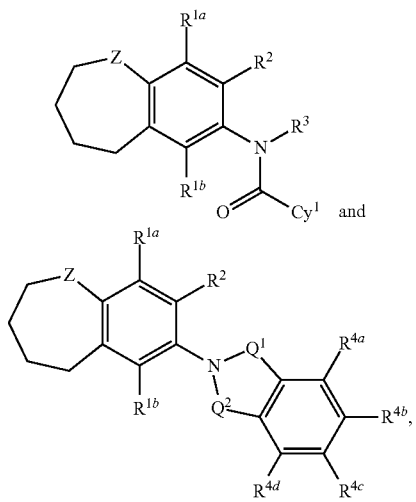

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy²; wherein Cy², when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein Cy¹ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy², or a pharmaceutically acceptable salt thereof, and a pharmaceutically acceptable carrier.

Also disclosed are methods for the treatment of a viral infection in a subject, the method comprising the step of administering to the subject an effective amount of at least one compound having a structure represented by a formula selected from:

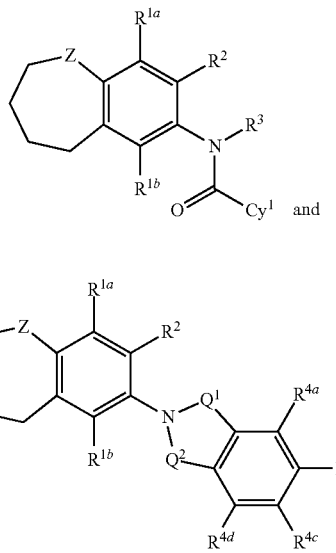

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy²; wherein Cy², when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein Cy¹ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy², or a pharmaceutically acceptable salt thereof.

Also disclosed are kits comprising at least one compound having a structure represented by a formula selected from:

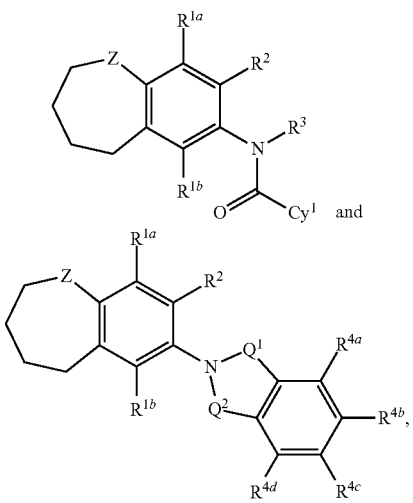

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, or a pharmaceutically acceptable salt thereof, and one or more of: (a) at least one antiviral agent; (b) a instructions for administering the at least one compound in connection with treating a viral infection; (c) instructions for administering the at least one compound in connection with reducing the risk of viral infection; or (d) instructions for treating a viral infection.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a viral infection. The term "patient" includes human and veterinary subjects. In some aspects of the disclosed methods, the subject has been diagnosed with a need for treatment of one or more viral infections prior to the administering step. In various aspects, the one or more disorders is selected from chikungunya, Venezuelan equine encephalitis, dengue, influenza, and zika.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{90}$," is intended to refer to the concentration of a substance (e.g., a compound or a drug) that is required for 90% inhibition of a biological process, or component of a process, including a protein, subunit, organelle, ribonucleoprotein, etc. In one aspect, an $EC_{90}$ can refer to the concentration of a substance that is required for 90% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1O(O)C-A^2-C(O)O)_a$— or -($A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^{\circ hd\ 2}$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet 3$, —$C(O)SR^\bullet$, —$(C_{1-4}$ straight or branched alkylene)C(O)OR$^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR$^*_2$, =NNHC(O)R$^*$, =NNHC(O)OR$^*$, =NNHS(O)$_2$R$^*$, =NR$^*$, =NOR$^*$, —O(C(R$^*_2$))$_{2-3}$O—, or —S(C(R$^*_2$))$_{2-3}$S—, wherein each independent occurrence of R$^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$^*_2$)$_{2-3}$O—, wherein each independent occurrence of R$^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^*$ include halogen, —R$^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R†)S(O)₂R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

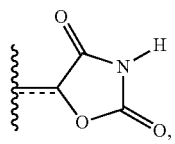

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as 3H and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

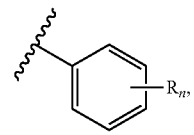

which is understood to be equivalent to a formula:

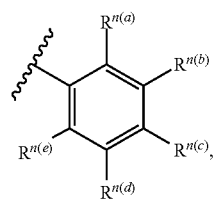

wherein n is typically an integer. That is, $R''$ is understood to represent five independent substituents, $R''^{(a)}$, $R''^{(b)}$, $R''^{(c)}$, $R''^{(d)}$, $R''^{(e)}$. In each such case, each of the five $R''$ can be hydrogen or a recited substituent. By "independent substituents," it is meant that each R substituent can be independently defined. For example, if in one instance $R''^{(a)}$ is halogen, then $R''^{(b)}$ is not necessarily halogen in that instance.

In some yet further aspects, a structure of a compound can be represented by a formula:

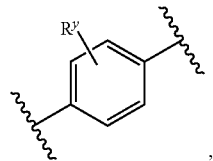

wherein $R^y$ represents, for example, 0-2 independent substituents selected from $A^1$, $A^2$, and $A^3$, which is understood to be equivalent to the groups of formulae:

wherein $R^y$ represents 0 independent substituents

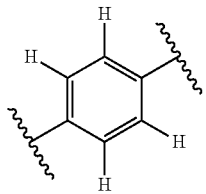

wherein $R^y$ represents 1 independent substituent

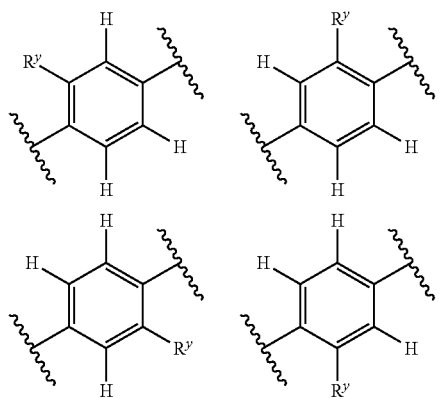

wherein $R^y$ represents 2 independent substituents

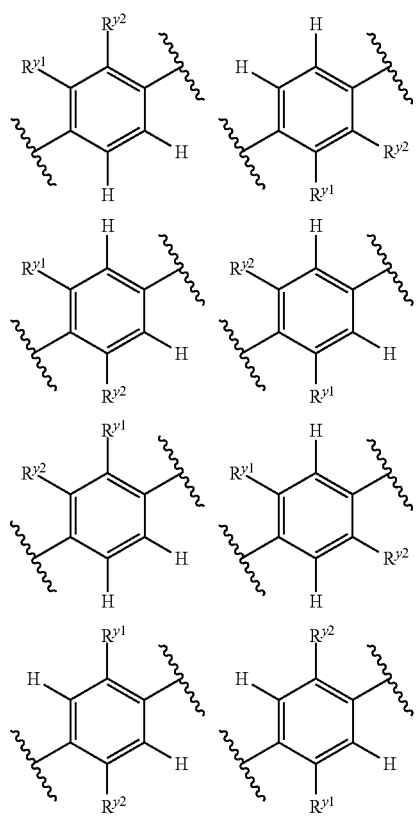

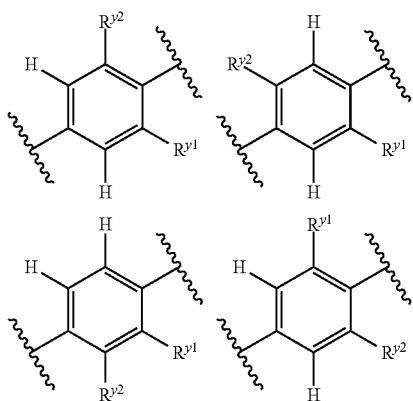

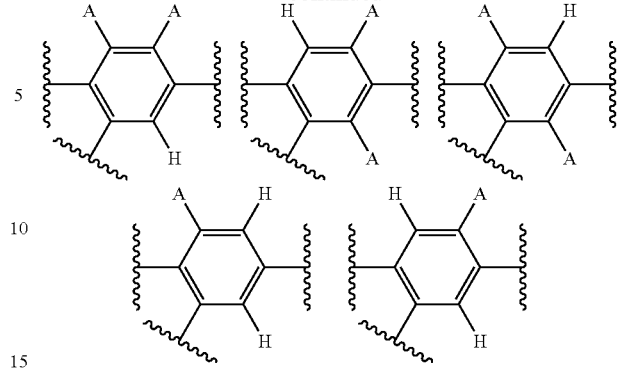

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

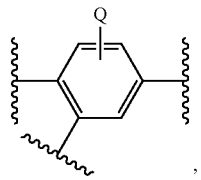

wherein, for example, Q comprises three substituents independently selected from hydrogen and A, which is understood to be equivalent to a formula:

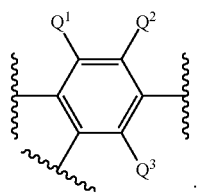

Again, by "independent substituents," it is meant that each Q substituent is independently defined as hydrogen or A, which is understood to be equivalent to the groups of formulae:

wherein Q comprises three substituents independently selected from H and A

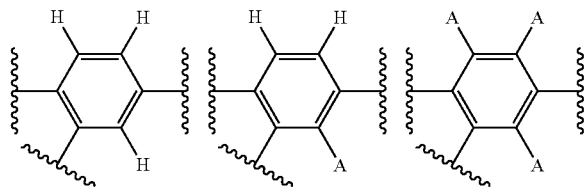

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with a viral infection, in particular, chikungunya, Venezuelan equine encephalitis, dengue, influenza, and zika.

In one aspect, the disclosed compounds exhibit antiviral activity.

In one aspect, the compounds of the invention are useful in inhibiting viral activity in a mammal. In a further aspect, the compounds of the invention are useful in inhibiting viral activity in at least one cell.

In one aspect, the compounds of the invention are useful in the treatment of viral disorders, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

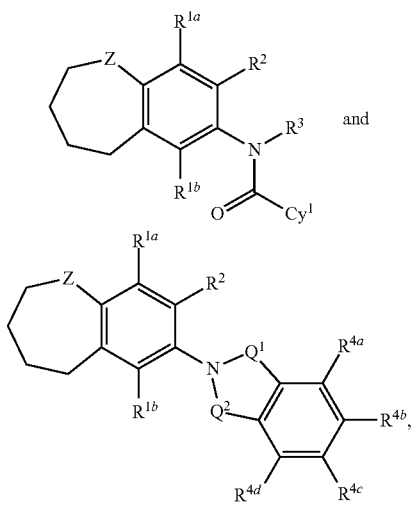

wherein each of $Q^1$ and $Q^2$ is independently selected from $CH_2$, $CH(OH)$, and $C(O)$, provided that at least one of $Q^1$ and $Q^2$ is $C(O)$; wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, provided that when $Cy^1$ is unsubstituted phenyl, then at least one of $R^{1a}$, $R^{1b}$, and $R^2$ is not hydrogen, or a pharmaceutically acceptable salt thereof.

In a further aspect, the compound has a structure represented by a formula:

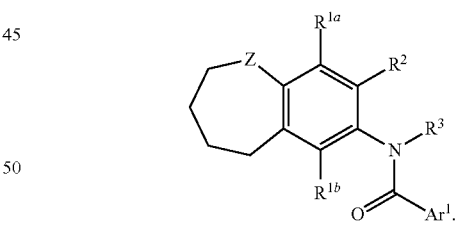

In a further aspect, the compound has a structure selected from:

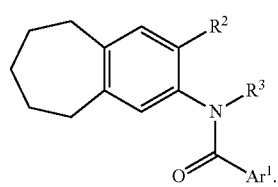

In a further aspect, the compound has a structure selected from:

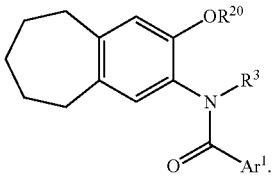

In a further aspect, the compound has a structure selected from:

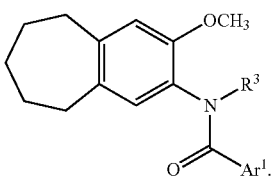

In a further aspect, the compound has a structure represented by a formula:

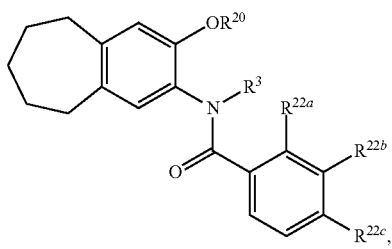

wherein each of $R^{22a}$, $R^{22b}$, and $R^{22c}$ is independently selected from hydrogen, halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, Cy$^1$, and Ar$^3$.

In a further aspect, the compound has a structure represented by a formula:

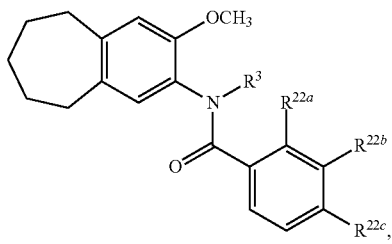

In a further aspect, the compound has a structure represented by a formula:

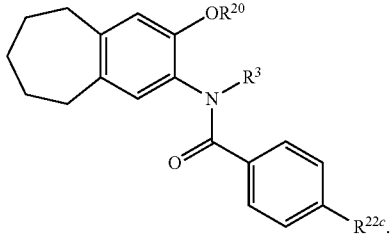

In a further aspect, the compound has a structure represented by a formula:

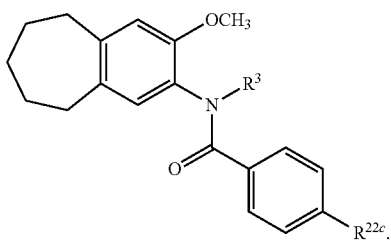

In one aspect, n is selected from 0, 1, 2, 3, and 4. In a further aspect, n is selected from 0, 1, 2, and 3. In a still further aspect, n is selected from 0, 1, and 2. In yet a further aspect, n is selected from 0 and 1. In an even further aspect, n is 4. In a still further aspect, n is 3. In yet a further aspect, n is 2. In an even further aspect, n is 1. In a still further aspect, n is 0.

a. Q$^1$ and Q$^2$ Groups

In one aspect, each of Q$^1$ and Q$^2$ is independently selected from CH$_2$, CH(OH), and C(O), provided that at least one of Q$^1$ and Q$^2$ is C(O). In a further aspect, each of Q$^1$ and Q$^2$ is independently selected from CH$_2$ and C(O). In a still further aspect, each of Q$^1$ and Q$^2$ is independently selected from CH(OH) and C(O). In yet a further aspect, each of Q$^1$ and Q$^2$ is C(O).

In a further aspect, Q$^1$ is C(O) and Q$^2$ is selected from CH$_2$ and CH(OH). In a still further aspect, Q$^1$ is C(O) and Q$^2$ is CH$_2$. In yet a further aspect, Q$^1$ is C(O) and Q$^2$ is CH(OH).

In a further aspect, Q$^2$ is C(O) and Q$^1$ is selected from CH$_2$ and CH(OH). In a still further aspect, Q$^2$ is C(O) and Q$^1$ is CH$_2$. In yet a further aspect, Q$^2$ is C(O) and Q$^1$ is CH(OH).

b. Z Groups

In one aspect, Z is selected from CH$_2$ and NH. In a further aspect, Z is CH$_2$. In a still further aspect, Z is NH.

c. $R^{1A}$ and $R^{1B}$ Groups

In one aspect, each of $R^{1a}$ and $R^{1b}$ is independently selected from hydrogen and —F. In a further aspect, each of $R^{1a}$ and $R^{1b}$ is —F. In a still further aspect, $R^{1a}$ and $R^{1b}$ is hydrogen.

In a further aspect, $R^{1a}$ is hydrogen and $R^{1b}$ is —F. In a still further aspect, $R^{1b}$ is hydrogen and $R^{1a}$ is —F.

d. R$^2$ Groups

In one aspect, R$^2$ is selected from hydrogen, halogen, —CN, —(CH$_2$)$_n$OR$^{20}$, and —OC(O)R$^{21}$. In a further aspect, R$^2$ is selected from hydrogen, —F, —Cl, —Br, —CN, —(CH$_2$)$_n$OR$^{20}$, and —OC(O)R$^{21}$. In a still further aspect, R$^2$ is hydrogen.

In a further aspect, $R^2$ is selected from hydrogen and halogen. In a still further aspect, $R^2$ is selected from hydrogen, —F, —Cl, and —Br. In yet a further aspect, $R^2$ is selected from hydrogen, —F, and —Cl. In an even further aspect, $R^2$ is selected from hydrogen and —Br. In a still further aspect, $R^2$ is selected from hydrogen and —Cl. In yet a further aspect, $R^2$ is selected from hydrogen and —F. In an even further aspect, $R^2$ is selected from hydrogen and —I.

In a further aspect, $R^2$ is selected from halogen. In a still further aspect, $R^2$ is selected from —F, —Cl, and —Br. In yet a further aspect, $R^2$ is selected from —F and —Cl. In an even further aspect, $R^2$ is —Br. In a still further aspect, $R^2$ is —Cl. In yet a further aspect, $R^2$ is —F. In an even further aspect, $R^2$ is —I.

In a further aspect, $R^2$ is selected from —CN, —(CH$_2$)$_n$OR$^{20}$, and —OC(O)R$^{21}$. In a still further aspect, $R^2$ is —CN. In yet a further aspect, $R^2$ is —(CH$_2$)$_n$OR$^{20}$. In an even further aspect, $R^2$ is —OC(O)R$^{21}$.

In a further aspect, $R^2$ is —OR$^{20}$. In a still further aspect, $R^2$ is —OH. In yet a further aspect, $R^2$ is —OCH$_2$CH$_3$. In an even further aspect, $R^2$ is —OCH$_3$.

e. $R^3$ Groups

In one aspect, $R^3$ is selected from hydrogen and C1-C4 alkyl. In a further aspect, $R^3$ is hydrogen.

In a further aspect, $R^3$ is selected from hydrogen, methyl, ethyl, n-propyl, and i-propyl. In a still further aspect, $R^3$ is selected from hydrogen, methyl, and ethyl. In yet a further aspect, $R^3$ is selected from hydrogen and ethyl. In an even further aspect, $R^3$ is selected from hydrogen and methyl.

In a further aspect, $R^3$ is selected from C1-C4 alkyl. In a still further aspect, $R^3$ is selected from methyl, ethyl, n-propyl, and i-propyl. In yet a further aspect, $R^3$ is selected from methyl and ethyl. In an even further aspect, $R^3$ is ethyl. In a still further aspect, $R^3$ is methyl.

f. $R^{4A}$, $R^{4B}$, $R^{4C}$, and $R^{4D}$ Groups

In one aspect, each of $R^{4a}$, $R^{4b}$, $R^{4c}$, and $R^{4d}$ is independently selected from hydrogen, halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$. In a further aspect, each of $R^{4a}$, $R^{4b}$, $R^{4c}$, and $R^{4d}$ is independently selected from hydrogen, halogen, —CO$_2$H, —CN, —OH, —NH$_2$, C1-C4 alkyl, C1-C4 haloalkyl, C1-C4 alkylnitrile, C1-C4 hydroxyalkyl, C1-C4 alkoxy, C1-C4 halohydroxyalkyl, C1-C4 aminoalkyl, C1-C4 alkylamino, (C1-C4)(C1-C4) dialkylamino, and Cy$^2$. In a still further aspect, each of $R^{4a}$, $R^{4b}$, $R^{4c}$, and $R^{4d}$ is hydrogen.

In a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C4 alkyl, C1-C4 haloalkyl, C1-C4 alkylnitrile, C1-C4 hydroxyalkyl, C1-C4 alkoxy, C1-C4 halohydroxyalkyl, C1-C4 aminoalkyl, C1-C4 alkylamino, (C1-C4)(C1-C4) dialkylamino, and Cy$^2$. In yet a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, —CH(CH$_2$F)(CH$_3$), —CH$_2$CN, —CH$_2$CH$_2$CN, —CH$_2$CH$_2$CH$_2$CN, —CH(CH$_2$CN)(CH$_3$), —CH$_2$OH, —CH$_2$CH$_2$OH, —CH$_2$CH$_2$CH$_2$OH, —CH(CH$_2$OH)(CH$_3$), —CH$_2$OCH$_3$, —CH$_2$CH$_2$OCH$_3$, —CH$_2$CH$_2$CH$_2$OCH$_3$, —CH(CH$_2$OCH$_3$)(CH$_3$), —CH(OH)CF$_3$, —CH(OH)CH$_2$CF$_3$, —C(OH)(CF$_3$)(CH$_3$), —C(OH)(CF$_3$)$_2$, —CH$_2$NH$_2$, —CH$_2$CH$_2$NH$_2$, —CH$_2$CH$_2$CH$_2$NH$_2$, —CH(CH$_2$NH$_2$)(CH$_3$), —NHCH$_3$, —NHCH$_2$CH$_3$, —NHCH$_2$CH$_2$CH$_3$, —NHCH(CH$_3$)$_2$, —N(CH$_3$)$_2$, —N(CH$_2$CH$_3$)$_2$, —N(CH$_2$CH$_2$CH$_3$)$_2$, —N(CH(CH$_3$)$_2$)$_2$, and Cy$^2$. In an even further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, —CH$_2$Cl, —CH$_2$CH$_2$Cl, —CH$_2$F, —CH$_2$CH$_2$F, —CH$_2$CN, —CH$_2$CH$_2$CN, —CH$_2$OH, —CH$_2$CH$_2$OH, —CH$_2$OCH$_3$, —CH$_2$CH$_2$OCH$_3$, —CH(OH)CF$_3$, —CH$_2$NH$_2$, —CH$_2$CH$_2$NH$_2$, —NHCH$_3$, —NHCH$_2$CH$_3$, —N(CH$_3$)$_2$, —N(CH$_2$CH$_3$)$_2$, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, —CH$_2$Cl, —CH$_2$F, —CH$_2$CN, —CH$_2$OH, —CH$_2$OCH$_3$, —CH(OH)CF$_3$, —CH$_2$NH$_2$, —NHCH$_3$, —N(CH$_3$)$_2$, and Cy$^2$.

In a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C8 alkyl, C1-C8 haloalkyl, C1-C8 alkylnitrile, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C4 alkyl, C1-C4 haloalkyl, C1-C4 alkylnitrile, and Cy$^2$. In yet a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, —CH(CH$_2$F)(CH$_3$), —CH$_2$CN, —CH$_2$CH$_2$CN, —CH$_2$CH$_2$CH$_2$CN, —CH(CH$_2$CN)(CH$_3$) and Cy$^2$. In an even further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, —CH$_2$Cl, —CH$_2$CH$_2$Cl, —CH$_2$F, —CH$_2$CH$_2$F, —CH$_2$CN, —CH$_2$CH$_2$CN, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, —CH$_2$Cl, —CH$_2$F, —CH$_2$CN, and Cy$^2$.

In a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C8 alkyl, C1-C8 hydroxyalkyl, C1-C8 alkoxy, C1-C8 halohydroxyalkyl, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C4 alkyl, C1-C4 hydroxyalkyl, C1-C4 alkoxy, C1-C4 halohydroxyalkyl, and Cy$^2$. In yet a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, n-propyl, i-propyl, —CH$_2$OH, —CH$_2$CH$_2$OH, —CH$_2$CH$_2$CH$_2$OH, —CH(CH$_2$OH)(CH$_3$), —CH$_2$OCH$_3$, —CH$_2$CH$_2$OCH$_3$, —CH$_2$CH$_2$CH$_2$OCH$_3$, —CH(CH$_2$OCH$_3$)(CH$_3$), —CH(OH)CF$_3$, —CH(OH)CH$_2$CF$_3$, —C(OH)(CF$_3$)(CH$_3$), —C(OH)(CF$_3$)$_2$, and Cy$^2$. In an even further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, —CH$_2$OH, —CH$_2$CH$_2$OH, —CH$_2$OCH$_3$, —CH$_2$CH$_2$OCH$_3$, —CH(OH)CF$_3$, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, —CH$_2$OH, —CH$_2$OCH$_3$, —CH(OH)CF$_3$, and Cy$^2$.

In a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, C1-C4 alkyl, C1-C4 aminoalkyl, C1-C4 alkylamino, (C1-C4)(C1-C4) dialkylamino, and Cy$^2$. In yet a further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, n-propyl, i-propyl, —CH$_2$NH$_2$, —CH$_2$CH$_2$NH$_2$, —CH$_2$CH$_2$CH$_2$NH$_2$, —CH(CH$_2$NH$_2$)(CH$_3$), —NHCH$_3$, —NHCH$_2$CH$_3$, —NHCH$_2$CH$_2$CH$_3$, —NHCH(CH$_3$)$_2$, —N(CH$_3$)$_2$, —N(CH$_2$CH$_3$)$_2$, —N(CH$_2$CH$_2$CH$_3$)$_2$, —N(CH(CH$_3$)$_2$)$_2$, and Cy$^2$. In an even further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, ethyl, —CH$_2$NH$_2$, —CH$_2$CH$_2$NH$_2$, —NHCH$_3$, —NHCH$_2$CH$_3$, —N(CH$_3$)$_2$, —N(CH$_2$CH$_3$)$_2$, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, —CH$_2$NH$_2$, —NHCH$_3$, —N(CH$_3$)$_2$, and Cy$^2$.

In a further aspect, each of $R^{4a}$, $R^{4b}$, $R^{4c}$, and $R^{4d}$ is independently selected from hydrogen, halogen, —CO$_2$H, —CN, —OH, —NH$_2$, C1-C8 alkyl, and Cy$^2$. In a still further aspect, each of $R^{4a}$, $R^{4b}$, $R^{4c}$, and $R^{4d}$ is independently selected from hydrogen, halogen, —CO$_2$H, —CN, —OH, —NH$_2$, C1-C4 alkyl, and Cy$^2$. In yet a further aspect, each of $R^{4a}$, $R^{4b}$, $R^{4c}$, and $R^{4d}$ is independently selected from hydrogen, halogen, —CO$_2$H, —CN, —OH, —NH$_2$, methyl, ethyl, n-propyl, i-propyl, and Cy$^2$. In an even further aspect, each of $R^{4a}$, $R^{4b}$, $R^{4c}$, and $R^{4d}$ is independently selected from hydrogen, halogen, —CO$_2$H, —CN, —OH, —NH$_2$, methyl, ethyl, and Cy$^2$. In a still further aspect, each of $R^{4a}$, $R^{4b}$, $R^{4c}$, and $R^{4d}$ is independently selected from hydrogen, halogen, —CO$_2$H, —CN, —OH, —NH$_2$, methyl, and Cy$^2$.

In a further aspect, each of $R^{4a}$, $R^{4b}$, $R^{4c}$, and $R^{4d}$ is independently selected from hydrogen and halogen. In a still further aspect, each of $R^{4a}$, $R^{4b}$, $R^{4c}$, and $R^{4d}$ is independently selected from hydrogen, —F, —Cl, and —Br. In yet a further aspect, each of $R^{4a}$, $R^{4b}$, $R^{4c}$, and $R^{4d}$ is independently selected from hydrogen, —F, and —Cl. In an even further aspect, each of $R^{4a}$, $R^{4b}$, $R^{4c}$, and $R^{4d}$ is independently selected from hydrogen and —I. In a still further aspect, each of $R^{4a}$, $R^{4b}$, $R^{4c}$, and $R^{4d}$ is independently selected from hydrogen and —Br. In yet a further aspect, each of $R^{4a}$, $R^{4b}$, $R^{4c}$, and $R^{4d}$ is independently selected from hydrogen and —Cl. In an even further aspect, each of $R^{4a}$, $R^{4b}$, $R^{4c}$, and $R^{4d}$ is independently selected from hydrogen and —F.

In a further aspect, each of $R^{4a}$, $R^{4b}$, $R^{4c}$, and $R^{4d}$ is independently selected from hydrogen and C1-C8 alkyl. In a still further aspect, each of $R^{4a}$, $R^{4b}$, $R^{4c}$, and $R^{4d}$ is independently selected from hydrogen, methyl, ethyl, n-propyl, i-propyl, n-butyl, i-butyl, sec-butyl, and t-butyl. In yet a further aspect, each of $R^{4a}$, $R^{4b}$, $R^{4c}$, and $R^{4d}$ is independently selected from hydrogen, methyl, ethyl, n-propyl, and i-propyl. In an even further aspect, each of $R^{4a}$, $R^{4b}$, $R^{4c}$, and $R^{4d}$ is independently selected from hydrogen, methyl, and ethyl. In a still further aspect, each of $R^{4a}$, $R^{4b}$, $R^{4c}$, and $R^{4d}$ is independently selected from hydrogen and ethyl. In yet a further aspect, each of $R^{4a}$, $R^{4b}$, $R^{4c}$, and $R^{4d}$ is independently selected from hydrogen and methyl.

In a further aspect, each of $R^{4a}$, $R^{4b}$, and $R^{4d}$ is hydrogen and $R^{4c}$ is selected from —F, —Cl, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$. In a still further aspect, each of $R^{4a}$, $R^{4b}$, and $R^{4d}$ is hydrogen and $R^{4c}$ is selected from —F, —Cl, —CO$_2$H, —CN, —OH, —NH$_2$, C1-C4 alkyl, C1-C4 haloalkyl, C1-C4 alkylnitrile, C1-C4 hydroxyalkyl, C1-C4 alkoxy, C1-C4 halohydroxyalkyl, C1-C4 aminoalkyl, C1-C4 alkylamino, (C1-C4)(C1-C4) dialkylamino, and Cy$^2$. In yet a further aspect, each of $R^{4a}$, $R^{4b}$, and $R^{4d}$ is hydrogen and $R^{4c}$ is selected from —F, —Cl, —CO$_2$H, —CN, —OH, —NH$_2$, methyl, ethyl, n-propyl, i-propyl, —CH$_2$Cl, —CH$_2$CH$_2$Cl, —CH$_2$CH$_2$CH$_2$Cl, —CH(CH$_2$Cl)(CH$_3$), —CH$_2$F, —CH$_2$CH$_2$F, —CH$_2$CH$_2$CH$_2$F, —CH(CH$_2$F)(CH$_3$), —CH$_2$CN, —CH$_2$CH$_2$CN, —CH$_2$CH$_2$CH$_2$CN, —CH(CH$_2$CN)(CH$_3$), —CH$_2$OH, —CH$_2$CH$_2$OH, —CH$_2$CH$_2$CH$_2$OH, —CH(CH$_2$OH)(CH$_3$), —CH$_2$OCH$_3$, —CH$_2$CH$_2$OCH$_3$, —CH$_2$CH$_2$CH$_2$OCH$_3$, —CH(CH$_2$OCH$_3$)(CH$_3$), —CH(OH)CF$_3$, —CH(OH)CH$_2$CF$_3$, —C(OH)(CF$_3$)(CH$_3$), —C(OH)(CF$_3$)$_2$, —CH$_2$NH$_2$, —CH$_2$CH$_2$NH$_2$, —CH$_2$CH$_2$CH$_2$NH$_2$, —CH(CH$_2$NH$_2$)(CH$_3$), —NHCH$_3$, —NHCH$_2$CH$_3$, —NHCH$_2$CH$_2$CH$_3$, —NHCH(CH$_3$)$_2$, —N(CH$_3$)$_2$, —N(CH$_2$CH$_3$)$_2$, —N(CH$_2$CH$_2$CH$_3$)$_2$, —N(CH(CH$_3$)$_2$)$_2$, and Cy$^2$. In an even further aspect, each of $R^{4a}$, $R^{4b}$, and $R^{4d}$ is hydrogen and $R^{4c}$ is selected from —F, —Cl, —CO$_2$H, —CN, —OH, —NH$_2$, methyl, ethyl, —CH$_2$Cl, —CH$_2$CH$_2$Cl, —CH$_2$F, —CH$_2$CH$_2$F, —CH$_2$CN, —CH$_2$CH$_2$CN, —CH$_2$OH, —CH$_2$CH$_2$OH, —CH$_2$OCH$_3$, —CH$_2$CH$_2$OCH$_3$, —CH(OH)CF$_3$, —CH$_2$NH$_2$, —CH$_2$CH$_2$NH$_2$, —NHCH$_3$, —NHCH$_2$CH$_3$, —N(CH$_3$)$_2$, —N(CH$_2$CH$_3$)$_2$, and Cy$^2$. In a still further aspect, each of $R^{4a}$, $R^{4b}$, $R^{4c}$, and $R^{4d}$ is independently selected from hydrogen, —F, —Cl, —CO$_2$H, —CN, —OH, —NH$_2$, methyl, —CH$_2$Cl, —CH$_2$F, —CH$_2$CN, —CH$_2$OH, —CH$_2$OCH$_3$, —CH(OH)CF$_3$, —CH$_2$NH$_2$, —NHCH$_3$, —N(CH$_3$)$_2$, and Cy$^2$.

In a further aspect, each of $R^{4a}$, $R^{4b}$, and $R^{4d}$ is hydrogen and $R^{4c}$ is selected from C1-C8 alkyl. In a still further aspect, each of $R^{4a}$, $R^{4b}$, and $R^{4d}$ is hydrogen and $R^{4c}$ is selected from methyl, ethyl, n-propyl, i-propyl, n-butyl, i-butyl, sec-butyl, and t-butyl. In yet a further aspect, each of $R^{4a}$, $R^{4b}$, and $R^{4d}$ is hydrogen and $R^{4c}$ is selected from methyl, ethyl, n-propyl, and i-propyl. In an even further aspect, each of $R^{4a}$, $R^{4b}$, and $R^{4d}$ is hydrogen and $R^{4c}$ is selected from methyl and ethyl. In a still further aspect, each of $R^{4a}$, $R^{4b}$, and $R^{4d}$ is hydrogen and $R^{4c}$ is t-butyl. In yet a further aspect, each of $R^{4a}$, $R^{4b}$, and $R^{4d}$ is hydrogen and $R^{4c}$ is n-butyl. In an even further aspect, each of $R^{4a}$, $R^{4b}$, and $R^{4d}$ is hydrogen and $R^{4c}$ is i-butyl. In a still further aspect, each of $R^{4a}$, $R^{4b}$, and $R^{4d}$ is hydrogen and $R^{4c}$ is s-butyl. In yet a further aspect, each of $R^{4a}$, $R^{4b}$, and $R^{4d}$ is hydrogen and $R^{4c}$ is n-propyl. In an even further aspect, each of $R^{4a}$, $R^{4b}$, and $R^{4d}$ is hydrogen and $R^{4c}$ is i-propyl. In a still further aspect, each of $R^{4a}$, $R^{4b}$, and $R^{4d}$ is hydrogen and $R^{4c}$ is ethyl. In yet a further aspect, each of $R^{4a}$, $R^{4b}$, and $R^{4d}$ is hydrogen and $R^{4c}$ is methyl.

g. $R^{20}$ Groups

In one aspect, $R^{20}$, when present, is selected from hydrogen, C1-C4 alkyl, C1-C4 haloalkyl, Ar$^1$, and —(C1-C4 alkyl)Ar$^1$. In a further aspect, $R^{20}$, when present, is hydrogen.

In a further aspect, $R^{20}$, when present, is selected from hydrogen, Ar$^1$, and —(C1-C4 alkyl)Ar$^1$. In a still further aspect, $R^{20}$, when present, is selected from hydrogen, Ar$^1$, —CH$_2$Ar$^1$, —CH$_2$CH$_2$Ar$^1$, —CH$_2$CH$_2$CH$_2$Ar$^1$, and —CH ($CH_3$)($CH_2Ar^1$). In yet a further aspect, $R^{20}$, when present, is selected from hydrogen, $Ar^1$, —$CH_2Ar^1$, and —$CH_2CH_2Ar^1$. In an even further aspect, $R^{20}$, when present, is selected from hydrogen, $Ar^1$, and —$CH_2Ar^1$.

In a further aspect, $R^{20}$, when present, is selected from $Ar^1$ and —(C1-C4 alkyl)$Ar^1$. In a still further aspect, $R^{20}$, when present, is selected from $Ar^1$, —$CH_2Ar^1$, —$CH_2CH_2Ar^1$, —$CH_2CH_2CH_2Ar^1$, and —CH($CH_3$)($CH_2Ar^1$). In yet a further aspect, $R^{20}$, when present, is selected from $Ar^1$, —$CH_2Ar^1$, and —$CH_2CH_2Ar^1$. In an even further aspect, $R^{20}$, when present, is selected from $Ar^1$ and —$CH_2Ar^1$. In a still further aspect, $R^{20}$, when present, is $Ar^1$. In yet a further aspect, $R^{20}$, when present, is —$CH_2Ar^1$.

In a further aspect, $R^{20}$, when present, is selected from hydrogen, C1-C4 alkyl, and C1-C4 haloalkyl. In a still further aspect, $R^{20}$, when present, is selected from hydrogen, methyl, ethyl, n-propyl, i-propyl, —$CH_2Cl$, —$CH_2CH_2Cl$, —$CH_2CH_2CH_2Cl$, —CH($CH_2Cl$)($CH_3$), —$CH_2F$, —$CH_2CH_2F$, —$CH_2CH_2CH_2F$, and —CH($CH_2F$)($CH_3$). In yet a further aspect, $R^{20}$, when present, is selected from hydrogen, methyl, ethyl, —$CH_2Cl$, —$CH_2CH_2Cl$, —$CH_2F$, and —$CH_2CH_2F$. In an even further aspect, $R^{20}$, when present, is selected from hydrogen, methyl, —$CH_2Cl$, and —$CH_2F$.

In a further aspect, $R^{20}$, when present, is selected from hydrogen and C1-C4 haloalkyl. In a still further aspect, $R^{20}$, when present, is selected from hydrogen, —$CH_2Cl$, —$CH_2CH_2Cl$, —$CH_2CH_2CH_2Cl$, —CH($CH_2Cl$)($CH_3$), —$CH_2F$, —$CH_2CH_2F$, —$CH_2CH_2CH_2F$, and —CH($CH_2F$)($CH_3$). In yet a further aspect, $R^{20}$, when present, is selected from hydrogen, —$CH_2Cl$, —$CH_2CH_2Cl$, —$CH_2F$, and —$CH_2CH_2F$. In an even further aspect, $R^{20}$, when present, is selected from hydrogen, —$CH_2Cl$, and —$CH_2F$.

In a further aspect, $R^{20}$, when present, is selected from hydrogen and C1-C4 alkyl. In a still further aspect, $R^{20}$, when present, is selected from hydrogen, methyl, ethyl, n-propyl, and i-propyl. In yet a further aspect, $R^{20}$, when present, is selected from hydrogen, methyl, and ethyl. In an even further aspect, $R^{20}$, when present, is selected from hydrogen and methyl. In a still further aspect, $R^{20}$, when present, is selected from hydrogen and ethyl.

h. $R^{21}$ Groups

In one aspect, $R^{21}$, when present, is selected from hydrogen, C1-C4 alkyl, C1-C4 haloalkyl, and $Ar^1$. In a further aspect, $R^{21}$, when present, is hydrogen.

In a further aspect, $R^{21}$, when present, is selected from hydrogen, C1-C4 alkyl, and $Ar^1$. In a still further aspect, $R^{21}$, when present, is selected from hydrogen, methyl, ethyl, n-propyl, i-propyl, and $Ar^1$. In yet a further aspect, $R^{21}$, when present, is selected from hydrogen, methyl, ethyl, and $Ar^1$. In an even further aspect, $R^{21}$, when present, is selected from hydrogen, methyl, and $Ar^1$.

In a further aspect, $R^{21}$, when present, is selected from hydrogen, C1-C4 haloalkyl, and $Ar^1$. In a still further aspect, $R^{21}$, when present, is selected from hydrogen, —$CH_2Cl$, —$CH_2CH_2Cl$, —$CH_2CH_2CH_2Cl$, —CH($CH_2Cl$)($CH_3$), —$CH_2F$, —$CH_2CH_2F$, —$CH_2CH_2CH_2F$, —CH($CH_2F$)($CH_3$), and $Ar^1$. In yet a further aspect, $R^{21}$, when present, is selected from hydrogen, —$CH_2Cl$, —$CH_2CH_2Cl$, —$CH_2F$, —$CH_2CH_2F$, and $Ar^1$. In an even further aspect, $R^{21}$, when present, is selected from hydrogen, —$CH_2Cl$, —$CH_2F$, and $Ar^1$.

In a further aspect, $R^{21}$, when present, is selected from hydrogen and C1-C4 alkyl. In a still further aspect, $R^{21}$, when present, is selected from hydrogen, methyl, ethyl, n-propyl, and i-propyl. In yet a further aspect, $R^{21}$, when present, is selected from hydrogen, methyl, and ethyl. In an even further aspect, $R^{21}$, when present, is selected from hydrogen and ethyl. In a still further aspect, $R^{21}$, when present, is selected from hydrogen and methyl.

In a further aspect, $R^{21}$, when present, is selected from C1-C4 alkyl. In a still further aspect, $R^{21}$, when present, is selected from methyl, ethyl, n-propyl, and i-propyl. In yet a further aspect, $R^{21}$, when present, is selected from methyl and ethyl. In an even further aspect, $R^{21}$, when present, is ethyl. In a still further aspect, $R^{21}$, when present, is methyl.

In a further aspect, $R^{21}$, when present, is selected from hydrogen and C1-C4 haloalkyl. In a still further aspect, $R^{21}$, when present, is selected from hydrogen, —$CH_2Cl$, —$CH_2CH_2Cl$, —$CH_2CH_2CH_2Cl$, —CH($CH_2Cl$)($CH_3$), —$CH_2F$, —$CH_2CH_2F$, —$CH_2CH_2CH_2F$, and —CH($CH_2F$)($CH_3$). In yet a further aspect, $R^{21}$, when present, is selected from hydrogen, —$CH_2Cl$, —$CH_2CH_2Cl$, —$CH_2F$, and —$CH_2CH_2F$. In an even further aspect, $R^{21}$, when present, is selected from hydrogen, —$CH_2Cl$, and —$CH_2F$.

In a further aspect, $R^{21}$, when present, is selected from C1-C4 haloalkyl. In a still further aspect, $R^{21}$, when present, is selected from —$CH_2Cl$, —$CH_2CH_2Cl$, —$CH_2CH_2CH_2Cl$, —CH($CH_2Cl$)($CH_3$), —$CH_2F$, —$CH_2CH_2F$, —$CH_2CH_2CH_2F$, and —CH($CH_2F$)($CH_3$). In yet a further aspect, $R^{21}$, when present, is selected from —$CH_2Cl$, —$CH_2CH_2Cl$, —$CH_2F$, and —$CH_2CH_2F$. In an even further aspect, $R^{21}$, when present, is selected from —$CH_2Cl$ and —$CH_2F$. In a still further aspect, $R^{21}$, when present, is —$CH_2Cl$. In yet a further aspect, $R^{21}$, when present, is —$CH_2F$.

In a further aspect, $R^{21}$, when present, is $Ar^1$.

i. $Ar^1$ Groups

In one aspect, $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy. In a further aspect, $Ar^1$, when present, is selected from C5-C6 aryl and C4-C5 heteroaryl and substituted with 0, 1, or 2 groups independently selected from halogen, C1-C4 alkyl, C1-C4 haloalkyl, C1-C4 hydroxyalkyl, and C1-C4 alkoxy. In a still further aspect, $Ar^1$, when present, is selected from C5-C6 aryl and C4-C5 heteroaryl and substituted with 0 or 1 group selected from halogen, C1-C4 alkyl, C1-C4 haloalkyl, C1-C4 hydroxyalkyl, and C1-C4 alkoxy. In yet a further aspect, $Ar^1$, when present, is selected from C5-C6 aryl and C4-C5 heteroaryl and monosubstituted with a group selected from halogen, C1-C4 alkyl, C1-C4 haloalkyl, C1-C4 hydroxyalkyl, and C1-C4 alkoxy. In a still further aspect, $Ar^1$, when present, is selected from C5-C6 aryl and C4-C5 heteroaryl and unsubstituted.

In a further aspect, $Ar^1$, when present, is C5-C6 aryl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Ar^1$, when present, is C5-C6 aryl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Ar^1$, when present, is C5-C6 aryl substituted with 0 or 1 group selected from halogen, C1-C4 alkyl, C1-C4 haloalkyl, C1-C4 hydroxyalkyl, and C1-C4 alkoxy. In an even further aspect, $Ar^1$, when present, is C5-C6 aryl monosubstituted with a group selected from halogen, C1-C4 alkyl, C1-C4 haloalkyl, C1-C4 hydroxyalkyl, and C1-C4 alkoxy. In a still further aspect, $Ar^1$, when present, is unsubstituted C5-C6 aryl.

In a further aspect, $Ar^1$, when present, is phenyl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Ar^1$, when present, is phenyl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Ar^1$, when present, is phenyl substituted with 0 or 1 group selected from halogen, C1-C4 alkyl, C1-C4 haloalkyl, C1-C4 hydroxyalkyl, and C1-C4 alkoxy. In an even further aspect, $Ar^1$, when present, is phenyl monosubstituted with a group selected from halogen, C1-C4 alkyl, C1-C4 haloalkyl, C1-C4 hydroxyalkyl, and C1-C4 alkoxy. In a still further aspect, $Ar^1$, when present, is unsubstituted phenyl.

In a further aspect, $Ar^1$, when present, is C4-C5 heteroaryl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Ar^1$, when present, is C4-C5 heteroaryl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Ar^1$, when present, is C4-C5 heteroaryl substituted with 0 or 1 group selected from halogen, C1-C4 alkyl, C1-C4 haloalkyl, C1-C4 hydroxyalkyl, and C1-C4 alkoxy. In an even further aspect, $Ar^1$, when present, is C4-C5 heteroaryl monosubstituted with a group selected from halogen, C1-C4 alkyl, C1-C4 haloalkyl, C1-C4 hydroxyalkyl, and C1-C4 alkoxy. In a still further aspect, $Ar^1$, when present, is unsubstituted C4-C5 heteroaryl.

In a further aspect, $Ar^1$, when present, is selected from furanyl, thiophenyl, pyrrolyl, pyridinyl, imidazolyl, and purinyl and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Ar^1$, when present, is selected from furanyl, thiophenyl, pyrrolyl, pyridinyl, imidazolyl, and purinyl and substituted with 0, 1, or 2 groups independently selected from halogen, C1-C4 alkyl, C1-C4 haloalkyl, C1-C4 hydroxyalkyl, and C1-C4 alkoxy. In yet a further aspect, $Ar^1$, when present, is selected from furanyl, thiophenyl, pyrrolyl, pyridinyl, imidazolyl, and purinyl and substituted with 0 or 1 group selected from halogen, C1-C4 alkyl, C1-C4 haloalkyl, C1-C4 hydroxyalkyl, and C1-C4 alkoxy. In an even further aspect, $Ar^1$, when present, is selected from furanyl, thiophenyl, pyrrolyl, pyridinyl, imidazolyl, and purinyl and monosubstituted with a group selected from halogen, C1-C4 alkyl, C1-C4 haloalkyl, C1-C4 hydroxyalkyl, and C1-C4 alkoxy. In a still further aspect, $Ar^1$, when present, is selected from furanyl, thiophenyl, pyrrolyl, pyridinyl, imidazolyl, and purinyl and unsubstituted.

j. $Cy^1$ Groups

In one aspect, $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, provided that when $Cy^1$ is unsubstituted phenyl, then at least one of $R^{1a}$, $R^{1b}$, and $R^2$ is not hydrogen. In a further aspect, $Cy^1$ is selected from C3-C10 cycloalkyl, C5-C6 aryl, and C4-C5 heteroaryl and substituted with 0 or 1 group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In a still further aspect, $Cy^1$ is selected from C3-C10 cycloalkyl, C5-C6 aryl, and C4-C5 heteroaryl and monosubstituted with a group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In yet a further aspect, $Cy^1$ is selected from C3-C10 cycloalkyl, C5-C6 aryl, and C4-C5 heteroaryl and unsubstituted.

In a further aspect, $Cy^1$ is C3-C10 cycloalkyl substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In a still further aspect, $Cy^1$ is C3-C10 cycloalkyl substituted with 0 or 1 group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In yet a further aspect, $Cy^1$ is C3-C10 cycloalkyl monosubstituted with a group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In an even further aspect, $Cy^1$ is unsubstituted C3-C10 cycloalkyl.

In a further aspect, $Cy^1$ is adamantine substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In a still further aspect, $Cy^1$ is adamantine substituted with 0 or 1 group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In yet a further aspect, $Cy^1$ is adamantine monosubstituted with a group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In an even further aspect, $Cy^1$ is unsubstituted adamantane.

In a further aspect, $Cy^1$ is selected from C5-C6 aryl and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In a still further aspect, $Cy^1$ is selected from C5-C6 aryl and C4-C5 heteroaryl and substituted with 0 or 1 group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In yet a further aspect, $Cy^1$ is selected from C5-C6 aryl and C4-C5 heteroaryl and monosubstituted with a group selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$. In an even further aspect, $Cy^1$ is selected from C5-C6 aryl and C4-C5 heteroaryl and unsubstituted.

In a further aspect, $Cy^1$ is C5-C6 aryl substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In a still further aspect, Cy$^1$ is C5-C6 aryl substituted with 0 or 1 group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In yet a further aspect, Cy$^1$ is C5-C6 aryl monosubstituted with a group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In an even further aspect, Cy$^1$ is unsubstituted C5-C6 aryl.

In a further aspect, Cy$^1$ is phenyl substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In a still further aspect, Cy$^1$ is phenyl substituted with 0 or 1 group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In yet a further aspect, Cy$^1$ is phenyl monosubstituted with a group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In an even further aspect, Cy$^1$ is unsubstituted phenyl.

In a further aspect, Cy$^1$ is phenyl substituted with a C1-C8 alkyl group. In a still further aspect, Cy$^1$ is phenyl substituted with a C1-C4 alkyl group. In yet a further aspect, Cy$^1$ is phenyl substituted with a group selected from methyl, ethyl, n-propyl, and i-propyl. In an even further aspect, Cy$^1$ is phenyl substituted with a group selected from methyl and ethyl. In a still further aspect, Cy$^1$ is phenyl substituted with a tert-butyl group. In yet a further aspect, Cy$^1$ is phenyl substituted with an iso-butyl group. In an even further aspect, Cy$^1$ is phenyl substituted with a n-butyl group. In a still further aspect, Cy$^1$ is phenyl substituted with a sec-butyl group. In yet a further aspect, Cy$^1$ is phenyl substituted with an iso-propyl group. In an even further aspect, Cy$^1$ is phenyl substituted with a n-propyl group. In a still further aspect, Cy$^1$ is phenyl substituted with an ethyl group. In yet a further aspect, Cy$^1$ is phenyl substituted with a methyl group.

In a further aspect, Cy$^1$ is C4-C5 heteroaryl substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, Cy$^1$, and Ar$^3$. In a still further aspect, Cy$^1$ is C4-C5 heteroaryl substituted with 0 or 1 group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In yet a further aspect, Cy$^1$ is C4-C5 heteroaryl monosubstituted with a group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In an even further aspect, Cy$^1$ is unsubstituted C4-C5 heteroaryl.

In a further aspect, Cy$^1$ is selected from thiazole, pyrazole, imidazole, furan, thiophene, isoxazole, pyrimidine, and pyridine and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, Cy$^1$, and Ar$^3$. In a still further aspect, Cy$^1$ is selected from thiazole, pyrazole, imidazole, furan, thiophene, isoxazole, pyrimidine, and pyridine and substituted with 0 or 1 group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In yet a further aspect, Cy$^1$ is selected from thiazole, pyrazole, imidazole, furan, thiophene, isoxazole, pyrimidine, and pyridine and monosubstituted with a group selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and Cy$^2$. In an even further aspect, Cy$^1$ is selected from thiazole, pyrazole, imidazole, furan, thiophene, isoxazole, pyrimidine, and pyridine and unsubstituted.

In a further aspect, Cy$^1$ is unsubstituted adamantine.

k. Cy$^2$ Groups

In one aspect, Cy$^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy. In a further aspect, Cy$^2$, when present, is selected from C3-C5 cycloalkyl, C2-C5 heterocycloalkyl, C5-C6 aryl, and C4-C5 heteroaryl and substituted with 0, 1, or 2 groups independently selected from halogen, C1-C4 alkyl, C1-C4 haloalkyl, C1-C4 hydroxyalkyl, and C1-C4 alkoxy. In a still further aspect, Cy$^2$, when present, is selected from C3-C5 cycloalkyl, C2-C5 heterocycloalkyl, C5-C6 aryl, and C4-C5 heteroaryl and substituted with 0 or 1 group selected from halogen, C1-C4 alkyl, C1-C4 haloalkyl, C1-C4 hydroxyalkyl, and C1-C4 alkoxy. In yet a further aspect, Cy$^2$, when present, is selected from C3-C5 cycloalkyl, C2-C5 heterocycloalkyl, C5-C6 aryl, and C4-C5 heteroaryl and monosubstituted with a group selected from halogen, C1-C4 alkyl, C1-C4 haloalkyl, C1-C4 hydroxyalkyl, and C1-C4 alkoxy. In an even further aspect, Cy$^2$, when present, is selected from C3-C5 cycloalkyl, C2-C5 heterocycloalkyl, C5-C6 aryl, and C4-C5 heteroaryl and unsubstituted.

In a further aspect, Cy$^2$, when present, is selected from C3-C5 cycloalkyl and C2-C5 heterocycloalkyl and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, Cy$^2$, when present, is selected from C3-C5 cycloalkyl and C2-C5 heterocycloalkyl and substituted with 0, 1, or 2 groups independently selected from halogen, C1-C4 alkyl, C1-C4 haloalkyl, C1-C4 hydroxyalkyl, and C1-C4 alkoxy. In yet a further aspect, Cy$^2$, when present, is selected from C3-C5 cycloalkyl and C2-C5 heterocycloalkyl and substituted with 0 or 1 group selected from halogen, C1-C4 alkyl, C1-C4 haloalkyl, C1-C4 hydroxyalkyl, and C1-C4 alkoxy. In an even further aspect, Cy$^2$, when present, is selected from C3-C5 cycloalkyl and C2-C5 heterocycloalkyl and monosubstituted with a group selected from halogen, C1-C4 alkyl, C1-C4 haloalkyl, C1-C4 hydroxyalkyl, and C1-C4 alkoxy. In a still further aspect, $Cy^2$, when present, is selected from C3-C5 cycloalkyl and C2-C5 heterocycloalkyl and unsubstituted.

In a further aspect, $Cy^2$, when present, is C3-C5 cycloalkyl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is C3-C5 cycloalkyl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is C3-C5 cycloalkyl substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is C3-C5 cycloalkyl monosubstituted with a group selected from halogen, C1-C4 alkyl, C1-C4 haloalkyl, C1-C4 hydroxyalkyl, and C1-C4 alkoxy. In a still further aspect, $Cy^2$, when present, is unsubstituted C3-C5 cycloalkyl.

In a further aspect, $Cy^2$, when present, is selected from cyclopropyl, cyclobutyl, and cyclopentyl and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is selected from cyclopropyl, cyclobutyl, and cyclopentyl and substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is selected from cyclopropyl, cyclobutyl, and cyclopentyl and substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is selected from cyclopropyl, cyclobutyl, and cyclopentyl and monosubstituted with a group selected from halogen, C1-C4 alkyl, C1-C4 haloalkyl, C1-C4 hydroxyalkyl, and C1-C4 alkoxy. In a still further aspect, $Cy^2$, when present, is selected from cyclopropyl, cyclobutyl, and cyclopentyl and unsubstituted.

In a further aspect, $Cy^2$, when present, is C2-C5 heterocycloalkyl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is C2-C5 heterocycloalkyl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is C2-C5 heterocycloalkyl substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is C2-C5 heterocycloalkyl monosubstituted with a group selected from halogen, C1-C4 alkyl, C1-C4 haloalkyl, C1-C4 hydroxyalkyl, and C1-C4 alkoxy. In a still further aspect, $Cy^2$, when present, is unsubstituted C2-C5 heterocycloalkyl.

In a further aspect, $Cy^2$, when present, is selected from azetidinyl, aziridinyl, morpholinyl, oxetanyl, oxiranyl, piperazinyl, piperidinyl, pyrrolidinyl, tetrahydro-2H-pyranyl, tetrahydro-2H-thiopyranyl, tetrahydrofuranyl, tetrahydrothiophenyl, thietanyl, thiiranyl, and thiomorpholinyl and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is selected from azetidinyl, aziridinyl, morpholinyl, oxetanyl, oxiranyl, piperazinyl, piperidinyl, pyrrolidinyl, tetrahydro-2H-pyranyl, tetrahydro-2H-thiopyranyl, tetrahydrofuranyl, tetrahydrothiophenyl, thietanyl, thiiranyl, and thiomorpholinyl and substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is selected from azetidinyl, aziridinyl, morpholinyl, oxetanyl, oxiranyl, piperazinyl, piperidinyl, pyrrolidinyl, tetrahydro-2H-pyranyl, tetrahydro-2H-thiopyranyl, tetrahydrofuranyl, tetrahydrothiophenyl, thietanyl, thiiranyl, and thiomorpholinyl and substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is selected from azetidinyl, aziridinyl, morpholinyl, oxetanyl, oxiranyl, piperazinyl, piperidinyl, pyrrolidinyl, tetrahydro-2H-pyranyl, tetrahydro-2H-thiopyranyl, tetrahydrofuranyl, tetrahydrothiophenyl, thietanyl, thiiranyl, and thiomorpholinyl and monosubstituted with a group selected from halogen, C1-C4 alkyl, C1-C4 haloalkyl, C1-C4 hydroxyalkyl, and C1-C4 alkoxy. In a still further aspect, $Cy^2$, when present, is selected from azetidinyl, aziridinyl, morpholinyl, oxetanyl, oxiranyl, piperazinyl, piperidinyl, pyrrolidinyl, tetrahydro-2H-pyranyl, tetrahydro-2H-thiopyranyl, tetrahydrofuranyl, tetrahydrothiophenyl, thietanyl, thiiranyl, and thiomorpholinyl and unsubstituted.

In a further aspect, $Cy^2$, when present, is morpholinyl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is morpholinyl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is morpholinyl substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is morpholinyl monosubstituted with a group selected from halogen, C1-C4 alkyl, C1-C4 haloalkyl, C1-C4 hydroxyalkyl, and C1-C4 alkoxy. In a still further aspect, $Cy^2$, when present, is unsubstituted morpholinyl.

In a further aspect, $Cy^2$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is selected from C5-C6 aryl and C4-C5 heteroaryl and substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is selected from C5-C6 aryl and C4-C5 heteroaryl and substituted with 0 or 1 group selected from halogen, C1-C4 alkyl, C1-C4 haloalkyl, C1-C4 hydroxyalkyl, and C1-C4 alkoxy. In an even further aspect, $Cy^2$, when present, is selected from C5-C6 aryl and C4-C5 heteroaryl and monosubstituted with a group selected from halogen, C1-C4 alkyl, C1-C4 haloalkyl, C1-C4 hydroxyalkyl, and C1-C4 alkoxy. In a still further aspect, $Cy^2$, when present, is selected from C5-C6 aryl and C4-C5 heteroaryl and unsubstituted.

In a further aspect, $Cy^2$, when present, is C5-C6 aryl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, $Cy^2$, when present, is C5-C6 aryl substituted with 0, 1, or 2 groups independently selected from halogen, C1-C4 alkyl, C1-C4 haloalkyl, C1-C4 hydroxyalkyl, and C1-C4 alkoxy. In yet a further aspect, $Cy^2$, when present, is C5-C6 aryl substituted with 0 or 1 group selected from halogen, C1-C4 alkyl, C1-C4 haloalkyl, C1-C4 hydroxyalkyl, and C1-C4 alkoxy. In an even further aspect, Cy$^2$, when present, is C5-C6 aryl monosubstituted with a group selected from halogen, C1-C4 alkyl, C1-C4 haloalkyl, C1-C4 hydroxyalkyl, and C1-C4 alkoxy. In a still further aspect, Cy$^2$, when present, is unsubstituted C5-C6 aryl.

In a further aspect, Cy$^2$, when present, is phenyl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, Cy$^2$, when present, is phenyl substituted with 0, 1, or 2 groups independently selected from halogen, C1-C4 alkyl, C1-C4 haloalkyl, C1-C4 hydroxyalkyl, and C1-C4 alkoxy. In yet a further aspect, Cy$^2$, when present, is phenyl substituted with 0 or 1 group selected from halogen, C1-C4 alkyl, C1-C4 haloalkyl, C1-C4 hydroxyalkyl, and C1-C4 alkoxy. In an even further aspect, Cy$^2$, when present, is phenyl monosubstituted with a group selected from halogen, C1-C4 alkyl, C1-C4 haloalkyl, C1-C4 hydroxyalkyl, and C1-C4 alkoxy. In a still further aspect, Cy$^2$, when present, is unsubstituted phenyl.

In a further aspect, Cy$^2$, when present, is C4-C5 heteroaryl substituted with 0, 1, 2, or 3 groups independently selected from halogen, C1-C4 alkyl, C1-C4 haloalkyl, C1-C4 hydroxyalkyl, and C1-C4 alkoxy. In a still further aspect, Cy$^2$, when present, is C4-C5 heteroaryl substituted with 0, 1, or 2 groups independently selected from halogen, C1-C4 alkyl, C1-C4 haloalkyl, C1-C4 hydroxyalkyl, and C1-C4 alkoxy. In yet a further aspect, Cy$^2$, when present, is C4-C5 heteroaryl substituted with 0 or 1 group selected from halogen, C1-C4 alkyl, C1-C4 haloalkyl, C1-C4 hydroxyalkyl, and C1-C4 alkoxy. In an even further aspect, Cy$^2$, when present, is C4-C5 heteroaryl monosubstituted with a group selected from halogen, C1-C4 alkyl, C1-C4 haloalkyl, C1-C4 hydroxyalkyl, and C1-C4 alkoxy. In a still further aspect, Cy$^2$, when present, is unsubstituted C4-C5 heteroaryl.

In a further aspect, Cy$^2$, when present, is selected from thiazole, pyrazole, imidazole, furan, thiophene, isoxazole, pyrimidine, and pyridine and substituted with 0, 1, 2, or 3 groups independently selected from halogen, C1-C4 alkyl, C1-C4 haloalkyl, C1-C4 hydroxyalkyl, and C1-C4 alkoxy. In a still further aspect, Cy$^2$, when present, is selected from thiazole, pyrazole, imidazole, furan, thiophene, isoxazole, pyrimidine, and pyridine and substituted with 0, 1, or 2 groups independently selected from halogen, C1-C4 alkyl, C1-C4 haloalkyl, C1-C4 hydroxyalkyl, and C1-C4 alkoxy. In yet a further aspect, Cy$^2$, when present, is selected from thiazole, pyrazole, imidazole, furan, thiophene, isoxazole, pyrimidine, and pyridine and substituted with 0 or 1 group selected from halogen, C1-C4 alkyl, C1-C4 haloalkyl, C1-C4 hydroxyalkyl, and C1-C4 alkoxy. In an even further aspect, Cy$^2$, when present, is selected from thiazole, pyrazole, imidazole, furan, thiophene, isoxazole, pyrimidine, and pyridine and monosubstituted with a group selected from halogen, C1-C4 alkyl, C1-C4 haloalkyl, C1-C4 hydroxyalkyl, and C1-C4 alkoxy. In a still further aspect, Cy$^2$, when present, is selected from thiazole, pyrazole, imidazole, furan, thiophene, isoxazole, pyrimidine, and pyridine and unsubstituted.

2. Example Compounds

In one aspect, a compound can be present as one or more of the following structures:

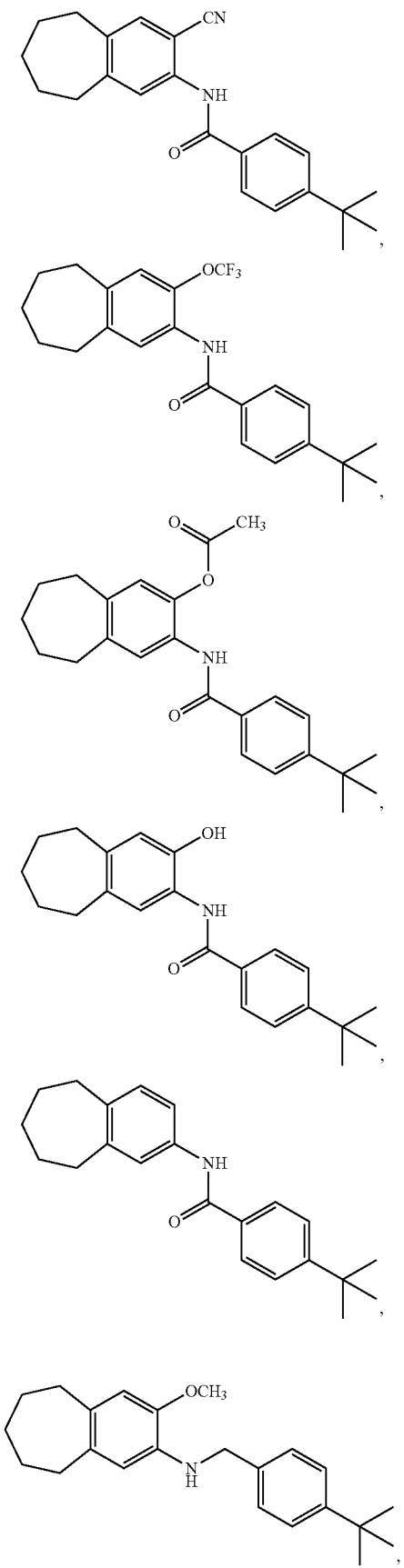

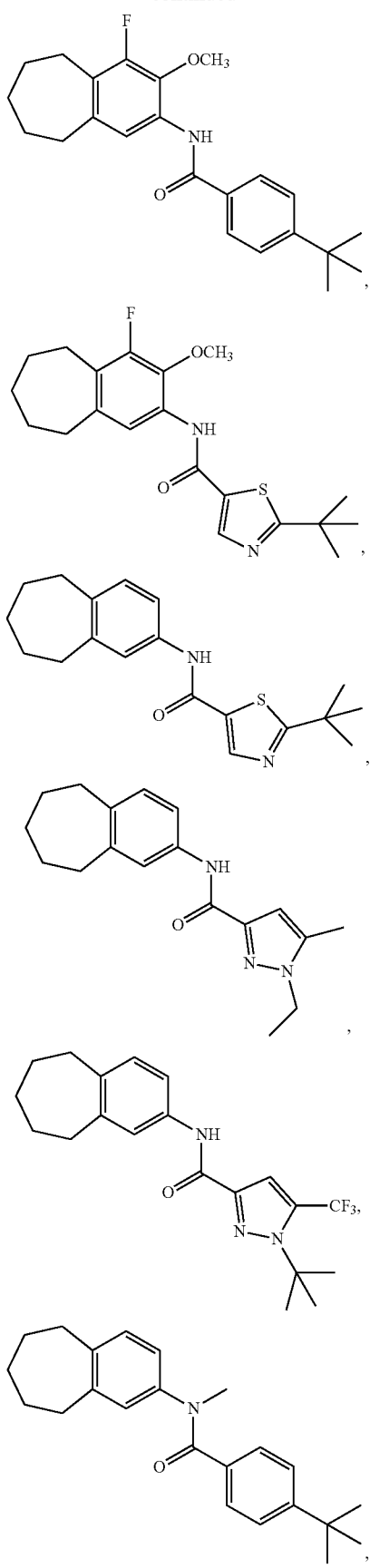
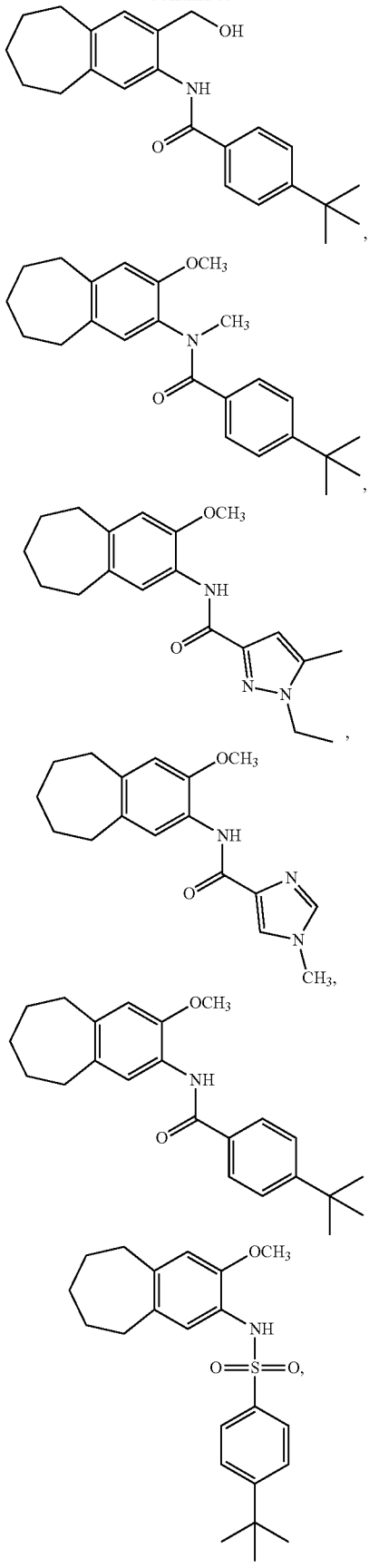

45
-continued
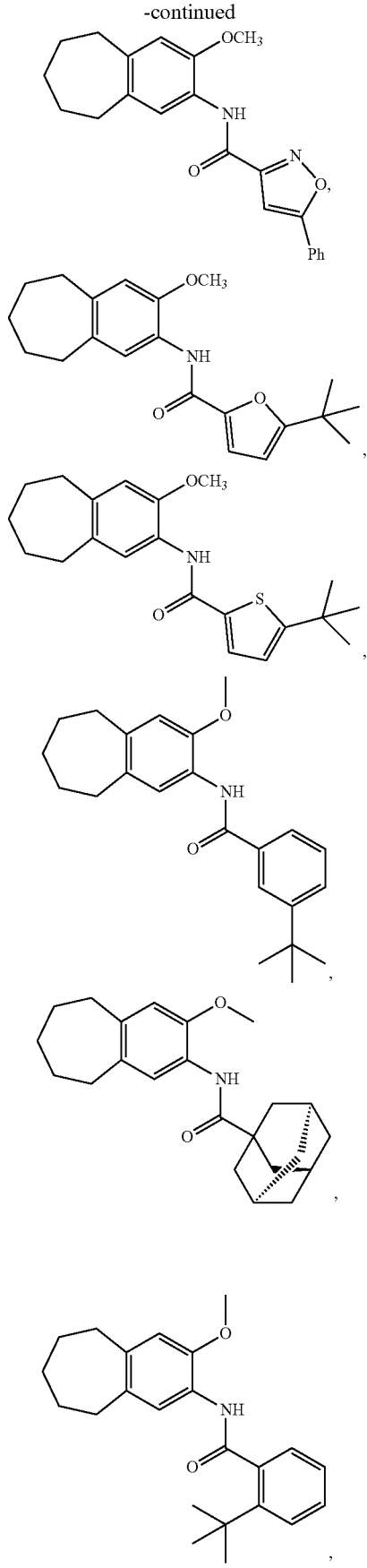
46
-continued
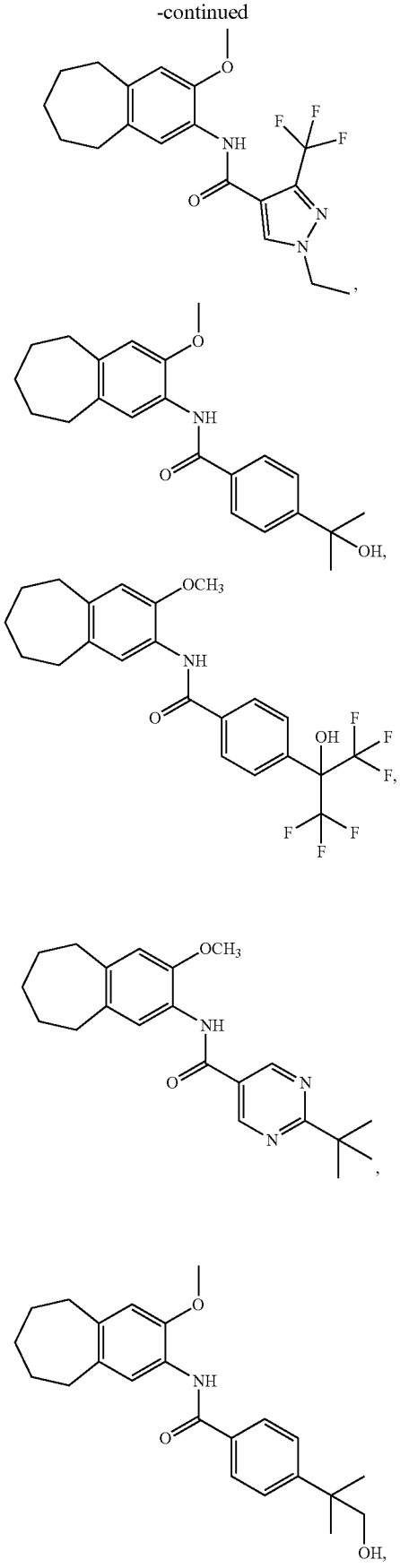

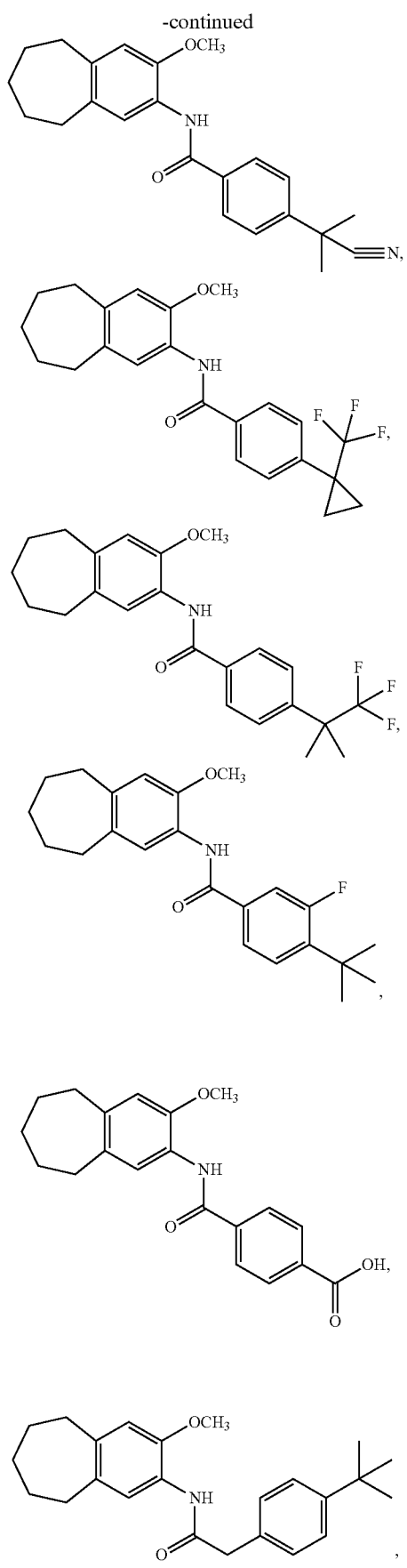
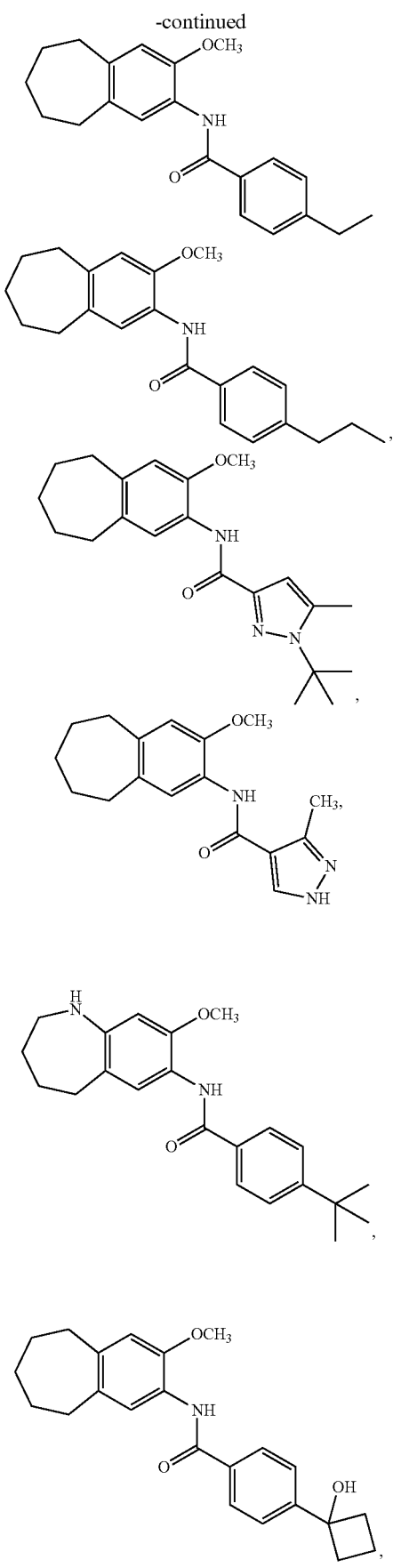

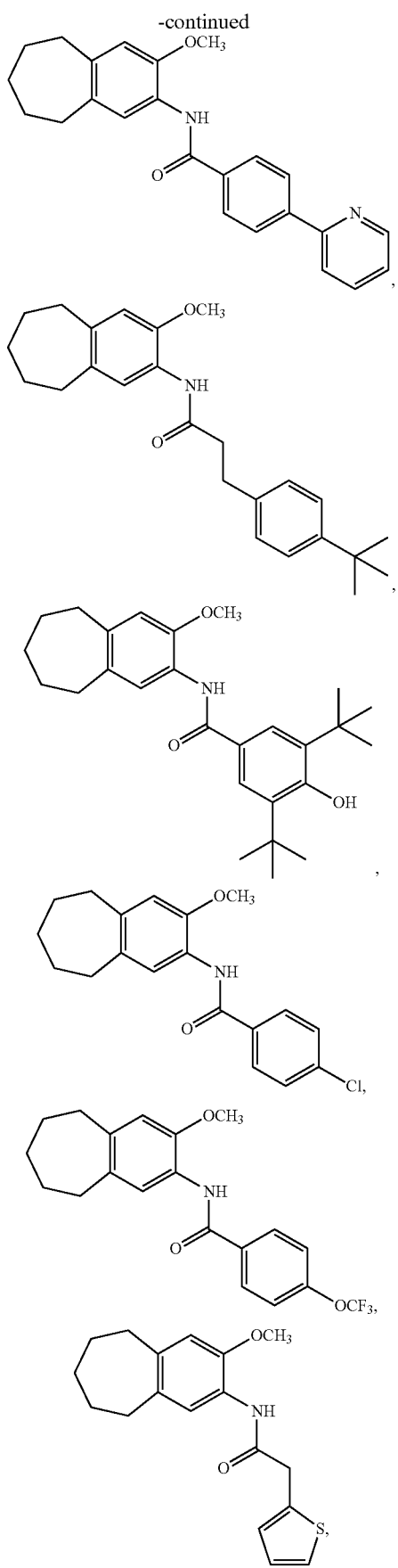
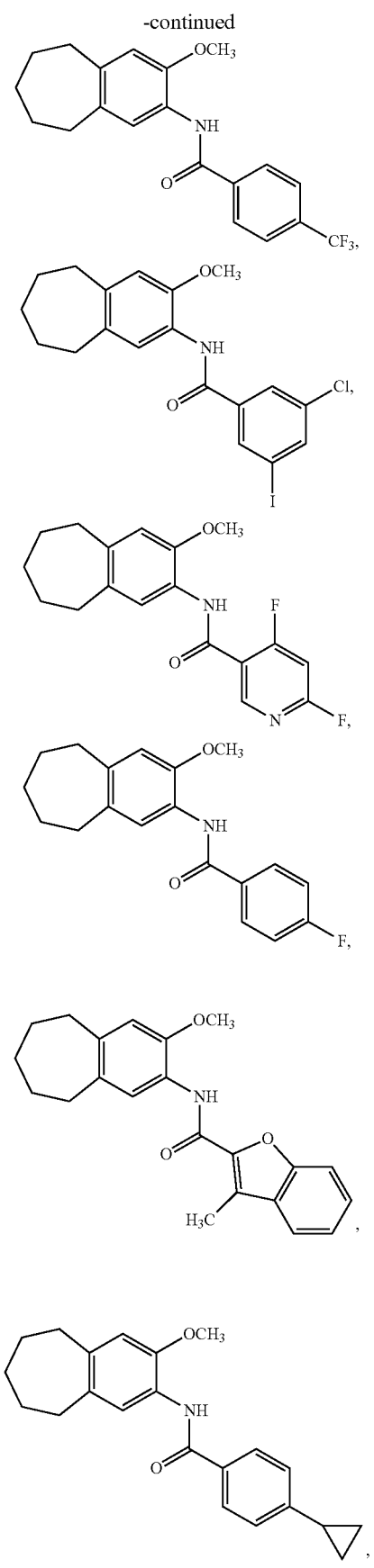

-continued
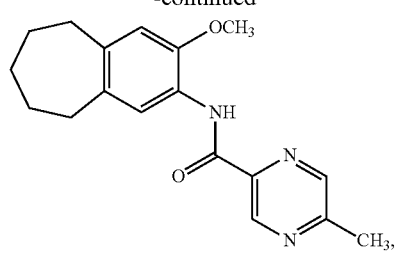
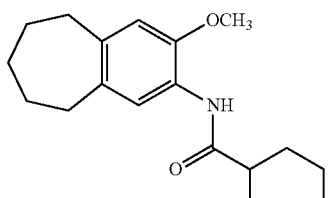
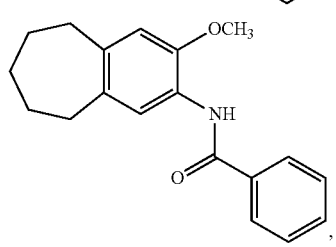
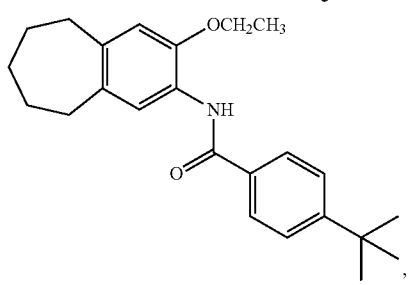
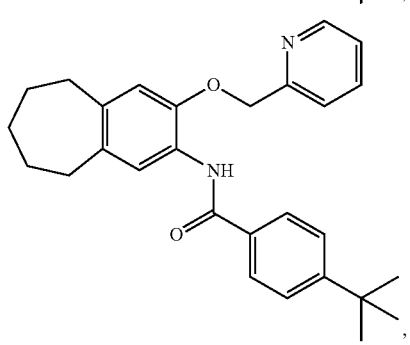
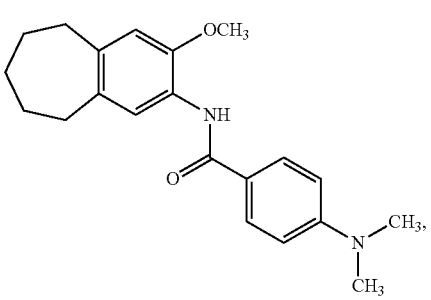
-continued
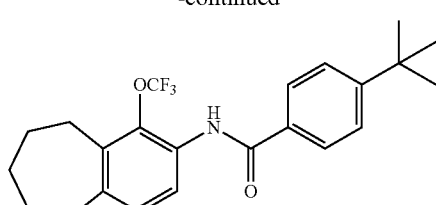
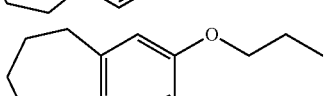
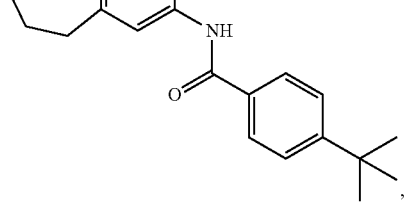
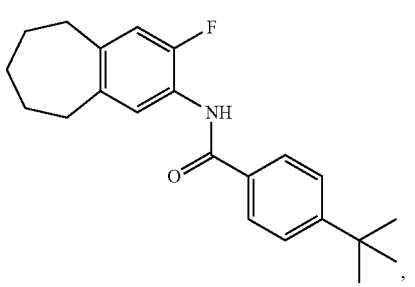
, and
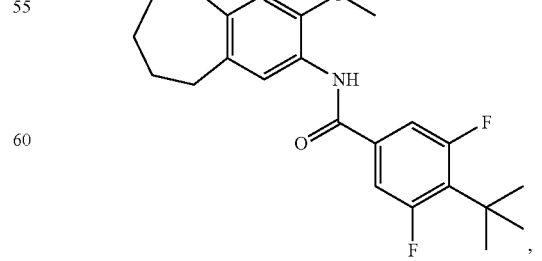
or a pharmaceutically acceptable salt thereof.

In one aspect, a compound can be present as one or more of the following structures:

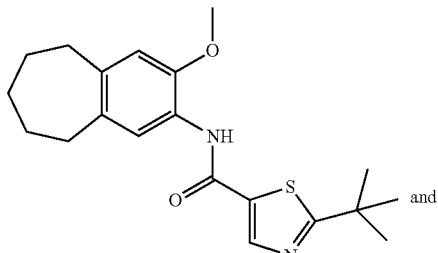

and

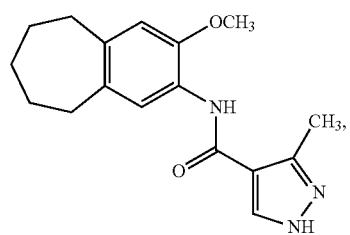

or a pharmaceutically acceptable salt thereof.

In one aspect, a compound can be present as one or more of the following structures:

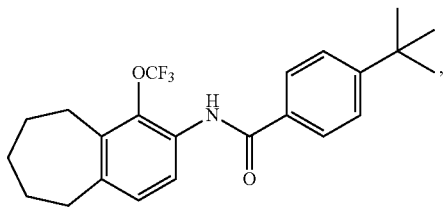 [SMILES: CC(C)(C)c1ccc(C(=O)Nc2ccc3c(c2OC(F)(F)F)CCCCC3)cc1]

or a pharmaceutically acceptable salt thereof.

In one aspect, a compound can be present as one or more of the following structures:

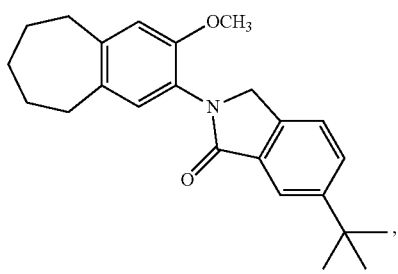

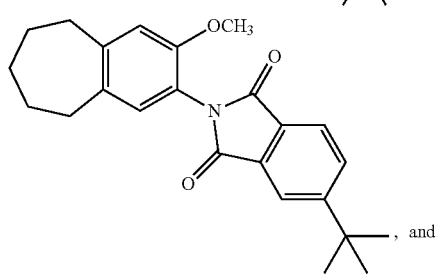

, and

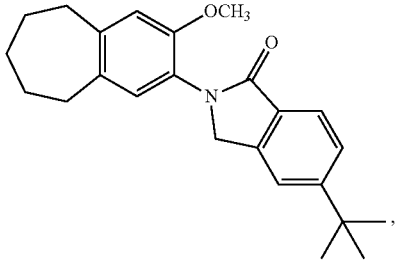

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of a viral infection, and such activity can be determined using the assay methods described herein.

In one aspect, a compound can be selected from:

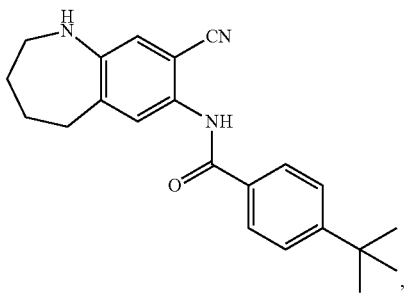

,

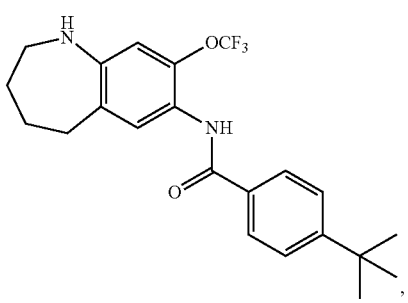

,

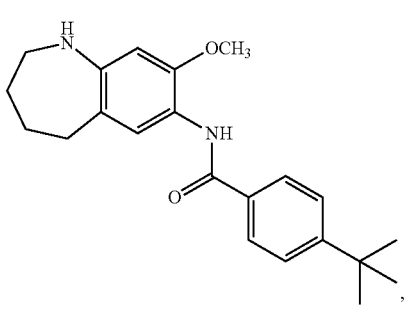

,

-continued
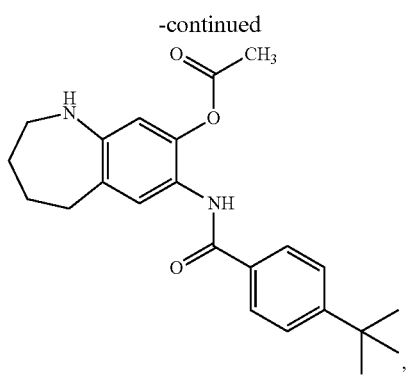
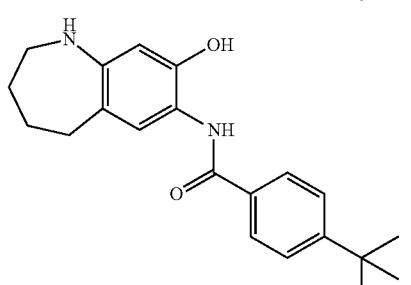
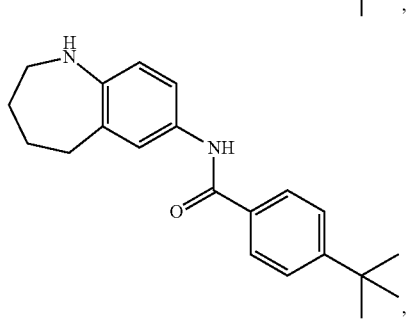
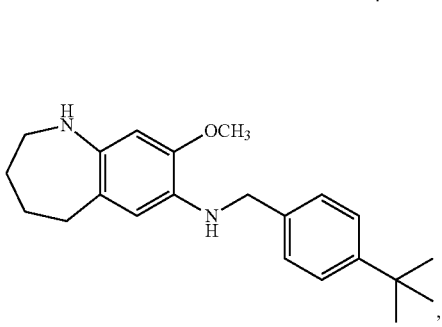
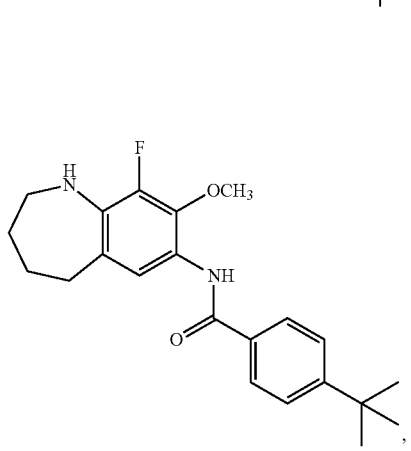
-continued
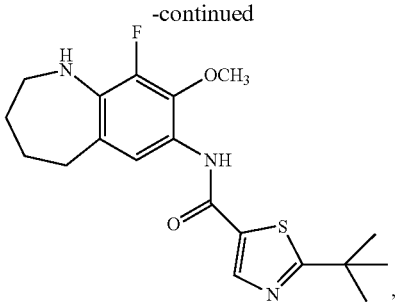
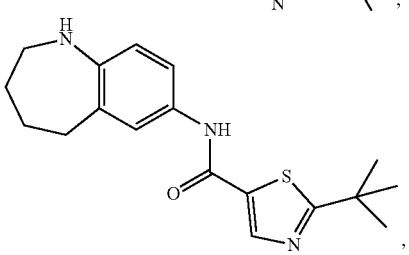
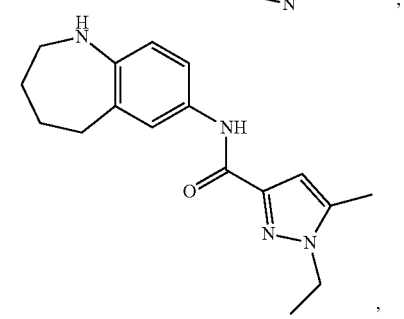
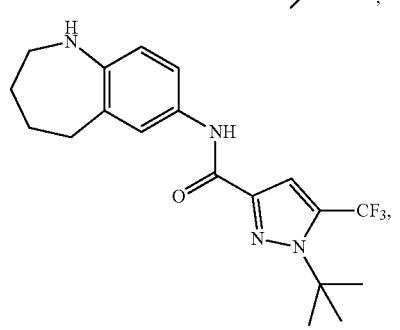
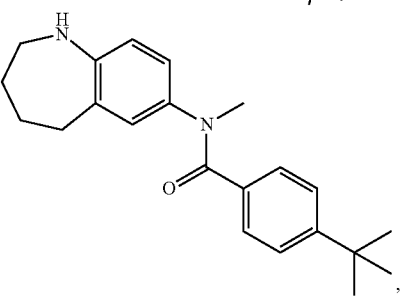
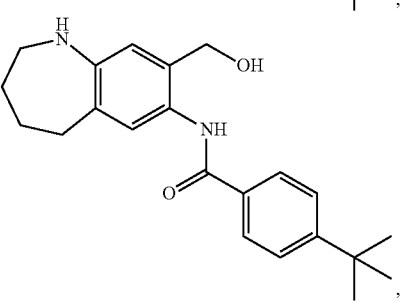

57
-continued
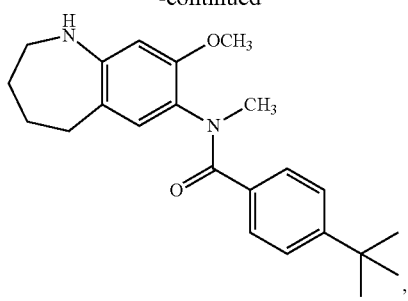
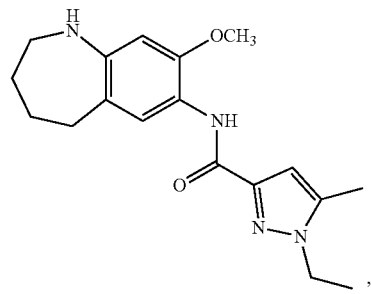
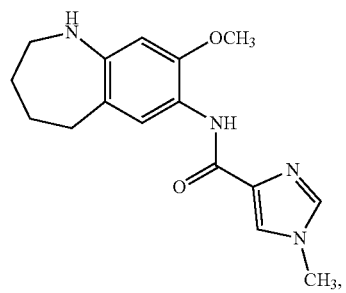
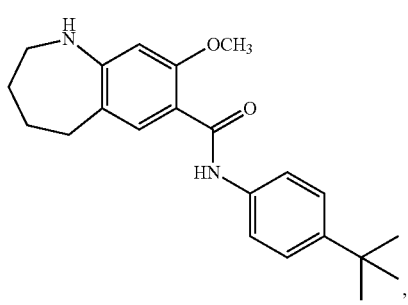
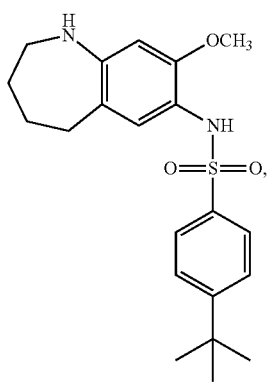
58
-continued
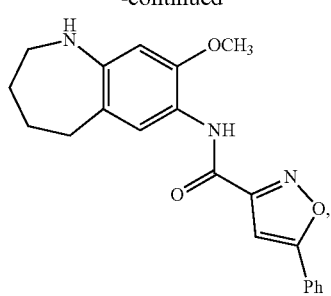
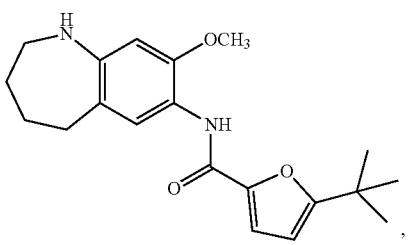
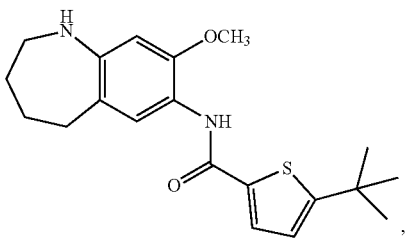
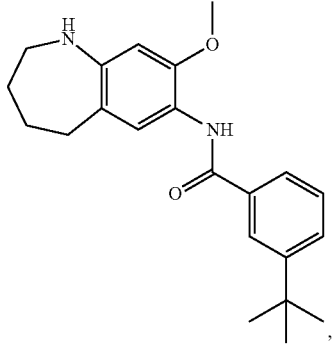
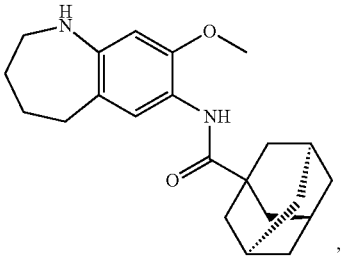
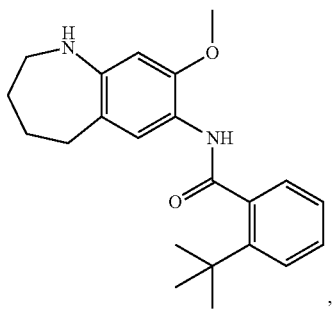

-continued
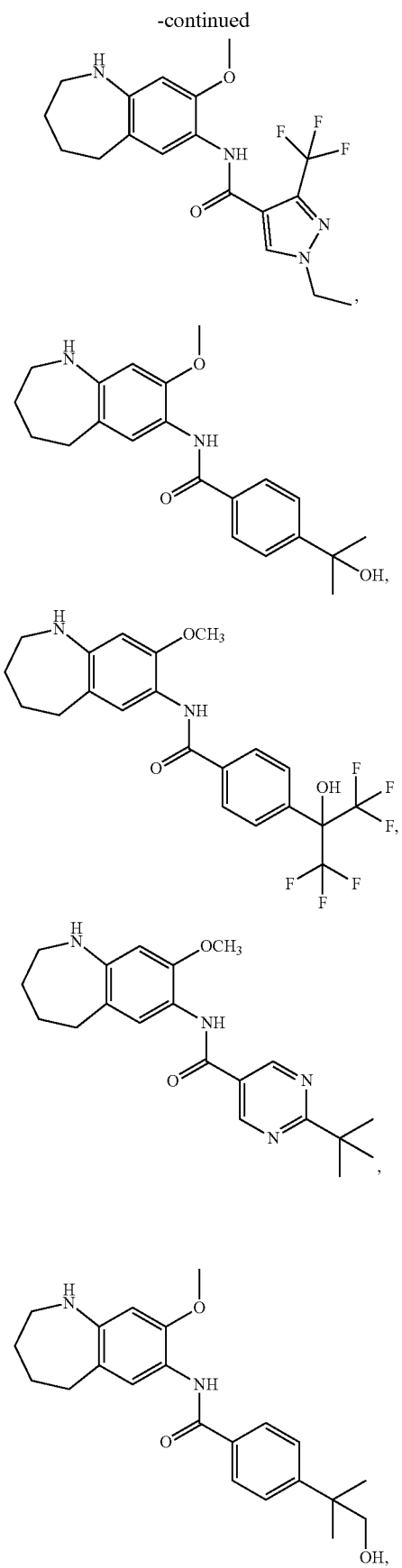
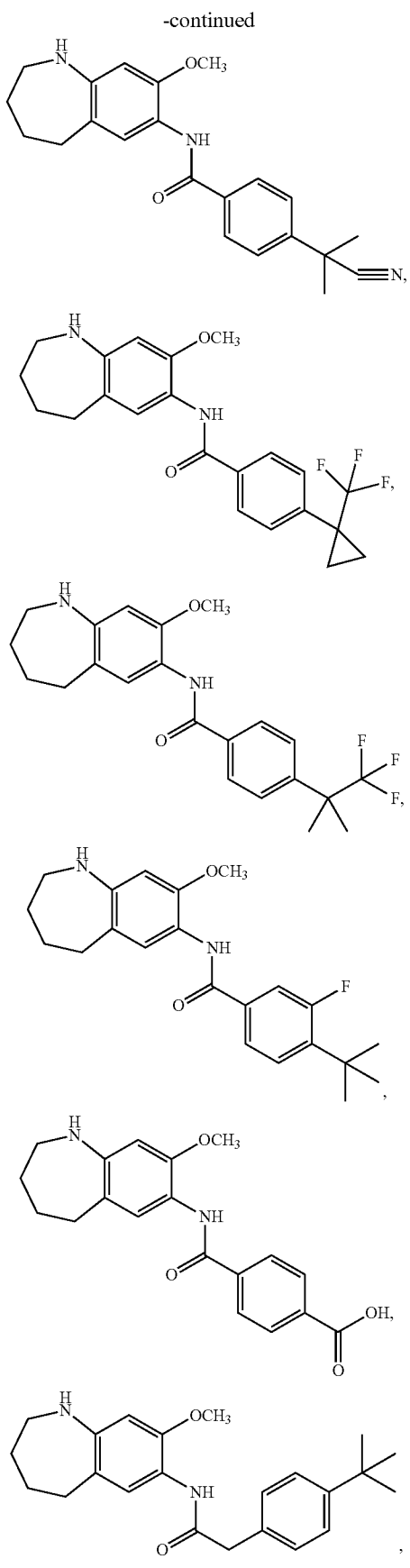

61
-continued
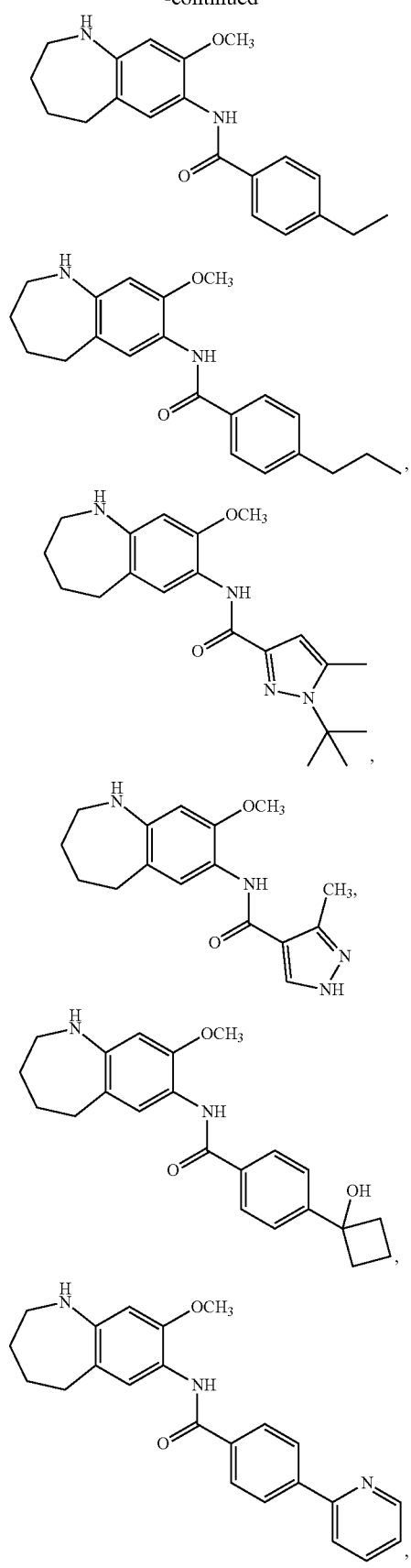
62
-continued
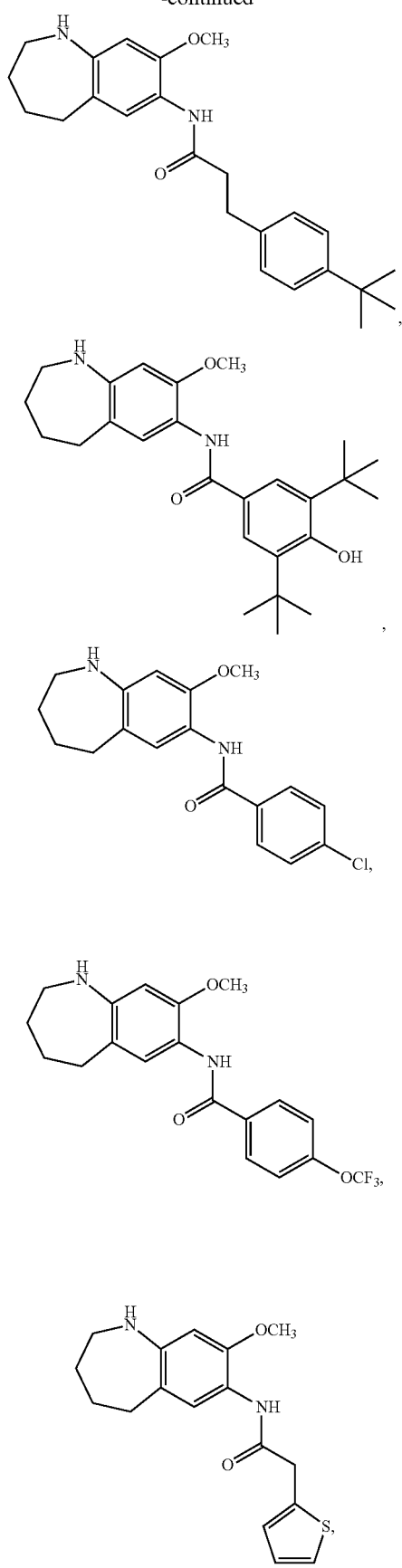

-continued
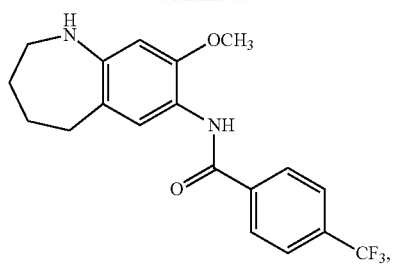
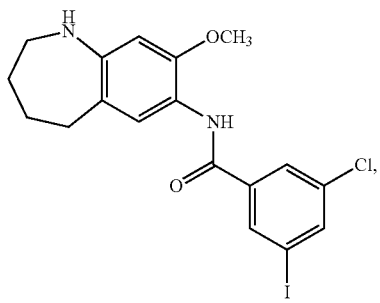
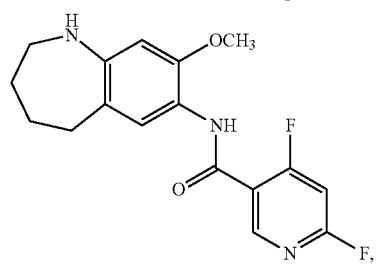
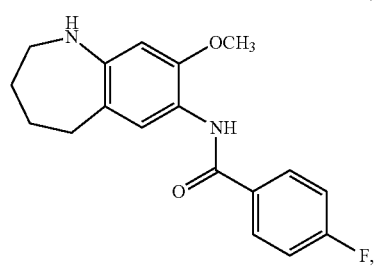
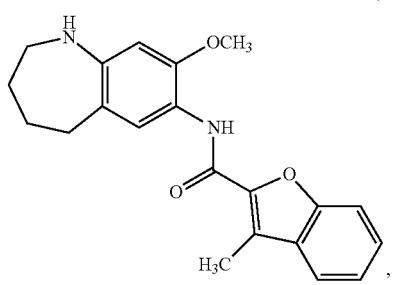
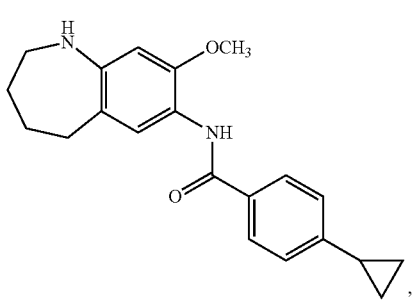
-continued
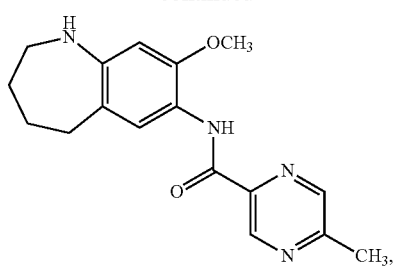
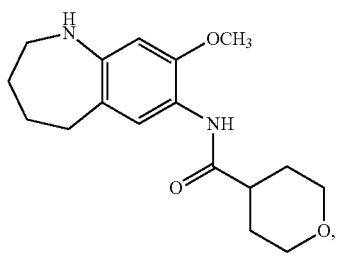
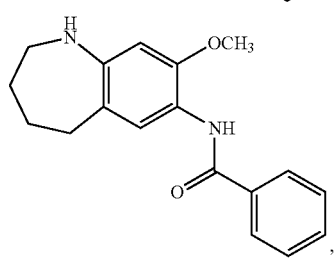
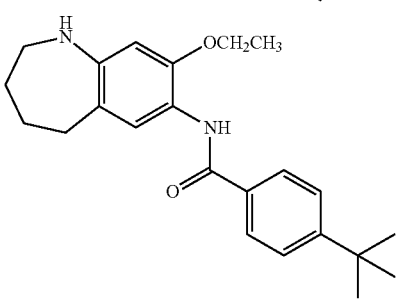
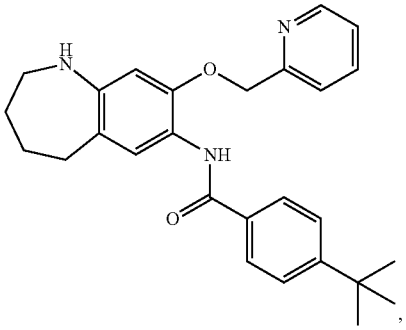
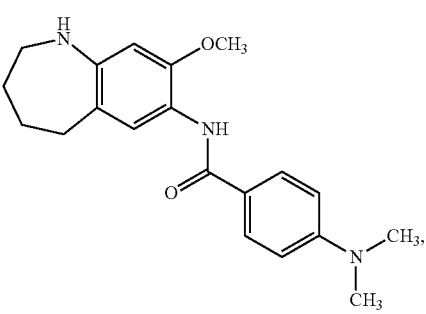

-continued

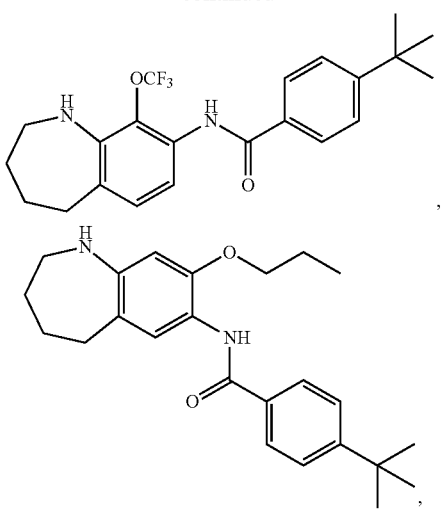

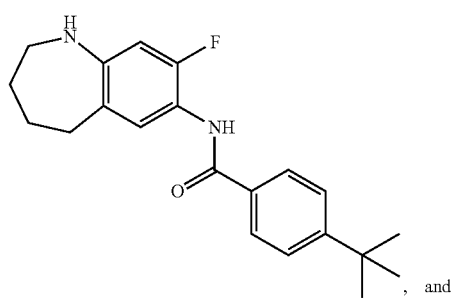

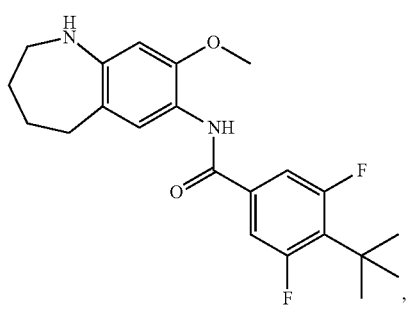

or a pharmaceutically acceptable salt thereof.

In one aspect, a compound can be selected from:

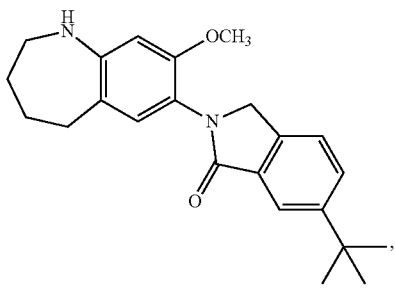

-continued

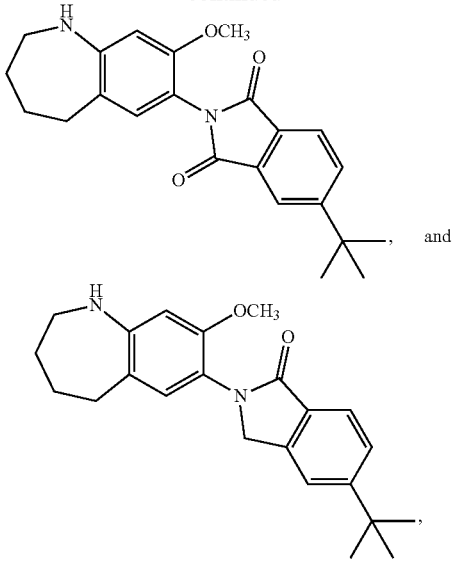

or a pharmaceutically acceptable salt thereof.

C. Pharmaceutical Compositions

In one aspect, the invention relates to pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

In one aspect, the invention relates to pharmaceutical compositions comprising a therapeutically effective amount of at least one compound having a structure represented by a formula selected from:

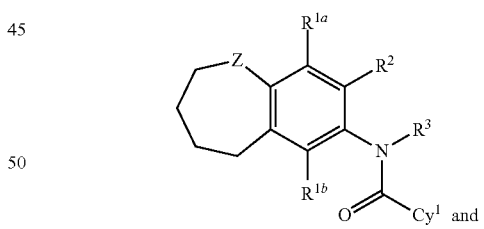

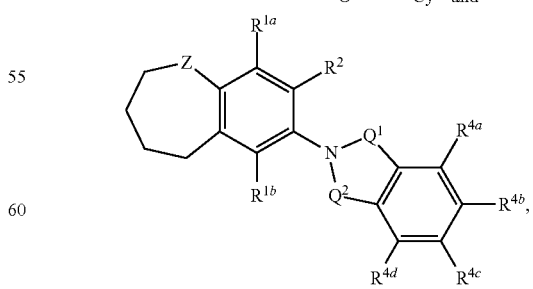

wherein each of $Q^1$ and $Q^2$ is independently selected from $CH_2$, $CH(OH)$, and $C(O)$, provided that at least one of $Q^1$ and $Q^2$ is $C(O)$; wherein Z is selected from $CH_2$ and NH;

wherein each of $R^{1a}$ and $R^{1b}$ is independently selected from hydrogen and —F; wherein $R^2$ is selected from hydrogen, halogen, —CN, —$(CH_2)_nOR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, or a pharmaceutically acceptable salt thereof, and a pharmaceutically acceptable carrier.

In a further aspect, when $Cy^1$ is unsubstituted phenyl, then at least one of $R^a$, $R^b$, and $R^2$ is not hydrogen.

The compounds are active against viral infections, and generally have $EC_{90}$ values against CHIKV ranging from 0.3 µM to 30 µM. $EC_{90}$ refers to the concentration of the compound that is required for 90% antagonism or inhibition of CHIKV. $EC_{90}$ also refers to the concentration of a substance that is required for 90% antagonism or inhibition of CHIKV in vivo. The activity of the compounds, including $EC_{90}$, is determined according to the procedures discussed below in the Examples section.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of a viral infection. In a still further aspect, the mammal has been diagnosed with a need for treatment of a viral infection prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of a virus. The method also includes the administration of a therapeutically effect amount of the compound for the treatment of patient having a predisposition for being afflicted with a virus. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the virus.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one agent known to treat a viral infection. In a still further aspect, the viral infection is selected from human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In yet a further aspect, the viral infection is selected from chikungunya, Venezuelan equine encephalitis, dengue, influenza, and zika.

In a further aspect, the composition further comprises at least one agent known to have a side effect of increasing the risk of a viral infection.

It is understood that the disclosed compositions can be prepared from the disclosed compounds. It is also understood that the disclosed compositions can be employed in the disclosed methods of using.

D. Methods of Making the Compounds

In various aspects, the inventions relates to methods of making compounds useful to treat viral infections, in particular, chikungunya, Venezuelan equine encephalitis, dengue, influenza, and zika. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, benzo annulene analogs can be prepared as shown below.

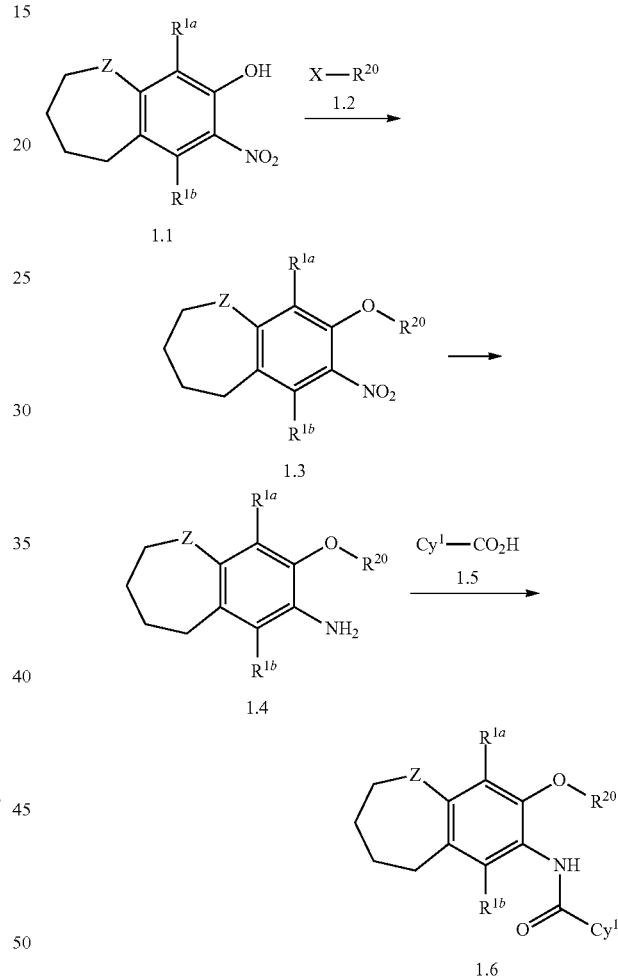

Compounds are represented in generic form, with substituents as noted in compound descriptions elsewhere herein and wherein X is a halide. A more specific example is set forth below.

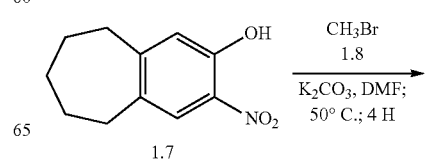

-continued

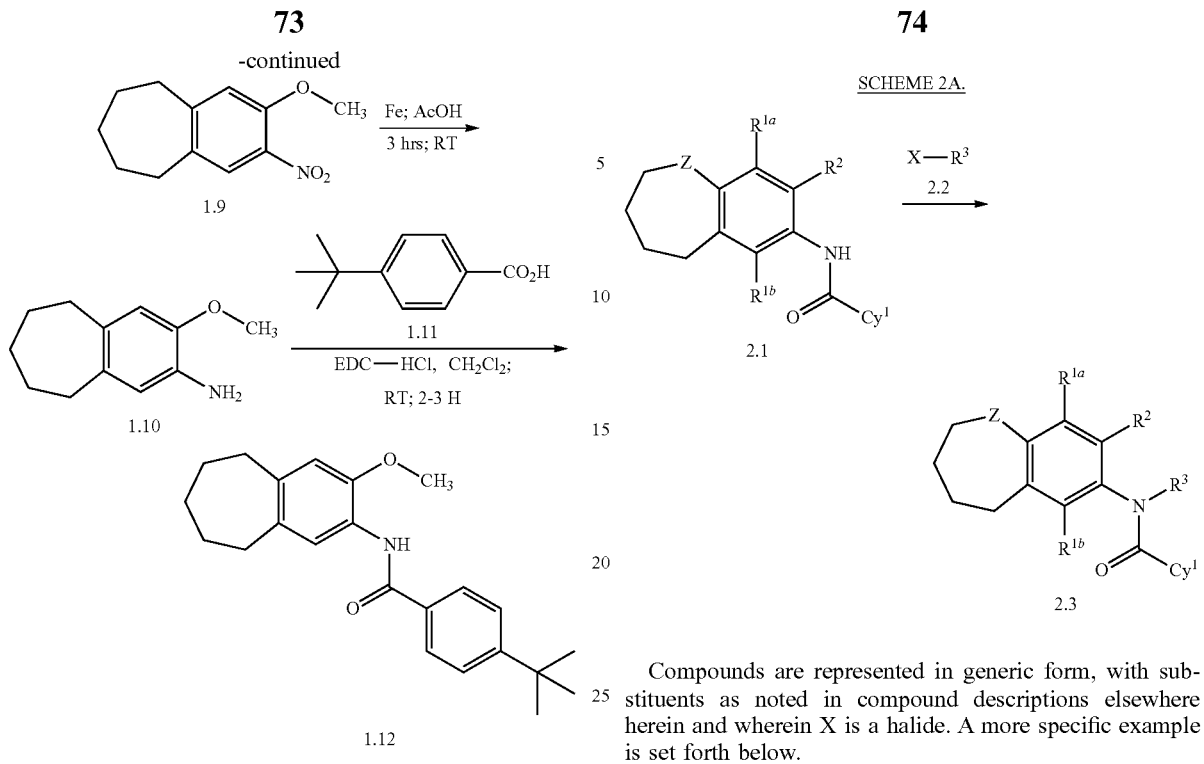

SCHEME 2A.

Compounds are represented in generic form, with substituents as noted in compound descriptions elsewhere herein and wherein X is a halide. A more specific example is set forth below.

In one aspect, compounds of type 1.6, and similar compounds, can be prepared according to reaction Scheme 1B above. Thus, compounds of type 1.9 can be prepared by an alkylation reaction of an appropriate alcohol, e.g., 1.7 as shown above, and an appropriate alkyl halide, e.g., 1.8 as shown above. Appropriate alcohols and appropriate alkyl halides are commercially available or prepared by methods known to one skilled in the art or as disclosed herein. The alkylation reaction is carried out in the presence of an appropriate base, e.g., potassium carbonate, in an appropriate solvent, e.g., dimethylformamide, at an appropriate temperature, e.g., 50° C., for an appropriate period of time, e.g., 4 hours. Compounds of type 1.10 can be prepared by reduction of an appropriate nitro compound, e.g., 1.9 as shown above. The reduction is carried out in the presence of an appropriate metal, e.g., iron, and an appropriate acid, e.g., acetic acid, for an appropriate period of time, e.g., 3 hours. Compounds of type 1.12 can be prepared by a coupling reaction of an appropriate amine, e.g., 1.10 as shown above, and an appropriate carboxylic acid, e.g., 1.11 as shown above. Appropriate carboxylic acids are commercially available or prepared by methods known to one skilled in the art. The coupling reaction is carried out in the presence of an appropriate coupling agent, e.g., 1-ethyl-3-(3-dimethylaminopropyl)carbodiimide hydrochloride (EDC-HCl), in an appropriate solvent, e.g., dichloromethane, for an appropriate period of time, e.g., 2-3 hours. As can be appreciated by one skilled in the art, the above reaction provides an example of a generalized approach wherein compounds similar in structure to the specific reactants above (compounds similar to compounds of type 1.1, 1.2, 1.3, 1.4, and 1.5), can be substituted in the reaction to provide substituted benzo annulenes similar to Formula 1.6.

2. Route II

In one aspect, benzo annulene analogs can be prepared as shown below.

SCHEME 2B.

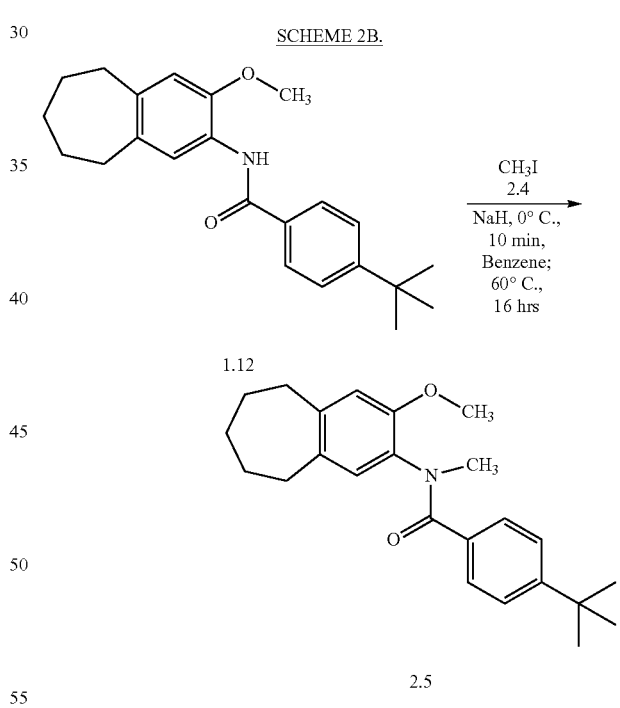

In one aspect, compounds of type 2.3, and similar compounds, can be prepared according to reaction Scheme 2B above. Thus, compounds of type 2.5 can be prepared by an alkylation reaction of an appropriate amine, e.g., 1.12 as shown above, and an appropriate alkyl halide, e.g., 2.4 as shown above. Appropriate alkyl halides are commercially available or prepared by methods known to one skilled in the art. The alkylation reaction is carried out in the presence of an appropriate base, e.g., sodium hydride, in an appropriate solvent, e.g., benzene. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted benzo annulenes similar to Formula 2.3.

3. Route III

In one aspect, benzo annulene analogs can be prepared as shown below.

SCHEME 3A.

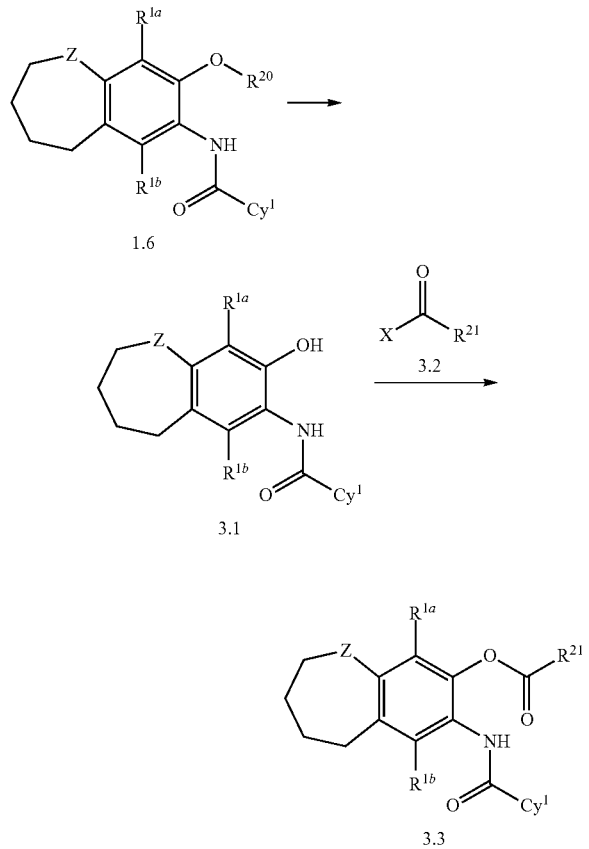

Compounds are represented in generic form, with substituents as noted in compound descriptions elsewhere herein and wherein X is a halide. A more specific example is set forth below.

SCHEME 3B.

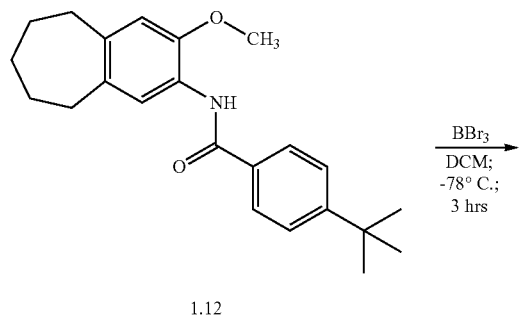

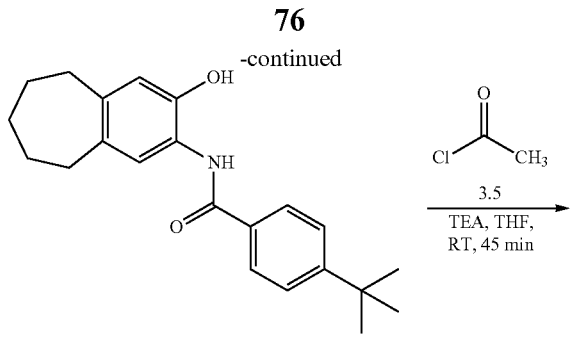

In one aspect, compounds of type 3.3, and similar compounds, can be prepared according to reaction Scheme 3B above. Thus, compounds of type 3.4 can be prepared by deprotection of an appropriate ether, e.g., 1.12 as shown above. The deprotection is carried out in the presence of an appropriate acid, e.g., boron tribromide, in an appropriate solvent, e.g., dichloromethane, at an appropriate temperature, e.g., −78° C., for an appropriate period of time, e.g., 3 hours. Compounds of type 3.6 can be prepared by acylation of an appropriate alcohol, e.g., 3.4 as shown above, with an appropriate acyl halide, e.g., 3.5 as shown above. Appropriate acyl halides are commercially available or prepared by methods known to one skilled in the art. The acylation is carried out in the presence of an appropriate base, e.g., triethylamine (TEA), in an appropriate solvent, e.g., tetrahydrofuran, for an appropriate period of time, e.g., 45 minutes. As can be appreciated by one skilled in the art, the above reaction provides an example of a generalized approach wherein compounds similar in structure to the specific reactants above (compounds similar to compounds of type 1.6, 3.1, and 3.2), can be substituted in the reaction to provide substituted benzo annulenes similar to Formula 3.3.

4. Route IV

In one aspect, benzo annulene analogs can be prepared as shown below.

SCHEME 4A.

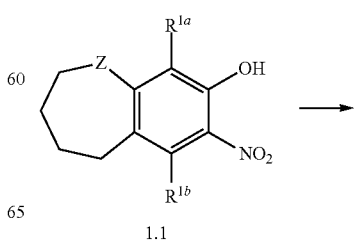

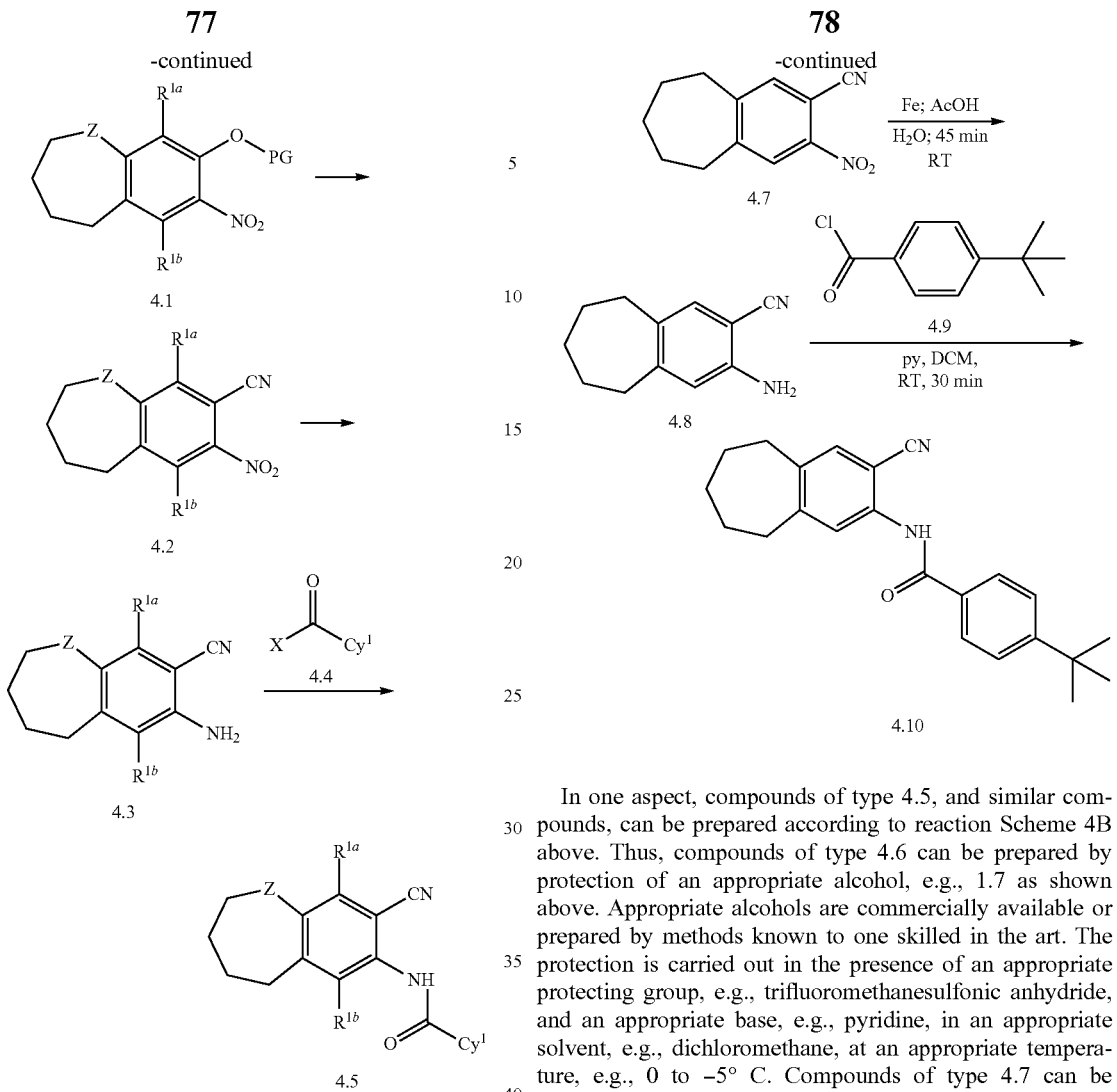

Compounds are represented in generic form, with substituents as noted in compound descriptions elsewhere herein, wherein PG is selected from trifyl and 4-(trifluoromethyl)benzenesulfonyl, and wherein X is a halide. A more specific example is set forth below.

SCHEME 4B.

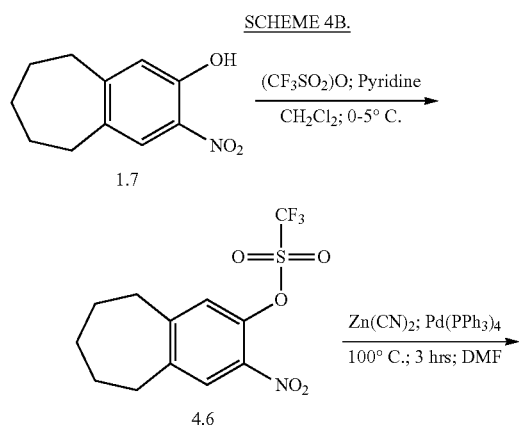

In one aspect, compounds of type 4.5, and similar compounds, can be prepared according to reaction Scheme 4B above. Thus, compounds of type 4.6 can be prepared by protection of an appropriate alcohol, e.g., 1.7 as shown above. Appropriate alcohols are commercially available or prepared by methods known to one skilled in the art. The protection is carried out in the presence of an appropriate protecting group, e.g., trifluoromethanesulfonic anhydride, and an appropriate base, e.g., pyridine, in an appropriate solvent, e.g., dichloromethane, at an appropriate temperature, e.g., 0 to −5° C. Compounds of type 4.7 can be prepared by displacement of an appropriate protected alcohol, e.g., 4.6 as shown above, with an appropriate cyano reagent, e.g., zinc cyanide as shown above. The displacement is carried out in the presence of an appropriate catalyst, e.g., tetrakis(triphenylphosphine)palladium (0), in an appropriate solvent, e.g., dimethylformamide, for an appropriate period of time, e.g., 3 hours, at an appropriate temperature, e.g., 100° C. Compounds of type 4.8 can be prepared by reduction of an appropriate nitro compound, e.g., 4.7 as shown above. The reduction is carried out in the presence of an appropriate metal, e.g., iron, and an appropriate acid, e.g., acetic acid, for an appropriate period of time, e.g., 45 minutes. Compounds of type 4.10 can be prepared by coupling of an appropriate amine, e.g., 4.8 as shown above, with an appropriate acyl halide, e.g., 4.9 as shown above. Appropriate acyl halides are commercially available or prepared by methods known to one skilled in the art. The coupling is carried out in the presence of an appropriate base, e.g., pyridine, in an appropriate solvent, e.g., dichloromethane, for an appropriate period of time, e.g., 30 minutes. As can be appreciated by one skilled in the art, the above reaction provides an example of a generalized approach wherein compounds similar in structure to the specific reactants above (compounds similar to compounds of type 1.1, 4.1, 4.2, 4.3, and 4.4), can be substituted in the reaction to provide substituted benzo annulenes similar to Formula 4.5.

5. Route V
In one aspect, benzo annulene analogs can be prepared as shown below.
SCHEME 5A.
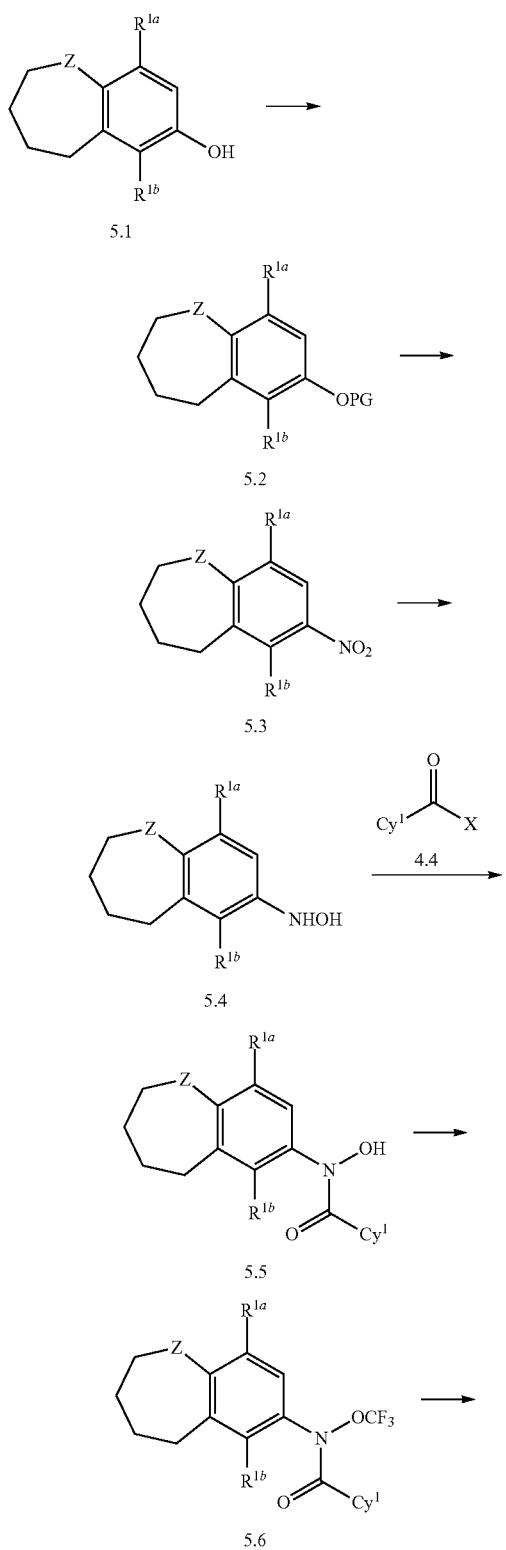
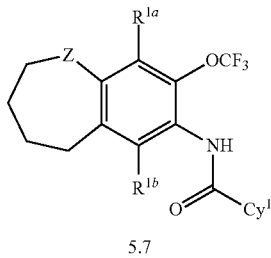
Compounds are represented in generic form, with substituents as noted in compound descriptions elsewhere herein, wherein PG is selected from trifyl and 4-(trifluoromethyl)benzenesulfonyl, and wherein X is a halide. A more specific example is set forth below.
SCHEME 5B.
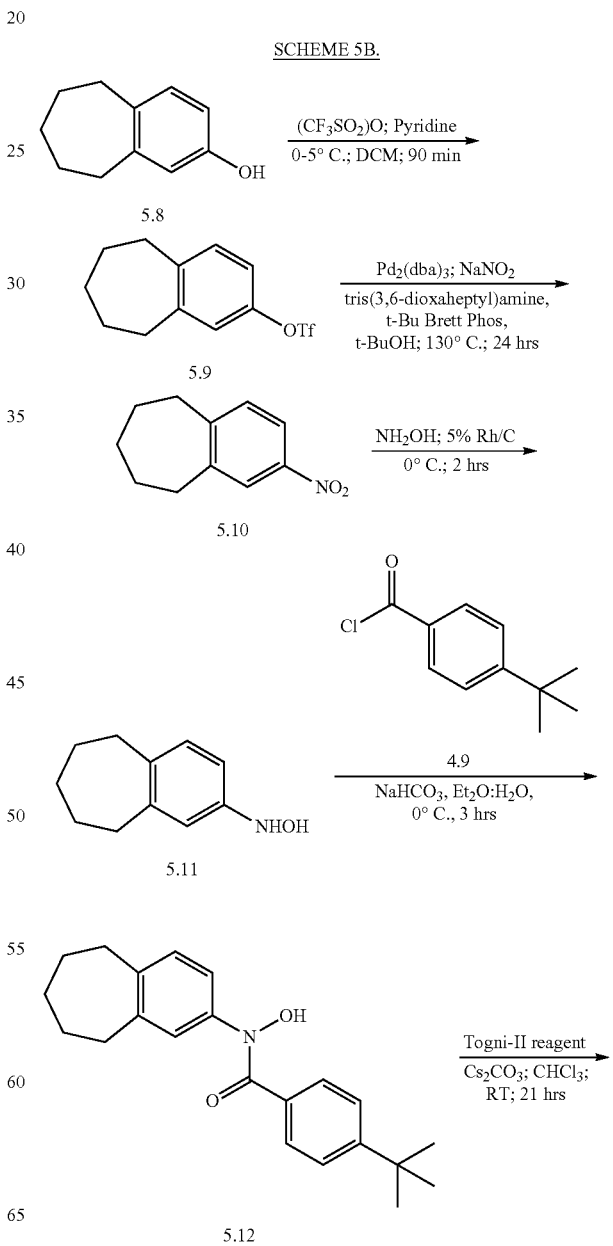

-continued

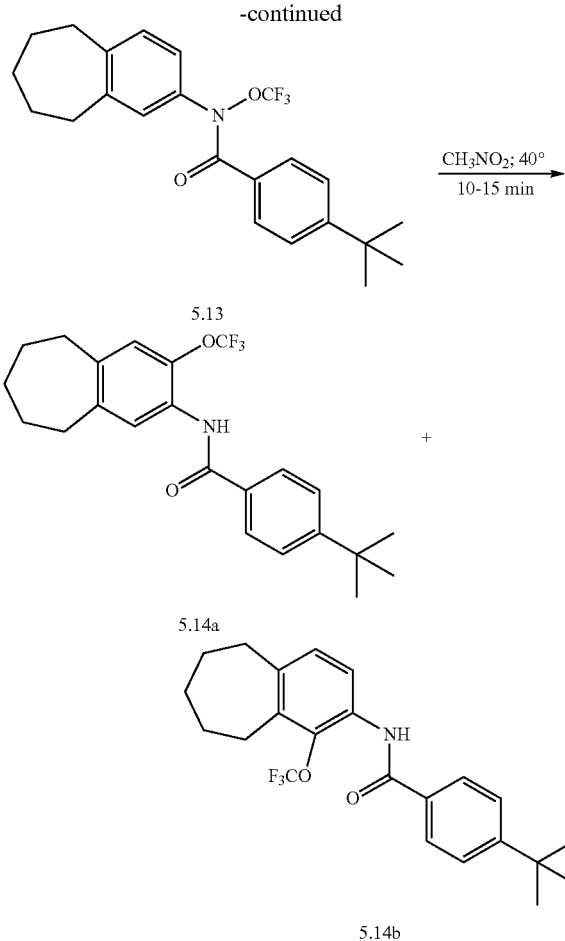

5.13

5.14a 5.14b

In one aspect, compounds of type 5.7, and similar compounds, can be prepared according to reaction Scheme 5B above. Thus, compounds of type 5.9 can be prepared by protection of an appropriate alcohol, e.g., 5.8 as shown above. Appropriate alcohols are commercially available or prepared by methods known to one skilled in the art. The protection is carried out in the presence of an appropriate protecting group, e.g., trifluoromethanesulfonic anhydride, and an appropriate base, e.g., pyridine, in an appropriate solvent, e.g., dichloromethane, at an appropriate temperature, e.g., 0 to −5° C., for an appropriate period of time, e.g., 90 minutes. Compounds of type 5.10 can be prepared by displacement of an appropriate protected alcohol, e.g., 5.9 as shown above, with an appropriate nitro reagent, e.g., sodium nitrite as shown above. The displacement is carried out in the presence of an appropriate catalyst, e.g., tris(dibenzylideneacetone)dipalladium (0), an appropriate amine, e.g., tris (3,6-dioxaheptyl)amine, and an appropriate ligand, e.g., t-Bu Brett Phos, in an appropriate solvent, e.g., tert-butyl alcohol, for an appropriate period of time, e.g., 24 hours, at an appropriate temperature, e.g., 130° C. Compounds of type 5.11 can be prepared by reduction of an appropriate nitro compound, e.g., 5.10 as shown above. The reduction is carried out in the presence of an appropriate hydroxyl amine, e.g., hydroxylamine, and an appropriate catalyst, e.g., 5% rhodium on Carbon, for an appropriate period of time, e.g., 2 hours, at an appropriate temperature, e.g., 0° C. Compounds of type 5.12 can be prepared by coupling of an appropriate amine, e.g., 5.11 as shown above, with an appropriate acyl halide, e.g., 4.9 as shown above. Appropriate acyl halides are commercially available or prepared by methods known to one skilled in the art. The coupling is carried out in the presence of an appropriate base, e.g., sodium carbonate, in an appropriate solvent system, e.g., diethyl ether and water, for an appropriate period of time, e.g., 3 hours, at an appropriate temperature, e.g., 0° C. Compounds of type 5.13 can be prepared by alkylation of an appropriate hydroxylamine, e.g., 5.12 as shown above. The alkylation is carried out in the presence of an appropriate catalyst, e.g., Togni-II reagent, and an appropriate base, e.g., cesium carbonate, in an appropriate solvent, e.g., trichloromethane, for an appropriate period of time, e.g., 21 hours. Compounds of type 5.14a and 5.14b can be prepared by intramolecular trifluoroalkoxy group migration of an appropriate trifluoromethoxyamine, e.g., 5.13 as shown above. The intramolecular trifluoroalkoxy group migration is carried out in the presence of an appropriate solvent, e.g., nitromethane, for an appropriate period of time, e.g., 10-15 minutes, at an appropriate temperature, e.g., 40° C. As can be appreciated by one skilled in the art, the above reaction provides an example of a generalized approach wherein compounds similar in structure to the specific reactants above (compounds similar to compounds of type 4.4, 5.1, 5.2, 5.3, 5.4, 5.5, and 5.6), can be substituted in the reaction to provide substituted benzo annulenes similar to Formula 5.7.

6. Route VI

In one aspect, benzo annulene analogs can be prepared as shown below.

SCHEME 6A.

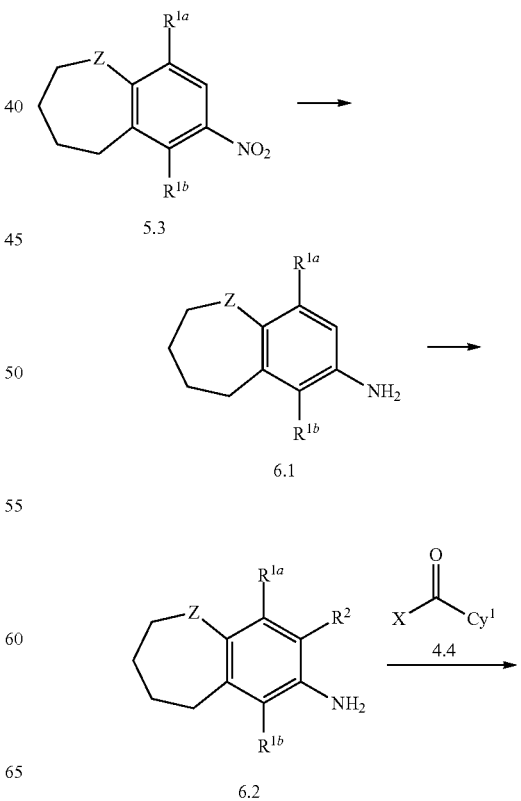

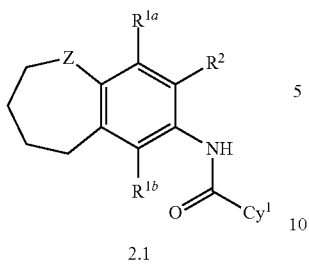

2.1

Compounds are represented in generic form, with substituents as noted in compound descriptions elsewhere herein and wherein X is a halide. A more specific example is set forth below.

SCHEME 6B.

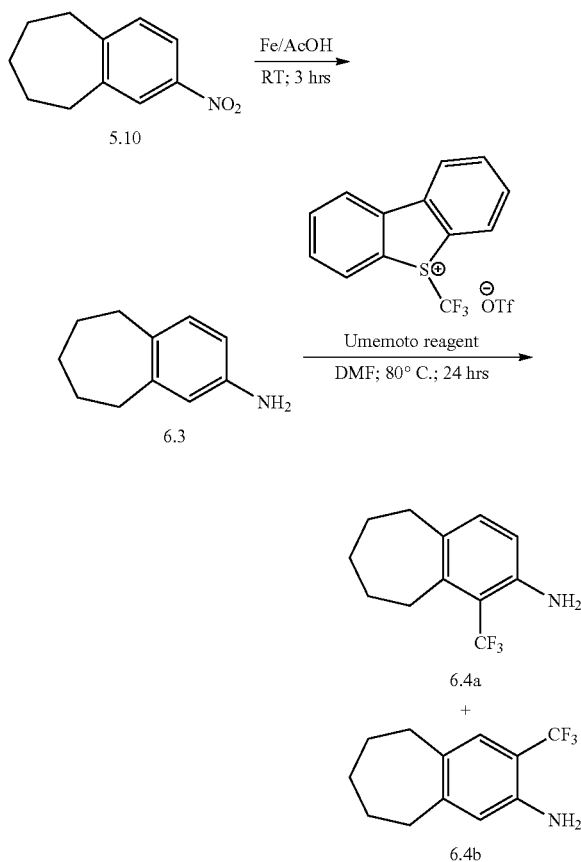

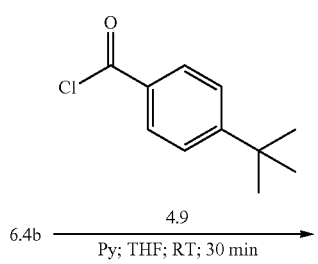

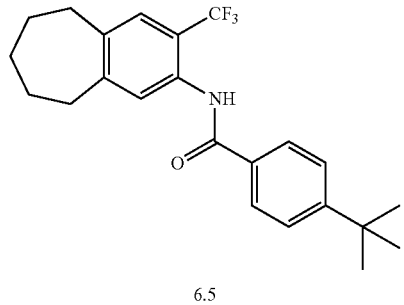

6.5

In one aspect, compounds of type 2.1, and similar compounds, can be prepared according to reaction Scheme 6B above. Thus, compounds of type 6.3 can be prepared by reduction of an appropriate nitro compound, e.g., 5.10 as shown above. Appropriate nitro compounds are commercially available or prepared by methods known to one skilled in the art. The reduction is carried out in the presence of an appropriate metal, e.g., iron, and an appropriate acid, e.g., acetic acid, for an appropriate period of time, e.g., 3 hours. Compounds of type 6.4a and 6.4b can be prepared by nucleophilic substitution of an appropriate protected aniline, e.g., 6.3 as shown above, and an appropriate nucleophile, e.g., Umemoto reagent as shown above. The nucleophilic substitution is carried out in an appropriate solvent, e.g., dimethylformamide, for an appropriate period of time, e.g., 24 hours, at an appropriate temperature, e.g., 80° C. Compounds of type 6.5 can be prepared by coupling of an appropriate amine, e.g., 6.4b as shown above, and an appropriate acyl halide, e.g., 4.9 as shown above. Appropriate acyl halides are commercially available or prepared by methods known to one skilled in the art. The couplings carried out in the presence of an appropriate base, e.g., pyridine, in an appropriate solvent, e.g., tetrahydrofuran, for an appropriate period of time, e.g., 30 minutes. As can be appreciated by one skilled in the art, the above reaction provides an example of a generalized approach wherein compounds similar in structure to the specific reactants above (compounds similar to compounds of type 4.4, 5.3, 6.1, and 6.2), can be substituted in the reaction to provide substituted benzo annulenes similar to Formula 2.1.

7. Route VII

In one aspect, benzo annulene analogs can be prepared as shown below.

SCHEME 7A.

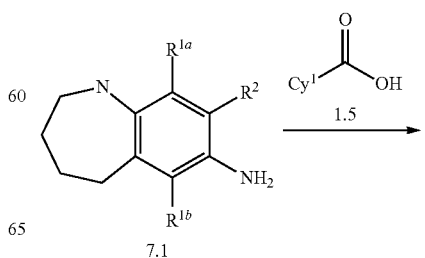

7.1

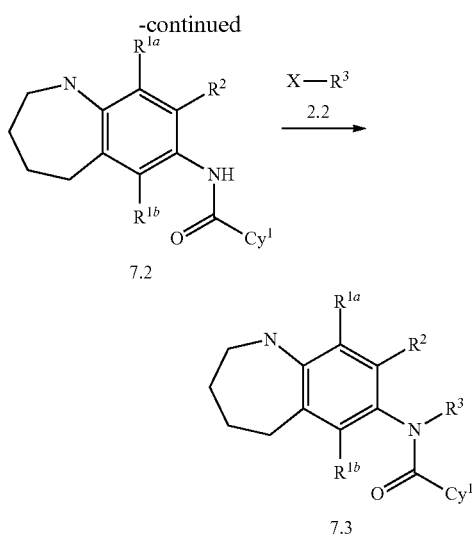

Compounds are represented in generic form, with substituents as noted in compound descriptions elsewhere herein and wherein X is a halide. A more specific example is set forth below.

commercially available or prepared by methods known to one skilled in the art. The coupling is carried out in the presence of an appropriate coupling agent, e.g., 1-ethyl-3-(3-dimethylaminopropyl)carbodiimide hydrochloride, in an appropriate solvent, e.g., dichloromethane, for an appropriate period of time, e.g., 3-5 hours. Compounds of type 7.6 can be prepared by alkylation of an appropriate amide, e.g., 7.5 as shown above, with an appropriate alkyl halide, e.g., 2.4 as shown above. Appropriate alkyl halides are commercially available or prepared by methods known to one skilled in the art. The alkylation is carried out in the presence of an appropriate base, e.g., sodium hydride, in an appropriate solvent, e.g., benzene, for an appropriate period of time, e.g., 6 hours. As can be appreciated by one skilled in the art, the above reaction provides an example of a generalized approach wherein compounds similar in structure to the specific reactants above (compounds similar to compounds of type 1.5, 2.2, 7.1, and 7.2), can be substituted in the reaction to provide substituted benzo annulenes similar to Formula 7.3.

8. Route VIII

In one aspect, benzo annulene analogs can be prepared as shown below.

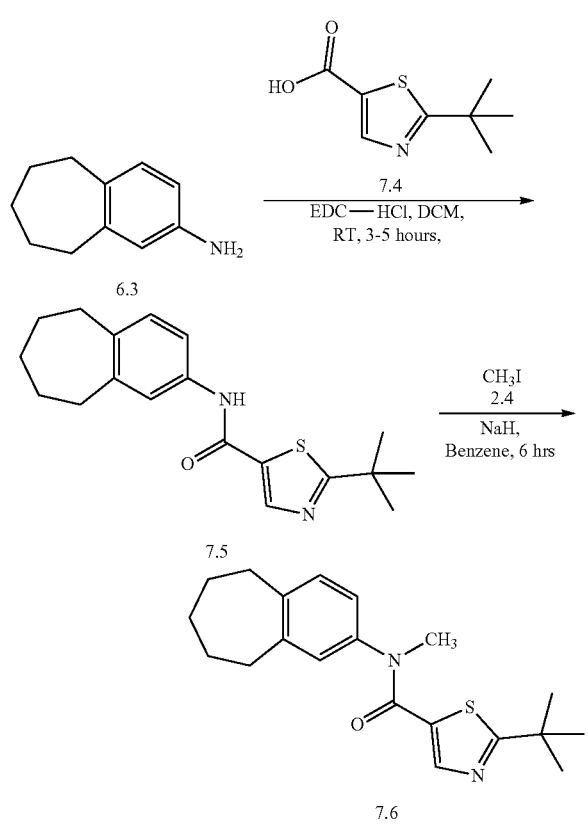

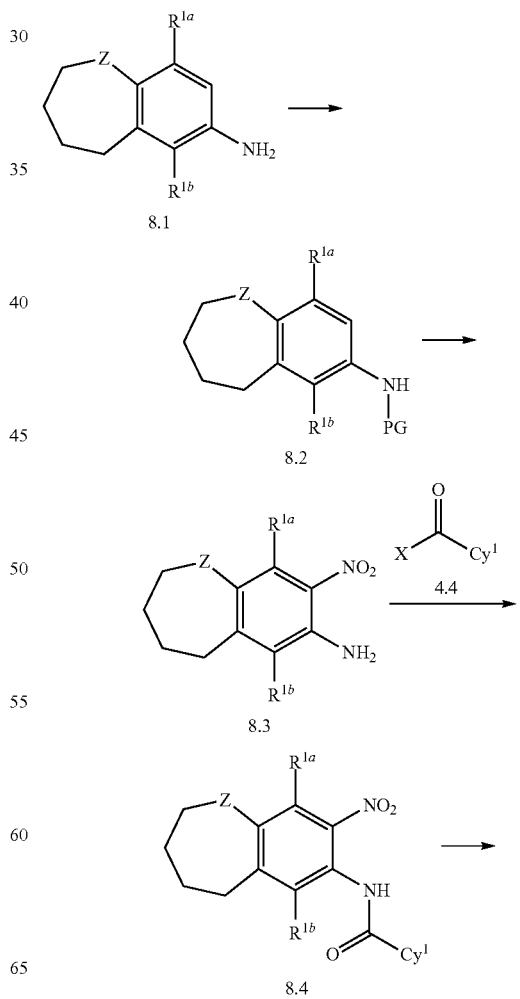

In one aspect, compounds of type 7.3, and similar compounds, can be prepared according to reaction Scheme 7B above. Thus, compounds of type 7.5 can be prepared by coupling of an appropriate aniline, e.g., 6.3 as shown above, and an appropriate carboxylic acid, e.g., 7.4 as shown above. Appropriate anilines and appropriate carboxylic acids are -continued

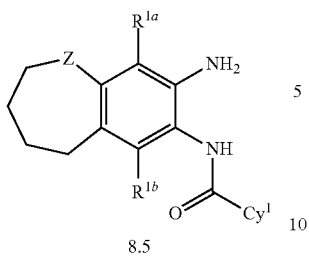

8.5

Compounds are represented in generic form, with substituents as noted in compound descriptions elsewhere herein, wherein PG is an amine protecting group, and wherein X is a halide. A more specific example is set forth below.

SCHEME 8B.

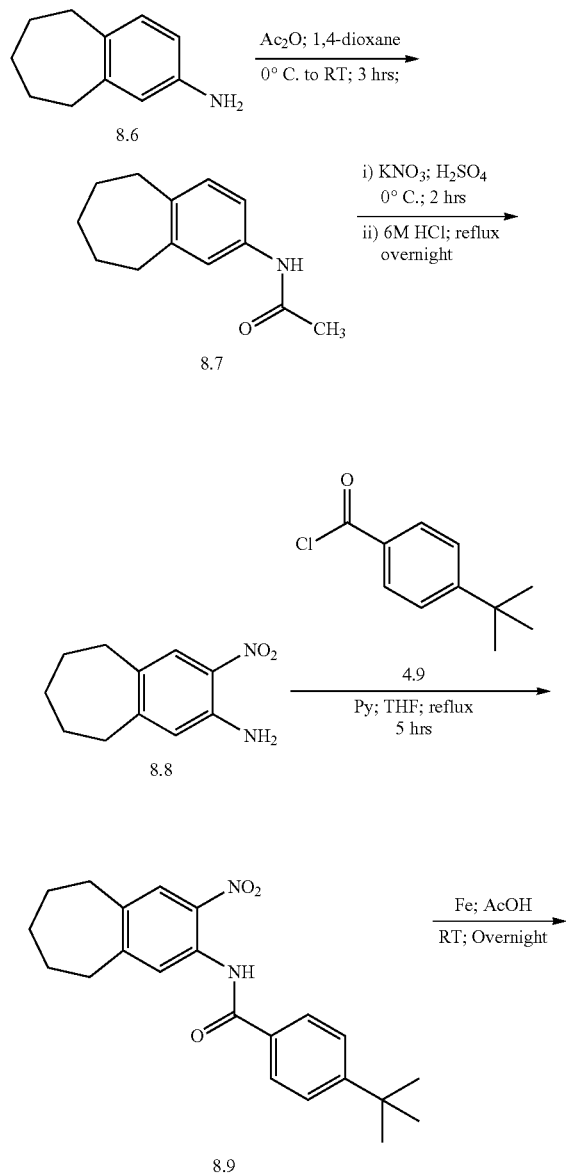

-continued

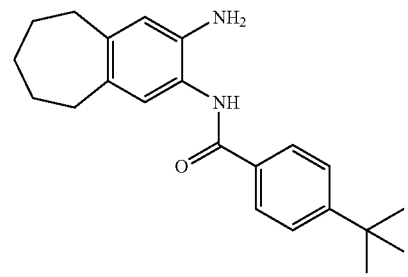

8.10

In one aspect, compounds of type 8.5, and similar compounds, can be prepared according to reaction Scheme 8B above. Thus, compounds of type 8.7 can be prepared by protection of an appropriate aniline, e.g., 8.6 as shown above. Appropriate anilines are commercially available or prepared by methods known to one skilled in the art. The protection is carried out in the presence of an appropriate protecting agent, e.g., acetic anhydride, in an appropriate solvent, e.g., 1,4-dioxane, for an appropriate period of time, e.g., 3 hours. Compounds of type 8.8 can be prepared by nitration of an appropriate arene, e.g., 8.7 as shown above. The nitration is carried out in the presence of an appropriate nitrate, e.g., potassium nitrate, and an appropriate acid, e.g., sulfuric acid, at an appropriate temperature, e.g., 0° C., for an appropriate period of time, e.g., 2 hours, followed by reaction with an appropriate acid, e.g., hydrochloric acid. Compounds of type 8.9 can be prepared by coupling of an appropriate amine, e.g., 8.8 as shown above, and an appropriate carboxylic acid, e.g., 4.9 as shown above. Appropriate carboxylic acids are commercially available or prepared by methods known to one skilled in the art. The coupling is carried out in the presence of an appropriate base, e.g., pyridine, in an appropriate solvent, e.g., tetrahydrofuran, for an appropriate period of time, e.g., 5 hours. Compounds of type 8.10 can be prepared by reduction of an appropriate nitro compound, e.g., 8.9 as shown above. The reduction is carried out in the presence of an appropriate metal, e.g., iron, and an appropriate acid, e.g., acetic acid. As can be appreciated by one skilled in the art, the above reaction provides an example of a generalized approach wherein compounds similar in structure to the specific reactants above (compounds similar to compounds of type 4.4, 8.1, 8.2, 8.3, and 8.4), can be substituted in the reaction to provide substituted benzo annulenes similar to Formula 8.5.

9. Route IX

In one aspect, benzo annulene analogs can be prepared as shown below.

SCHEME 9A.

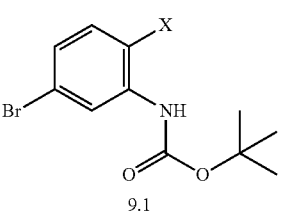

9.1

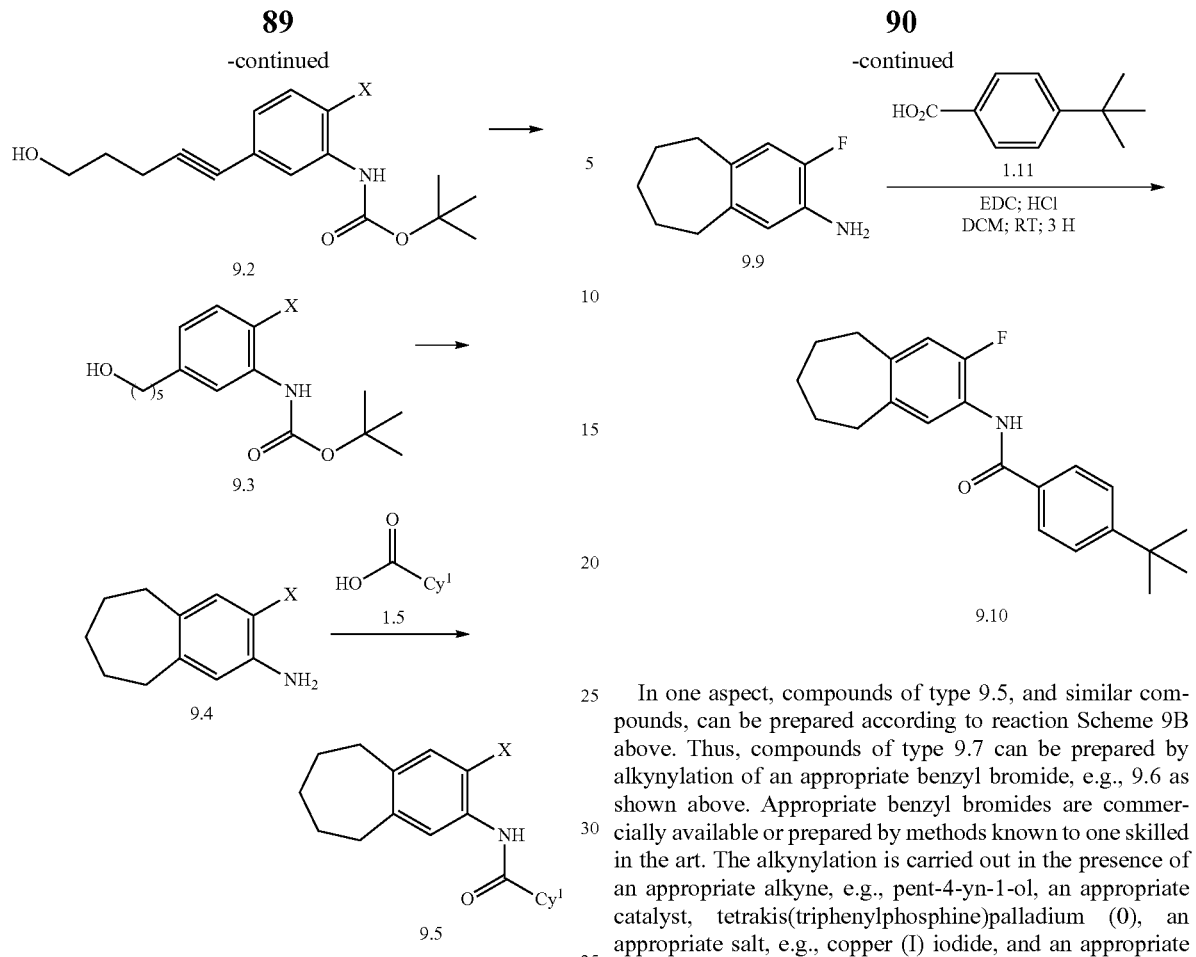

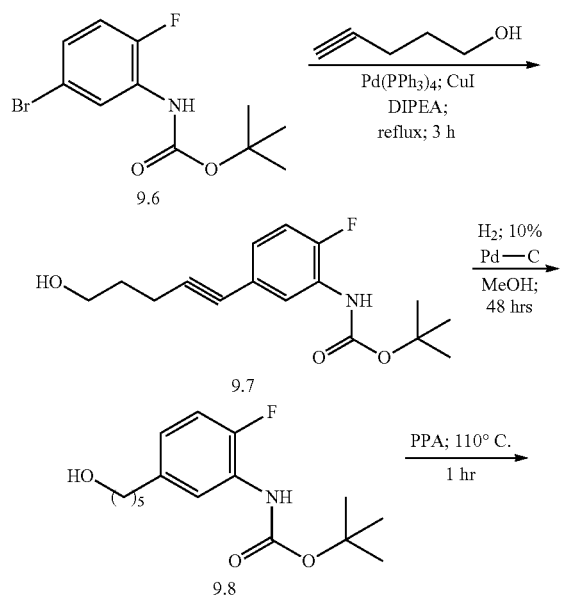

Compounds are represented in generic form, with substituents as noted in compound descriptions elsewhere herein and wherein X is a halide. A more specific example is set forth below.

In one aspect, compounds of type 9.5, and similar compounds, can be prepared according to reaction Scheme 9B above. Thus, compounds of type 9.7 can be prepared by alkynylation of an appropriate benzyl bromide, e.g., 9.6 as shown above. Appropriate benzyl bromides are commercially available or prepared by methods known to one skilled in the art. The alkynylation is carried out in the presence of an appropriate alkyne, e.g., pent-4-yn-1-ol, an appropriate catalyst, tetrakis(triphenylphosphine)palladium (0), an appropriate salt, e.g., copper (I) iodide, and an appropriate base, e.g., N,N-diisopropylethylamine, for an appropriate period of time, e.g., 3 hours. Compounds of type 9.8 can be prepared by reduction of an appropriate alkyne, e.g., 9.7 as shown above. The reduction is carried out in the presence of an appropriate hydrogen source, e.g., hydrogen gas, and an appropriate catalyst, e.g., 10% palladium on Carbon, in an appropriate solvent, e.g., methanol, for an appropriate period of time, e.g., 48 hours. Compounds of type 9.9 can be prepared by cyclization of an appropriate alcohol, e.g., 9.8 as shown above. The cyclization is carried out in the presence of an appropriate amine, e.g., phenylpropanolamine, for an appropriate period of time, e.g., 1 hour, at an appropriate temperature, e.g., 110° C. Compounds of type 9.10 can be prepared by coupling of an appropriate amine, e.g., 9.9 as shown above, and an appropriate carboxylic acid, e.g., 1.11 as shown above. Appropriate carboxylic acids are commercially available or prepared by methods known to one skilled in the art. The coupling is carried out in the presence of an appropriate coupling agent, e.g., 1-ethyl-3-(3-dimethylaminopropyl)carbodiimide hydrochloride (EDC-HCl), in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 1.5, 9.1, 9.2, 9.3, and 9.4), can be substituted in the reaction to provide substituted benzo annulenes similar to Formula 9.5.

10. Route X

In one aspect, benzo annulene analogs can be prepared as shown below.

SCHEME 10A.

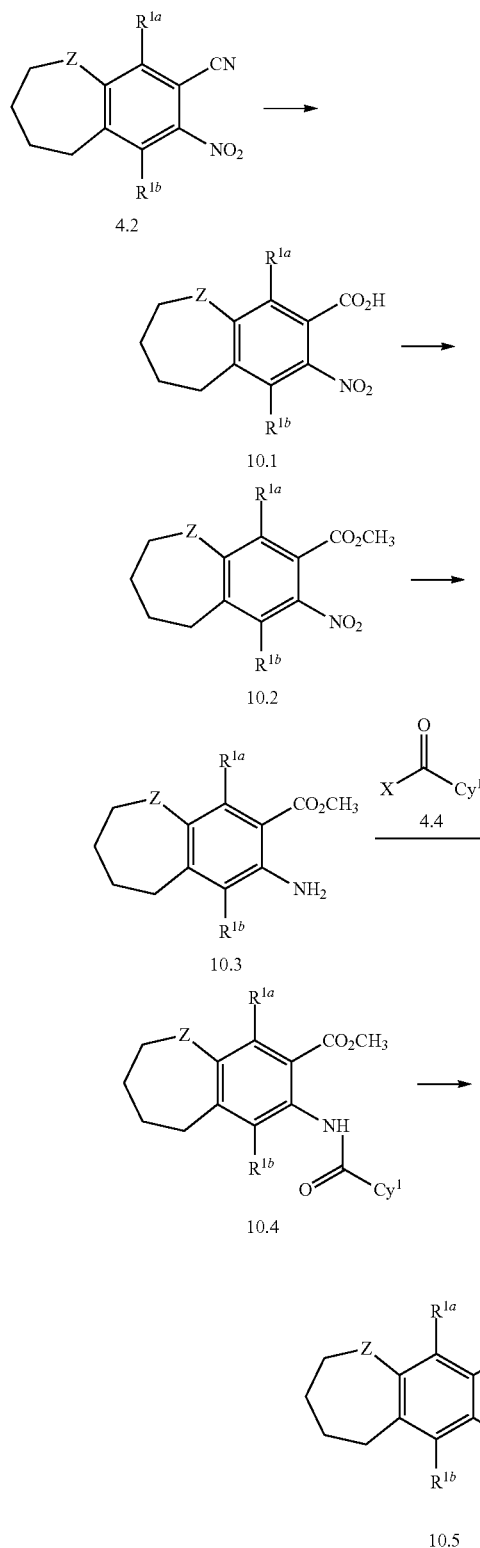

Compounds are represented in generic form, with substituents as noted in compound descriptions elsewhere herein and wherein X is a halide. A more specific example is set forth below.

SCHEME 10B.

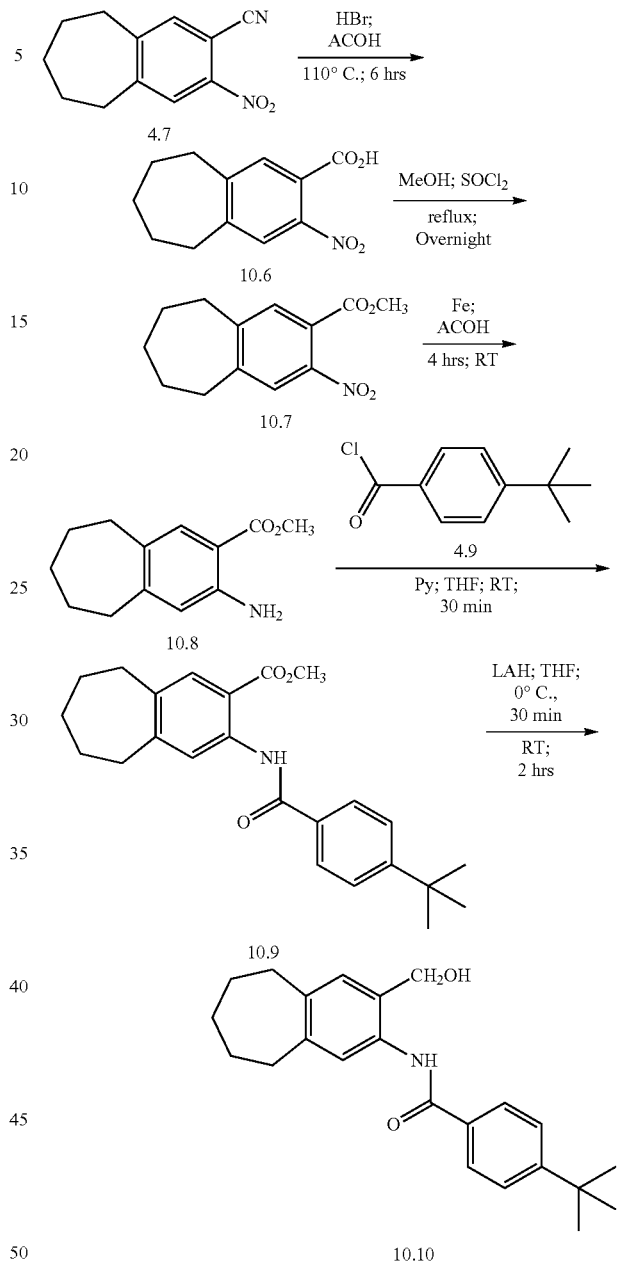

In one aspect, compounds of type 10.5, and similar compounds, can be prepared according to reaction Scheme 10B above. Thus, compounds of type 10.6 can be prepared by hydrolysis of an appropriate nitrile, e.g., 4.7 as shown above. Appropriate nitriles are commercially available or prepared by methods known to one skilled in the art. The hydrolysis is carried out in the presence of an appropriate acid, e.g., hydrobromic acid, in an appropriate solvent, e.g., acetic acid, for an appropriate period of time, e.g., 6 hours, at an appropriate temperature, e.g., 110° C. Compounds of type 10.7 can be prepared by esterification of an appropriate carboxylic acid, e.g., 10.6 as shown above. The esterification is carried out in the presence of an appropriate activating agent, e.g., thionyl chloride, and an appropriate alcohol, e.g., methanol. Compounds of type 10.8 can be prepared by reduction of an appropriate nitro compound, e.g., 10.7 as shown above. The reduction is carried out in the presence of an appropriate metal, e.g., iron, and an appropriate acid, e.g., acetic acid, for an appropriate period of time, e.g., 4 hours. Compounds of type 10.9 can be prepared by coupling of an appropriate amine, e.g., 10.8 as shown above, and an appropriate acyl halide, e.g., 4.9 as shown above. Appropriate acyl halides are commercially available or prepared by methods known to one skilled in the art. The coupling is carried out in the presence of an appropriate base, e.g., pyridine, in an appropriate solvent, e.g., tetrahydrofuran, for an appropriate period of time, e.g., 30 minutes. Compounds of type 10.10 can be prepared by reduction of an appropriate ester, e.g., 10.9 as shown above. The reduction is carried out in the presence of an appropriate base, e.g., lithium aluminum hydride, in an appropriate solvent, e.g., tetrahydrofuran, for an appropriate period of time, e.g., 30 minutes. As can be appreciated by one skilled in the art, the above reaction provides an example of a generalized approach wherein compounds similar in structure to the specific reactants above (compounds similar to compounds of type 4.2, 4.4, 10.1, 10.2, 10.3, and 10.4), can be substituted in the reaction to provide substituted benzo annulenes similar to Formula 10.5.

11. Route XI

In one aspect, benzo annulene analogs can be prepared as shown below.

SCHEME 11A.

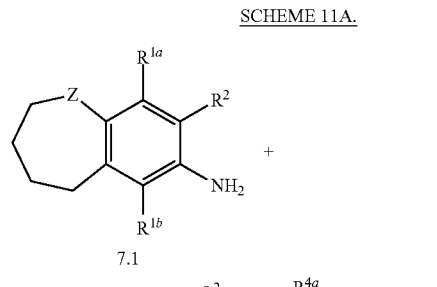

7.1

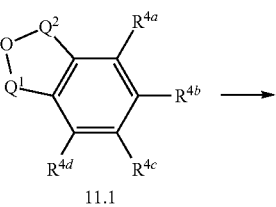

11.1

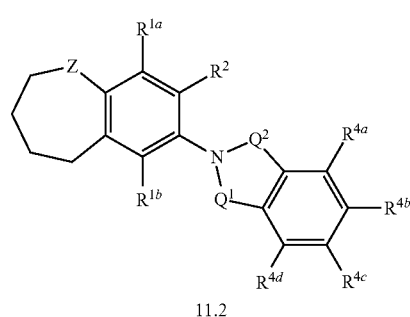

11.2

Compounds are represented in generic form, with substituents as noted in compound descriptions elsewhere herein. A more specific example is set forth below.

SCHEME 11B.

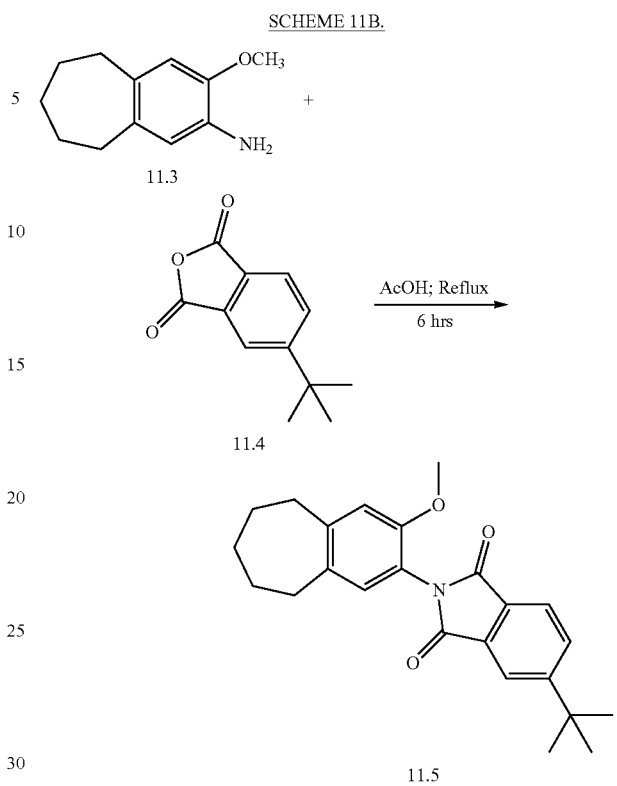

In one aspect, compounds of type 11.2, and similar compounds, can be prepared according to reaction Scheme 11B above. Thus, compounds of type 11.5 can be prepared by hydrolysis of an appropriate aniline, e.g., 11.3 as shown above, and an appropriate furan, e.g., 11.4 as shown above. Appropriate anilines and appropriate furans are commercially available or prepared by methods known to one skilled in the art. The hydrolysis is carried out in the presence of an appropriate acid, e.g., acetic acid, for an appropriate period of time, e.g., 6 hours. As can be appreciated by one skilled in the art, the above reaction provides an example of a generalized approach wherein compounds similar in structure to the specific reactants above (compounds similar to compounds of type 7.1 and 11.1), can be substituted in the reaction to provide substituted benzo annulenes similar to Formula 11.2.

12. Route XII

In one aspect, benzo annulene analogs can be prepared as shown below.

SCHEME 12A.

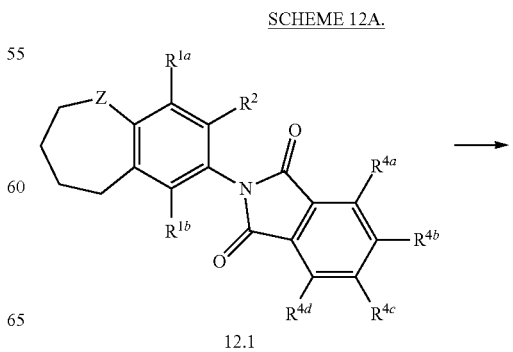

12.1

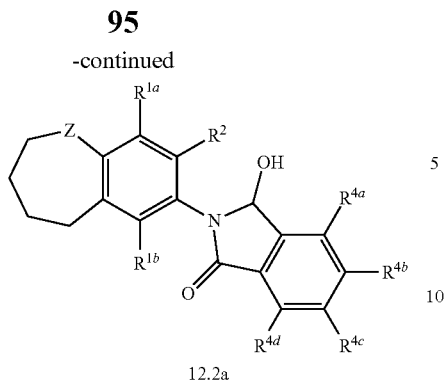

12.2a

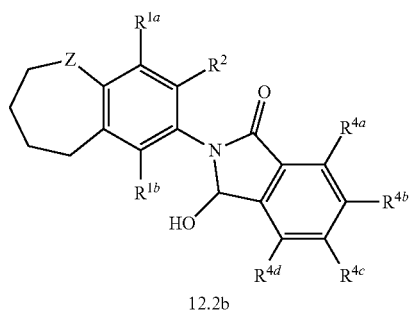

12.2b

Compounds are represented in generic form, with substituents as noted in compound descriptions elsewhere herein. A more specific example is set forth below.

SCHEME 12B.

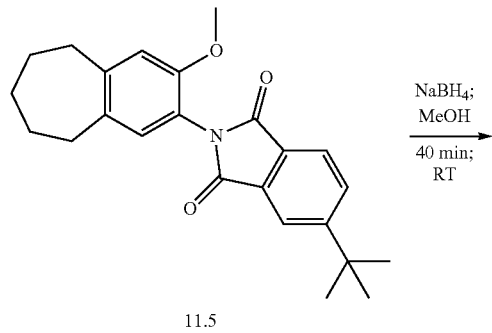

11.5

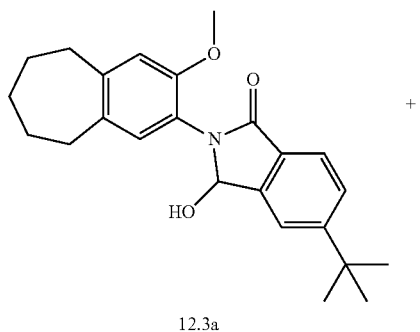

12.3a

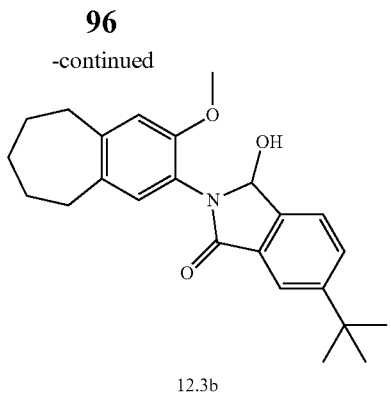

12.3b

In one aspect, compounds of type 12.2a and 12.2b, and similar compounds, can be prepared according to reaction Scheme 12B above. Thus, compounds of type 12.3a and 12.3b can be prepared by reduction of an appropriate phthalimide, e.g., 11.5 as shown above. The reduction is carried out in the presence of an appropriate reducing agent, e.g., sodium borohydride, in an appropriate solvent, e.g., methanol, for an appropriate period of time, e.g., 40 minutes. As can be appreciated by one skilled in the art, the above reaction provides an example of a generalized approach wherein compounds similar in structure to the specific reactants above (compounds similar to compounds of type 12.1), can be substituted in the reaction to provide substituted benzo annulenes similar to Formula 12.2a and 12.2b.

13. Route XIII

In one aspect, benzo annulene analogs can be prepared as shown below.

SCHEME 13A.

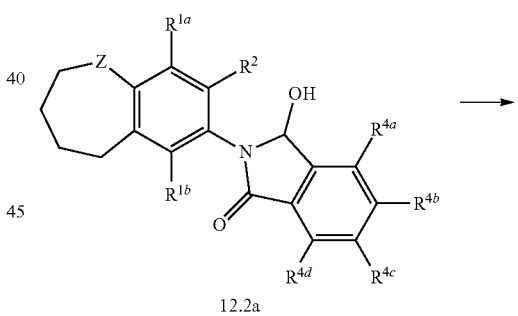

12.2a

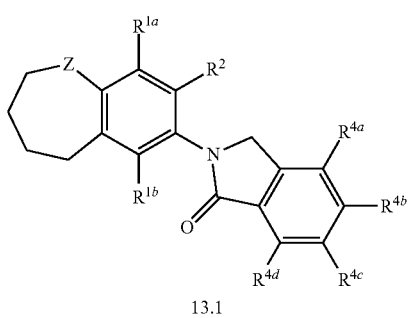

13.1

Compounds are represented in generic form, with substituents as noted in compound descriptions elsewhere herein. A more specific example is set forth below.

SCHEME 13B.

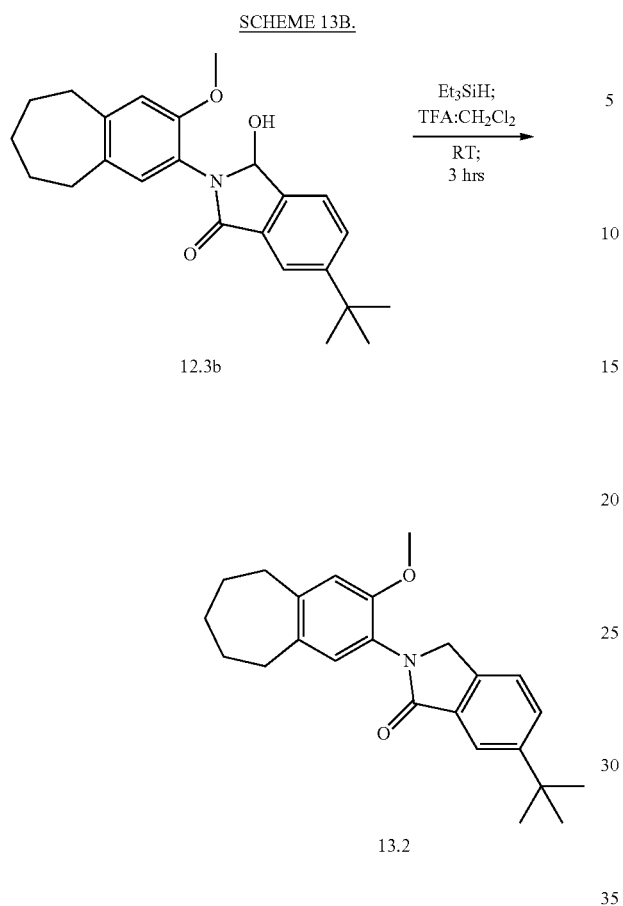

In one aspect, compounds of type 13.1, and similar compounds, can be prepared according to reaction Scheme 13B above. Thus, compounds of type 13.2 can be prepared by reduction of an appropriate alcohol, e.g., 12.3b as shown above. The reduction is carried out in the presence of an appropriate reducing agent, e.g., triethylsilane, and an appropriate acid, e.g., trifluoroacetic acid, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 12.2a), can be substituted in the reaction to provide substituted benzo annulenes similar to Formula 13.1.

14. Route XIV

In one aspect, benzo annulene analogs can be prepared as shown below.

SCHEME 14A.

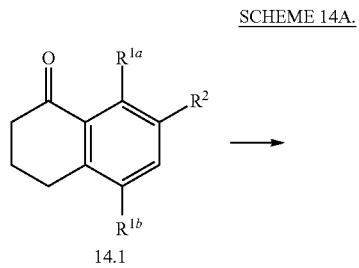

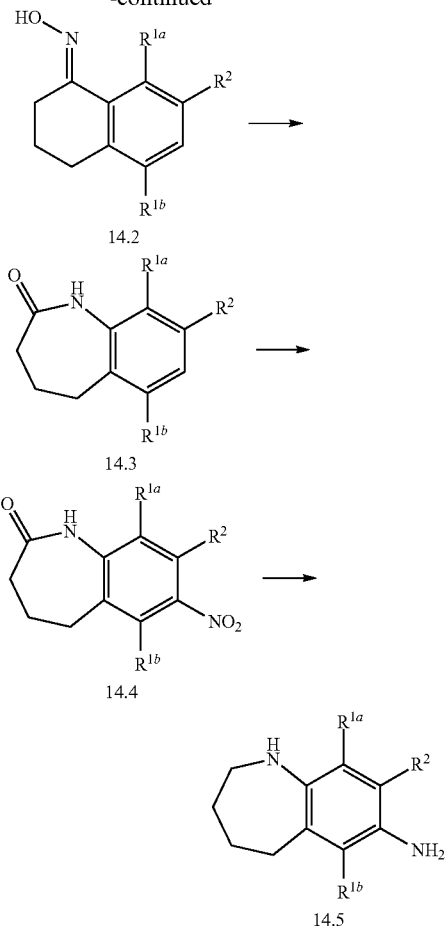

Compounds are represented in generic form, with substituents as noted in compound descriptions elsewhere herein. A more specific example is set forth below.

SCHEME 14B.

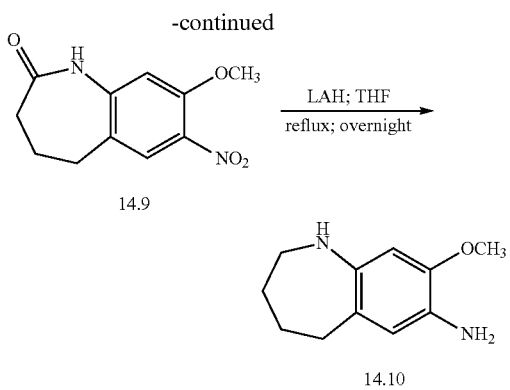

14.9

14.10

In one aspect, compounds of type 14.5, and similar compounds, can be prepared according to reaction Scheme 14B above. Thus, compounds of type 14.7 can be prepared by nucleophilic substitution of an appropriate ketone, e.g., 14.6 as shown above. Appropriate ketones are commercially available or prepared by methods known to one skilled in the art. The nucleophilic substitution is carried out in the presence of an appropriate nucleophile, e.g., hydroxylamine hydrochloride, and an appropriate base, e.g., sodium acetate, in an appropriate solvent system, e.g., ethanol and water. Compounds of type 14.8 can be prepared by ring expansion of an appropriate oxime, e.g., 14.7 as shown above. The ring expansion is carried out in the presence of an appropriate amine, e.g., phenylpropanolamine, at an appropriate temperature, e.g., 70° C., for an appropriate period of time, e.g., 16 hours. Compounds of type 14.9 can be prepared by nitration of an appropriate arene, e.g., 14.8 as shown above. The nitration is carried out in the presence of an appropriate nitrate, e.g., potassium nitrate, and an appropriate acid, e.g., trifluoroacetic anhydride, in an appropriate solvent, e.g., acetonitrile. Compounds of type 14.10 can be prepared by reduction of an appropriate nitro compound, e.g., 14.9 as shown above. The reduction is carried out in the presence of an appropriate reducing agent, e.g., lithium aluminum hydride, in an appropriate solvent, e.g., tetrahydrofuran. As can be appreciated by one skilled in the art, the above reaction provides an example of a generalized approach wherein compounds similar in structure to the specific reactants above (compounds similar to compounds of type 14.1, 14.2, 14.3, and 14.4), can be substituted in the reaction to provide substituted benzo annulenes similar to Formula 14.5.

E. Methods of Using the Compounds

The compounds and pharmaceutical compositions of the invention are useful in treating or controlling disorders associated with a viral infection, in particular, chikungunya, Venezuelan equine encephalitis, dengue, influenza, and zika.

Examples of viral infections for which the compounds and compositions can be useful in treating, include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as chikungunya, Venezuelan equine encephalitis, dengue, influenza, and zika.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a viral infection, such as chikungunya, Venezuelan equine encephalitis, dengue, influenza, and zika.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with a viral infection, in particular, chikungunya, Venezuelan equine encephalitis, dengue, influenza, and zika. Thus, provided is a method comprising administering a therapeutically effective amount of a composition comprising a disclosed compound to a subject. In a further aspect, the method can be a method for treating a viral infection.

a. Treating a Viral Infection

In one aspect, disclosed are methods of treating a disorder associated a viral infection in a mammal, the method comprising the step of administering to the mammal an effective amount of at least one disclosed compound, or a pharmaceutically acceptable salt thereof.

In one aspect, disclosed are methods the treatment of a viral infection in a subject, the method comprising the step of administering to the subject an effective amount of at least one compound having a structure represented by a formula selected from:

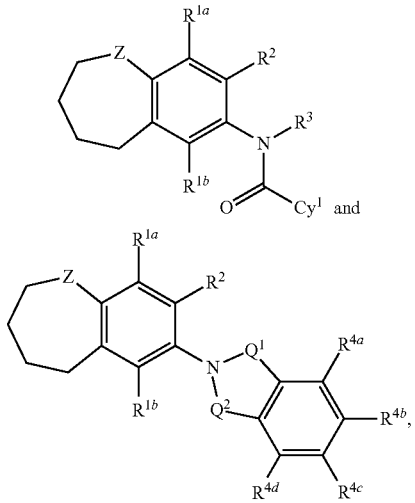

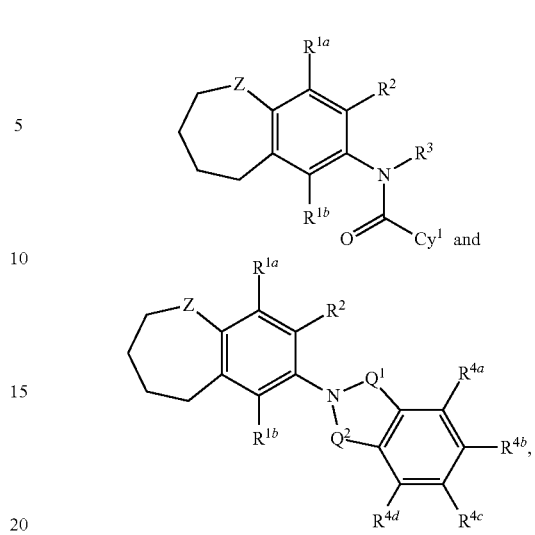

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —OC(O)$R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, or a pharmaceutically acceptable salt thereof.

In one aspect, disclosed are methods for the treatment of a disorder associated with a viral infection in a mammal, the method comprising the step of administering to the mammal an effective amount of at least one compound having a structure represented by a formula selected from:

wherein each of $Q^1$ and $Q^2$ is independently selected from $CH_2$, CH(OH), and C(O), provided that at least one of $Q^1$ and $Q^2$ is C(O); wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_nOR^{20}$, and —OC(O)$R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, provided that when $Cy^1$ is unsubstituted phenyl, then at least one of $R^{1a}$, $R^{1b}$, and $R^2$ is not hydrogen, or a pharmaceutically acceptable salt thereof.

Examples of viral infections include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika.

In a further aspect, the subject has been diagnosed with a need for treatment of the disorder prior to the administering step. In a still further aspect, the subject has been diagnosed with a need for treatment of the viral infection prior to the administering step.

In a further aspect, the subject is a mammal. In a still further aspect, the mammal is a human.

In a further aspect, the method further comprises the step of identifying a subject in need of treatment of the viral infection.

In a further aspect, the disorder is associated with a viral infection. In a still further aspect, the viral infection is selected from human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In yet a further aspect, the viral infection is selected from chikungunya, Venezuelan equine encephalitis, dengue, influenza, and zika.

In a further aspect, the method further comprises the step of administering a therapeutically effective amount of at least one antiviral agent. In a still further aspect, the at least one agent is selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxil fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

In a further aspect, the effective amount is a therapeutically effective amount. In a still further aspect, the effective amount is a prophylactically effective amount.

2. Methods of Inhibiting a Viral Infection in a Mammal

In one aspect, disclosed are methods of inhibiting a viral infection in a mammal, the method comprising the step of administering to the mammal a therapeutically effective amount of at least one disclosed compound, or a pharmaceutically acceptable salt thereof.

In a further aspect, the compound exhibits inhibition of a viral infection. In a still further aspect, the compound exhibits a decrease in a viral infection. In yet a further aspect, the viral infection is CHIKV.

In a further aspect, the compound exhibits inhibition of CHIKV activity with an $EC_{90}$ of less than about 30 µM. In a still further aspect, the compound exhibits inhibition of CHIKV activity with an $EC_{90}$ of less than about 25 µM. In yet a further aspect, the compound exhibits inhibition of CHIKV activity with an $EC_{90}$ of less than about 20 µM. In an even further aspect, the compound exhibits inhibition of CHIKV activity with an $EC_{90}$ of less than about 15 µM. In a still further aspect, the compound exhibits inhibition of CHIKV activity with an $EC_{90}$ of less than about 10 µM. In yet a further aspect, the compound exhibits inhibition of CHIKV activity with an $EC_{90}$ of less than about 5 µM. In an even further aspect, the compound exhibits inhibition of CHIKV activity with an $EC_{90}$ of less than about 1 µM. In a still further aspect, the compound exhibits inhibition of CHIKV activity with an $EC_{90}$ of less than about 0.5 µM.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

3. Methods of Inhibiting a Viral Infection in at Least One Cell

In one aspect, disclosed are methods for inhibiting a viral infection in at least one cell, the method comprising the step of contacting the at least one cell with an effective amount of at least one disclosed compound, or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

4. Use of Compounds

In one aspect, the invention relates to the use of a disclosed compound or a product of a disclosed method. In a further aspect, a use relates to the manufacture of a medicament for the treatment of a viral infection in a mammal.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for antagonism of a viral infection. In one aspect, the use is characterized in that the mammal is a human. In one aspect, the use is characterized in that the disorder is a viral infection.

In a further aspect, the use relates to the manufacture of a medicament for the treatment of a viral infection in a mammal.

In a further aspect, the use relates to antagonism of a viral infection in a mammal. In a further aspect, the use relates to modulating viral activity in a mammal. In a still further aspect, the use relates to modulating viral activity in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a viral infection in a mammal. In a further aspect, the viral infection is selected from chikungunya, Venezuelan equine encephalitis, dengue, influenza, and zika.

5. Manufacture of a Medicament

In one aspect, the invention relates to a method for the manufacture of a medicament for treating a viral infection in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, the invention relates to a kit comprising at least one compound having a structure represented by a formula selected from:

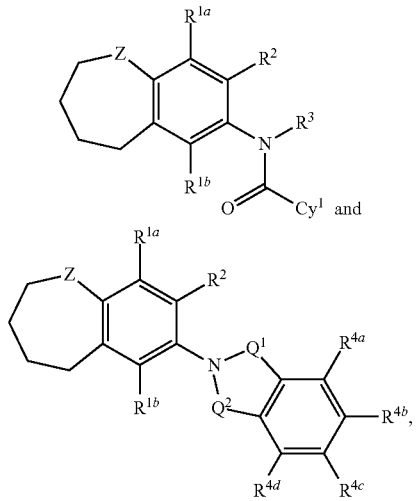

wherein each of $Q^1$ and $Q^2$ is independently selected from $CH_2$, $CH(OH)$, and $C(O)$, provided that at least one of $Q^1$ and $Q^2$ is $C(O)$; wherein Z is selected from $CH_2$ and NH; wherein each of $R^{1a}$ and $R^{1b}$ is independently selected from hydrogen and —F; wherein $R^2$ is selected from hydrogen, halogen, —CN, —$(CH_2)_n OR^{20}$, and —$OC(O)R^{21}$; wherein n is selected from 0, 1, 2, 3, and 4; wherein $R^{20}$, when present, is selected from hydrogen, C1-C4 alkyl, C1-C4 haloalkyl, $Ar^1$, and —(C1-C4 alkyl)$Ar^1$; wherein $Ar^1$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; wherein $R^{21}$, when present, is selected from hydrogen, C1-C4 alkyl, C1-C4 haloalkyl, and $Ar^1$; wherein $R^3$ is selected from hydrogen and C1-C4 alkyl; and wherein each of $R^{4a}$, $R^{4b}$, $R^{4c}$, and $R^{4d}$ is independently selected from hydrogen, halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$; wherein $Cy^2$, when present, is selected from C3-C5 cycloalkyl, C2-C5 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, C5-C6 aryl, and C4-C5 heteroaryl and substituted with 0, 1, or 2 groups independently selected from halogen, —$CO_2H$, —CN, —OH, —$NH_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, or a pharmaceutically acceptable salt thereof, and one or more of: (a) at least one antiviral agent; (b) a instructions for administering the at least one compound in connection with treating a viral infection; (c) instructions for administering the at least one compound in connection with reducing the risk of viral infection; or (d) instructions for treating a viral infection.

In a further aspect, when Cy¹ is unsubstituted phenyl, then at least one of $R^{1a}$, $R^{1b}$, and $R^2$ is not hydrogen.

In a further aspect, the viral infection is selected from human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In a still further aspect, the viral infection is selected from chikungunya, Venezuelan equine encephalitis, dengue, influenza, and zika.

In a still further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following preparations and examples are given to enable those skilled in the art to more clearly understand and to practice the present invention. They should not be considered as limiting the scope of the invention, but merely as being illustrative and representative.

1. General Experimental Methods

The reactions were performed under a dry argon atmosphere and reaction temperatures were measured externally. Anhydrous solvents over molecular sieves were purchased from Aldrich and used as such in reactions. Purification of compounds was performed on an Isco Teledyne Combiflash Rf200 with four channels to carryout sequential purification. Universal RediSep solid sample loading pre-packed cartridges (5.0 g Silica) were used to absorb crude product and purified on 12 g silica RediSep Rf Gold Silica (20-40 μm spherical silica) columns using appropriate solvent gradients. Pure samples were dried overnight under high vacuum over $P_2O_5$ at 78° C. before analyses. The reactions were monitored by thin-layer chromatography (TLC) on pre-coated silica gel ($60F_{254}$) aluminium plates (0.25 mm) from E. Merck and visualized using UV light (254 nm). Pure samples were dried overnight under high vacuum over $P_2O_5$ at 78° C. before analyses. The HR-mass spectral data were obtained on an Agilent LC-MSTOF by electrospray ionization (ESI). ¹H NMR spectra were recorded at 400 MHz on Agilent/Varian MR-400 spectrometer in $CDCl_3$ or DMSO-$d_6$ as solvents. The chemical shifts (δ) are in ppm downfield from standard tetramethylsilane (TMS). Coupling constants (J) are reported in Hertz (Hz). Purity of final compounds was checked by HPLC using Waters HPLC equipped with a 3100 Mass Detector using Sunfire C18 column (5 μm, 4.6×150 mm) using Acetonitrile-$H_2O$ (both containing 0.1% formic acid) 10-90% in 15 min.

2. Chemistry Experimentals a. Synthesis of 3-Nitro-6,7,8,9-tetrahydro-5H-benzo[7]annulen-2-ol

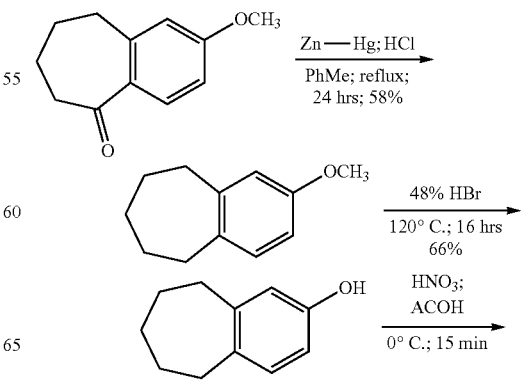

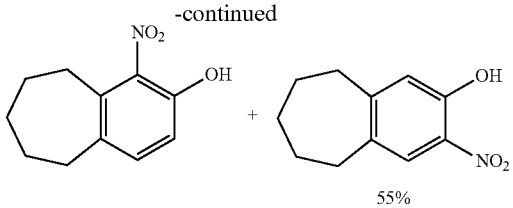

55%

Step 1: To a mixture of zinc (121 g, 1.86 mol) and mercury(II) chloride (11.42 g, 42 mmol) was added a solution of HCl [9.2 mL in 256 mL of deionized $H_2O$]. The reaction mixture was stirred at room temperature for 10 min and decanted. The resulted slurry was suspended in an aqueous solution of HCl [230 mL in 101 mL deionized water] and added toluene (130 mL) and compound 2-methoxy-6,7,8,9-tetrahydro-5H-benzo[7]annulen-5-one (16 g, 84 mmol). The reaction mixture was refluxed for 24 h at 110° C. It was cooled to room temperature and poured into ice cold water (1 L). The resulting mixture was extracted with EtOAc. The organic layer was dried over $Na_2SO_4$, filtered and solvent was evaporated. The crude residue was purified by pre-packed Silica gel column on ISCO using 19:1 (Hexanes:EtOAc). Yield: (8.60 g, 58%). $^1$H NMR (400 MHz, $CDCl_3$) δ 7.03 (d, J=8.2 Hz, 1H), 6.71 (d, J=2.7 Hz, 1H), 6.64 (dd, J=8.2, 2.7 Hz, 1H), 3.80 (s, 3H), 2.77 (dd, J=11.0, 6.4 Hz, 4H), 1.84 (d, J=5.5 Hz, 2H), 1.66 (dd, J=12.9, 5.3 Hz, 4H).

Step 2: 2-Methoxy-6,7,8,9-tetrahydro-5H-benzo[7]annulene (4.70 g, 26.7 mmol) was dissolved in HBr (3 mL, 55.2 mmol) and AcOH (3 mL, 52.4 mmol). The mixture was refluxed for 24 h. After completion of reaction it was diluted with water and extracted with EtOAc. The organic layer was washed with aq. $NaHCO_3$, dried over anhydrous $Na_2SO_4$, filtered and concentrated. The product was purified by column chromatography using 7:3 (Hexanes:EtOAc); Yield: (2.86 g, 68%). $^1$H NMR (400 MHz, $CDCl_3$) δ 6.95 (d, J=8.0 Hz, 1H), 6.60 (d, J=2.7 Hz, 1H), 6.54 (dd, J=8.0, 2.7 Hz, 1H), 2.75-2.68 (m, 4H), 1.86-1.77 (m, 2H), 1.62 (dq, J=9.6, 5.6 Hz, 4H).

Step 3: 6,7,8,9-Tetrahydro-5H-benzo[7]annulen-2-ol (150 mg, 0.92 mmol) was dissolved in AcOH (2.12 mL) and water (0.2 mL). The reaction mixture was cooled to 5° C. and a mixture of fuming nitric acid (0.041 mL, 0.93 mmol) and acetic acid (0.5 mL) was added drop wise. The mixture was then stirred for 15 min at 5° C. and water was added. The reaction mixture was extracted with $CH_2Cl_2$. The organic layer was washed with water and dried over anhydrous Na2SO4. The crude product was purified by column chromatography using 19:1 (Hexanes:EtOAc). Yield: 105 mg (55%). $^1$H NMR (400 MHz, $CDCl_3$) δ 10.52 (s, 1H), 7.80 (s, 1H), 6.89 (s, 1H), 2.78 (dd, J=11.1, 9.0 Hz, 4H), 1.83 (p, J=6.1, 5.6 Hz, 2H), 1.65 (dt, J=10.7, 5.3 Hz, 4H).

b. General Synthesis of Compounds 3, 17, 21, 31-33, 36-46, 48-53, 56, 57, and 66-86

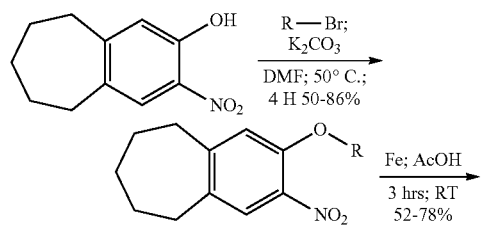

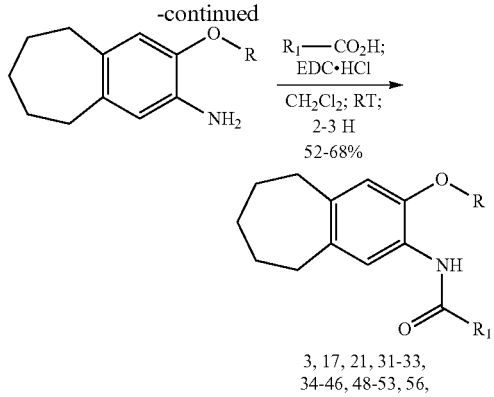

3, 17, 21, 31-33, 34-46, 48-53, 56, 57, and 66-86

Step 1: A heterogeneous mixture of nitrophenol (1 mmol), corresponding alkyl/aryl halide (1.1 mmol) and $K_2CO_3$ (2 mmol) in anhydrous DMF (3 mL) was stirred at 50° C. for 4 h. The reaction mixture was diluted with EtOAc and any precipitate was removed by filtration. The filtrate was concentrated and the resulting residue was purified by column chromatography.

Step 2: Product from Step-1 (1 mmol) was dissolved in 6 mL AcOH followed by the addition of Fe powder (5 mmol) and reaction mixture was stirred for 3 h at room temperature. The reaction mixture was filtered through short celite pad and washed with EtOAc. The filtrate was diluted with water and extracted with EtOAc. The organic layer was washed with aq. $NaHCO_3$, brine, dried over anhydrous $Na_2SO_4$ and concentrated. The crude product was purified by column chromatography.

Step 3: Product from Step-2 (1 mmol) was dissolved in 5 mL of anhydrous $CH_2Cl_2$. To this solution, corresponding carboxylic acid (1 mmol) was added followed by EDC (2.2 mmol) and the reaction mixture was stirred for 2-3 h at room temperature. The reaction mixture was diluted with water and extracted with $CH_2Cl_2$ The organic layer was dried over anhydrous $Na_2SO_4$ and solvent was evaporated. The crude product was purified by column chromatography.

i. 4-(tert-Butyl)-N-(3-methoxy-6,7,8,9-tetrahydro-5H-benzo[7]annulen-2-yl)benzamide (3)

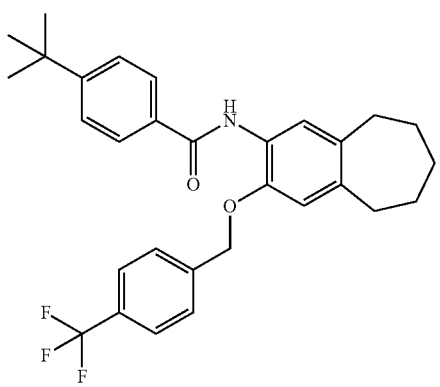

Yield: 50 mg (70%). $^1$H NMR ($CDCl_3$) δ 8.43 (s, 1H), 8.29 (s, 1H), 7.88-7.77 (m, 2H), 7.56-7.43 (m, 2H), 6.67 (s, 1H), 3.88 (s, 3H), 2.85-2.67 (m, 4H), 1.82-1.79 (m, 2H), 1.70-1.56 (m, 4H), 1.35 (s, 9H). HR-ESIMS: m/z 352.2198

[M+H]+ calcd for $C_{23}H_{30}NO_2$, found 352.2227. HPLC Purity: 97% (Retention Time=21.2 min).

i. 4-(tert-Butyl)-N-(3-((4-(trifluoromethyl)benzyl)oxy)-6,7,8,9-tetrahydro-5H-benzo[7]annulen-2-yl)benzamide (17)

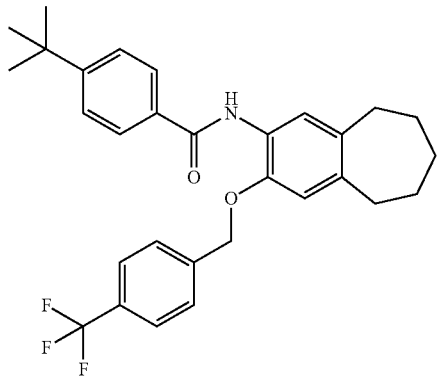 [SMILES: CC(C)(C)c1ccc(C(=O)Nc2cc3c(cc2OCc2ccc(C(F)(F)F)cc2)CCCCC3)cc1]

Yield: 7.3 mg (68%). 1H NMR (CDCl3) δ 8.47 (s, 1H), 8.34 (s, 1H), 7.77-7.75 (m, 3H), 7.73-7.65 (m, 3H), 7.60 (d, J=8.2 Hz, 2H), 6.76 (s, 1H), 5.18 (s, 2H), 2.81-2.74 (m, 4H), 1.83-1.65 (m, 6H), 1.34 (s, 9H). HR-ESIMS: m/z 496.2385 [M+H]+ calcd for $C_{30}H_{33}F_3NO_2$, found 496.2426.

ii. 4-(tert-Butyl)-N-(3-(2-methoxyethoxy)-6,7,8,9-tetrahydro-5H-benzo[7]annulen-2-yl)benzamide (21)

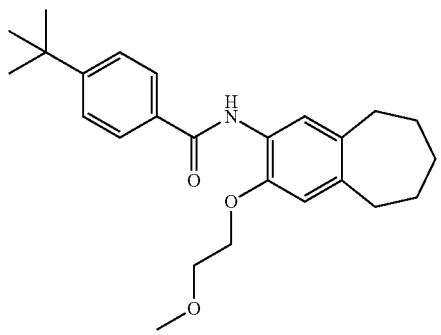 [SMILES: COCCOc1cc2c(cc1NC(=O)c1ccc(C(C)(C)C)cc1)CCCCC2]

Yield: 6 mg (53%); 1H NMR (CDCl3) δ 8.79 (s, 1H), 8.32 (s, 1H), 7.87 (d, J=8.6 Hz, 2H), 7.49 (d, J=8.6 Hz, 2H), 6.74 (s, 1H), 4.31-4.08 (m, 2H), 3.81-3.52 (m, 2H), 3.36 (s, 3H), 2.74 (d, J=24.0 Hz, 4H), 1.92-1.71 (m, 2H), 1.63 (d, J=5.1 Hz, 4H), 1.48-1.27 (m, 9H). HR-ESIMS: m/z 396.2460 [M+H]+ calcd for $C_{25}H_{34}NO_3$, found 396.2425. HPLC Purity: 100% (Retention Time=18.8 min).

iii. 1-Ethyl-N-(3-methoxy-6,7,8,9-tetrahydro-5H-benzo[7]annulen-2-yl)-5-methyl-1H-pyrazole-3-carboxamide (31)

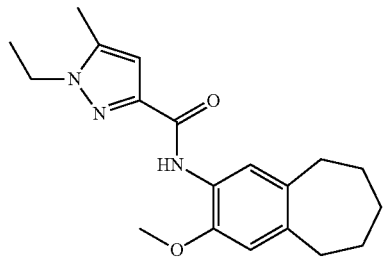 [SMILES: CCn1nc(C(=O)Nc2cc3c(cc2OC)CCCCC3)cc1C]

Yield: 37 mg (60%). 1H NMR (CDCl3) δ 9.15 (s, 1H), 8.27 (s, 1H), 6.66 (s, 1H), 6.59 (s, 1H), 4.12 (q, J=7.2 Hz, 2H), 3.89 (s, 3H), 2.75 (t, J=9.9 Hz, 4H), 2.31 (s, 3H), 1.80 (d, J=5.3 Hz, 6H), 1.46 (t, J=7.3 Hz, 3H). HR-ESIMS: m/z 328.1947 [M+H]+ calcd for $C_{19}H_{26}N_3O_2$, found 328.2050. HPLC Purity: 100% (Retention Time=3 min).

iv. N-(3-methoxy-6,7,8,9-tetrahydro-5H-benzo[7]annulen-2-yl)-1-methyl-1H-imidazole-4-carboxamide (32)

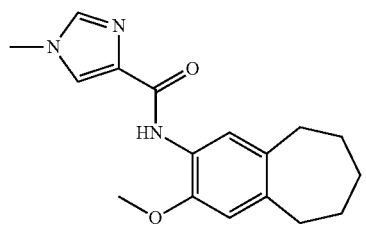 [SMILES: COc1cc2c(cc1NC(=O)c1cn(C)cn1)CCCCC2]

Yield: 28 mg (33%). 1H NMR (CDCl3) δ 9.37 (s, 1H), 8.29 (s, 1H), 7.57 (s, 1H), 7.41 (s, 1H), 6.67 (s, 1H), 3.90 (d, J=0.8 Hz, 3H), 3.75 (s, 3H), 2.76 (t, J=10.4 Hz, 4H), 1.64 (s, 4H), 1.26 (s, 2H). HR-ESIMS: m/z 300.1634 [M+H]+ calcd for $C_{17}H_{22}N_3O_2$, found 300.1692. HPLC Purity: 100% (Retention Time=2.7 min).

v. N-(3-methoxy-6,7,8,9-tetrahydro-5H-benzo[7]annulen-2-yl)-2-methylthiazole-5-carboxamide (33)

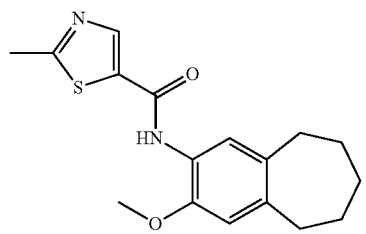 [SMILES: COc1cc2c(cc1NC(=O)c1cnc(C)s1)CCCCC2]

Yield: 17.2 mg (48%). 1H NMR (CDCl3) δ 9.64 (s, 1H), 8.29 (s, 1H), 8.01 (s, 1H), 6.68 (s, 1H), 3.92 (s, 3H), 2.77 (s, 6H), 1.81 (d, J=5.2 Hz, 2H), 1.62 (d, J=12.6 Hz, 5H). ESI-MS: m/z 217 [M+H]+.

vi. N-(3-methoxy-6,7,8,9-tetrahydro-5H-benzo[7]annulen-2-yl)-5-phenylisoxazole-3-carboxamide (36)

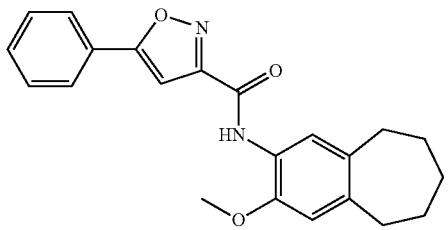 [SMILES: COc1cc2c(cc1NC(=O)c1cc(-c3ccccc3)on1)CCCCC2]

Yield: 71 mg (60%). ¹H NMR (CDCl₃) δ 9.12 (s, 1H), 8.22 (s, 1H), 7.82 (dt, J=5.5, 1.9 Hz, 2H), 7.57-7.40 (m, 2H), 7.03 (d, J=1.9 Hz, 1H), 6.70 (s, 1H), 3.91 (d, J=1.8 Hz, 3H), 2.78 (t, J=9.5 Hz, 4H), 1.82 (d, J=4.5 Hz, 2H). 1.58-1.26 (m, 4H). HR-ESIMS: m/z 363.1630 [M+H]⁺ calcd for $C_{22}H_{23}N_2O_3$, found 363.1689. HPLC Purity: 100% (Retention Time=3.5 min).

vii. 5-(tert-Butyl)-N-(3-methoxy-6,7,8,9-tetrahydro-5H-benzo[7]annulen-2-yl)furan-2-carboxamide (37)

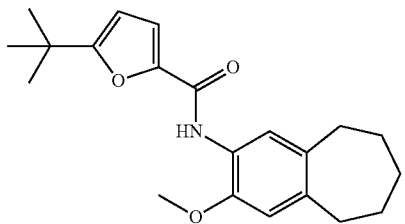 [SMILES: COc1cc2c(cc1NC(=O)c1ccc(C(C)(C)C)o1)CCCCC2]

Yield: 27 mg, 50%. ¹H NMR (CDCl₃) δ 8.59 (s, 1H), 8.22 (s, 1H), 7.07 (dd, J=3.4, 1.4 Hz, 1H), 6.67 (s, 1H), 6.15-6.09 (m, 1H), 3.90 (d, J=1.3 Hz, 3H), 2.80-2.71 (m, 4H), 1.81 (d, J=5.2 Hz, 2H), 1.61 (d, J=19.6 Hz, 4H), 1.39-1.21 (m, 9H). HR-ESIMS: m/z 342.1991 [M+H]⁺ calcd for $C_{21}H_{28}NO_3$, found 342.2063. HPLC Purity: 100% (Retention Time=3 min).

viii. 5-(tert-Butyl)-N-(3-methoxy-6,7,8,9-tetrahydro-5H-benzo[7]annulen-2-yl)thiophene-2-carboxamide (38)

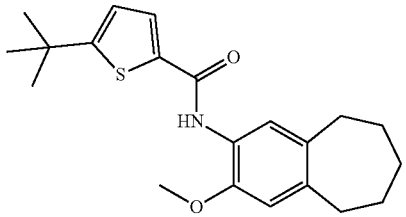 [SMILES: COc1cc2c(cc1NC(=O)c1ccc(C(C)(C)C)s1)CCCCC2]

Yield: 18 mg (32%). ¹H NMR (CDCl₃) δ 8.19 (s, 2H), 7.43 (d, J=3.8 Hz, 1H), 6.84 (d, J=3.8 Hz, 1H), 6.66 (s, 1H), 3.89 (s, 3H), 2.84-2.67 (m, 4H), 1.79 (d, J=6.3 Hz, 2H), 1.63 (d, J=5.4 Hz, 4H), 1.41 (s, 9H). HR-ESIMS: m/z 358.1762 [M+H]⁺ calcd for $C_{21}H_{28}NO_2S$, found 358.1832. HPLC Purity: 100% (Retention Time=3.2 min).

ix. N-(3-Methoxy-6,7,8,9-tetrahydro-5H-benzo[7]annulen-2-yl)-5-methylpyrazine-2-carboxamide (39)

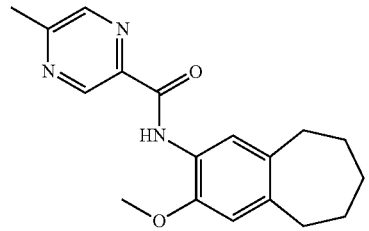 [SMILES: COc1cc2c(cc1NC(=O)c1cnc(C)cn1)CCCCC2]

Yield: 61 mg (72%). ¹H NMR (CDCl₃) δ 9.35 (d, J=1.4 Hz, 1H), 8.46 (d, J=1.3 Hz, 1H), 8.34 (s, 1H), 6.70 (s, 1H), 3.93 (s, 3H), 2.78 (t, J=11.2 Hz, 4H), 2.68 (s, 3H), 1.83-1.80 (m, 2H), 1.74-1.58 (m, 4H). HR-ESIMS: m/z 312.1634 [M+H]⁺ calcd for $C_{18}H_{22}N_3O_2$, found: 312.1718. HPLC Purity: 98% (Retention Time=2.9 min).

x. N-(3-Methoxy-6,7,8,9-tetrahydro-5H-benzo[7]annulen-2-yl)benzo[c][1,2,5]oxadiazole-5-carboxamide (40)

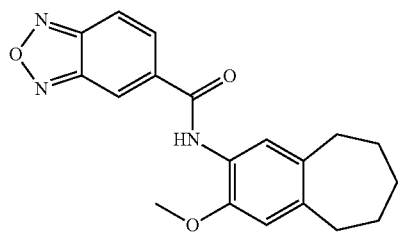 [SMILES: COc1cc2c(cc1NC(=O)c1ccc3nonc3c1)CCCCC2]

Yield: 73 mg (75%). ¹H NMR (CDCl₃) δ 8.31 (t, J=1.2 Hz, 1H), 8.23 (s, 1H), 8.04-7.78 (m, 2H), 6.72 (s, 1H), 3.92 (s, 3H), 2.90-2.60 (m, 4H), 1.83 (d, J=5.0 Hz, 2H), 1.66-1.65 (m, 4H). HR-ESIMS: m/z 338.1426 [M+H]⁺ calcd for $C_{19}H_{20}N_3O_3$, found 338.1498. HPLC Purity: 100% (Retention Time=2.9 min).

xi. 3-(tert-Butyl)-N-(3-methoxy-6,7,8,9-tetrahydro-5H-benzo[7]annulen-2-yl)benzamide (41)

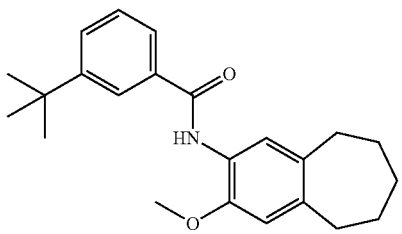 [SMILES: COc1cc2c(cc1NC(=O)c1cccc(C(C)(C)C)c1)CCCCC2]

Yield: 69 (66%). ¹H NMR (CDCl₃) δ 8.44 (s, 1H), 8.31 (s, 1H), 7.98 (t, J=1.9 Hz, 1H), 7.79-7.49 (m, 2H), 7.41 (t, J=7.7 Hz, 1H), 6.69 (s, 1H), 3.89 (s, 3H), 2.78 (ddd, J=11.6, 7.1, 3.8 Hz, 3H), 1.82 (d, J=5.4 Hz, 2H), 1.77-1.49 (m, 4H), 1.37 (s, 9H). HR-ESIMS: m/z 351.2198 [M+H]+ calcd for C₂₃H₂₉NO₂, found 352.2265. HPLC Purity: 100% (Retention Time=18.7 min).

xii. (3r,5r,7r)-N-(3-methoxy-6,7,8,9-tetrahydro-5H-benzo[7]annulen-2-yl)adamantane-1-carboxamide (42)

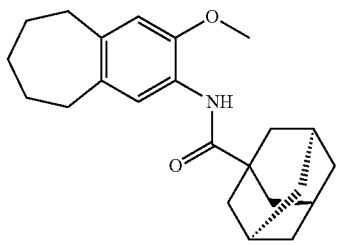 [SMILES: COc1cc2c(cc1NC(=O)C13C[C@H]4C[C@@H](C1)C[C@@H](C3)C4)CCCCC2]

Yield: 73 mg (58%). ¹H NMR (CDCl₃) δ 8.21 (s, 1H), 7.98 (s, 1H), 6.63 (s, 1H), 3.86 (s, 3H), 2.72 (dt, J=7.2, 3.1 Hz, 4H), 2.09 (s, 3H), 1.96 (d, J=2.9 Hz, 5H), 1.77 (dd, J=12.6, 3.9 Hz, 7H), 1.76-1.12 (m, 7H). HR-ESIMS: m/z 354.2355 [M+H]+ calcd for C₂₃H₃₂NO₂, found: 354.2419. HPLC Purity: 100% (Retention Time=19.9 min).

xiii. 2-(tert-Butyl)-N-(3-methoxy-6,7,8,9-tetrahydro-5H-benzo[7]annulen-2-yl)benzamide (43)

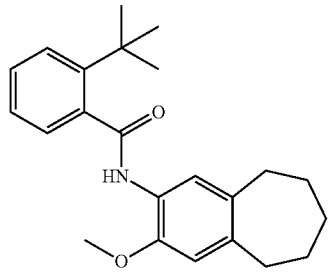 [SMILES: COc1cc2c(cc1NC(=O)c1ccccc1C(C)(C)C)CCCCC2]

Yield: 59 mg (57%). H NMR (CDCl₃) δ 8.27 (s, 1H), 7.89 (s, 1H), 7.52 (dd, J=8.1, 1.1 Hz, 1H), 7.36 (ddd, J=16.1, 7.6, 1.7 Hz, 2H), 7.23 (dd, J=7.5, 1.2 Hz, 1H), 6.66 (s, 1H), 3.80 (s, 3H), 2.86-2.70 (m, 4H), 1.65 (d, J=4.7 Hz, 4H), 1.46 (s, 9H). HR-ESIMS: m/z 352.2198 [M+H]+ calcd for C₂₃H₃₀NO₂, found 352.2266. HPLC Purity: 100% (Retention Time=18.4 min).

xiv. 2-(tert-Butyl)-N-(3-methoxy-6,7,8,9-tetrahydro-5H-benzo[7]annulen-2-yl)thiazole-5-carboxamide (44)

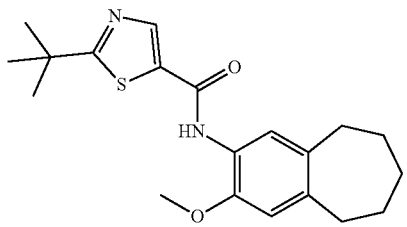 [SMILES: COc1cc2c(cc1NC(=O)c1cnc(C(C)(C)C)s1)CCCCC2]

Yield: 55 mg (77%). ¹H NMR (CDCl₃) δ 8.16 (s, 1H), 8.14 (s, 1H), 8.11 (s, 1H), 6.67 (s, 1H), 3.89 (s, 3H), 2.80-2.71 (m, 6H), 1.81 (s, 2H), 1.47 (s, 10H), 1.49-1.44 (m, 1H). HR-ESIMS: m/z 359.1715 [M+H]+ calcd for C₂₀H₂₇N₂O₂S, found 359.1718. HPLC Purity: 100% (Retention Time=3.1 min).

xv. 1-Ethyl-N-(3-methoxy-6,7,8,9-tetrahydro-5H-benzo[7]annulen-2-yl)-3-(trifluoromethyl)-1H-pyrazole-4-carboxamide (45)

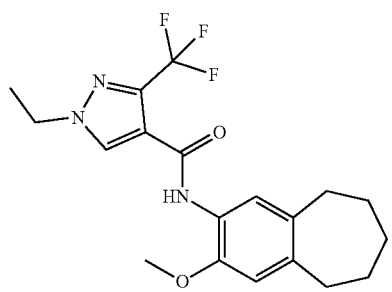 [SMILES: CCn1cc(C(=O)Nc2cc3c(cc2OC)CCCCC3)c(C(F)(F)F)n1]

Yield: 49 mg (61%). ¹H NMR (CDCl₃) δ 8.35 (s, 1H), 8.19 (s, 1H), 8.01 (s, 1H), 6.67 (s, 1H), 4.38-4.06 (m, 2H), 3.99-3.70 (m, 3H), 2.92-2.54 (m, 4H), 1.97-1.17 (m, 9H). HR-ESIMS: m/z 382.1664 [M+H]+ calcd for C₁₉H₂₃F₃N₃O₂, found 382.1726. HPLC Purity: 95% (Retention Time=11.7 min).

xvi. 4-(2-Hydroxypropan-2-yl)-N-(3-methoxy-6,7,8,9-Tetrahydro-5H-benzo[7]annulen-2-yl)benzamide (46)

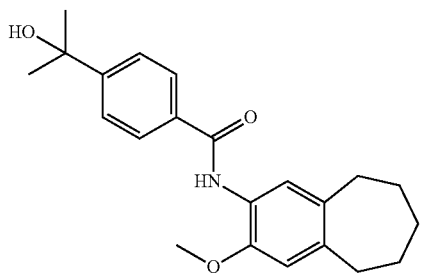 [SMILES: COc1cc2c(cc1NC(=O)c1ccc(C(C)(C)O)cc1)CCCCC2]

Yield: 35 mg (63%). ¹H NMR (CDCl₃) δ 8.43 (s, 1H), 8.28 (s, 1H), 7.84 (d, J=8.6 Hz, 2H), 7.66-7.54 (m, 2H), 6.68 (s, 1H), 3.89 (s, 3H), 2.77 (s, 4H), 1.86-1.75 (m, 2H), 1.61 (s, 10H). HR-ESIMS: m/z 354.1991 [M+H]+ calcd for C₂₂H₂₈NO₃, found 354.2064. HPLC Purity: 100% (Retention Time=10.2 min).

xvii. 4-(1,1,1,3,3,3-Hexafluoro-2-hydroxypropan-2-yl)-N-(3-methoxy-6,7,8,9-tetrahydro-5H-benzo[7]annulen-2-yl)benzamide (48)

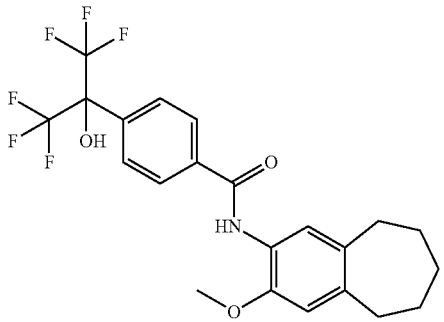 [SMILES: COc1cc2c(cc1NC(=O)c1ccc(C(O)(C(F)(F)F)C(F)(F)F)cc1)CCCCC2]

Yield: 56 mg (58%). $^1$H NMR (CDCl$_3$) δ 8.45 (s, 1H), 8.24 (s, 1H), 7.86 (q, J=8.7 Hz, 4H), 6.69 (s, 1H), 4.54 (s, 1H), 3.89 (s, 3H), 2.97-2.65 (m, 4H), 1.83 (s, 2H), 1.77-1.48 (m, 4H). HR-ESIMS: m/z 462.1426 [M+H]$^+$ calcd for C$_{22}$H$_{22}$F$_6$NO$_3$, found: 462.1482. HPLC Purity: 100% (Retention Time=4.5 min).

xviii. 2-(tert-Butyl)-N-(3-methoxy-6,7,8,9-tetrahydro-5H-benzo[7]annulen-2-yl)pyrimidine-5-carboxamide (49)

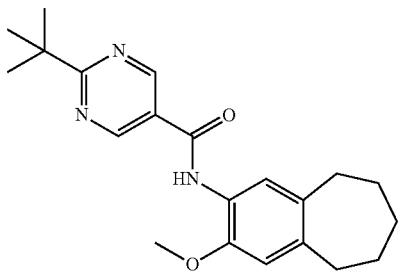 [SMILES: COc1cc2c(cc1NC(=O)c1cnc(C(C)(C)C)nc1)CCCCC2]

Yield: 45 mg (61%). $^1$H NMR (CDCl$_3$) δ 9.15 (s, 2H), 8.37 (s, 1H), 8.23 (s, 1H), 6.69 (s, 1H), 3.89 (s, 3H), 2.99-2.48 (m, 4H), 1.91-1.71 (m, 2H), 1.71-1.53 (m, 4H), 1.56-1.03 (m, 9H). HR-ESIMS: m/z 354.2103 [M+H]$^+$ calcd for C$_{21}$H$_{28}$N$_3$O$_2$, found 354.2182. HPLC Purity: 98% (Retention Time=16.4 min).

xix. 4-(2-Cyanopropan-2-yl)-N-(3-methoxy-6,7,8,9-tetrahydro-5H-benzo[7]annulen-2-yl)benzamide (50)

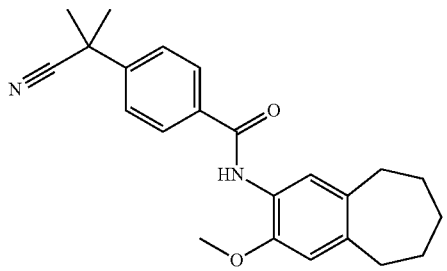 [SMILES: COc1cc2c(cc1NC(=O)c1ccc(C(C)(C)C#N)cc1)CCCCC2]

Yield: 20 mg (54%). $^1$H NMR (CDCl$_3$) δ 8.43 (s, 1H), 8.27 (s, 1H), 7.97-7.84 (m, 2H), 7.67-7.54 (m, 2H), 6.69 (s, 1H), 3.89 (s, 3H), 2.77 (t, J=10.7 Hz, 4H), 1.82 (d, J=5.0 Hz, 2H), 1.70-1.44 (m, 10H). HR-ESIMS: m/z 363.1994 [M+H]$^+$ calcd for C$_{23}$H$_{27}$N$_2$O$_2$, found 363.2070. HPLC Purity: 100% (Retention Time=12.3 min).

xx. N-(3-methoxy-6,7,8,9-tetrahydro-5H-benzo[7]annulen-2-yl)-4-(1-(trifluoromethyl)cyclopropyl)benzamide (51)

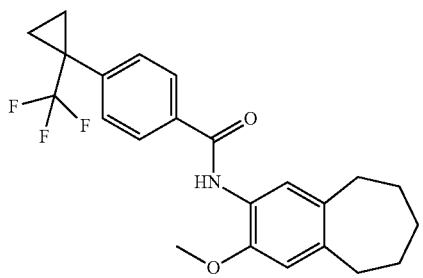 [SMILES: COc1cc2c(cc1NC(=O)c1ccc(C3(C(F)(F)F)CC3)cc1)CCCCC2]

Yield: 23 mg (54%). $^1$H NMR (CDCl$_3$) δ 8.42 (s, 1H), 8.27 (s, 1H), 7.93-7.75 (m, 2H), 7.58 (d, J=8.1 Hz, 2H), 6.68 (s, 1H), 3.89 (s, 3H), 2.77 (t, J=10.9 Hz, 4H), 1.82 (s, 2H), 1.64 (d, J=5.1 Hz, 4H), 1.49-1.34 (m, 2H), 1.14-0.94 (m, 2H). HR-ESIMS: m/z 404.1759[M+H]$^+$ calcd for C$_{23}$H$_{25}$F$_3$NO$_2$, found 404.1834. HPLC Purity: 100% (Retention Time=16.0 min).

xxi. N-(3-methoxy-6,7,8,9-tetrahydro-5H-benzo[7]annulen-2-yl)-4-(1,1,1-trifluoro-2-methylpropan-2-yl)benzamide (52)

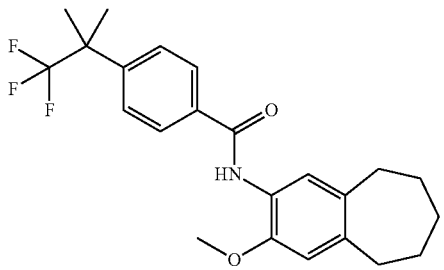 [SMILES: COc1cc2c(cc1NC(=O)c1ccc(C(C)(C)C(F)(F)F)cc1)CCCCC2]

Yield: 35 mg (67%). $^1$H NMR (CDCl$_3$) δ 8.44 (s, 1H), 8.29 (s, 1H), 7.96-7.78 (m, 2H), 7.62 (d, J=8.2 Hz, 2H), 6.68 (s, 1H), 3.89 (s, 3H), 2.85-2.69 (m, 4H), 1.82 (d, J=5.3 Hz, 2H), 1.72-1.51 (m, 9H). HR-ESIMS: m/z 405.1916 [M+H]$^+$ calcd for C$_{23}$H$_{26}$F$_3$NO$_2$, found 406.1988. HPLC Purity: 100% (Retention Time=5.2 min).

xxii. 4-(tert-Butyl)-3-fluoro-N-(3-methoxy-6,7,8,9-tetrahydro-5H-benzo[7]annulen-2-yl)benzamide (53)

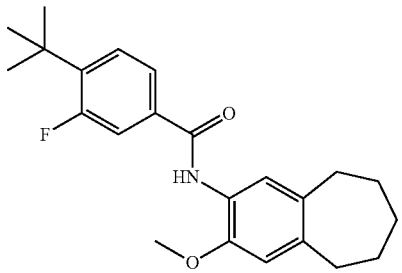 [SMILES: COc1cc2c(cc1NC(=O)c1ccc(C(C)(C)C)c(F)c1)CCCCC2]

Yield: 36 mg (52%). $^1$H NMR (CDCl$_3$) δ 8.39 (s, 1H), 8.26 (s, 1H), 7.63-7.46 (m, 2H), 7.41 (t, J=8.1 Hz, 1H), 6.68 (s, 1H), 3.89 (s, 3H), 2.77 (t, J=10.7 Hz, 4H), 1.82 (s, 2H), 1.71-1.58 (m, 4H), 1.41 (d, J=1.0 Hz, 9H). HR-ESIMS: m/z 370.2104 [M+H]$^+$ calcd for C$_{23}$H$_{29}$FNO$_2$, found 370.2182. HPLC Purity: 100% (Retention Time=5.5 min).

xxiii. 4-Ethyl-N-(3-methoxy-6,7,8,9-tetrahydro-5H-benzo[7]annulen-2-yl)benzamide (56)

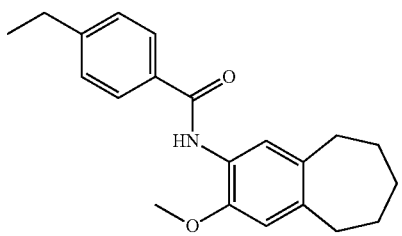 [SMILES: CCc1ccc(C(=O)Nc2cc3c(cc2OC)CCCCC3)cc1]

Yield: 46 mg (85%). $^1$H NMR (CDCl$_3$) δ 8.43 (s, 1H), 8.29 (s, 1H), 7.91-7.72 (m, 2H), 7.40-7.27 (m, 2H), 6.68 (s, 1H), 2.87-2.65 (m, 6H), 1.87-1.73 (m, 2H), 1.74-1.55 (m, 4H), 1.27 (t, J=7.6 Hz, 3H). HR-ESIMS: m/z 324.1885 [M+H]$^+$ calcd for C$_{21}$H$_{26}$NO$_2$, found 324.1953. HPLC Purity: 93% (Retention Time=14.8 min).

xxiv. N-(3-methoxy-6,7,8,9-tetrahydro-5H-benzo[7]annulen-2-yl)-4-propylbenzamide (57)

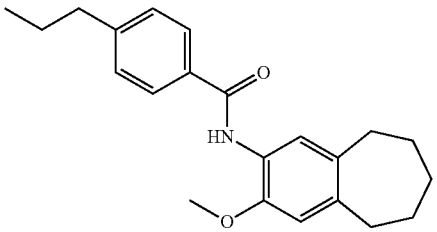 [SMILES: CCCc1ccc(C(=O)Nc2cc3c(cc2OC)CCCCC3)cc1]

Yield: 30 mg (78%). $^1$H NMR (CDCl$_3$) δ 8.42 (s, 1H), 8.29 (s, 1H), 7.87-7.70 (m, 2H), 7.35-7.25 (m, 2H), 6.68 (s, 1H), 2.99-2.27 (m, 6H), 1.81 (q, J=5.9 Hz, 2H), 1.77-1.42 (m, 6H), 0.96 (t, J=7.3 Hz, 3H). HR-ESIMS: m/z 338.2042 [M+H]$^+$ calcd for C$_{22}$H$_{28}$NO$_2$, found 338.2113. HPLC Purity: 93% (Retention Time=17.6 min).

xxv. 4-(1-Hydroxycyclobutyl)-N-(3-methoxy-6,7,8,9-tetrahydro-5H-benzo[7]annulen-2-yl)benzamide (66)

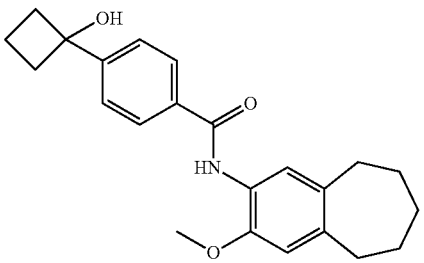 [SMILES: COc1cc2c(cc1NC(=O)c1ccc(C3(O)CCC3)cc1)CCCCC2]

Yield: 34 mg (71%). $^1$H NMR (CDCl$_3$) δ 8.44 (s, 1H), 8.29 (s, 1H), 8.04-7.79 (m, 2H), 7.75-7.45 (m, 2H), 6.68 (s, 1H), 3.89 (s, 3H), 2.88-2.69 (m, 4H), 2.65-2.46 (m, 2H), 2.48-2.34 (m, 2H), 2.16-1.94 (m, 1H), 1.96-1.70 (m, 3H), 1.70-1.51 (m, 4H). HR-ESIMS: m/z 366.1991 [M+H]$^+$ calcd for C$_{23}$H$_{28}$NO$_3$, found 366.2000. HPLC Purity: 94% (Retention Time=14.5 min).

xxvi. N-(3-Methoxy-6,7,8,9-tetrahydro-5H-benzo[7]annulen-2-yl)-4-(pyridin-2-yl)benzamide (67)

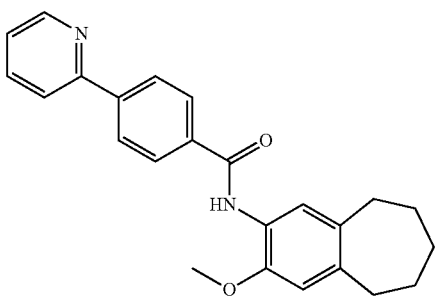 [SMILES: COc1cc2c(cc1NC(=O)c1ccc(-c3ccccn3)cc1)CCCCC2]

Yield: 38 mg (65%). $^1$H NMR (CDCl$_3$) δ 8.73 (dt, J=4.8, 1.3 Hz, 1H), 8.50 (s, 1H), 8.31 (s, 1H), 8.21-8.02 (m, 2H), 8.04-7.81 (m, 2H), 7.87-7.64 (m, 2H), 6.69 (s, 1H), 3.91 (s, 3H), 3.20-2.40 (m, 4H), 1.82 (d, J=5.3 Hz, 2H), 1.75-1.37 (m, 4H). HR-ESIMS: m/z 373.1838 [M+H]$^+$ calcd for C$_{24}$H$_{25}$N$_2$O$_2$, found 373.2000. HPLC Purity: 98% (Retention Time=15.2 min).

xxvii. 3-(4-(tert-Butyl)phenyl)-N-(3-methoxy-6,7,8,9-tetrahydro-5H-benzo[7]annulen-2-yl)propanamide (68)

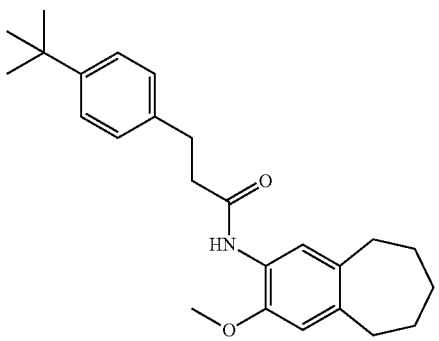 [SMILES: COc1cc2c(cc1NC(=O)CCc1ccc(C(C)(C)C)cc1)CCCCC2]

Yield: 68 mg (86%). $^1$H NMR (CDCl$_3$) δ 8.15 (s, 1H), 7.61 (s, 1H), 7.32 (d, J=8.3 Hz, 2H), 7.19 (d, J=8.2 Hz, 2H), 6.62 (s, 1H), 3.81 (s, 3H), 3.10-2.95 (m, 2H), 2.81-2.63 (m, 6H), 1.81 (p, J=5.9 Hz, 2H), 1.61 (s, 4H), 1.31 (s, 9H). HR-ESIMS: m/z 380.2511 [M+H]$^+$ calcd for C$_{25}$H$_{34}$NO$_2$, found 380.3000. HPLC Purity: 98% (Retention Time=8.9 min).

xxviii. N-(3-methoxy-6,7,8,9-tetrahydro-5H-benzo[7]annulen-2-yl)-3-methyl-1H-pyrazole-4-carboxamide (69)

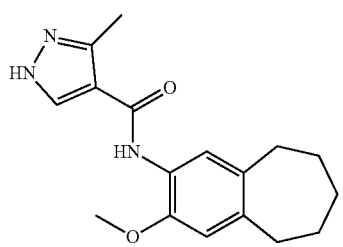 [SMILES: COc1cc2c(cc1NC(=O)c1c[nH]nc1C)CCCCC2]

Yield: 26 mg (33%). $^1$H NMR (CDCl$_3$) δ 8.20 (s, 1H), 8.05 (s, 1H), 7.89 (s, 1H), 6.67 (s, 1H), 3.89 (s, 3H), 2.95-2.65 (m, 4H), 2.63 (s, 3H), 1.91-1.72 (m, 2H), 1.65-1.62 (m, 4H). HR-ESIMS: m/z 300.1634 [M+H]$^+$ calcd for C$_{17}$H$_{22}$N$_3$O$_2$, found 380.3000. HPLC Purity: 100% (Retention Time=2.4 min).

xxix. 3,5-Di-tert-butyl-4-hydroxy-N-(3-methoxy-6,7,8,9-tetrahydro-5H-benzo[7]annulen-2-yl)benzamide (70)

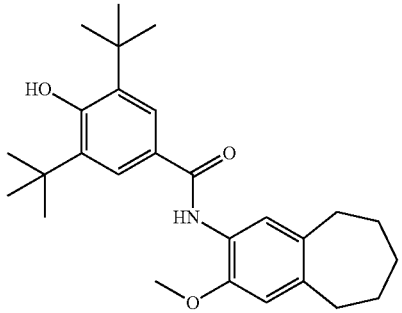 [SMILES: COc1cc2c(cc1NC(=O)c1cc(C(C)(C)C)c(O)c(C(C)(C)C)c1)CCCCC2]

Yield: 84 mg (63%). $^1$H NMR (CDCl$_3$) δ 8.27 (s, 1H), 7.72 (s, 2H), 6.67 (s, 1H), 5.58 (s, 1H), 3.88 (s, 3H), 2.76 (t, J=10.7 Hz, 4H), 1.85-1.79 (m, 2H), 1.71-1.59 (m, 4H), 1.48 (s, 18H). HR-ESIMS: m/z 423.2773 [M+H]$^+$ calcd for C$_{27}$H$_{37}$NO$_3$, found 423.2842. HPLC Purity: 100% (Retention Time=3.3 min).

xxx. 4-Chloro-N-(3-methoxy-6,7,8,9-tetrahydro-5H-benzo[7]annulen-2-yl)benzamide (71)

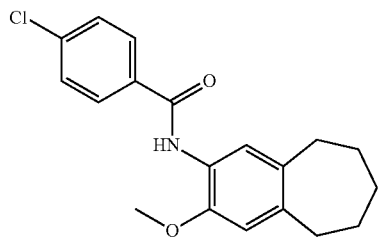 [SMILES: COc1cc2c(cc1NC(=O)c1ccc(Cl)cc1)CCCCC2]

Yield: 79 mg (83%). $^1$H NMR (CDCl$_3$) δ 8.37 (s, 1H), 8.25 (s, 1H), 7.93-7.66 (m, 2H), 7.57-7.32 (m, 2H), 6.68 (s, 1H), 3.89 (s, 3H), 2.77 (t, J=10.6 Hz, 4H), 1.82-1.79 (m, 2H), 1.74-1.55 (m, 4H). HR-ESIMS: m/z 330.1183 [M+H]$^+$ calcd for C$_{19}$H$_{21}$ClNO$_2$, found 330.1255. HPLC Purity: 100% (Retention Time=3.1 min).

xxxi. N-(3-Methoxy-6,7,8,9-tetrahydro-5H-benzo[7]annulen-2-yl)-4-(trifluoromethoxy)benzamide (72)

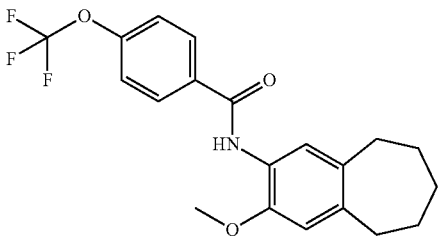 [SMILES: COc1cc2c(cc1NC(=O)c1ccc(OC(F)(F)F)cc1)CCCCC2]

Yield: 101 mg (73%). $^1$H NMR (CDCl$_3$) δ 8.25 (s, 1H), 7.96-7.88 (m, 2H), 7.32 (d, J=8.0 Hz, 2H), 6.69 (s, 1H), 3.89 (s, 3H), 2.77 (t, J=10.6 Hz, 4H), 1.82 (d, J=5.3 Hz, 2H), 1.68-1.60 (m, 4H). HR-ESIMS: m/z 380.1395 [M+H]+ calcd for $C_{20}H_{21}F_3NO_3$, found 380.1466. HPLC Purity: 100% (Retention Time=3.1 min).

xxxii. N-(3-Methoxy-6,7,8,9-tetrahydro-5H-benzo[7]annulen-2-yl)-2-(thiophen-2-yl)acetamide (73)

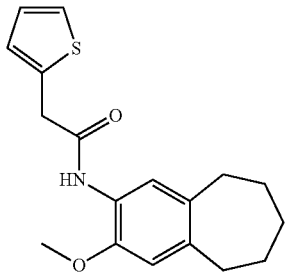 [SMILES: COc1cc2c(cc1NC(=O)Cc1cccs1)CCCCC2]

Yield: 61 mg (74%). $^1$H NMR (CDCl$_3$) δ 8.09 (s, 1H), 7.86 (s, 1H), 7.27-7.23 (m, 1H), 7.02 (d, J=3.7 Hz, 2H), 6.58 (s, 1H), 3.93 (s, 2H), 3.73 (s, 3H), 2.82-2.64 (m, 4H), 1.87-1.70 (m, 2H), 1.65-1.53 (m, 4H). HR-ESIMS: m/z 316.1293 [M+H]+ calcd for $C_{18}H_{22}NO_2S$, found 316.1366. HPLC Purity: 100% (Retention Time=2.8 min).

xxxiii. N-(3-methoxy-6,7,8,9-tetrahydro-5H-benzo[7]annulen-2-yl)-4-(trifluoromethyl)benzamide (74)

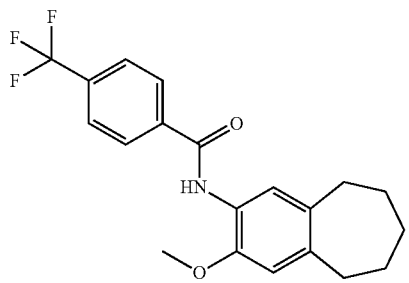 [SMILES: COc1cc2c(cc1NC(=O)c1ccc(C(F)(F)F)cc1)CCCCC2]

Yield: 86 mg (83%). $^1$H NMR (CDCl$_3$) δ 8.43 (s, 1H), 8.26 (s, 1H), 7.98 (d, J=8.1 Hz, 2H), 7.75 (d, J=8.2 Hz, 2H), 6.69 (s, 1H), 3.89 (s, 3H), 2.78 (t, J=10.7 Hz, 4H), 1.83 (p, J=6.1 Hz, 2H), 1.64-1.60 (m, 4H). HR-ESIMS: m/z 364.1446 [M+H]+ calcd for $C_{20}H_{21}F_3NO_2$, found 364.1518. HPLC Purity: 100% (Retention Time=3.0 min).

xxxiv. 4-Chloro-2-iodo-N-(3-methoxy-6,7,8,9-tetrahydro-5H-benzo[7]annulen-2-yl)benzamide (75)

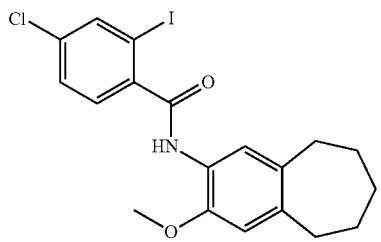 [SMILES: COc1cc2c(cc1NC(=O)c1ccc(Cl)cc1I)CCCCC2]

Yield: 87 mg (73%). $^1$H NMR (CDCl$_3$) δ 8.25 (s, 1H), 8.05-7.82 (m, 2H), 7.50-7.32 (m, 2H), 6.68 (s, 1H), 3.84 (s, 3H), 2.87-2.63 (m, 4H), 1.83-1.80 (m, 2H), 1.65 (d, J=5.0 Hz, 4H). HR-ESIMS: m/z 456.0149 [M+H]+ calcd for $C_{19}H_{20}ClINO_2$, found 456.0218. HPLC Purity: 100% (Retention Time=3.2 min).

xxxv. 4-(Dimethylamino)-N-(3-methoxy-6,7,8,9-tetrahydro-5H-benzo[7]annulen-2-yl)benzamide (76)

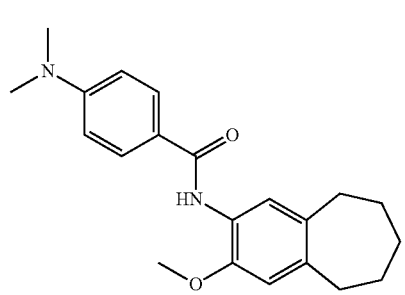 [SMILES: COc1cc2c(cc1NC(=O)c1ccc(N(C)C)cc1)CCCCC2]

Yield: 27 mg (33%). $^1$H NMR (CDCl$_3$) δ 8.35 (s, 1H), 8.30 (s, 1H), 7.89-7.68 (m, 2H), 6.79-6.63 (m, 3H), 3.89 (d, J=1.3 Hz, 3H), 3.04 (d, J=1.3 Hz, 6H), 2.76 (t, J=11.3 Hz, 4H), 1.82-1.80 (m, 2H), 1.64 (d, J=5.0 Hz, 4H). HR-ESIMS: m/z 339.1994 [M+H]+ calcd for $C_{21}H_{27}N_2O_2$, found: 339.2057. HPLC Purity: 100% (Retention Time=3.3 min).

xxxvi. 3,5-Difluoro-N-(3-methoxy-6,7,8,9-tetrahydro-5H-benzo[7]annulen-2-yl)picolinamide (77)

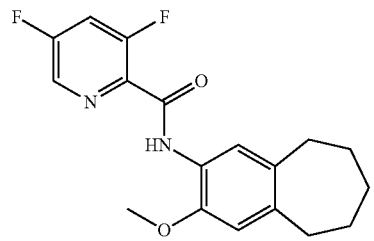 [SMILES: COc1cc2c(cc1NC(=O)c1ncc(F)cc1F)CCCCC2]

Yield: 61 mg (58%). $^1$H NMR (CDCl$_3$) δ 8.54-8.14 (m, 2H), 7.35 (ddd, J=10.3, 8.1, 2.3 Hz, 1H), 6.69 (s, 1H), 3.92 (s, 3H), 2.95-2.50 (m, 4H), 1.82-1.79 (m, 2H), 1.64-1.54 (m, 4H). HR-ESIMS: m/z 333.1336 [M+H]+ calcd for $C_{18}H_{19}F_2N_2O_2$, found 333.1398. HPLC Purity: 100% (Retention Time=3.3 min).

xxxvii. 4-Fluoro-N-(3-methoxy-6,7,8,9-tetrahydro-5H-benzo[7]annulen-2-yl)benzamide (78)

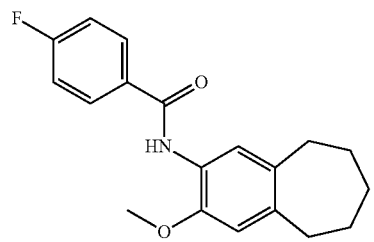 [SMILES: COc1cc2c(cc1NC(=O)c1ccc(F)cc1)CCCCC2]

Yield: 88 mg (83%). $^1$H NMR (CDCl$_3$) δ 8.25 (s, 1H), 7.95-7.77 (m, 2H), 7.23-7.05 (m, 2H), 6.68 (s, 1H), 3.89 (s, 3H), 2.77 (t, J=10.8 Hz, 4H), 1.93-1.74 (m, 2H), 1.74-1.58 (m, 4H). HR-ESIMS: m/z 314.1478 [M+H]$^+$ calcd for C$_{19}$H$_{21}$FNO$_2$, found 314.1545. HPLC Purity: 100% (Retention Time=3.3 min).

xxxviii. N-(3-methoxy-6,7,8,9-tetrahydro-5H-benzo[7]annulen-2-yl)-3-methylbenzofuran-2-carboxamide (79)

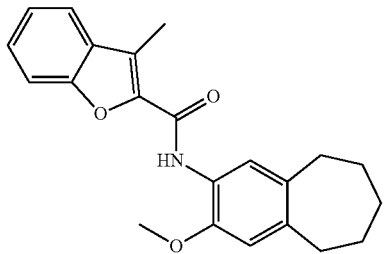 [SMILES: COc1cc2c(cc1NC(=O)c1oc3ccccc3c1C)CCCCC2]

Yield: 68 mg (85%). $^1$H NMR (CDCl$_3$) δ 8.91 (s, 1H), 8.30 (s, 1H), 7.68-7.59 (m, 1H), 7.54 (d, J=8.3 Hz, 1H), 7.48-7.40 (m, 1H), 7.36-7.27 (m, 1H), 6.70 (s, 1H), 3.95 (s, 3H), 2.88-2.72 (m, 4H), 2.69 (s, 3H), 1.81-1.82 (m, 2H), 1.64 (d, J=3.4 Hz, 4H). HR-ESIMS: m/z 350.1678 [M+H]$^+$ calcd for C$_{22}$H$_{24}$NO$_3$, found 350.1750. HPLC Purity: 100% (Retention Time=3.3 min).

xxxix. 4-Cyclopropyl-N-(3-methoxy-6,7,8,9-tetrahydro-5H-benzo[7]annulen-2-yl)benzamide (80)

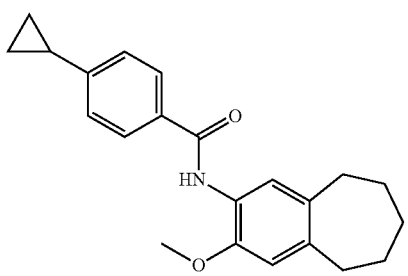 [SMILES: COc1cc2c(cc1NC(=O)c1ccc(C3CC3)cc1)CCCCC2]

Yield: 37 mg (46%). $^1$H NMR (CDCl$_3$) δ 8.40 (s, 1H), 8.28 (s, 1H), 7.85-7.68 (m, 2H), 7.22-7.03 (m, 2H), 6.67 (s, 1H), 3.88 (s, 3H), 2.77 (t, J=11.3 Hz, 4H), 1.95 (ddd, J=13.5, 8.4, 5.0 Hz, 1H), 1.79-1.66 (m, 2H), 1.70-1.58 (m, 4H), 1.12-1.00 (m, 2H), 0.77 (dt, J=6.7, 4.8 Hz, 2H). HR-ESIMS: m/z 336.1885 [M+H]$^+$ calcd for C$_{22}$H$_{26}$NO$_2$; found: 336.1959. HPLC Purity: 100% (Retention Time=3.3 min).

xl. N-(3-methoxy-6,7,8,9-tetrahydro-5H-benzo[7]annulen-2-yl)-5-methylpyrazine-2-carboxamide (81)

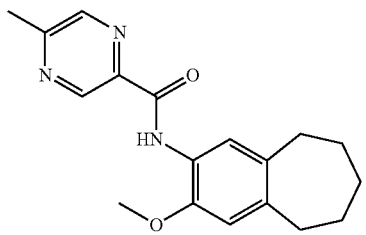 [SMILES: COc1cc2c(cc1NC(=O)c1cnc(C)cn1)CCCCC2]

Yield: 61 mg (72%). $^1$H NMR (CDCl$_3$) δ 9.35 (d, J=1.4 Hz, 1H), 8.46 (d, J=1.3 Hz, 1H), 8.34 (s, 1H), 6.70 (s, 1H), 3.93 (s, 3H), 2.78 (t, J=11.2 Hz, 4H), 2.68 (s, 3H), 1.83-1.80 (m, 2H), 1.74-1.58 (m, 4H). HR-ESIMS: m/z 312.1634 [M+H]$^+$ calcd for C$_{18}$H$_{22}$N$_3$O$_2$, found: 312.1718. HPLC Purity: 100% (Retention Time=2.8 min).

xli. N-(3-methoxy-6,7,8,9-tetrahydro-5H-benzo[7]annulen-2-yl)tetrahydro-2H-pyran-4-carboxamide (82)

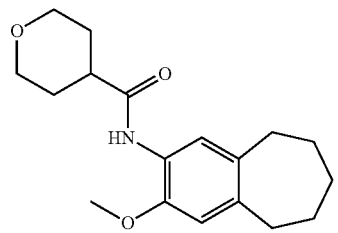 [SMILES: COc1cc2c(cc1NC(=O)C1CCOCC1)CCCCC2]

Yield: 51 mg (70%). $^1$H NMR (CDCl$_3$) δ 8.15 (s, 1H), 7.72 (s, 1H), 6.64 (s, 1H), 4.06 (dt, J=11.6, 3.2 Hz, 2H), 3.85 (s, 3H), 3.47 (td, J=11.4, 2.8 Hz, 2H), 2.73 (dt, J=6.9, 3.0 Hz, 4H), 2.58-2.45 (m, 1H), 1.99-1.75 (m, 6H), 1.64-1.56 (m, 4H). HR-ESIMS: m/z 304.1834 [M+H]$^+$ calcd for C$_{18}$H$_{26}$NO$_3$, found: 304.1910. HPLC Purity: 100% (Retention Time=2.6 min).

xlii. N-(3-methoxy-6,7,8,9-tetrahydro-5H-benzo[7]annulen-2-yl)benzamide (83)

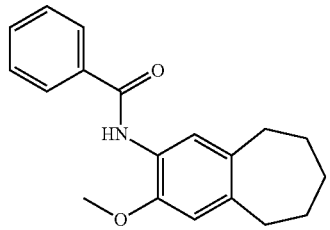 [SMILES: COc1cc2c(cc1NC(=O)c1ccccc1)CCCCC2]

Yield: 69 mg (74%). $^1$H NMR (CDCl$_3$) δ 8.44 (s, 1H), 8.29 (s, 1H), 7.96-7.77 (m, 2H), 7.62-7.39 (m, 3H), 6.68 (s, 1H), 3.89 (d, J=1.0 Hz, 3H), 2.77 (t, J=11.6 Hz, 4H), 1.82 (d, J=5.1 Hz, 2H), 1.73-1.52 (m, 4H). HR-ESIMS: m/z 296.1572 [M+H]$^+$ calcd for C$_{19}$H$_{22}$NO$_2$, found 296.1646. HPLC Purity: 100% (Retention Time=3.1 min).

xliii. 4-(tert-Butyl)-N-(3-ethoxy-6,7,8,9-tetrahydro-5H-benzo[7]annulen-2-yl)benzamide (84)

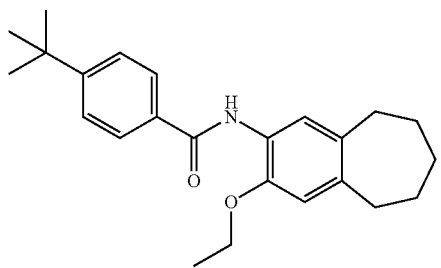 [SMILES: CCOc1cc2c(cc1NC(=O)c1ccc(C(C)(C)C)cc1)CCCCC2]

Yield: 8 mg (52%). $^1$H NMR (CDCl$_3$) δ 8.31 (s, 1H), 8.09-7.71 (m, 2H), 7.51 (d, J=8.6 Hz, 2H), 6.67 (s, 1H), 4.12 (q, J=7.0 Hz, 2H), 3.00-2.47 (m, 4H), 1.82-1.80 (m, 2H), 1.64-1.60 (m, 4H), 1.46 (t, J=7.0 Hz, 3H), 1.36 (s, 9H). HR-ESIMS: m/z 366.2355 [M+H]$^+$ calcd for C$_{24}$H$_{32}$NO$_2$, found 366.2430. HPLC Purity: 100% (Retention Time=3.4 min).

xliv. 4-(tert-Butyl)-N-(3-(pyridin-2-ylmethoxy)-6,7,8,9-tetrahydro-5H-benzo[7]annulen-2-yl)benzamide (85)

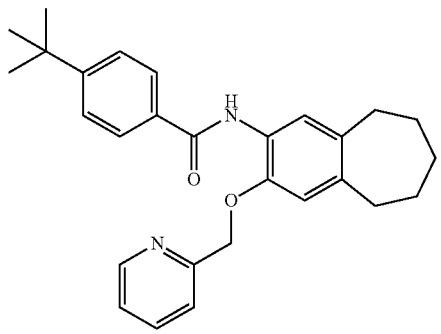 [SMILES: CC(C)(C)c1ccc(C(=O)Nc2cc3c(cc2OCc2ccccn2)CCCCC3)cc1]

Yield: 6 mg (72%). $^1$H NMR (CDCl$_3$) δ 8.99 (s, 1H), 8.54 (d, J=4.5 Hz, 1H), 8.31 (s, 1H), 7.88 (d, J=8.3 Hz, 2H), 7.69 (d, J=7.7 Hz, 1H), 7.49 (d, J=8.3 Hz, 2H), 7.37 (d, J=7.6 Hz, 1H), 6.76 (s, 1H), 5.27 (s, 2H), 2.74 (dd, J=31.4, 10.3 Hz, 4H), 1.81 (s, 2H), 1.76-1.50 (m, 4H), 1.36 (s, 9H). ESI MS: 429 [M+H]$^+$.

xlv. 4-(tert-Butyl)-N-(3-propoxy-6,7,8,9-tetrahydro-5H-benzo[7]annulen-2-yl)benzamide (86)

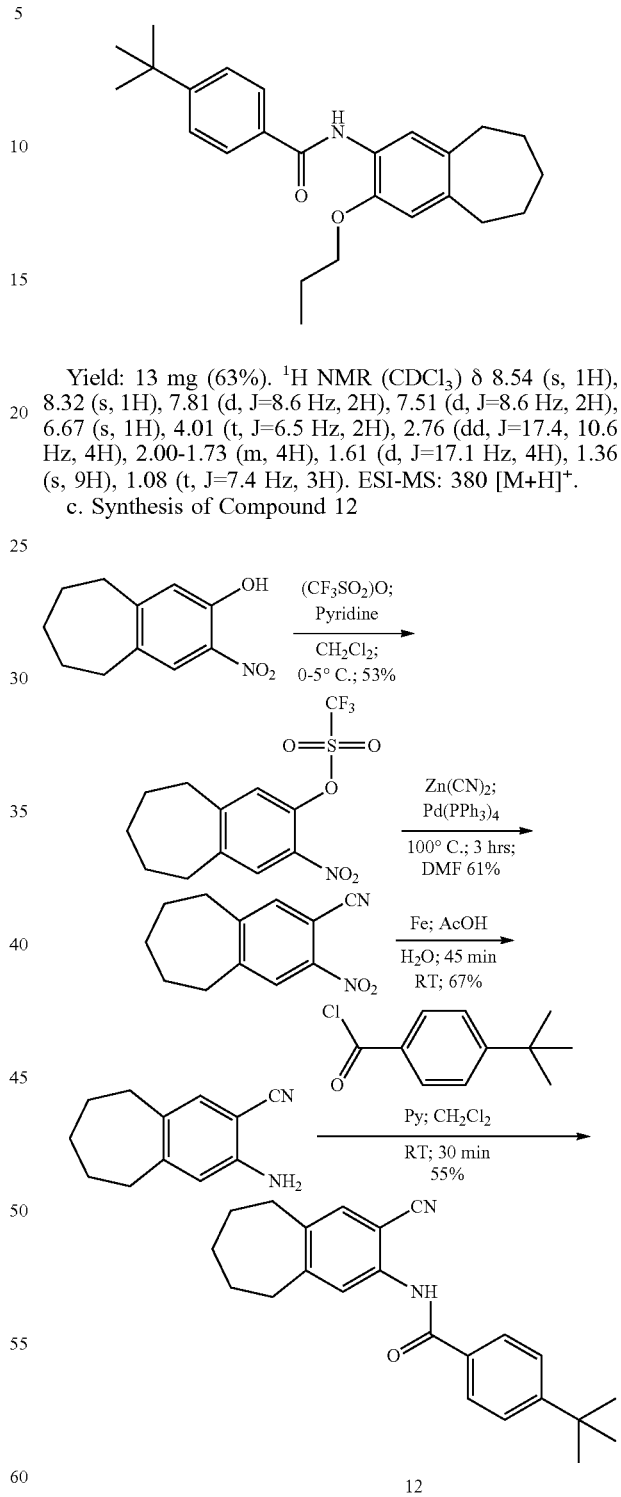

Yield: 13 mg (63%). $^1$H NMR (CDCl$_3$) δ 8.54 (s, 1H), 8.32 (s, 1H), 7.81 (d, J=8.6 Hz, 2H), 7.51 (d, J=8.6 Hz, 2H), 6.67 (s, 1H), 4.01 (t, J=6.5 Hz, 2H), 2.76 (dd, J=17.4, 10.6 Hz, 4H), 2.00-1.73 (m, 4H), 1.61 (d, J=17.1 Hz, 4H), 1.36 (s, 9H), 1.08 (t, J=7.4 Hz, 3H). ESI-MS: 380 [M+H]$^+$.

c. Synthesis of Compound 12

Step-1: 3-Nitro-6,7,8,9-tetrahydro-5H-benzo[7]annulen-2-ol (97 mg, 0.47 mmol) was dissolved in 3 mL of anhydrous dichloromethane. To this, pyridine (76 μL, 0.94 mmol) was added under nitrogen environment and cooled in ice-bath. Trifluoromethanesulfonic anhydride (79 μL, 0.47 mmol) was added drop wise to the cold mixture and stirred for 1.5 h at the same temperature. The reaction was quenched with 1M HCl and extracted with dichloromethane. The organic layer was washed with aq. NaHCO$_3$, followed by brine and purified on Silica gel preparative plate. Yield: 84 mg (53%). $^1$H NMR (CDCl$_3$) δ 7.91 (s, 1H), 7.14 (s, 1H), 2.89 (dt, J=7.4, 3.8 Hz, 4H), 1.89 (p, J=6.0 Hz, 2H), 1.78-1.63 (m, 4H). ESI-MS: m/z 340 [M+H]$^+$.

Step-2: 3-Nitro-6,7,8,9-tetrahydro-5H-benzo[7]annulen-2-yl trifluoromethanesulfonate (146 mg, 0.43 mmol), dicyanozinc (30 mg, 0.26 mmol) and tetrakispalladium(0) (50 mg, 0.04 mmol) were suspended in anhydrous DMF and heated for 3 h at 100° C. After completion of reaction, it was diluted with water and extracted with EtOAc. The organic layer was washed with ice-cold water, followed by brine and dried over anhydrous Na$_2$SO$_4$. It was concentrated and crude product was purified on Silica gel preparative plate. Yield: 57 mg (61%). $^1$H NMR (CDCl$_3$) δ 8.06 (s, 1H), 7.60 (s, 1H), 2.94 (t, J=11.4 Hz, 4H), 1.91 (p, J=5.9 Hz, 2H), 1.71 (d, J=5.4 Hz, 4H). ESI-MS: m/z 217 [M+H]$^+$.

Step-3: 3-Nitro-6,7,8,9-tetrahydro-5H-benzo[7]annulene-2-carbonitrile (55 mg, 0.25 mmol) was dissolved in AcOH—H$_2$O (3:0.3, mL) and Fe (28 mg, 0.51 mmol) was added. The reaction mixture was stirred for 30 min at room temperature. After completion of reaction, it was filtered through celite pad and washed with EtOAc. The filtrate was diluted with water, and extracted with EtOAc. The organic layer washed with aq. NaHCO$_3$, followed by brine, dried over anhydrous Na$_2$SO$_4$ and concentrated. The crude product was purified by column chromatography. Yield: 32 mg (67%). $^1$H NMR (CDCl$_3$) δ 7.09 (s, 1H), 6.51 (s, 1H), 4.21 (s, 2H), 2.68 (ddd, J=13.5, 8.9, 5.5 Hz, 4H), 1.79 (p, J=5.9 Hz, 2H), 1.60 (d, J=13.7 Hz, 2H). ESI-MS: m/z 187 [M+H]$^+$.

Step-4: 4-(tert-Butyl)-N-(3-cyano-6,7,8,9-tetrahydro-5H-benzo[7]annulen-2-yl)benzamide (12). To a anhydrous dichloromethane (10 mL) solution of 3-amino-6,7,8,9-tetrahydro-5H-benzo[7]annulene-2-carbonitrile (25 mg, 0.13 mmol) was added pyridine (0.02 mL, 0.27 mmol) followed by 4-(tert-butyl)benzoyl chloride (29 mg, 0.15 mmol). The reaction mixture was stirred for 30 min at room temperature and after completion of reaction it was diluted with DCM. It was washed 2M HCl, followed by NaHCO$_3$ and brine. The organic layer was dried over anhydrous Na$_2$SO$_4$ and concentrated. The crude product was purified on Silica gel preparative plate. Yield: 26 mg (55%). $^1$H NMR (CDCl$_3$) δ 8.37 (s, 1H), 8.28 (s, 1H), 7.91-7.79 (m, 2H), 7.60-7.42 (m, 2H), 2.92-2.67 (m, 4H), 1.85 (p, J=5.9 Hz, 2H), 1.68 (d, J=11.4 Hz, 4H), 1.36 (s, 9H). HR-ESIMS: m/z 347.2045 [M+H]$^+$ calcd for C$_{23}$H$_{26}$N$_2$O, found 347.2035. HPLC Purity: 100% (Retention Time=3.1 min).

d. Synthesis of Compounds 13 and 87

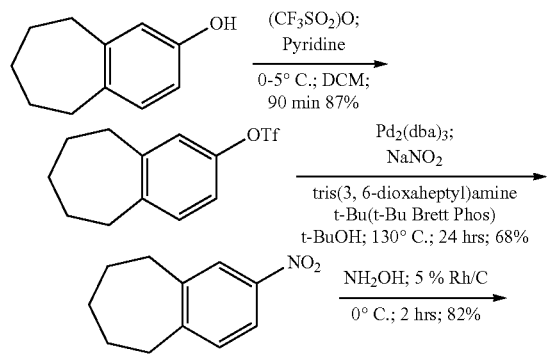

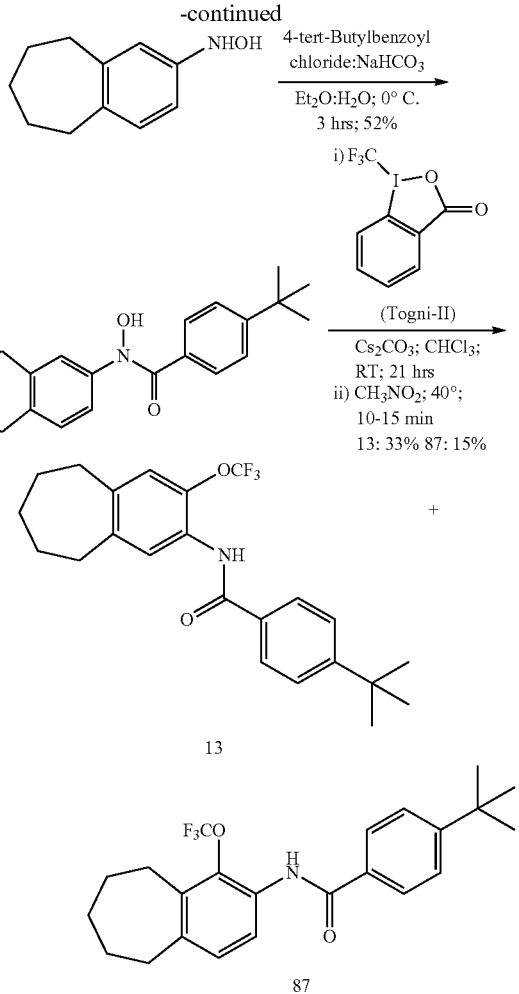

Step-1: To a anhydrous dichloromethane (10 mL) solution of 6,7,8,9-tetrahydro-5H-benzo[7]annulen-2-ol (93 mg, 0.57 mmol) pyridine (93 μL, 1.15 mmol) was added followed by trifluoromethanesulfonic anhydride (107 μL, 0.63 mmol) drop wise in an ice-bath. The reaction mixture was stirred for 1.5 h at the same temperature. After completion of reaction, it was diluted with 1M HCl and extracted with DCM. The organic layer was washed with aq. NaHCO$_3$ followed by brine and dried over anhydrous Na$_2$SO$_4$ and concentrated. The crude product was purified on Silica gel preparative plate. Yield: 147 mg (87%). $^1$H NMR (CDCl$_3$) δ 7.13 (d, J=8.2 Hz, 1H), 7.04-6.88 (m, 2H), 2.88-2.69 (m, 4H), 1.85 (p, J=5.9 Hz, 2H), 1.62 (s, 4H). ESI-MS: m/z 295 [M+H]$^+$.

Step-2: 6,7,8,9-Tetrahydro-5H-benzo[7]annulen-2-yl trifluoromethanesulfonate (130 mg, 0.44 mmol) was dissolved in 3 mL anhydrous t-BuOH at room temperature. To this solution, sodium nitrite (61 mg, 0.88 mmol), Pd$_2$(dba)$_3$ (4 mg, 4.42 μmol), tris(2-(2-methoxyethoxy)ethyl)amine (7 mg, 0.02 mmol) and t-BuBrett Phos (2 mg, 0.004 mmol) were added. The reaction mixture was heated at 130° C. for 24 h and after completion of reaction, it was filtered. The filtrate was concentrated and residue was purified by column chromatography. Yield: 57 mg (68%). $^1$H NMR (CDCl$_3$) δ 7.99-7.90 (m, 2H), 7.23 (d, J=8.1 Hz, 1H), 2.92-2.84 (m, 5H), 1.71-1.64 (m, 5H). ESI-MS: m/z 192 [M+H]$^+$.

Step-3: 2-Nitro-6,7,8,9-tetrahydro-5H-benzo[7]annulene (54 mg, 0.28 mmol) was dissolved in anhydrous THF and cooled to 0° C. To this solution, 5% Rh/C (3 mg, 0.03 mmol) was added followed by hydroxylamine (9 mg, 0.28 mmol). The reaction mixture was stirred for 2 h at 0° C. Reaction solvent was removed and directly loaded on Silica gel preparative plate for purification. Yield: 41 mg (82%). ¹H NMR (CDCl₃) δ 7.01 (d, J=7.9 Hz, 1H), 6.77 (d, J=2.3 Hz, 1H), 6.73 (dd, J=7.9, 2.4 Hz, 1H), 2.86 (dd, J=10.6, 5.2 Hz, 4H), 1.81 (d, J=5.7 Hz, 4H), 1.67 (d, J=6.2 Hz, 2H). ESI-MS: m/z 178 [M+H]⁺.

Step-4: N-(6,7,8,9-tetrahydro-5H-benzo[7]annulen-2-yl) hydroxylamine (38 mg, 0.21 mmol) was dissolved in 1:1 Et₂O:H₂O and cooled to 0° C. To this solution was added sodium bicarbonate (36 mg, 0.43 mmol) followed by the drop wise addition of 4-(tert-butyl)benzoyl chloride (42 mg, 0.21 mmol) and the reaction mass stirred at same temperature for 3 h. The reaction mixture was filtered and extracted with Et₂O. The organic layer was dried over anhydrous Na₂SO₄ and concentrated to dryness. The crude product was purified on Silica gel preparative plate. Yield: 38 mg (52%). ¹H NMR (CDCl₃) δ 7.49 (d, J=8.2 Hz, 1H), 7.37 (d, J=8.4 Hz, 2H), 7.28 (s, 1H), 7.05-6.94 (m, 2H), 6.90 (d, J=8.1 Hz, 1H), 2.73 (dd, J=29.3, 10.9 Hz, 4H), 1.81 (s, 2H), 1.37-1.19 (m, 9H). ESI-MS: m/z 338 [M+H]⁺.

Step-5: 4-(tert-Butyl)-N-hydroxy-N-(6,7,8,9-tetrahydro-5H-benzo[7]annulen-2-yl)benzamide (28 mg, 0.08 mmol) was dissolved in anhydrous CHCl₃ (5 mL) under N₂ atmosphere. To this solution, Cs₂CO₃ (2.7 mg, 8.30 μmol) was added followed by Togni-II reagent (52.4 mg, 0.17 mmol) and the reaction mixture was stirred 21 h at room temperature. The solvent was evaporated and solid was further dissolved in Nitromethane (3 mL) and heated at 40° C. for 15 min. Solvent was removed and the crude product was purified on Silica gel preparative plate to produce products 13 and 87.

i. 4-(tert-butyl)-N-(3-(trifluoromethoxy)-6,7,8,9-tetrahydro-5H-benzo[7]annulen-2-yl)benzamide (13)

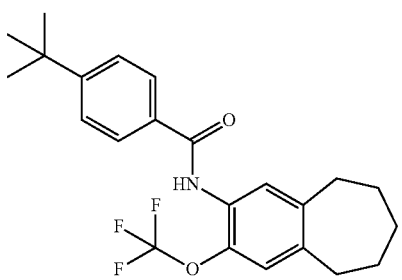 [SMILES: CC(C)(C)c1ccc(C(=O)Nc2cc3c(cc2OC(F)(F)F)CCCCC3)cc1]

Yield: 11 mg (33%). ¹H NMR (CDCl₃) δ 8.31 (s, 1H), 8.07 (s, 1H), 7.80 (d, J=8.4 Hz, 2H), 7.53 (d, J=8.3 Hz, 2H), 7.02 (s, 1H), 2.98-2.62 (m, 4H), 1.83 (d, J=5.3 Hz, 2H), 1.66 (s, 4H), 1.36 (d, J=0.9 Hz, 9H). HR-ESIMS: m/z 406.1916 [M+H]⁺ calcd for C₂₃H₂₇F₃NO₂, found 406.1987. HPLC Purity: 100% (Retention Time=3.2 min).

ii. 4-(tert-butyl)-N-(1-(trifluoromethoxy)-6,7,8,9-tetrahydro-5H-benzo[7]annulen-2-yl)benzamide (87)

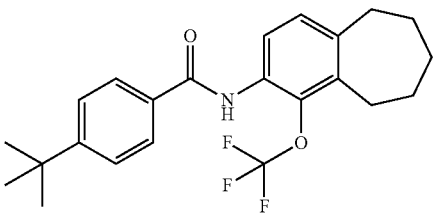 [SMILES: CC(C)(C)c1ccc(C(=O)Nc2ccc3c(c2OC(F)(F)F)CCCCC3)cc1]

Yield: 5.5 mg (15%). ¹H NMR (CDCl₃) δ 8.19 (d, J=8.3 Hz, 1H), 8.10 (s, 1H), 7.81 (d, J=8.4 Hz, 2H), 7.52 (d, J=8.4 Hz, 2H), 7.12 (d, J=8.2 Hz, 1H), 3.06-2.65 (m, 4H), 1.84 (d, J=5.2 Hz, 2H), 1.65 (d, J=5.3 Hz, 4H), 1.36 (d, J=1.2 Hz, 9H). HR-ESIMS: m/z 406.1916 [M+H]⁺ calcd for C₂₃H₂₇F₃NO₂, found 406.1990. HPLC Purity: 100% (Retention Time=3.2 min).

e. Synthesis of Compound 14

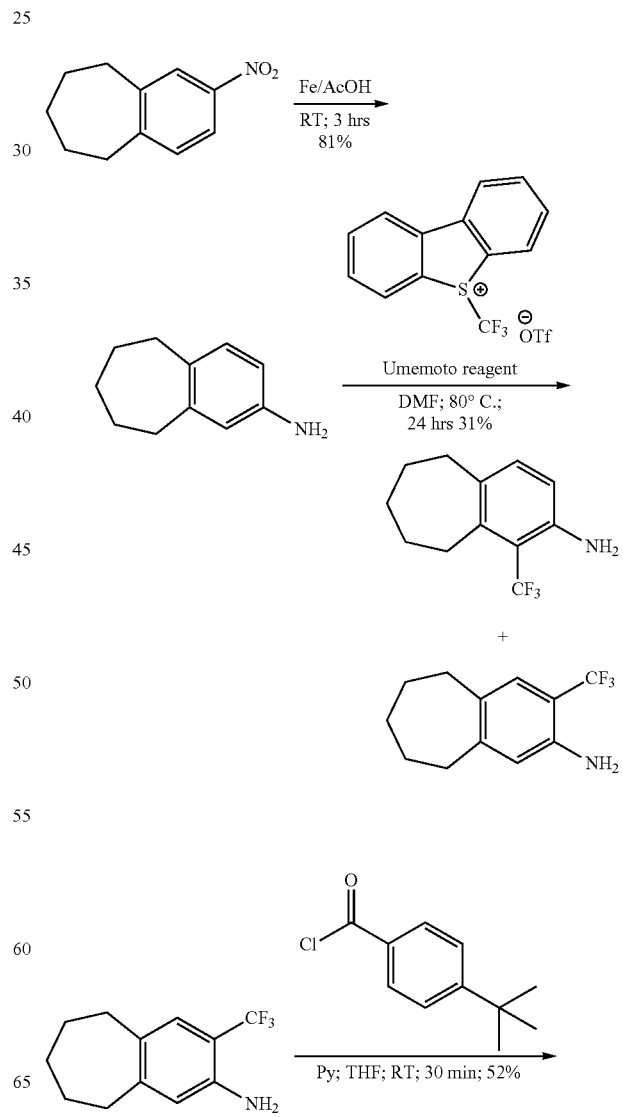

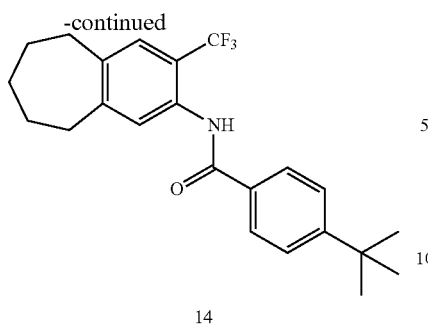

14

Step-1: Synthesis of 6,7,8,9-Tetrahydro-5H-benzo[7]annulen-2-amine. To an AcOH (10 mL) solution of 2-nitro-6,7,8,9-tetrahydro-5H-benzo[7]annulene (254 mg, 1.33 mmol) was added Fe (371 mg, 6.64 mmol) and reaction mixture was stirred at room temperature for 4 h. The reaction was neutralized with aq. NaHCO$_3$ and extracted with EtOAc. The organic layer was washed with water followed by brine and concentrated. The material obtained was directly used for next step without purification. Yield: 173 mg (81%). $^1$H NMR (CDCl$_3$) δ 6.88 (d, J=7.8 Hz, 1H), 6.48 (d, J=2.4 Hz, 1H), 6.42 (dd, J=7.8, 2.4 Hz, 1H), 2.76-2.61 (m, 4H), 1.77 (s, 2H), 1.61 (tt, J=11.3, 5.9 Hz, 4H). ESI-MS: m/z 162 [M+H]$^+$.

Step-2: Synthesis of 3-(Trifluoromethyl)-6,7,8,9-tetrahydro-5H-benzo[7]annulen-2-amine. To a dry DMF (10 mL) solution of 6,7,8,9-tetrahydro-5H-benzo[7]annulen-2-amine (73 mg, 0.45 mmol) was added 5-(trifluoromethyl)-5H-dibenzo[b,d]thiophen-5-ium (57 mg, 0.23 mmol). The reaction mixture was stirred for 8 h at 80° C. After completion of reaction, it was diluted with cold water and extracted with EtOAc. The organic layer was dried over anhydrous Na$_2$SO$_4$ and solvent was removed under reduced pressure. The crude product was purified on Silica gel preparative plate. Yield: 29 mg (31%). $^1$H NMR (CDCl$_3$) δ 8.31 (d, J=1.5 Hz, 1H), 6.81 (d, J=1.8 Hz, 1H), 2.82-2.54 (m, 4H), 1.82 (dtd, J=15.0, 11.5, 5.8 Hz, 4H), 1.62 (dt, J=11.2, 4.9 Hz, 2H). ESI-MS: m/z 230[M+H]$^+$.

Step-3: Synthesis of 4-(tert-butyl)-N-(3-(trifluoromethyl)-6,7,8,9-tetrahydro-5H-benzo[7]annulen-2-yl)benzamide (14). To a dry THF (5 mL) solution of 3-(trifluoromethyl)-6,7,8,9-tetrahydro-5H-benzo[7]annulen-2-amine (7.7 mg, 0.034 mmol) was added 4-tert-butylbenzoyl chloride (6.7 mg, 0.037 mmol) followed by pyridine (5.43 µL, 0.067 mmol). The reaction mixture was stirred at room temperature for 30 min and after completion of the reaction, it was diluted with 1M HCl. It was extracted with EtOAc and organic layer was washed with aq. NaHCO$_3$ followed by brine. The organic layer was dried over anhydrous Na$_2$SO$_4$ and solvent was removed under reduced pressure. The crude product was purified on Silica gel preparative plate. Yield: 6.8 mg (52%). $^1$H NMR (CDCl$_3$) δ 8.16 (s, 1H), 7.81 (d, J=8.6 Hz, 2H), 7.62-7.46 (m, 2H), 7.35 (s, 1H), 2.84 (dd, J=21.2, 10.9 Hz, 4H), 1.85 (d, J=5.6 Hz, 2H), 1.68 (s, 4H), 1.54 (s, 9H). HR-ESIMS: m/z 390.1966 [M+H]$^+$ calcd for C$_{23}$H$_{27}$F$_3$NO, found 390.2033. HPLC Purity: 95% (Retention Time=18.5 min).

f. Synthesis of Compounds 15 and 16

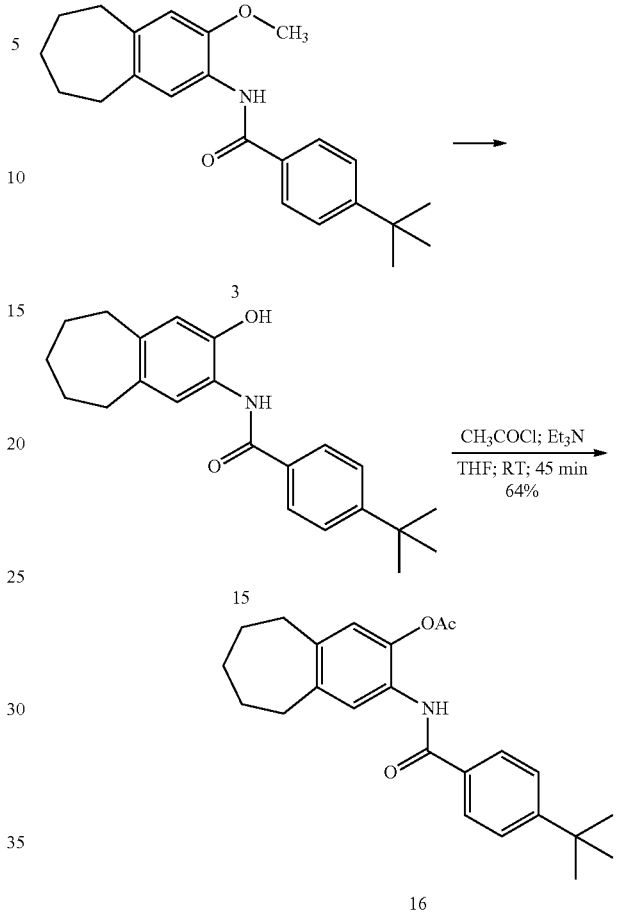

i. Synthesis of 4-(tert-butyl)-N-(3-hydroxy-6,7,8,9-tetrahydro-5H-benzo[7]annulen-2-yl)benzamide (15)

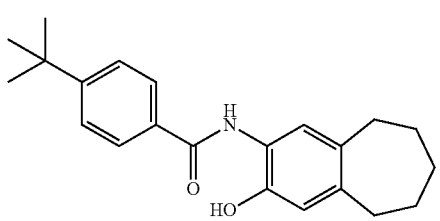 [SMILES: CC(C)(C)c1ccc(C(=O)Nc2cc3c(cc2O)CCCCC3)cc1]

To a cooled (−78° C.) anhydrous dichloromethane (10 mL) solution of 4-(tert-butyl)-N-(3-methoxy-6,7,8,9-tetrahydro-5H-benzo[7]annulen-2-yl)benzamide (3) (64 mg, 0.18 mmol) was added dropwise BBr$_3$ (0.052 mL, 0.55 mmol) [1M BBr$_3$ solution in DCM] and the reaction mixture was stirred at same temperature for 3 h. The reaction was quenched by 2% aqueous Na$_2$CO$_3$ solution and extracted with dichloromethane. The organic layer was washed with brine, and dried over Na$_2$SO$_4$. Solvent was removed under reduced pressure and purified on Silica gel preparative plate. Yield: 44 mg (71%). $^1$H NMR (CDCl$_3$) δ 8.70 (s, 1H), 7.85-7.79 (m, 1H), 7.62-7.37 (m, 2H), 6.82 (d, J=16.5 Hz, 2H), 2.93-2.47 (m, 4H), 1.54 (d, J=0.4 Hz, 4H), 1.36 (s, 9H).

HR-ESIMS: m/z 338.2042 [M+H]⁺ calcd for $C_{22}H_{28}NO_2$, found 339.2044. HPLC Purity: 99% (Retention Time=19.2 min).

ii. Synthesis of 3-(4-(tert-Butyl)benzamido)-6,7,8,9-tetrahydro-5H-benzo[7]annulen-2-yl acetate (16)

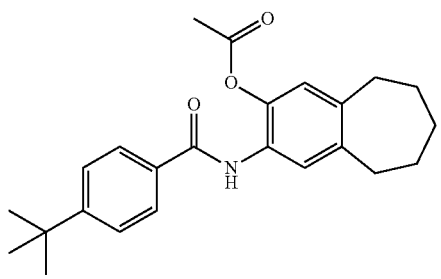 [SMILES: CC(=O)Oc1cc2c(cc1NC(=O)c1ccc(C(C)(C)C)cc1)CCCCC2]

To a dry THF (2 mL) solution of 4-(tert-butyl)-N-(3-hydroxy-6,7,8,9-tetrahydro-5H-benzo[7]annulen-2-yl)benzamide (22 mg, 0.065 mmol) and added triethylamine (0.027 mL, 0.196 mmol) followed by AcCl (5.10 µL, 0.072 mmol). The reaction mixture was stirred for 45 min at room temperature. It was diluted with water extracted with EtOAc and organic layer was washed with 1M HCl. Further organic layer was washed with aq. NaHCO₃, dried over anhydrous Na₂SO₄ and solvent was removed under reduced pressure. Crude product was purified by column chromatography. Yield: 16 mg (64%). ¹H NMR (CDCl₃) δ 7.94 (s, 1H), 7.77 (d, J=8.4 Hz, 2H), 7.51 (d, J=8.4 Hz, 2H), 6.90 (s, 1H), 2.77 (dd, J=22.9, 10.8 Hz, 4H), 2.34 (s, 3H), 1.92-1.77 (m, 2H), 1.75-1.50 (m, 4H), 1.36 (s, 9H). HR-ESIMS: m/z 380.2147 [M+H]⁺ calcd for $C_{24}H_{30}NO_3$, found 380.2044. HPLC Purity: 99% (Retention Time=19.2 min).

g. Synthesis of Compounds 19 and 25-28

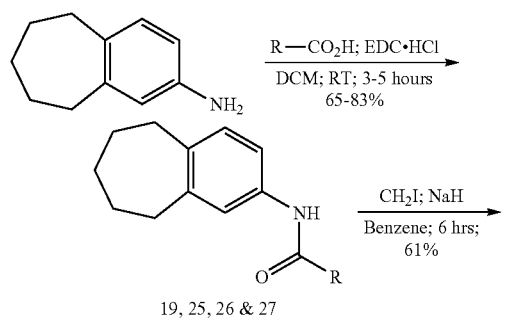

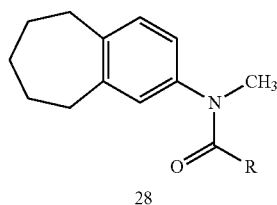

i. Synthesis of 4-(tert-Butyl)-N-(6,7,8,9-tetrahydro-5H-benzo[7]annulen-2-yl)benzamide (19)

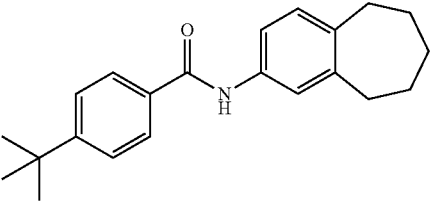 [SMILES: CC(C)(C)c1ccc(C(=O)Nc2ccc3c(c2)CCCCC3)cc1]

To an anhydrous DCM (2 mL) solution of 6,7,8,9-tetrahydro-5H-benzo[7]annulen-2-amine (28 mg, 0.174 mmol) was added 4-(tert-butyl)benzoic acid (34 mg, 0.191 mmol) followed by EDC (73 mg, 0.382 mmol). The reaction mixture was stirred for 1 hr at room temperature and concentrated. The crude product was directly loaded on the column for the purification. Yield: 46 mg (83%). ¹H NMR (CDCl₃) δ 7.90-7.83 (m, 1H), 7.83-7.74 (m, 2H), 7.52-7.42 (m, 2H), 7.40 (d, J=2.2 Hz, 1H), 7.35 (dd, J=8.0, 2.3 Hz, 1H), 7.07 (d, J=8.0 Hz, 1H), 2.89-2.62 (m, 4H), 1.82 (d, J=5.4 Hz, 2H), 1.74-1.54 (m, 4H), 1.35 (s, 9H). HR-ESIMS: m/z 322.2093 [M+H]⁺ calcd for $C_{22}H_{28}NO$, found 322.2159. HPLC Purity: 100% (Retention Time=17.3 min).

ii. Synthesis of 2-(tert-butyl)-N-(6,7,8,9-tetrahydro-5H-benzo[7]annulen-2-yl)thiazole-5-carboxamide (25)

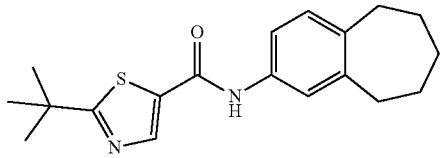 [SMILES: CC(C)(C)c1ncc(C(=O)Nc2ccc3c(c2)CCCCC3)s1]

To an anhydrous DCM (5 mL) solution of 6,7,8,9-tetrahydro-5H-benzo[7]annulen-2-amine (21.4 mg, 0.133 mmol) was added 2-(tert-butyl)thiazole-5-carboxylic acid (27 mg, 0.146 mmol) followed by EDC (56 mg, 0.292 mmol) at room temperature. The reaction mixture was stirred for 3 h at room temperature. It was diluted with water and extracted with DCM and organic layer was dried over anhydrous Na₂SO₄. The solvent was removed under reduced pressure and purified by column chromatography. Yield: 32 mg (73%). ¹H NMR (CDCl₃) δ 8.10 (s, 1H), 7.56 (s, 1H), 7.33-7.26 (m, 2H), 7.07 (d, J=7.9 Hz, 1H), 2.82-2.71 (m, 4H), 1.82 (d, J=5.3 Hz, 2H), 1.69-1.60 (m, 4H), 1.46 (s, 9H). HR-ESIMS: m/z 329.1609 [M+H]⁺ calcd for $C_{19}H_{25}N_2OS$, found 329.1685. HPLC Purity: 95% (Retention Time=0.94 min).

iii. Synthesis of 1-ethyl-5-methyl-N-(6,7,8,9-tetrahydro-5H-benzo[7]annulen-2-yl)-1H-pyrazole-3-carboxamide (26)

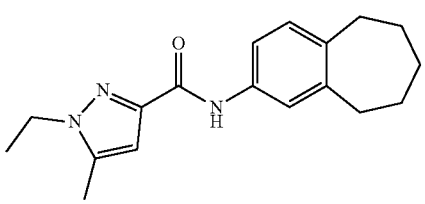 [SMILES: CCn1nc(C(=O)Nc2ccc3c(c2)CCCCC3)cc1C]

To an anhydrous DCM (5 mL) solution of 6,7,8,9-tetrahydro-5H-benzo[7]annulen-2-amine (25 mg, 0.155 mmol) was added 1-ethyl-5-methyl-1H-pyrazole-3-carboxylic acid (26 mg, 0.171 mmol) followed by N1-((ethylimino)methylene)-N3,N3-dimethylpropane-1,3-diamine hydrochloride (65.4 mg, 0.341 mmol). The reaction mixture was stirred for 3 h at room temperature. After completion of reaction, it was diluted with water and extracted with DCM. The organic layer was dried over anhydrous $Na_2SO_4$ and solvent was removed under vacuo. The crude product was purified by column chromatography. Yield: 30 mg (65%). $^1$H NMR ($CDCl_3$) δ 8.59 (s, 1H), 7.47-7.34 (m, 2H), 7.06 (d, J=7.7 Hz, 1H), 6.61 (d, J=0.7 Hz, 1H), 4.11 (q, J=7.3 Hz, 2H), 2.77 (dd, J=11.0, 9.0 Hz, 4H), 2.31 (d, J=0.6 Hz, 3H), 1.82 (d, J=5.5 Hz, 2H), 1.64 (q, J=5.3 Hz, 4H), 1.45 (t, J=7.3 Hz, 3H). HR-ESIMS: m/z 298.1841 [M+H]$^+$ calcd for $C_{18}H_{24}N_3O$, found 298.1917. HPLC Purity: 100% (Retention Time=0.90 min).

iv. Synthesis of 1-(tert-butyl)-N-(6,7,8,9-tetrahydro-5H-benzo[7]annulen-2-yl)-5-(trifluoromethyl)-1H-pyrazole-3-carboxamide (27)

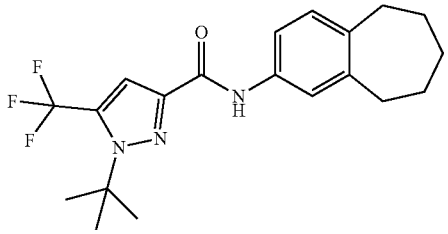 [SMILES: CC(C)(C)n1nc(C(=O)Nc2ccc3c(c2)CCCCC3)cc1C(F)(F)F]

To an anhydrous DCM (5 mL) solution of 6,7,8,9-tetrahydro-5H-benzo[7]annulen-2-amine (39.0 mg, 0.242 mmol) was added 1-(tert-butyl)-5-(trifluoromethyl)-1H-pyrazole-3-carboxylic acid (63 mg, 0.27 mmol) followed by N1-((ethylimino)methylene)-N3,N3-dimethylpropane-1,3-diamine hydrochloride (102 mg, 0.53 mmol). The reaction mixture was stirred for 3 h at room temperature. After completion of the reaction, it was diluted with water and extracted with DCM. The organic layer was dried over anhydrous $Na_2SO_4$ and solvent was evaporated. The crude product was purified by column chromatography. Yield: 60 mg (65%). $^1$H NMR ($CDCl_3$) δ 7.32 (s, 1H), 7.28 (d, J=3.6 Hz, 1H), 7.07 (d, J=8.0 Hz, 1H), 6.73 (m, 5H), 2.81-2.72 (m, 5H), 1.85-1.77 (m, 2H), 1.71 (s, 12H). HR-ESIMS: m/z 380.1871 [M+H]$^+$ calcd for $C_{20}H_{24}F_3N_3O$, found 380.1871.

v. Synthesis of 4-(tert-butyl)-N-methyl-N-(6,7,8,9-tetrahydro-5H-benzo[7]annulen-2-yl)benzamide (28)

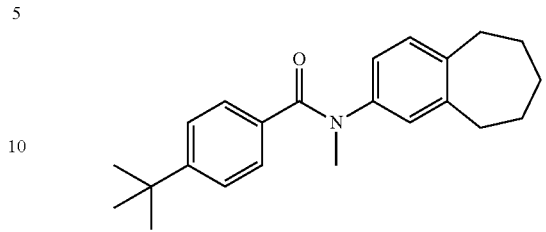

To an anhydrous benzene (2 mL) solution of 4-(tert-butyl)-N-(6,7,8,9-tetrahydro-5H-benzo[7]annulen-2-yl)benzamide (45 mg, 0.14 mmol) was added NaH (4.03 mg, 0.168 mmol) at 0° C. The reaction mixture was stirred at room temperature for 10 min and added methyliodide (0.013 mL, 0.210 mmol) and the reaction mixture was heated for 6 h at 60° C. The solvent was removed and the residue was diluted with water and extracted with DCM. The organic layer was dried over anhydrous $Na_2SO_4$ and solvent was removed under vacuo. The crude product was purified by column chromatography. Yield: 29 mg (61%); $^1$H NMR ($CDCl_3$) δ 7.21 (d, J=8.5 Hz, 2H), 7.16 (d, J=8.5 Hz, 2H), 6.93 (d, J=7.9 Hz, 1H), 6.76 (dd, J=7.9, 2.2 Hz, 1H), 6.70 (d, J=1.8 Hz, 1H), 3.46 (s, 3H), 2.65 (ddd, J=39.5, 6.9, 4.0 Hz, 4H), 1.87-1.71 (m, 2H), 1.64-1.35 (m, 4H), 1.23 (s, 9H). ESI-MS: m/z 336[M+H]$^+$.

h. Synthesis of Compounds 20 and 22

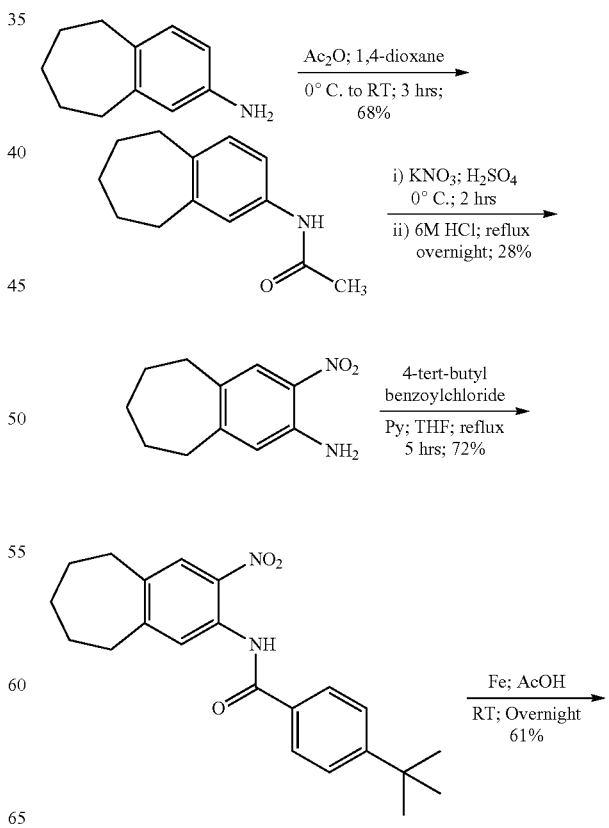

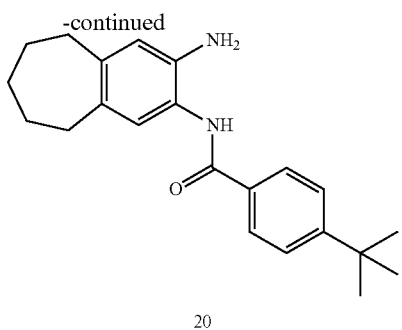

i. Synthesis of 4-(tert-butyl)-N-(3-nitro-6,7,8,9-tetrahydro-5H-benzo[7]annulen-2-yl)benzamide (22)

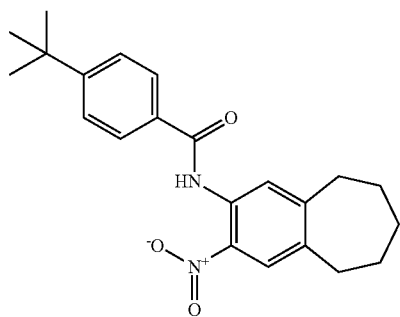

Step-1: Synthesis of N-(6,7,8,9-tetrahydro-5H-benzo[7]annulen-2-yl)acetamide: 6,7,8,9-Tetrahydro-5H-benzo[7]annulen-2-amine (150 mg, 0.93 mmol) was dissolved in 1,4-dioxane (4 mL) and to this solution, Ac$_2$O (0.18 mL, 1.86 mmol) was added drop wise at 0° C. The reaction mixture was stirred for 3 h at room temperature, after completion of the reaction monitored by TLC, solvent removed under reduced pressure. The crude reaction mixture was diluted with water and extracted with DCM. The organic layer was washed with aqueous NaHCO$_3$ followed by brine. The organic layer was dried over anhydrous Na$_2$SO$_4$ and solvent was removed under reduced pressure. The product was purified on a Silica gel preparative plate. Yield: 129 mg (68%). $^1$H NMR (CDCl$_3$) δ 7.25-7.12 (m, 2H), 7.02 (s, 1H), 2.75 (dt, J=7.3, 4.2 Hz, 4H), 2.15 (s, 3H), 1.86-1.79 (m, 2H), 1.65-1.59 (m, 4H). ESI-MS: m/z 204 [M+H]$^+$.

Step-2: Synthesis of 3-nitro-6,7,8,9-tetrahydro-5H-benzo[7]annulen-2-amine: A solution of potassium nitroperoxous acid (68 mg, 0.67 mmol) in 0.3 mL H$_2$SO$_4$ was added dropwise to a stirred suspension of N-(6,7,8,9-tetrahydro-5H-benzo[7]annulen-2-yl)acetamide (125 mg, 0.61 mmol) in sulfuric acid (1.83 mL, 34 mmol) at 0° C. The reaction mixture was stirred at 0° C. for 2 h and then poured in ice/water mixture. The mixture was extracted with DCM, dried over anhydrous Na$_2$SO$_4$ and concentrated to dryness. The residue was refluxed overnight in 3 mL of 6 M HCl and diluted with water. A pH of 7.5 was achieved by adding aq. NaOH and then extracted with DCM. The organic layer was dried over anhydrous Na$_2$SO$_4$ and solvent was removed under reduced pressure. Crude product was purified on a Silica gel preparative plate. Yield: 35 mg (28%). $^1$H NMR (CDCl$_3$) δ 7.83 (s, 1H), 6.54 (s, 1H), 5.93 (s, 2H), 2.82-2.58 (m, 4H), 1.79 (q, J=5.8 Hz, 2H), 1.63 (dt, J=13.4, 6.7 Hz, 4H). ESI-MS: m/z 207 [M+H]$^+$.

Step-3: 3-Nitro-6,7,8,9-tetrahydro-5H-benzo[7]annulen-2-amine (25 mg, 0.12 mmol) was dissolved in THF (2 mL) and to this solution, 4-(tert-butyl)benzoyl chloride (26 mg, 0.13 mmol) was added followed by the addition of pyridine (19 mg, 0.24 mmol) at 0° C. Further the reaction mixture was stirred overnight at room temperature. Solvent was removed under reduced pressure and crude product was purified on a Silica gel preparative plate. Yield: 32 mg (72%). $^1$H NMR (CDCl$_3$) δ 11.36 (s, 1H), 8.78 (s, 1H), 8.00 (s, 1H), 7.98-7.85 (m, 2H), 7.63-7.46 (m, 2H), 2.86 (dd, J=29.0, 11.0 Hz, 4H), 1.86 (s, 2H), 1.76-1.62 (m, 4H), 1.36 (s, 9H). HR-ESIMS: m/z 367.2016 [M+H]$^+$ calcd for C$_{22}$H$_{27}$N$_2$O$_3$, found 367.2009. HPLC Purity: 100% (Retention Time=18.4 min).

ii. Synthesis of N-(3-amino-6,7,8,9-tetrahydro-5H-benzo[7]annulen-2-yl)-4-(tert-butyl)benzamide (20)

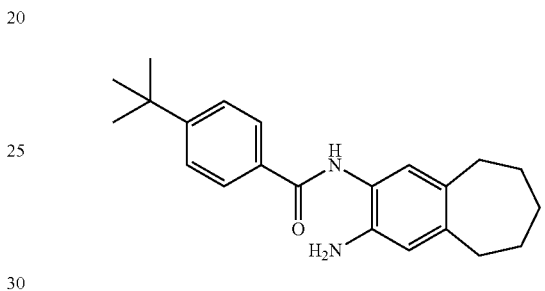

4-(tert-butyl)-N-(3-nitro-6,7,8,9-tetrahydro-5H-benzo[7]annulen-2-yl)benzamide (30 mg, 0.08 mmol) was dissolved in 1 mL AcOH and to this solution, Fe (23 mg, 0.41 mmol) was added at room temperature. The reaction mixture was stirred overnight and after completion of reaction, it was diluted with water and extracted with EtOAc. The organic layer was washed with aq. NaHCO$_3$, dried over anhydrous Na$_2$SO$_4$. Solvent was removed under reduced pressure and crude product was purified by column chromatography. Yield: 17 mg (61%). $^1$H NMR (CDCl$_3$) δ 7.83 (d, J=8.5 Hz, 2H), 7.69 (d, J=27.0 Hz, 1H), 7.59-7.37 (m, 2H), 7.05 (s, 1H), 6.61 (s, 1H), 3.73 (s, 2H), 2.69 (dt, J=7.3, 3.7 Hz, 4H), 1.79 (d, J=5.4 Hz, 2H), 1.71-1.52 (m, 4H), 1.35 (s, 9H). HR-ESI MS: m/z 337.2202 [M+H]$^+$ calcd for C$_{22}$H$_{29}$N20, found 337.2266. HPLC Purity: 98.7% (Retention Time=12.9 min).

i. General Synthesis of Compounds 23 and 24

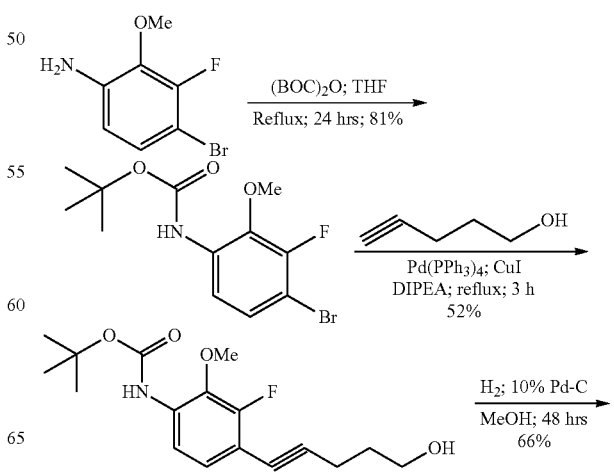

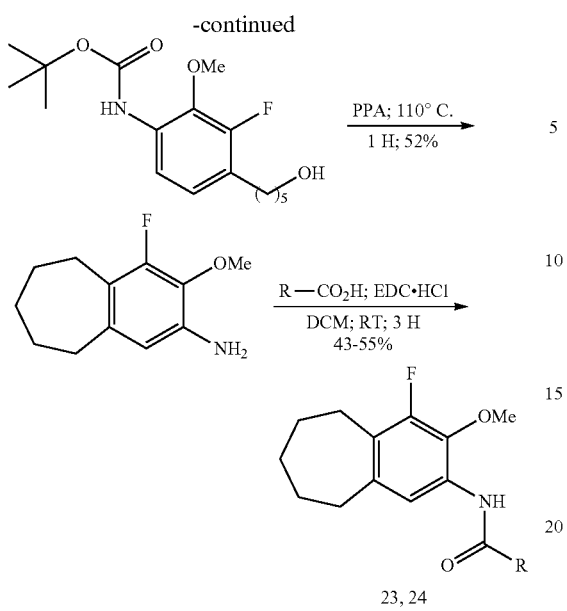

Step-1: Synthesis of tert-butyl(4-bromo-3-fluoro-2-methoxyphenyl)carbamate: 4-Bromo-3-fluoro-2-methoxyaniline (900 mg, 4.09 mmol) was dissolved in anhydrous THF (10 mL) and to this solution, Boc anhydride (950 µL, 4.09 mmol) was added. The reaction mixture was refluxed for 24 h and then cooled to room temperature. The solvent was removed and residue was purified on ISCO using Silica gel pre-packed column. Yield: 1.06 g (81%). $^1$H NMR (CDCl$_3$) δ 7.81 (d, J=8.9 Hz, 1H), 7.22-7.11 (m, 1H), 7.05 (s, 1H), 3.98 (d, J=2.0 Hz, 3H), 1.52 (s, 9H). ESI-MS: m/z 321 [M+H]$^+$.

Step-2: Synthesis of tert-butyl(3-fluoro-4-(5-hydroxy-pent-1-yn-1-yl)-2-methoxyphenyl)carbamate: Pd(PPh$_3$)$_4$ (72 mg, 0.06 mmol), copper(I) iodide (24 mg, 0.12 mmol) and pent-4-yn-1-ol (105 mg, 1.25 mmol) were added to a solution of tert-butyl (4-bromo-3-fluoro-2-methoxyphenyl)carbamate (200 mg, 0.63 mmol) in diisopropylethylamine (223 µL, 1.56 mmol) under an argon atmosphere. The reaction mixture was stirred under reflux for 3 h. After cooling to room temperature, the precipitate was removed via filtration and washed with EtOAc. The solvent was removed under reduced pressure and residue was purified on ISCO using Silica gel pre-packed column. Yield: 105 mg (52%); $^1$H NMR (CDCl$_3$) δ 7.81 (d, J=8.7 Hz, 1H), 7.10 (s, 1H), 7.04 (dd, J=8.7, 7.4 Hz, 1H), 3.96 (d, J=1.9 Hz, 3H), 3.83 (t, J=6.1 Hz, 2H), 2.57 (t, J=6.9 Hz, 2H), 1.99-1.78 (m, 2H), 1.52 (s, 9H). ESI-MS: m/z 324[M+H]$^+$.

Step-3: Synthesis of tert-butyl (3-fluoro-4-(5-hydroxypentyl)-2-methoxyphenyl)carbamate: tert-butyl (3-fluoro-4-(5-hydroxypent-1-yn-1-yl)-2-methoxyphenyl)carbamate (105 mg, 0.32 mmol) was dissolved in EtOH:MeOH:THF (2/2/0.2 mL) and to it was added 66 mg of 10% Pd/C. The reaction mixture was stirred under hydrogen atmosphere overnight. The reaction mixture was filtered and concentrated. The residue was purified on ISCO using pre-packed Silica gel column. Yield: 70.1 mg (66%). $^1$H NMR (CDCl$_3$) δ 7.74 (d, J=9.3 Hz, 1H), 6.99 (s, 1H), 6.81 (t, J=8.2 Hz, 1H), 3.94 (d, J=1.7 Hz, 3H), 3.63 (t, J=6.6 Hz, 2H), 2.58 (t, J=7.5 Hz, 2H), 1.74-1.46 (m, 15H). ESI-MS: m/z 328 [M+H]$^+$.

Step-4: 4-Fluoro-3-methoxy-6,7,8,9-tetrahydro-5H-benzo[7]annulen-2-amine: tert-butyl (3-fluoro-4-(5-hydroxypentyl)-2-methoxyphenyl)carbamate (100 mg, 0.31 mmol) was dissolved in 100 mg of PPA and heated for 1 h at 110° C. The reaction mixture was diluted with deionized water, neutralized with 1M NaOH and extracted with EtOAc. The organic layer was dried over anhydrous Na$_2$SO$_4$ and solvent removed under reduced pressure. The residue was purified on ISCO using pre-packed Silica gel column. Yield: 33 mg (52%). $^1$H NMR (CDCl$_3$) δ 6.48-6.29 (m, 1H), 3.96-3.66 (m, 3H), 2.90-2.38 (m, 4H), 2.10-1.28 (m, 6H). HR-ESIMS: m/z 210.1288 [M+H]$^+$ calcd for C$_{12}$H$_{17}$FNO, found 210.1293.

i. Synthesis of 4-(tert-butyl)-N-(4-fluoro-3-methoxy-6,7,8,9-tetrahydro-5H-benzo[7]annulen-2-yl)benzamide (23)

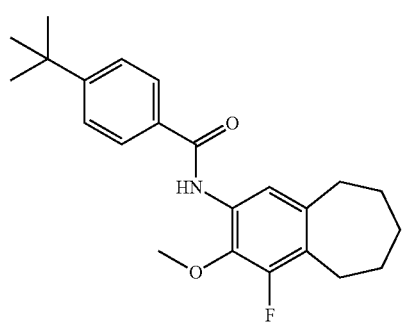 [SMILES: COc1c(NC(=O)c2ccc(C(C)(C)C)cc2)cc2c(c1F)CCCCC2]

4-Fluoro-3-methoxy-6,7,8,9-tetrahydro-5H-benzo[7]annulen-2-amine (20 mg, 0.10 mmol) was dissolved in DCM (3 mL) and to this solution, 4-(tert-butyl)benzoic acid (19 mg, 0.11 mmol) was added followed by EDC (40 mg, 0.21 mmol). The reaction mixture was stirred for 5 h at room temperature. The reaction mixture was diluted with deionized water and extracted with DCM. The organic layer was dried over anhydrous Na$_2$SO$_4$ and solvent was removed under reduced pressure. The product was purified on Silica gel preparative plate. 15 mg (43%). $^1$H NMR (400 MHz, CDCl$_3$) δ 8.45 (s, 1H), 8.18 (s, 1H), 7.88-7.74 (m, 2H), 7.59-7.43 (m, 2H), 3.97 (d, J=1.6 Hz, 3H), 2.90 (d, J=5.1 Hz, 1H), 2.76-2.59 (m, 2H), 1.95-1.81 (m, 2H), 1.77-1.41 (m, 5H), 1.44-1.30 (m, 9H). HR-ESIMS: m/z 370.2181 [M+H]$^+$ calcd for C$_{23}$H$_{29}$FNO$_2$, found 370.2104. HPLC Purity: 93% (Retention Time=19.1 min).

ii. Synthesis of 2-(tert-Butyl)-N-(4-fluoro-3-methoxy-6,7,8,9-tetrahydro-5H-benzo[7]annulen-2-yl)thiazole-5-carboxamide (24)

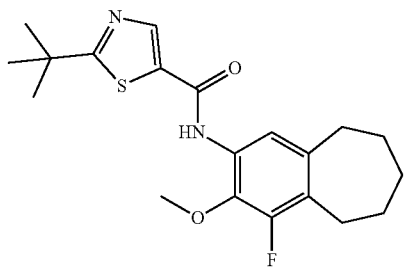 [SMILES: COc1c(NC(=O)c2cnc(C(C)(C)C)s2)cc2c(c1F)CCCCC2]

4-Fluoro-3-methoxy-6,7,8,9-tetrahydro-5H-benzo[7]annulen-2-amine (20 mg, 0.10 mmol) was dissolved in DCM (3 mL) and to this solution, 2-(tert-butyl)thiazole-5-carboxylic acid (19.5 mg, 0.11 mmol) was added followed by the addition of EDC (40 mg, 0.21 mmol). The reaction mixture was stirred for 5 h at room temperature. The reaction mixture was diluted with deionized water and extracted with DCM. The organic layer was dried over anhydrous $Na_2SO_4$ and solvent was removed under reduced pressure. The product was purified on Silica gel preparative plate. Yield: 19.7 mg (55%). $^1$H NMR (CDCl$_3$) δ 8.17 (bs, 1H), 8.13 (s, 1H), 8.03 (s, 1H), 3.99 (d, J=1.8 Hz, 3H), 2.98-2.80 (m, 1H), 2.67 (d, J=6.5 Hz, 2H), 1.85 (d, J=5.5 Hz, 3H), 1.56 (s, 4H), 1.48 (s, 9H). HR-ESIMS: m/z 377.1693 [M+H]$^+$ calcd for $C_{20}H_{26}FNO_2S$, found 377.1697. HPLC Purity: 100% (Retention Time=4.5 min).

j. Synthesis of Compound 29

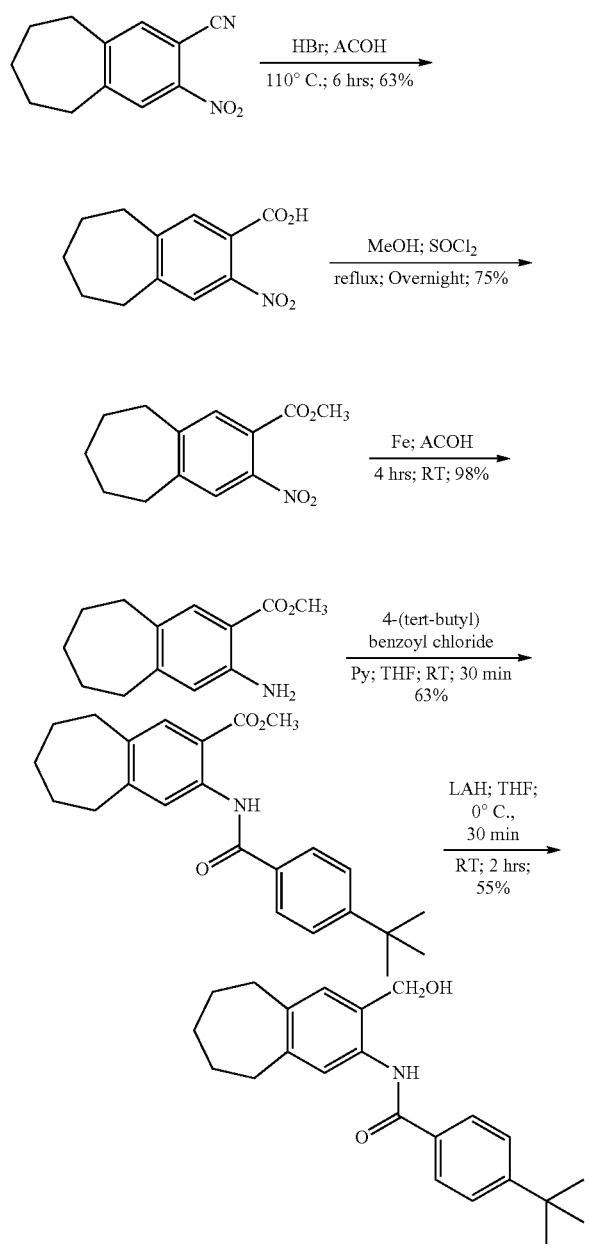

Step-1: Synthesis of 3-nitro-6,7,8,9-tetrahydro-5H-benzo[7]annulene-2-carboxylic acid. 3-Nitro-6,7,8,9-tetrahydro-5H-benzo[7]annulene-2-carbonitrile (55.0 mg, 0.25 mmol) was dissolved in 48% HBr (345 µL, 6.36 mmol) and AcOH (146 µL, 2.54 mmol) and heated 6 h at 110° C. The reaction was diluted with water and extracted with EtOAc. The organic layer was dried over anhydrous $Na_2SO_4$ and solvent removed under reduced pressure. Yield: 38 mg (63%). It was used as such in the next step.

Step-2: Synthesis of methyl 3-nitro-6,7,8,9-tetrahydro-5H-benzo[7]annulene-2-carboxylate: 3-Nitro-6,7,8,9-tetrahydro-5H-benzo[7]annulene-2-carboxylic acid (38 mg 0.161 mmol) was dissolved in MeOH (2 mL) and cooled to at 0° C. To the cooled solution, SOCl$_2$ (18.6 µL, 0.25 mmol) was added and then refluxed overnight. Reaction mixture was cooled to room temperature and solvent was evaporated. The residue was dissolve in DCM and washed with aq. NaHCO$_3$ followed by deionized water. The organic layer was dried over anhydrous $Na_2SO_4$ and concentrated. The product was purified on pre-packed Silica gel column on ISCO. Yield: 29 mg (75%). $^1$H NMR (CDCl$_3$) δ 7.65 (s, 1H), 7.43 (s, 1H), 3.90 (s, 3H), 2.95-2.79 (m, 4H), 1.87 (d, J=5.5 Hz, 2H), 1.77-1.60 (m, 4H).

Step-3: Synthesis of methyl 3-amino-6,7,8,9-tetrahydro-5H-benzo[7]annulene-2-carboxylate: Methyl 3-nitro-6,7,8,9-tetrahydro-5H-benzo[7]annulene-2-carboxylate (29 mg, 0.12 mmol) was dissolved in AcOH (146 µL, 2.54 mmol) and to this solution, iron (34 mg, 0.6 mmol) was added. The reaction mixture was stirred at room temperature for 4 h. The reaction mixture was diluted with deionized water and extracted with EtOAc. The organic layer was dried over anhydrous $Na_2SO_4$ and solvent was removed. Yield: 25 mg (98%) Used as such in next step. $^1$H NMR (CDCl$_3$) δ 7.57 (s, 1H), 6.44 (s, 1H), 3.84 (s, 3H), 2.76-2.57 (m, 4H), 1.77 (d, J=5.4 Hz, 2H), 1.61 (dd, J=12.7, 5.0 Hz, 4H). ESI-MS: m/z 188 [M-OCH$_3$]+.

Step-4: Synthesis of methyl 3-(4-(tert-butyl)benzamido)-6,7,8,9-tetrahydro-5H-benzo[7]annulene-2-carboxylate: Methyl 3-amino-6,7,8,9-tetrahydro-5H-benzo[7]annulene-2-carboxylate (25 mg, 0.11 mmol) was dissolved in dry THF (2 mL) and to this solution 4-(tert-butyl)benzoyl chloride (25 mg, 0.12 mmol) was added followed by pyridine (0.02 mL, 0.23 mmol). The reaction mixture was stirred for 30 min at room temperature. It was diluted with 1M HCl and extracted with EtOAc. The organic layer was dried over anhydrous $Na_2SO_4$ and concentrated. The crude product was purified on Silica gel preparative plate. Yield: 27 mg (63%). $^1$H NMR (CDCl$_3$) δ 8.72 (s, 1H), 8.07-7.87 (m, 2H), 7.79 (s, 1H), 7.64-7.47 (m, 2H), 3.93 (s, 3H), 3.02-2.65 (m, 4H), 1.83 (d, J=5.3 Hz, 2H), 1.77-1.59 (m, 4H), 1.36 (d, J=2.1 Hz, 9H). ESI-MS: m/z 380 [M+H]$^+$.

Step-5: Methyl 3-(4-(tert-butyl)benzamido)-6,7,8,9-tetrahydro-5H-benzo[7]annulene-2-carboxylate (17 mg, 0.04 mmol) was dissolved in anhydrous THF (3 mL) and to this solution, LAH (5 mg, 0.13 mmol) was added at 0° C. The reaction was stirred for 30 minutes at 0° C. and the further stirred at room temperature for 2 h. The reaction was diluted with satd. NH$_4$Cl solution and extracted with DCM. The organic was layer dried over anhydrous $Na_2SO_4$ and concentrated to dryness followed by purification on a pre-packed Silica gel column in ISCO. Yield: 8.4 mg (55%). $^1$H NMR (CDCl$_3$) δ 9.29 (s, 1H), 8.00 (s, 1H), 7.93-7.81 (m, 2H), 7.55-7.44 (m, 2H), 6.94 (s, 1H), 4.71 (d, J=5.9 Hz, 2H), 2.87-2.69 (m, 4H), 2.33 (t, J=6.0 Hz, 1H), 1.82 (d, J=5.4 Hz, 2H), 1.68-1.59 (m, 4H), 1.35 (s, 9H). HR-ESIMS: m/z 352.2198 [M–H]$^+$ calcd for $C_{23}H_{30}NO_2$, found 334.2158 [M-OH]$^+$. HPLC Purity: 100% (Retention Time=2.9 min).

k. Synthesis of Compound 30

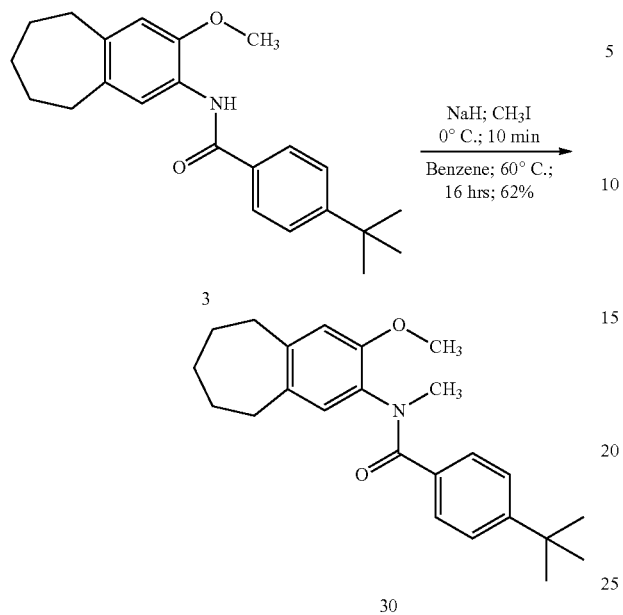

4-(tert-butyl)-N-(3-methoxy-6,7,8,9-tetrahydro-5H-benzo[7]annul en-2-yl)benzamide (31 mg, 0.09 mmol) was dissolved in 2 mL of anhydrous benzene and to this solution NaH (2.5 mg, 0.11 mmol) added at 0° C. The reaction mixture was stirred for 10 min at room temperature and added methyliodide (0.011 mL, 0.18 mmol). The reaction mixture was heated overnight at 60° C. Yield: 20 mg (62%). $^1$H NMR (CDCl$_3$) δ 7.19-7.13 (m, 4H), 6.65 (s, 1H), 6.53 (s, 1H), 3.69 (s, 3H), 3.33 (s, 3H), 2.68-2.55 (m, 4H), 1.75-1.73 (m, 2H), 1.59-1.52 (m, 4H), 1.21 (s, 9H). HR-ESI MS: m/z 366.2427 [M+H]$^+$ calcd for C$_{24}$H$_{31}$NO$_2$, found 366.2426 HPLC Purity: 100% (Retention Time=3.1 min).

l. Synthesis of Compound 47

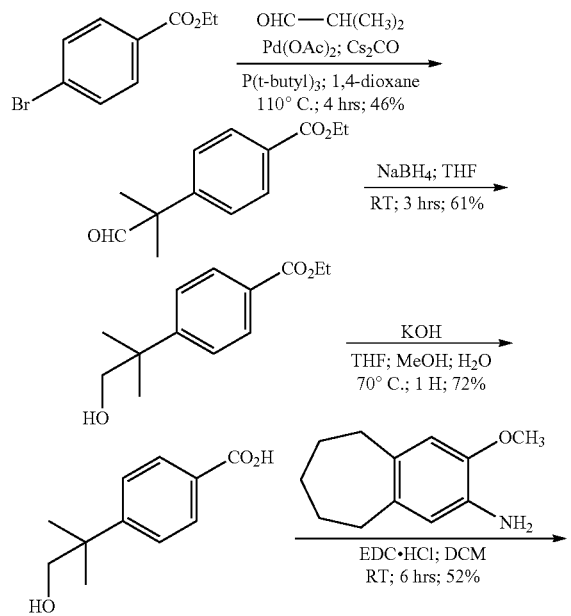

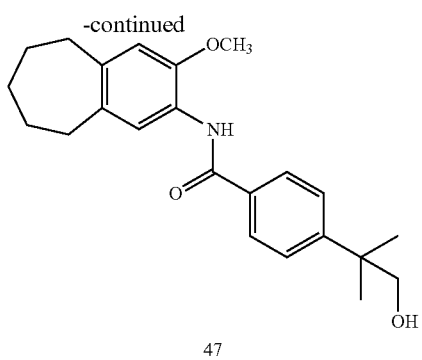

47

Step-1: Synthesis of ethyl 4-(2-methyl-1-oxopropan-2-yl)benzoate: To a suspension of ethyl 4-bromobenzoate (2.29 g, 10 mmol), isobutyraldehyde (1.8 mL, 20 mmol), diacetoxypalladium (45 mg, 0.2 mmol) and tri-tert-butylphosphine (81 mg, 0.4 mmol) in 5 mL of anhydrous dioxane was added oven dried CsCO$_3$ (782 mg, 2.4 mmol). The resulting mixture was stirred for 4 h at 110° C. The reaction mixture was cooled to room temperature, deionized water was added and extracted with EtOAc. The organic layer was dried over anhydrous Na$_2$SO$_4$ and solvent was removed. The product was purified on pre-packed Silica gel column using ISCO. Yield: 1.01 g (46%). $^1$H NMR (CDCl$_3$) δ 9.51 (d, J=0.6 Hz, 1H), 8.08-8.00 (m, 2H), 7.38-7.30 (m, 2H), 4.42-4.32 (m, 2H), 1.49 (s, 6H), 1.38 (td, J=7.1, 0.5 Hz, 3H).

Step-2: Synthesis of ethyl 4-(1-hydroxy-2-methylpropan-2-yl)benzoate: Ethyl 4-(2-methyl-1-oxopropan-2-yl)benzoate (1.0 g, 4.54 mmol) was dissolved in dry THF (6 mL) and to this solution was added NaBH$_4$ (344 mg, 9.08 mmol) in portions at room temperature. The reaction mixture was stirred at for 3 h at room temperature. After completion of reaction, it was diluted with water (slow addition) and extracted with EtOAc. The organic layer was dried over anhydrous Na$_2$SO$_4$, solvent removed under reduced pressure and the compound was recrystallized with Hexanes. Yield: 616 mg (61%). $^1$H NMR (CDCl$_3$) δ 8.17-7.77 (m, 2H), 7.57-7.30 (m, 2H), 4.35 (q, J=7.1 Hz, 2H), 3.62 (s, 2H), 1.37 (t, J=7.1 Hz, 3H), 1.34 (s, 6H).

Step-3: 4-(1-Hydroxy-2-methylpropan-2-yl)benzoic acid. Ethyl 4-(1-hydroxy-2-methylpropan-2-yl)benzoate (300 mg, 1.35 mmol) was dissolved in THF:MeOH (1 mL, 0.5 mL) and to this solution was added KOH in 0.5 mL water. The reaction mixture heated at 70° C. for 1 h. The reaction was cooled to room temperature, diluted with water and neutralized with 1M HCl, followed by extraction with EtOAc. The organic layer dried over anhydrous Na$_2$SO$_4$ and concentrated. The partially impure product was titrated with hexanes to get pure compound as a white solid and used as such in next step. Yield: 972 mg (72%). $^1$H NMR (CDCl$_3$) δ 7.94 (d, J=8.7 Hz, 2H), 7.42 (d, J=8.7 Hz, 2H), 3.83 (s, 2H) 1.30 (s, 6H).

Step-4: 3-Methoxy-6,7,8,9-tetrahydro-5H-benzo[7]annulen-2-amine (30 mg, 0.16 mmol) was dissolved in dry DCM (3 mL) and to this solution was added 4-(1-hydroxy-2-methylpropan-2-yl)benzoic acid (31 mg, 0.16 mmol) followed by EDC (66 mg, 0.35 mmol). The reaction mixture was stirred for 6 h at room temperature, diluted with water and extracted with EtOAc. The organic layer was dried over anhydrous Na$_2$SO$_4$ and solvent was removed under vacuo. The product was purified on pre-packed Silica gel column using ISCO. Yield: 30 mg (52%). $^1$H NMR (CDCl$_3$) δ 8.43 (s, 1H), 8.29 (s, 1H), 7.92-7.73 (m, 2H), 7.58-7.42 (m, 2H), 6.68 (s, 1H), 3.88 (s, 3H), 3.66 (s, 2H), 2.77 (t, J=11.3 Hz, 4H), 1.82 (p, J=6.0 Hz, 2H), 1.73-1.56 (m, 4H), 1.37 (s, 6H). HR-ESIMS: m/z 368.2220 [M+H]+ calcd for $C_{23}H_{30}NO_3$, found 368.2220. HPLC Purity: 100% (Retention Time=10.8 min).

m. Synthesis of Compound 52

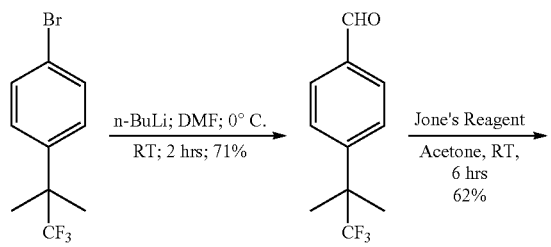

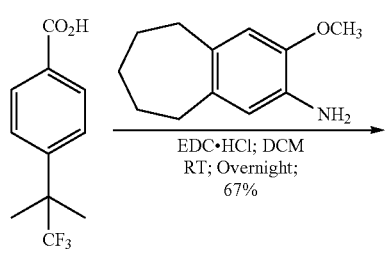

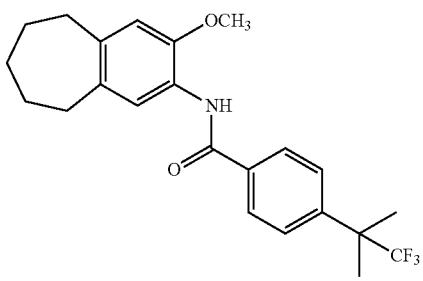

Step-1: Synthesis of 4-(1,1,1-trifluoro-2-methylpropan-2-yl)benzaldehyde: 1-bromo-4-(1,1,1-trifluoro-2-methylpropan-2-yl)benzene (200 mg, 0.75 mmol) was dissolved in anhydrous ether (3 mL) under argon and to this solution was added n-BuLi (48.0 mg, 0.75 mmol) at 0° C. The reaction mixture was stirred for 30 min at the same temperature, followed by the addition of dry DMF (0.058 mL, 0.75 mmol). Further the reaction mixture was stirred for 2 h at room temperature. The reaction mixture was diluted with 10% HCl solution and extracted with EtOAc. The organic layer was dried over anhydrous $Na_2SO_4$, filtered concentrated under vacuo. Used as such for next step reaction. Yield: 115 mg (71%). $^1$H NMR (CDCl$_3$) δ 10.03 (s, 1H), 8.15-7.75 (m, 2H), 7.67 (d, J=8.2 Hz, 2H), 1.61 (s, 6H).

Step-2: Synthesis of 4-(1,1,1-trifluoro-2-methylpropan-2-yl)benzoic acid: 4-(1,1,1-Trifluoro-2-methylpropan-2-yl)benzaldehyde (100 mg, 0.463 mmol) was dissolved in 1 mL acetone and to this solution was added 0.3 mL Jones reagent. The reaction mixture was for 6 h at room temperature. It was diluted with water and extracted with EtOAc. The organic layer was dried over anhydrous $Na_2SO_4$, concentrated and used as such for next step. Yield: 67 mg (62%). $^1$H NMR (CDCl$_3$) δ 8.23-8.00 (m, 2H), 7.62 (d, J=8.3 Hz, 2H), 1.62 (s, 6H).

Step-3: Synthesis of N-(3-methoxy-6,7,8,9-tetrahydro-5H-benzo[7]annulen-2-yl)-4-(1,1,1-trifluoro-2-methylpropan-2-yl)benzamide (52): 3-Methoxy-6,7,8,9-tetrahydro-5H-benzo[7]annulen-2-amine (25 mg, 0.13 mmol) was dissolved in DCM (3 mL) to this solution was added 4-(1,1,1-trifluoro-2-methylpropan-2-yl)benzoic acid (33 mg, 0.14 mmol) followed by EDC (55 mg, 0.29 mmol). The reaction mixture was stirred for 5 h at room temperature. It was diluted with water and extracted with DCM. The organic layer was dried over anhydrous $Na_2SO_4$ and solvent removed under vacuo. The product was purified on prepacked Silica gel column using ISCO. Yield: 35 mg (67%). $^1$H NMR (CDCl$_3$) δ 8.44 (s, 1H), 8.29 (s, 1H), 7.96-7.78 (m, 2H), 7.62 (d, J=8.2 Hz, 2H), 6.68 (s, 1H), 3.89 (s, 3H), 2.85-2.69 (m, 4H), 1.82 (d, J=5.3 Hz, 2H), 1.72-1.51 (m, 10H). HR-ESIMS: m/z 406.1988 [M+H]+ calcd for $C_{23}H_{27}F_3NO_2$, found 406.1988. HPLC Purity: 100% (Retention Time=5.2 min).

n. Synthesis of Compounds 59 and 60

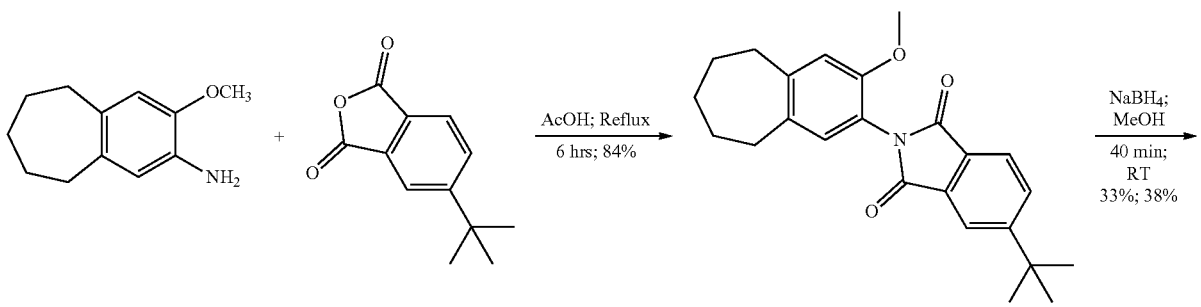

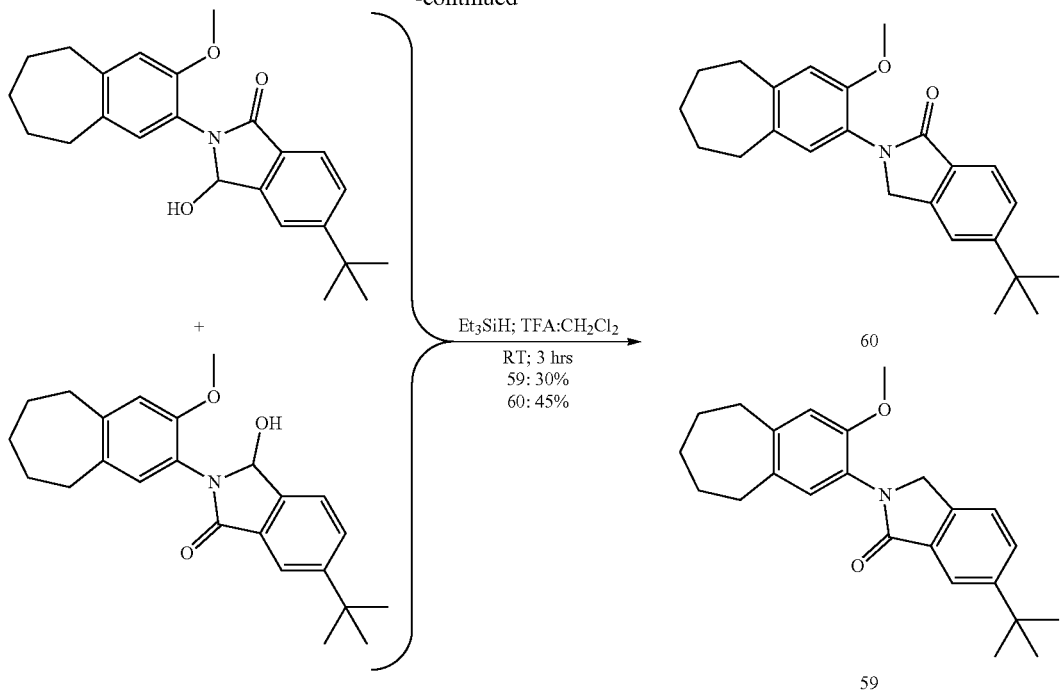

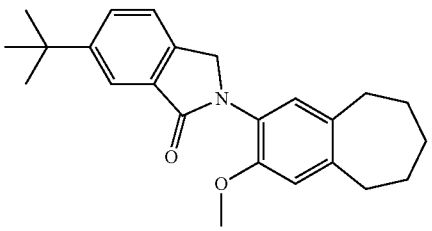 [SMILES: COc1cc2c(cc1N1Cc3ccc(C(C)(C)C)cc3C1=O)CCCCC2]

Step-1: Synthesis of 5-(tert-butyl)-2-(3-methoxy-6,7,8,9-tetrahydro-5H-benzo[7]annulen-2-yl)isoindoline-1,3-dione: 3-Methoxy-6,7,8,9-tetrahydro-5H-benzo[7]annulen-2-amine (50 mg, 0.26 mmol) was dissolved in AcOH (4 mL) and to this solution was added 5-(tert-butyl)isobenzofuran-1,3-dione (53 mg, 0.26 mmol). The reaction mixture was refluxed for 6 h and cooled to room temperature. It was poured in ice cold water (100 mL) and precipitate was filtered off. The solid was washed with water (3×25 mL) and dried under vacuum. Yield: 83 mg (84%). $^1$H NMR (CDCl$_3$) δ 7.96 (d, J=1.1 Hz, 1H), 7.85 (d, J=7.9 Hz, 1H), 7.77 (dd, J=7.9, 1.7 Hz, 1H), 6.94 (s, 1H), 6.79 (s, 1H), 3.75 (s, 3H), 2.90-2.64 (m, 4H), 1.83 (d, J=5.5 Hz, 2H), 1.66 (dd, J=9.4, 4.4 Hz, 4H), 1.40 (d, J=2.1 Hz, 9H). ESI-MS: m/z 378 [M+H]$^+$.

Step-2: 5-(tert-Butyl)-2-(3-methoxy-6,7,8,9-tetrahydro-5H-benzo[7]annulen-2-yl)isoindoline-1,3-dione (80 mg, 0.21 mmol) was dissolved in MeOH (3 mL) and NaBH$_4$ (32 mg, 0.85 mmol) was added in two portions. The reaction mixture was stirred at room temperature for 40 min and concentrated to dryness. The mass was diluted with deionized water and extracted with DCM. The organic layer was dried over anhydrous Na$_2$SO$_4$ and solvent was removed under vacuum. Used for next step. The sample was dissolved in 1:1 DCM-TFA (3 mL) and added triethylsilane (508 µL, 3.18 mmol) at room temperature. The reaction mixture was stirred for 3 h and concentrated. The residue was diluted with aq. NaHCO$_3$ and extracted with DCM. The organic layer was dried over anhydrous Na$_2$SO$_4$ and concentrated under vacuum. The crude product were purified using pre-packed Silica column on ISCO that gave 59 and 60.

i. 6-(tert-Butyl)-2-(3-methoxy-6,7,8,9-tetrahydro-5H-benzo[7]annulen-2-yl)isoindolin-1-ONE (59)

Yield: 23 mg (30%). $^1$H NMR (CDCl$_3$) δ 7.97 (d, J=1.4 Hz, 1H), 7.62 (dd, J=8.0, 1.9 Hz, 1H), 7.41 (dd, J=8.0, 0.7 Hz, 1H), 7.12 (s, 1H), 6.77 (s, 1H), 4.72 (s, 2H), 3.78 (s, 3H), 2.77 (ddd, J=21.3, 7.1, 3.9 Hz, 4H), 1.83 (q, J=6.2, 5.8 Hz, 2H), 1.66 (tt, J=10.3, 4.6 Hz, 4H), 1.38 (s, 9H). ESI-MS: m/z 364 [M+H]$^+$. HR-ESIMS: m/z 364.2198 [M+H]$^+$ calcd for C$_{24}$H$_{30}$NO$_2$, found 364.2264. HPLC Purity: 98.4% (Retention Time=14.9 min).

ii. 5-(tert-Butyl)-2-(3-methoxy-6,7,8,9-tetrahydro-5H-benzo[7]annulen-2-yl)isoindolin-1-one (60)

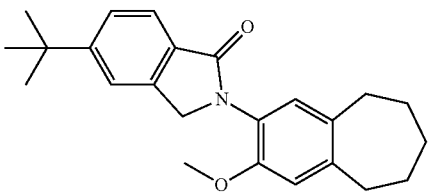 [SMILES: COc1cc2c(cc1N1Cc3cc(C(C)(C)C)ccc3C1=O)CCCCC2]

Yield: 35 mg (45%). $^1$H NMR (CDCl$_3$) δ 7.86 (d, J=8.1 Hz, 1H), 7.53 (dd, J=8.1, 1.6 Hz, 1H), 7.51-7.47 (m, 1H), 7.13 (s, 1H), 6.77 (s, 1H), 4.75 (s, 2H), 3.78 (s, 3H), 2.77 (ddd, J=21.2, 7.1, 3.8 Hz, 4H), 1.82 (d, J=5.3 Hz, 2H), 1.66 (dt, J=10.1, 5.1 Hz, 4H), 1.38 (s, 9H). HR-ESI MS: m/z 364.2198 [M+H]$^+$ calcd for C$_{24}$H$_{30}$NO$_2$, found 364.2264. HPLC Purity: 97% (Retention Time=14.9 min).

o. Synthesis of Compound 88

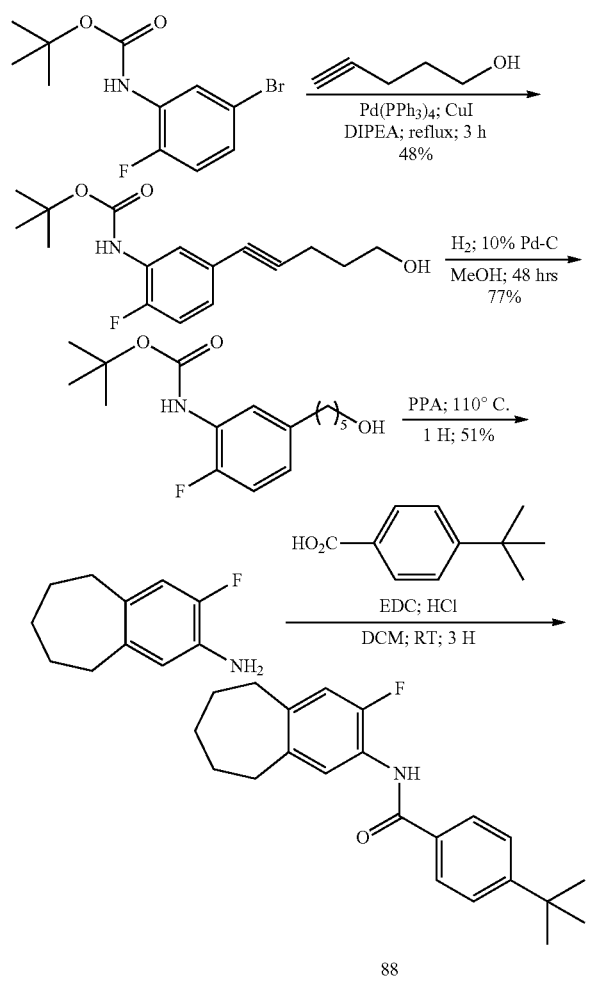

Step-1: Synthesis of tert-butyl (2-fluoro-5-(5-hydroxypent-1-yn-1-yl)phenyl)carbamate: Pd(PPh$_3$)$_4$ (0.13 g, 0.34 mmol), copper(I) iodide (0.13 g, 0.69 mmol) and pent-4-yn-1-ol (0.58 g, 6.89 mmol) were added to a dry DMF (3 mL) solution of tert-butyl (5-bromo-2-fluorophenyl)carbamate (1.0 g, 3.45 mmol) and DIPEA (8 mL, 45.8 mmol). The reaction mixture was stirred under reflux for 3 h. After cooling to room temperature, the precipitate was removed via filtration and washed with EtOAc. The filtrate was concentrated in vacuo to produce 485 mg (48%) of crude product and used as such in the next step. $^1$H NMR (CDCl$_3$) δ 8.15-7.91 (m, 1H), 7.20-6.96 (m, 2H), 6.71 (s, 1H), 3.81 (t, J=6.1 Hz, 2H), 2.52 (t, J=7.0 Hz, 2H), 1.96-1.69 (m, 2H), 1.52 (s, 9H).

Step-2: tert-Butyl (2-fluoro-5-(5-hydroxypent-1-yn-1-yl)phenyl)carbamate (485 mg, 1.65 mmol) was dissolved in EtOH-MeOH-THF (2/2/0.2 mL) mixture and to it was added 100 mg of Pd/C (10 w/w %). The reaction mixture was stirred under hydrogen atmosphere for 2 days at room temperature and filtered through celite. The filtrate was concentrated and purified using pre-packed Silica column on ISCO. Yield: 379 mg (77%). $^1$H NMR (CDCl$_3$) δ 7.92 (s, 1H), 6.91 (m, 2H), 6.88 (s, 1H), 4.11 (m, 1H), 3.62 (t, J=6.1 Hz, 2H), 2.56 (t, J=7.0 Hz, 2H), 1.63-1.61 (m, 2H), 1.52 (s, 9H), 1.41-1.22 (m, 4H). ESI-MS: m/z 388 [M+H]$^+$.

Step 3: Synthesis of 3-fluoro-6,7,8,9-tetrahydro-5H-benzo[7]annulen-2-amine: tert-Butyl (2-fluoro-5-(5-hydroxypentyl)phenyl)carbamate (100 mg, 0.34 mmol) was dissolved in 0.5 g of polyphosphoric acid (PPA) at room temperature and further heated to 110° C. for 1 h. The reaction mixture was poured to ice cold water and stirred for 30 min. It was neutralized with 1M NaOH and then extracted with EtOAc. Further the EtOAc layer was washed with deionized water followed by brine. The organic phase was dried over anhydrous Na$_2$SO$_4$ and solvent was removed under reduced pressure. The crude material was purified on preparative Silica gel plate. Yield: 30 mg (51%). $^1$H NMR (CDCl$_3$) δ 6.78-6.36 (m, 2H), 2.70 (dq, J=58.8, 6.2 Hz, 4H), 2.21-1.24 (m, 6H). ESI-MS: m/z 180 [M+H]$^+$.

Step-4: 4-(tert-Butyl)-N-(3-fluoro-6,7,8,9-tetrahydro-5H-benzo[7]annulen-2-yl)benzamide (88): 3-Fluoro-6,7,8,9-tetrahydro-5H-benzo[7]annulen-2-amine (18 mg, 0.100 mmol) was dissolved in dry dichloromethane (3 mL). To this solution was added 4-(tert-butyl)benzoic acid (19.7 mg, 0.11 mmol) followed by EDC (42 mg, 0.22 mmol). The reaction mixture was stirred for 3 h at room temperature. The reaction mixture was diluted with water and extracted with DCM. The organic layer dried over anhydrous Na$_2$SO$_4$ and solvent was removed under reduced pressure. The crude product was purified on Silica gel preparative plate. Yield: 19 mg (58%). $^1$H NMR (CDCl$_3$) δ 8.29 (d, J=8.1 Hz, 1H), 7.95 (s, 1H), 7.89-7.70 (m, 2H), 7.64-7.40 (m, 2H), 6.81 (d, J=11.8 Hz, 1H), 3.00-2.86 (m, 1H), 2.70 (d, J=5.6 Hz, 2H), 1.89 (d, J=5.6 Hz, 2H), 1.77-1.67 (m, 1H), 1.46-1.10 (m, 12H), 0.88 (s, 1H). HR-ESIMS: m/z 340.1998 [M+H]$^+$ calcd for $_{22}$H$_{27}$FNO, found 340.2074. HPLC Purity: 100% (Retention Time=3.1 min).

p. Synthesis of Compound 90

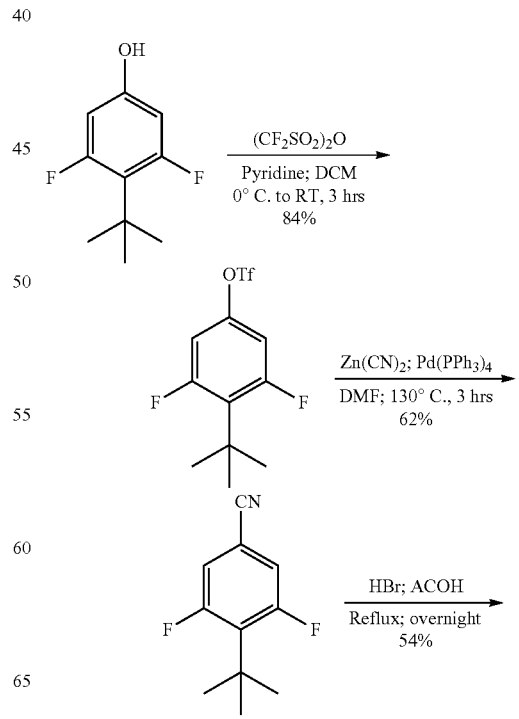

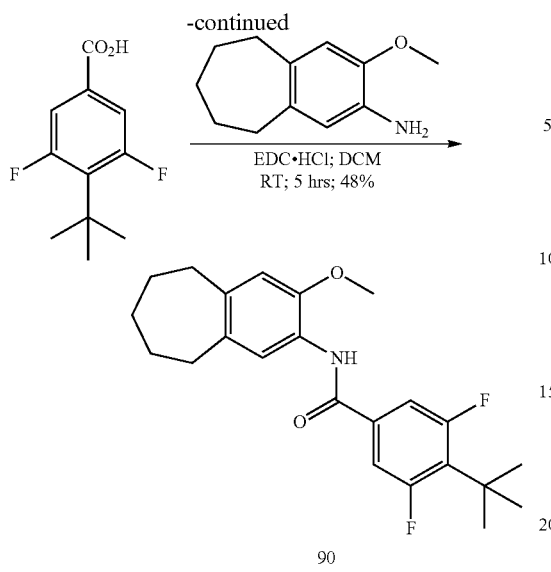

q. Synthesis of Compounds 62 and 91

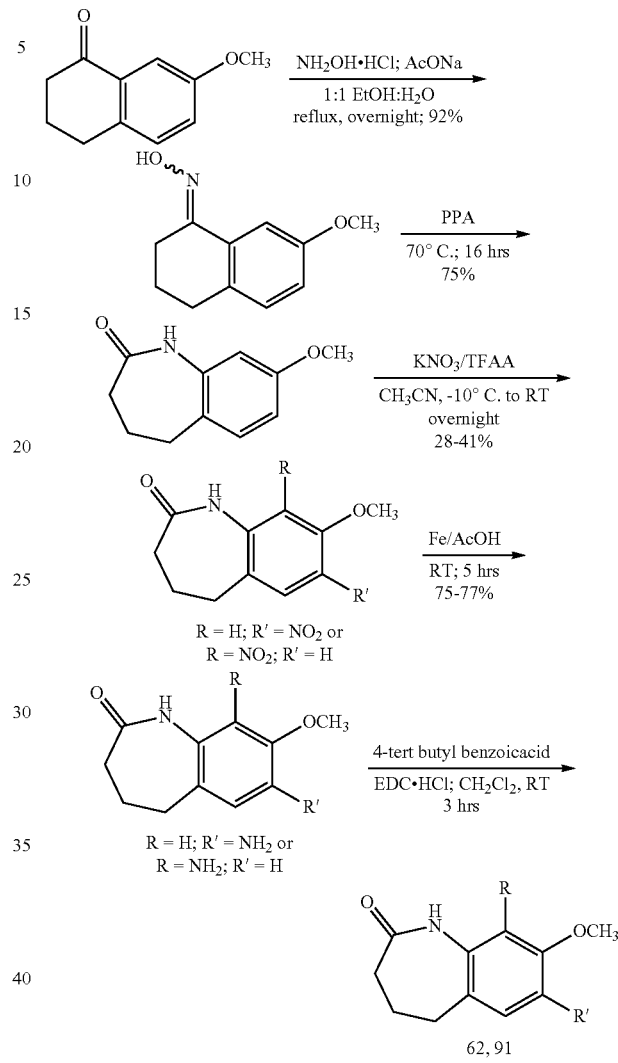

Step-1: 4-(tert-butyl)-3,5-difluorophenol (800 mg, 4.30 mmol) was dissolved in DCM (6 mL) and cooled to 0° C. To this solution, pyridine (0.70 mL, 8.59 mmol) was added followed by trifluoromethanesulfonic anhydride (0.73 mL, 4.30 mmol) drop wise addition at 0° C. and further stirred for 3 h at room temperature. The reaction mixture was diluted with water and extracted with DCM. The organic layer was washed with aq. $NaHCO_3$, dried over $Na_2SO_4$ and concentrated. Purification of crude product was performed on ISCO using pre-packed Silica gel column. Yield: 1.15 g (84%). $^1$H NMR ($CDCl_3$) δ 6.82 (d, J=10.2 Hz, 2H), 1.47 (s, 9H).

Step-2: 4-(tert-Butyl)-3,5-difluorophenyl trifluoromethanesulfonate (0.82 g, 2.58 mmol) was suspended in dry DMF (5 mL). To this solution, dicyanozinc (0.18 g, 1.55 mmol) was added followed by the addition of $Pd(PPh_3)_4$ (0.30 g, 0.26 mmol) at room temperature. The reaction mixture was then heated at 130° C. for 3 h and then filtered. The filtrate was diluted with cold water and extracted with EtOAc. The organic layer was dried over anhydrous $Na_2SO_4$ and concentrated. Yield: 311 mg (62%) was used as such for next step.

Step-3: 4-(tert-Butyl)-3,5-difluorobenzonitrile (311 mg, 1.6 mmol) was dissolved in HBr—AcOH (1:1, 4 mL) and refluxed overnight. The reaction mixture was diluted with water and extracted with EtOAc. The organic layer was dried over anhydrous $Na_2SO_4$ and concentrated. Yield: 184 mg (54%) was used for next step without further purification.

Step-4: Synthesis of 4-(tert-butyl)-3,5-difluoro-N-(3-methoxy-6,7,8,9-tetrahydro-5H-benzo[7]annulen-2-yl)benzamide (90): 3-Methoxy-6,7,8,9-tetrahydro-5H-benzo[7]annulen-2-amine (25 mg, 0.13 mmol) was dissolved in DCM (3 mL). To this solution, 4-tert-butyl 3,5-difluorophenylcarboxylic acid and EDC (30 mg, 0.143 mmol) were added. The reaction mixture was stirred for 5 h at room temperature and was concentrated. Crude product was purified by Silica gel preparative plate. Yield: 24 mg (48%). $^1$H NMR ($CDCl_3$) δ 8.22 (s, 1H), 7.30 (d, J=11.1 Hz, 2H), 6.68 (s, 1H), 3.90 (s, 3H), 2.85-2.61 (m, 4H), 1.81 (d, J=5.7 Hz, 2H), 1.64 (d, J=4.7 Hz, 4H), 1.56-1.38 (m, 9H). ESI-MS: m/z 388 [M+H]$^+$.

Step-1:
7-Methoxy-3,4-dihydronaphthalen-1(2H)-one oxime: 7-Methoxy-3,4-dihydronaphthalen-1(2H)-one (5.00 g, 28.4 mmol) was dissolved in 1:1 ethanol and water (20 mL) and to this solution was added hydroxylamine hydrochloride (2.37 g, 34.0 mmol) followed by sodium acetate (4.66 g, 56.7 mmol). The reaction mixture was heated to reflux for overnight, after completion reaction monitored by TLC, solvent removed under reduced pressure, diluted with 250 mL of ice cold water to precipitate out the compound which was filtered, collected solid was washed with 100 mL deionized water. Yield: 4.99 g (92%). $^1$H NMR ($CDCl_3$) δ 8.65 (s, 1H), 7.42 (d, J=2.7 Hz, 1H), 7.06 (d, J=8.4 Hz, 1H), 6.86 (dd, J=8.4, 2.7 Hz, 1H), 3.81 (s, 3H), 2.80 (t, J=6.7 Hz, 2H), 2.74-2.66 (m, 2H), 1.91-1.80 (m, 2H). ESI-MS: m/z 192 [M+H]$^+$.

Step-2: Synthesis of 8-methoxy-1,3,4,5-tetrahydro-2H-benzo[b]azepin-2-one: 7-methoxy-3,4-dihydronaphthalen-1(2H)-one oxime (1.34 g, 7.0 mmol) was added to PPA (35.6 g, 200 mmol) and reaction mixture stirred overnight at 70° C. The reaction mixture was diluted with ice cold water and stirred for 30 min. It was then extracted with EtOAc and concentrated. Purification of crude product was performed on ISCO using pre-packed Silica gel column. Yield: 1.00 g (75%). $^1$H NMR (CDCl$_3$) δ 7.54 (s, 1H), 7.11 (d, J=8.3 Hz, 1H), 6.69 (dd, J=8.3, 2.6 Hz, 1H), 6.53 (d, J=2.6 Hz, 1H), 3.79 (s, 3H), 2.74 (t, J=7.2 Hz, 2H), 2.36 (t, J=7.3 Hz, 2H), 2.19 (q, J=7.5 Hz, 2H). ESI-MS: m/z 192 [M+H]$^+$.

Step-3: Synthesis of 8-methoxy-9-nitro-4,5-dihydro-1H-benzo[b]azepin-2(3H)-one. 8-methoxy-4,5-dihydro-1H-benzo[b]azepin-2(3H)-one (300 mg, 1.57 mmol) was dissolved in dry CH$_3$CN (5 mL) and was cooled at −10° C. Trifluoroacetic anhydride (0.776 mL, 5.49 mmol) was added to the above solution followed by potassium nitroperoxous acid (174 mg, 1.73 mmol). After overnight stirring at room temperature, the reaction was partitioned between aq. sodium hydroxide and DCM. The organic layer dried over anhydrous Na$_2$SO$_4$, and concentrated. Purification of crude product was performed on ISCO using pre-packed Silica gel column to produce two isomers. 8-Methoxy-9-nitro-4,5-dihydro-1H-benzo[b]azepin-2(3H)-one. Yield: 152 mg (41%). $^1$H NMR (CDCl$_3$) δ 7.30 (d, J=8.6 Hz, 1H), 6.83 (d, J=8.6 Hz, 1H), 3.92 (s, 3H), 2.80 (t, J=7.2 Hz, 2H), 2.38 (t, J=7.2 Hz, 2H), 2.23 (p, J=7.2 Hz, 2H). ESI-MS: m/z 237 [M+H]$^+$. 8-Methoxy-7-nitro-4,5-dihydro-1H-benzo[b]azepin-2(3H)-one. Yield: 104 mg (28%). $^1$H NMR (CDCl$_3$) δ 8.30 (s, 1H), 7.84 (s, 1H), 6.68 (s, 1H), 3.97 (d, J=0.9 Hz, 3H), 2.81 (t, J=7.2 Hz, 2H), 2.43 (t, J=7.3 Hz, 2H), 2.26 (p, J=7.2 Hz, 2H). ESI-MS: m/z 237 [M+H]$^+$.

Step-4: (a) Synthesis of 9-amino-8-methoxy-1,3,4,5-tetrahydro-2H-benzo[b]azepin-2-one: 8-methoxy-9-nitro-4,5-dihydro-1H-benzo[b]azepin-2(3H)-one (80 mg, 0.34 mmol) was dissolved in AcOH (969 μL, 16.93 mmol) and to this was added 3 drops of deionized water followed by the addition of Fe (95 mg, 1.69 mmol). The reaction mixture was stirred 5 h at room temperature. The reaction mixture was filtered through short pad of celite and washed with EtOAc. The filtrate was diluted with water and extracted with EtOAc. The organic layer was washed with aq. NaHCO$_3$, dried over anhydrous Na$_2$SO$_4$ and concentrated. Purification of crude product was performed on pre-packed Silica gel column. Yield: 46 mg (66%). $^1$H NMR (CDCl$_3$) δ 7.26 (s, 1H), 6.64 (d, J=8.2 Hz, 1H), 6.58 (d, J=8.2 Hz, 1H), 3.86 (s, 3H), 2.71 (t, J=7.2 Hz, 2H), 2.34 (t, J=7.2 Hz, 2H), 2.16 (p, J=7.0 Hz, 2H). ESI-MS: m/z 207 [M+H]$^+$.

Step-4: (b) Synthesis of 7-amino-8-methoxy-1,3,4,5-tetrahydro-2H-benzo[b]azepin-2-one: 8-methoxy-7-nitro-4,5-dihydro-1H-benzo[b]azepin-2(3H)-one (44 mg, 0.19 mmol) was dissolved in AcOH (559 μL, 9.31 mmol) and to this was added 3 drops of deionized water followed by the addition of Fe (52 mg, 0.93 mmol). The reaction mixture was stirred 5 h at room temperature. The reaction mixture was filtered through short pad celite and washed with EtOAc. The filtrate was diluted with water and extracted with EtOAc. The organic layer was washed with aq. NaHCO$_3$, dried over anhydrous Na$_2$SO$_4$ and concentrated. Purification of crude product was performed on ISCO using pre-packed Silica gel column. Yield: 30 mg (77%). $^1$H NMR (CDCl$_3$) δ 6.56 (s, 1H), 6.43 (s, 1H), 3.83 (d, J=1.0 Hz, 3H), 2.66 (t, J=7.2 Hz, 2H), 2.32 (t, J=7.2 Hz, 2H), 2.26-2.06 (m, 2H). ESI-MS: m/z 207 [M+H]$^+$.

Step 5: (a) Synthesis of 4-(tert-butyl)-N-(8-methoxy-2-oxo-2,3,4,5-tetrahydro-1H-benzo[b]azepin-9-yl)benzamide (62): 9-Amino-8-methoxy-4,5-dihydro-1H-benzo[b]azepin-2(3H)-one (11 mg, 0.053 mmol) was dissolved in 3 mL of anhydrous DCM and to this solution was added 4-(tert-butyl)benzoic acid (14.3 mg, 0.080 mmol) followed by EDC (22.5 mg, 0.117 mmol). The reaction mixture was stirred overnight at room temperature, diluted with water and extracted with DCM. The organic layer was dried over anhydrous Na$_2$SO$_4$ and concentrated. The product was purified on a Silica gel preparative plate. Yield: 5 mg (26%). $^1$H NMR (CDCl$_3$) δ 7.87 (d, J=8.5 Hz, 2H), 7.52 (d, J=8.5 Hz, 2H), 7.09 (d, J=8.4 Hz, 1H), 6.73 (d, J=8.5 Hz, 1H), 3.87 (s, 3H), 2.82 (t, J=7.0 Hz, 2H), 2.26 (d, J=6.3 Hz, 2H), 2.18 (d, J=9.8 Hz, 2H), 1.36 (s, 9H). HR-ESIMS: m/z 367.2016 [M+H]$^+$ calcd for C$_{22}$H$_{27}$N$_2$O$_3$, found 367.2013. HPLC Purity: 100% (Retention Time=10.5 min).

Step-5: (b) Synthesis of 4-(tert-butyl)-N-(8-methoxy-2-oxo-2,3,4,5-tetrahydro-1H-benzo[b]azepin-7-yl)benzamide (91): 7-Amino-8-methoxy-4,5-dihydro-1H-benzo[b]azepin-2(3H)-one (14.70 mg, 0.071 mmol) was dissolved in 2 mL of anhydrous DCM and to this solution was added 4-(tert-butyl)benzoic acid (15.2 mg, 0.086 mmol) followed by EDC (30.1 mg, 0.157 mmol). The reaction mixture was stirred 3 h at room temperature, diluted with water and extracted with DCM. The organic layer was dried over anhydrous Na$_2$SO$_4$ and concentrated. The product was purified on a Silica gel preparative plate. Yield: 11 mg (42%). $^1$H NMR (CDCl$_3$) δ 8.46 (s, 2H), 7.88-7.77 (m, 2H), 7.57-7.49 (m, 2H), 3.91 (s, 3H), 2.79 (t, J=7.1 Hz, 2H), 2.36 (t, J=7.2 Hz, 2H), 2.24 (q, J=7.1 Hz, 2H), 1.36 (s, 9H). HR-ESI MS: m/z 367.2016 [M+H]$^+$ calcd for C$_{22}$H$_{27}$N$_2$O$_3$, found 367.2011. HPLC Purity: 97% (Retention Time=11.1 min).

r. Synthesis of Compound 63

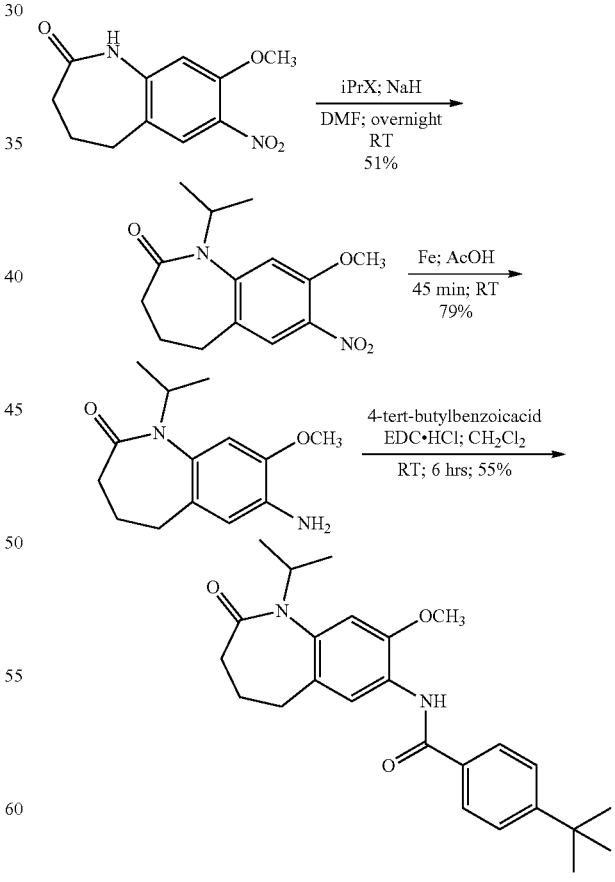

Step-1: Synthesis of 1-isopropyl-8-methoxy-7-nitro-1,3,4,5-tetrahydro-2H-benzo[b]azepin-2-one: 8-Methoxy-7-nitro-4,5-dihydro-1H-benzo[b]azepin-2(3H)-one (86 mg, 0.36 mmol) was dissolved in anhydrous DMF (2 mL) to this solution was added NaH (13.1 mg, 0.55 mmol) portion wise at 0° C. followed by 2-iodopropane (124 mg, 0.73 mmol). The reaction mixture was stirred 3 h at room temperature, diluted with water and extracted with EtOAc. The organic layer was dried over anhydrous $Na_2SO_4$ and concentrated. Purification of crude product was performed on ISCO using pre-packed Silica gel column. Yield: 51.7 mg (51%). $^1$H NMR (CDCl$_3$) δ 7.76 (s, 1H), 6.89 (s, 1H), 4.85-4.78 (m, 1H), 2.35 (m, 2H), 2.30-2.28 (s, 2H), 1.14 (d, J=6.9 Hz, 6H), 1.08 (d, J=7.0 Hz, 3H). ESI-MS: m/z 279 [M+H]$^+$.

Step-2: Synthesis of 7-amino-1-isopropyl-8-methoxy-1,3,4,5-tetrahydro-2H-benzo[b]azepin-2-one: 1-Isopropyl-8-methoxy-7-nitro-4,5-dihydro-H-benzo[b]azepin-2(3H)-one (37 mg, 0.133 mmol) was dissolved in AcOH (3 mL) and to this solution Fe (37 mg, 0.66 mmol) was added. The reaction mixture was stirred at room temperature for 45 min, filtered through short pad of celite and washed with EtOAc. The filtrate was diluted with water and extracted with EtOAc. The organic layer was washed with aq. NaHCO$_3$, dried over anhydrous Na$_2$SO$_4$ and concentrated. The material was used as such for next step. Yield: 26 mg (79%). $^1$H NMR (CDCl$_3$) δ 6.53 (s, 1H), 6.50 (s, 1H), 3.81 (s, 3H), 3.61 (s, 1H), 2.90 (s, 2H), 2.66-2.56 (m, 2H), 1.66-1.61 (m, 2H), 1.20-1.14 (m, 6H). ESI-MS: m/z 249 [M+H]$^+$.

Step-3: Synthesis of 4-(tert-butyl)-N-(1-isopropyl-8-methoxy-2-oxo-2,3,4,5-tetrahydro-1H-benzo[b]azepin-7-yl)benzamide (63): 7-Amino-1-isopropyl-8-methoxy-4,5-dihydro-1H-benzo[b]azepin-2(3H)-one (26.0 mg, 0.105 mmol) was dissolved in dry DCM (3 mL) and to this solution was added 4-(tert-butyl)benzoic acid (21 mg, 0.115 mmol) EDC (44.2 mg, 0.230 mmol). The reaction mixture was stirred for 6 h at room temperature, diluted with water and extracted with DCM. The organic layer was dried over anhydrous Na$_2$SO$_4$ filtered and concentrated under reduced pressure. The product was purified on a Silica gel preparative plate. Yield: 13.26 mg (31%). $^1$H NMR (CDCl$_3$) δ 8.50 (s, 1H), 8.42 (s, 1H), 8.02-7.70 (m, 2H), 7.66-7.34 (m, 2H), 6.74 (s, 1H), 4.85 (hept, J=6.9 Hz, 1H), 3.92 (s, 3H), 2.86-2.48 (m, 2H), 2.38-1.83 (m, 4H), 1.36 (s, 9H), 1.08 (d, J=7.0 Hz, 6H). HR-ESI MS: m/z 409.2485 [M+H]$^+$ calcd for C$_{25}$H$_{33}$N$_2$O$_3$, found 409.2480. HPLC Purity: 99% (Retention Time=15.54 min).

s. Synthesis of Compound 64

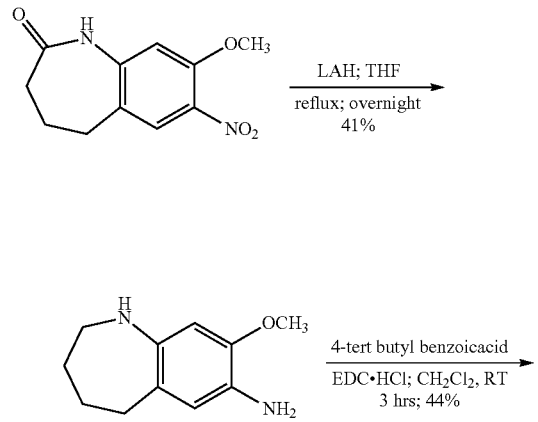

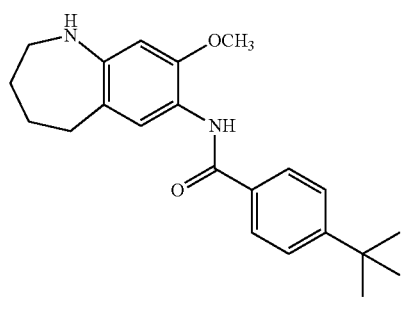

64

Step-1: Synthesis of 8-methoxy-2,3,4,5-tetrahydro-1H-benzo[b]azepin-7-amine: 8-methoxy-7-nitro-4,5-dihydro-1H-benzo[b]azepin-2(3H)-one (134 mg, 0.57 mmol) was dissolved in anhydrous THF (4 mL) and to this solution was added LAH (43 mg, 1.13 mmol) at 0° C. The reaction mixture was refluxed overnight. It was diluted with 0.2 mL water and 0.4 mL 1M NaOH solution and stirred for 15 min. The aqueous layer was extracted with EtOAc. The organic layer dried over anhydrous Na$_2$SO$_4$ and concentrated. Purification of crude product was performed on ISCO using pre-packed Silica gel column. Yield: 45 mg (41%). $^1$H NMR (CDCl$_3$) δ 6.52 (s, 1H), 6.28 (s, 1H), 3.79 (s, 3H), 3.01-2.92 (m, 2H), 2.69-2.59 (m, 2H), 1.76 (p, J=5.7 Hz, 2H), 1.58 (q, J=5.6 Hz, 2H). ESI-MS: m/z 193 [M+H]$^+$.

Step-2: Synthesis of 4-(tert-butyl)-N-(8-methoxy-2,3,4,5-tetrahydro-1H-benzo[b]azepin-7-yl)benzamide (64): 8-Methoxy-2,3,4,5-tetrahydro-1H-benzo[b]azepin-7-amine (19 mg, 0.096 mmol) was dissolved in anhydrous DCM (2 mL) and to this solution was added 4-(tert-butyl)benzoic acid (19 mg, 0.11 mmol) followed by EDC (41 mg, 0.21 mmol). The reaction mixture was stirred for 3 h at room temperature and concentrated. The product was purified on a Silica gel preparative plate. Yield: 15 mg (44%). $^1$H NMR (CDCl$_3$) δ 8.29 (bs, 1H), 8.26 (s, 1H), 7.81 (d, J=8.6 Hz, 2H), 7.49 (d, J=8.6 Hz, 2H), 6.33 (s, 1H), 3.85 (s, 3H), 3.09-2.97 (m, 2H), 2.82-2.71 (m, 2H), 1.78 (M, 2H), 1.64 (q, J=5.4 Hz, 2H), 1.35 (s, 9H). ESI-MS: m/z 353 [M+H]$^+$.

t. Synthesis of Compound 65

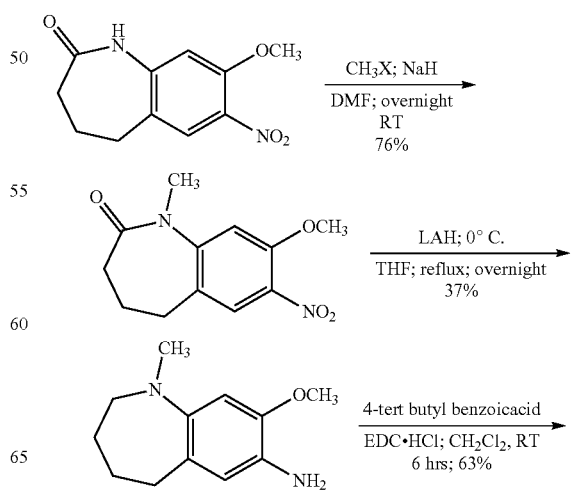

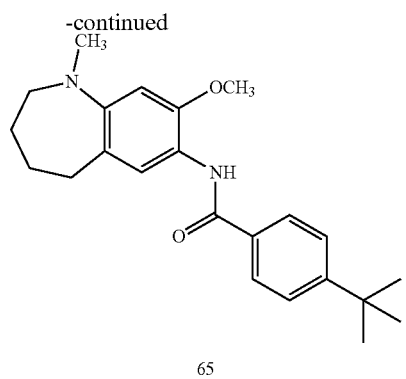

65

Step-1: Synthesis of 8-methoxy-1-methyl-7-nitro-1,3,4,5-tetrahydro-2H-benzo[b]azepin-2-one: 8-Methoxy-7-nitro-4,5-dihydro-1H-benzo[b]azepin-2(3H)-one (96 mg, 0.41 mmol) was dissolved in anhydrous DMF (3 mL). To this solution, NaH (15 mg, 0.61 mmol) was added at 0° C. followed by iodomethane (0.05 mL, 0.81 mmol). The reaction mixture was stirred overnight at room temperature, diluted with ice cold water and extracted with EtOAc. The organic layer was dried over anhydrous $Na_2SO_4$ and concentrated. The crude product was purified on Silica gel pre-packed ISCO column. $^1$H NMR ($CDCl_3$) δ 7.77 (s, 1H), 6.83 (s, 1H), 3.97 (s, 3H), 3.37 (s, 3H), 2.71 (t, J=7.2 Hz, 2H), 2.34 (t, J=7.2 Hz, 2H), 2.18 (p, J=7.1 Hz, 2H). ESI-MS: m/z 251 [M+H]$^+$.

Step-2: Synthesis of 8-methoxy-1-methyl-2,3,4,5-tetrahydro-1H-benzo[b]azepin-7-amine: 8-Methoxy-1-methyl-7-nitro-4,5-dihydro-1H-benzo[b]azepin-2(3H)-one (37 mg, 0.15 mmol) was dissolved in dry THF (4 mL) and to it was added aluminum(III) lithium hydride (11 mg, 0.30 mmol) at 0° C. Further, the reaction mixture was refluxed overnight and cooled to room temperature. Solvent was evaporated and crude product was purified on preparative Silica gel plate. $^1$H NMR ($CDCl_3$) δ 6.52 (s, 1H), 6.51 (s, 1H), 3.84 (s, 3H), 2.83 (d, J=3.3 Hz, 3H), 2.83-2.74 (m, 2H), 2.72-2.59 (m, 2H), 1.82-1.69 (m, 2H), 1.58-1.48 (m, 2H). ESI-MS: m/z 207 [M+H]$^+$.

Step-3: Synthesis of 4-(tert-butyl)-N-(8-methoxy-1-methyl-2,3,4,5-tetrahydro-1H-benzo[b]azepin-7-yl)benzamide (65): 8-Methoxy-1-methyl-2,3,4,5-tetrahydro-1H-benzo[b]azepin-7-amine (10 mg, 0.05 mmol) was dissolved in dry DCM (2 mL) and to this solution was added 4-(tert-butyl)benzoic acid (9.5 mg, 0.053 mmol) and EDC (20 mg, 0.11 mmol). The reaction mixture was stirred overnight at room temperature and concentrated. The product was purified on a Silica gel preparative plate. Yield: 7 mg (38%). $^1$H NMR ($CDCl_3$) δ 8.32 (s, 1H), 8.27 (s, 1H), 7.81 (d, J=8.7 Hz, 2H), 7.50 (d, J=8.7 Hz, 2H), 6.53 (s, 1H), 3.90 (s, 3H), 2.89 (d, J=4.3 Hz, 3H), 2.78 (d, J=11.6 Hz, 2H), 1.82-1.66 (m, 2H), 1.79-1.76 (m, 2H), 1.56-1.54 (m, 2H), 1.25 (s, 9H). HR-ESIMS: m/z 367.2380 [M+H]$^+$ calcd for $C_{23}H_{31}N_2O_2$, found 367.2375. HPLC Purity: 99% (Retention Time=11.75 min).

3. Evaluation of Antiviral Activity Against Chikungunya Virus

The compounds below in Table 1 were synthesized with methods identical or analogous to those described herein. The requisite starting materials were commercially available, described in the literature, or readily synthesized by one skilled in the art of organic synthesis. Table 1 below illustrates the effects of the disclosed compounds on Chikungunya virus.

TABLE 1

| No. | Structure | MW | $EC_{90}$ (μM) CHIKV | $CC_{50}$ (μM) CHIKV |
|---|---|---|---|---|
| 3 | [structure with OCH$_3$, NH, benzoyl] | 351.5 | 1.5 | >30 |
| 12 | [structure with CN, NH, 4-tert-butylbenzoyl] | 346.4 | 4.4 | 17 |

TABLE 1-continued

| No. | Structure | MW | EC$_{90}$ (µM) CHIKV | CC$_{50}$ (µM) CHIKV |
|---|---|---|---|---|
| 13 | 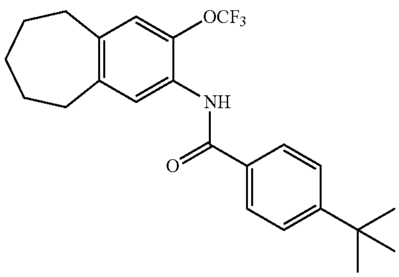 [SMILES: CC(C)(C)c1ccc(C(=O)Nc2cc3c(cc2OC(F)(F)F)CCCCC3)cc1] | 405.5 | 13.7 | >25 |
| 14 | 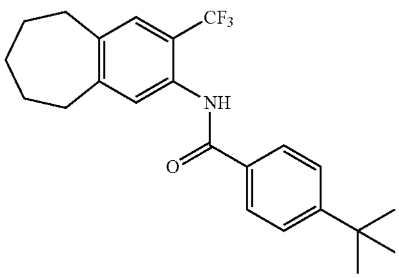 [SMILES: CC(C)(C)c1ccc(C(=O)Nc2cc3c(cc2C(F)(F)F)CCCCC3)cc1] | 389.5 | >30 | >30 |
| 15 | 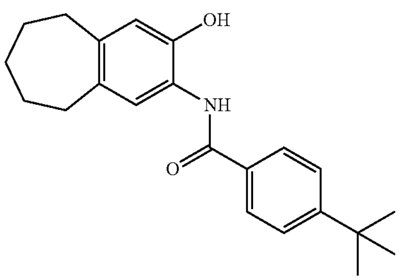 | 337.5 | 0.4 | >30 |
| 16 | 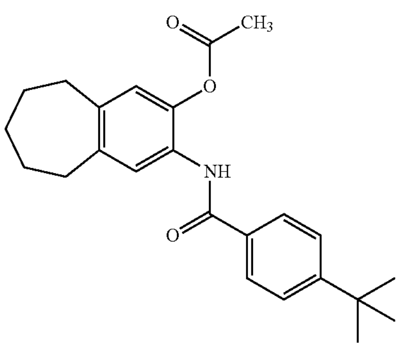 [SMILES: CC(=O)Oc1cc2c(cc1NC(=O)c1ccc(C(C)(C)C)cc1)CCCCC2] | 379.5 | 2.8 | >30 |
| 17 | 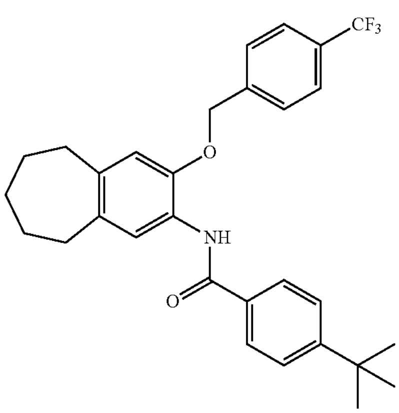 [SMILES: CC(C)(C)c1ccc(C(=O)Nc2cc3c(cc2OCc2ccc(C(F)(F)F)cc2)CCCCC3)cc1] | 495.6 | >30 | >30 |

TABLE 1-continued

| No. | Structure | MW | EC$_{90}$ (μM) CHIKV | CC$_{50}$ (μM) CHIKV |
|---|---|---|---|---|
| 19 | 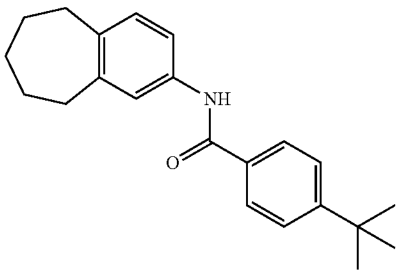 [SMILES: CC(C)(C)c1ccc(C(=O)Nc2ccc3c(c2)CCCCC3)cc1] | 321.5 | 0.7 | 79.1 |
| 20 | 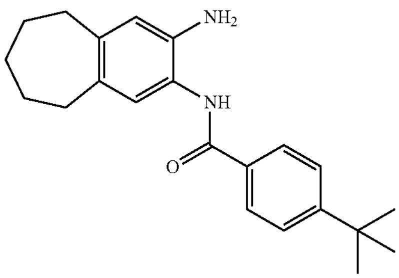 [SMILES: CC(C)(C)c1ccc(C(=O)Nc2cc3c(cc2N)CCCCC3)cc1] | 336.5 | >30 | >30 |
| 21 | 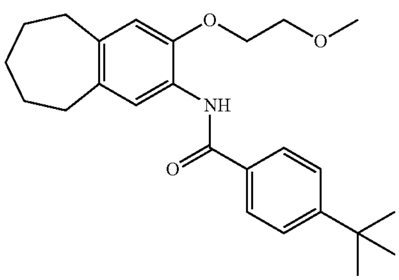 [SMILES: COCCOc1cc2c(cc1NC(=O)c1ccc(C(C)(C)C)cc1)CCCCC2] | 395.5 | >30 | >30 |
| 22 | 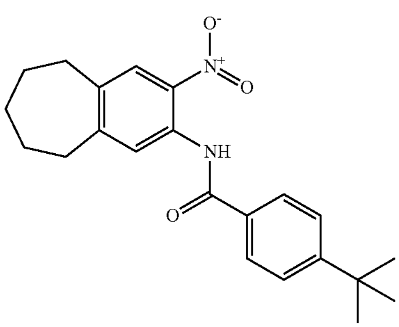 [SMILES: CC(C)(C)c1ccc(C(=O)Nc2cc3c(cc2[N+](=O)[O-])CCCCC3)cc1] | 366.5 | >30 | >30 |
| 23 | 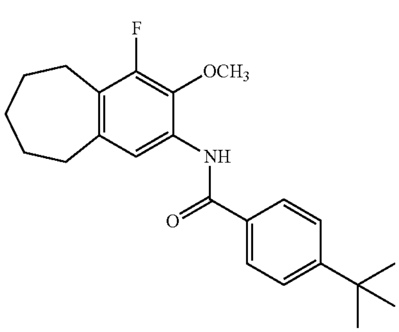 [SMILES: COc1c(NC(=O)c2ccc(C(C)(C)C)cc2)cc2c(c1F)CCCCC2] | 369.5 | 12.5 | >30 |

TABLE 1-continued

| No. | Structure | MW | EC$_{90}$ (μM) CHIKV | CC$_{50}$ (μM) CHIKV |
|---|---|---|---|---|
| 24 | 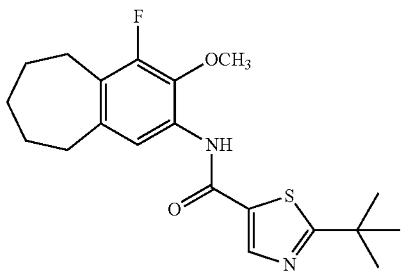 [SMILES: COc1c(NC(=O)c2cnc(C(C)(C)C)s2)cc2c(c1F)CCCCC2] | 376.5 | >10 | >30 |
| 25 | 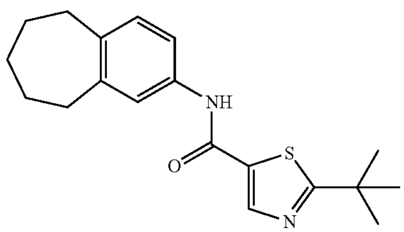 [SMILES: CC(C)(C)c1ncc(C(=O)Nc2ccc3c(c2)CCCCC3)s1] | 328.5 | 22.6 | 15.7 |
| 26 | 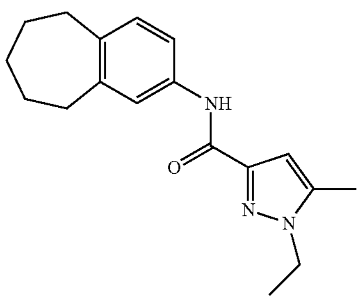 [SMILES: CCn1nc(C(=O)Nc2ccc3c(c2)CCCCC3)cc1C] | 397.4 | >30 | >30 |
| 27 | 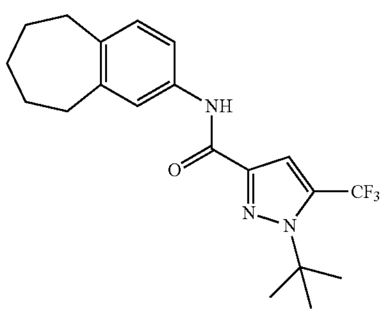 [SMILES: CC(C)(C)n1nc(C(=O)Nc2ccc3c(c2)CCCCC3)cc1C(F)(F)F] | 379.4 | >10 | >30 |
| 28 | 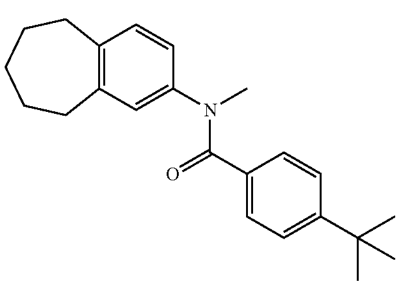 [SMILES: CN(C(=O)c1ccc(C(C)(C)C)cc1)c1ccc2c(c1)CCCCC2] | 335.5 | >10 | >30 |

TABLE 1-continued

| No. | Structure | MW | EC$_{90}$ (μM) CHIKV | CC$_{50}$ (μM) CHIKV |
|---|---|---|---|---|
| 29 | 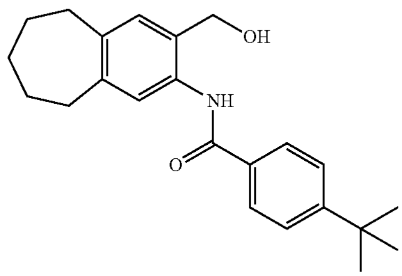 [SMILES: CC(C)(C)c1ccc(C(=O)Nc2cc3c(cc2CO)CCCCC3)cc1] | 351.5 | >10 | >30 |
| 30 | 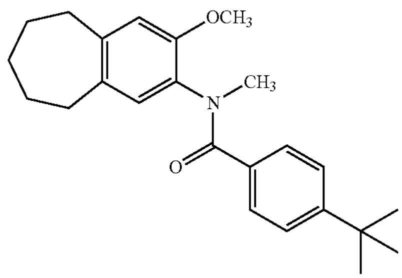 [SMILES: COc1cc2c(cc1N(C)C(=O)c1ccc(C(C)(C)C)cc1)CCCCC2] | 365.5 | 14.5 | >30 |
| 31 | 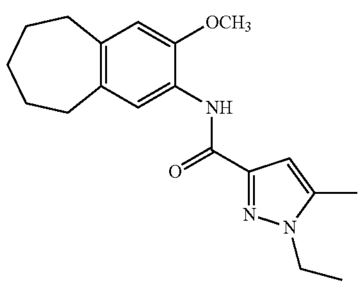 [SMILES: CCn1nc(C(=O)Nc2cc3c(cc2OC)CCCCC3)cc1C] | 327.4 | 0.79 | >30 |
| 32 | 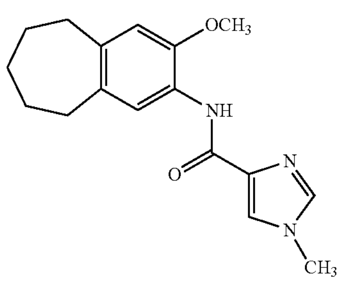 [SMILES: COc1cc2c(cc1NC(=O)c1cn(C)cn1)CCCCC2] | 299.3 | 55.6 | >30 |
| 33 | 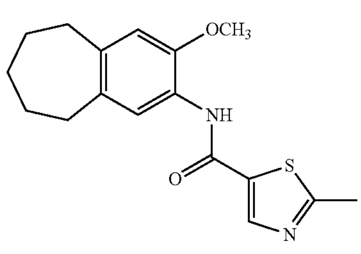 [SMILES: COc1cc2c(cc1NC(=O)c1cnc(C)s1)CCCCC2] | 316.4 | >30 | >30 |

TABLE 1-continued

| No. | Structure | MW | EC$_{90}$ (μM) CHIKV | CC$_{50}$ (μM) CHIKV |
|---|---|---|---|---|
| 36 | 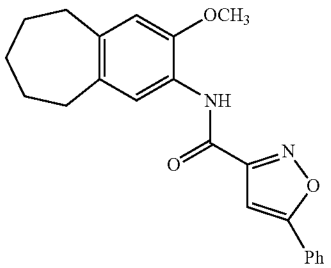 [SMILES: COc1cc2c(cc1NC(=O)c1cc(-c3ccccc3)on1)CCCCC2] | 362.4 | 9 | >30 |
| 37 | 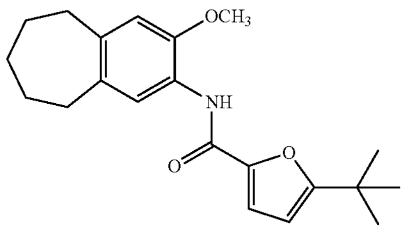 [SMILES: COc1cc2c(cc1NC(=O)c1ccc(C(C)(C)C)o1)CCCCC2] | 341.4 | 23.2 | >30 |
| 38 | 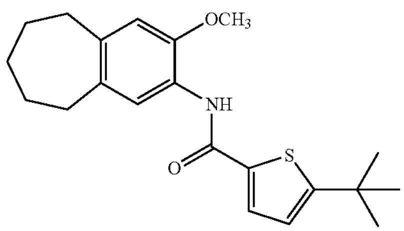 [SMILES: COc1cc2c(cc1NC(=O)c1ccc(C(C)(C)C)s1)CCCCC2] | 357.5 | 3.1 | 32 |
| 39 | 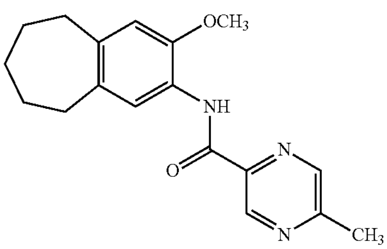 [SMILES: COc1cc2c(cc1NC(=O)c1cnc(C)cn1)CCCCC2] | 311.3 | >30 | >30 |
| 40 | 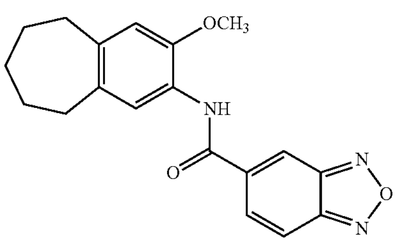 [SMILES: COc1cc2c(cc1NC(=O)c1ccc3nonc3c1)CCCCC2] | 337.3 | >30 | >30 |
| 41 | 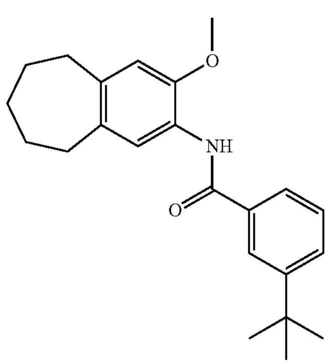 [SMILES: COc1cc2c(cc1NC(=O)c1cccc(C(C)(C)C)c1)CCCCC2] | 351.5 | 34.1 | >30 |

TABLE 1-continued

| No. | Structure | MW | EC$_{90}$ (µM) CHIKV | CC$_{50}$ (µM) CHIKV |
|---|---|---|---|---|
| 42 | 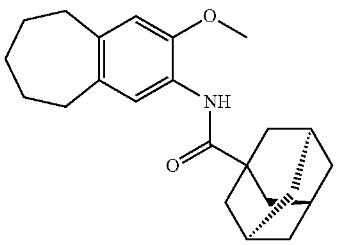 [SMILES: COc1cc2c(cc1NC(=O)C13C[C@H]4C[C@@H](C1)C[C@@H](C3)C4)CCCCC2] | 353.5 | 12.1 | >30 |
| 43 | 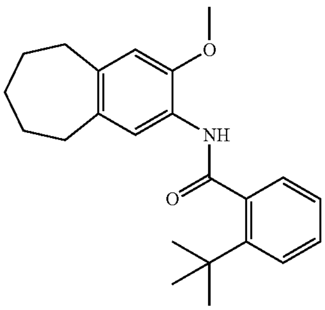 [SMILES: COc1cc2c(cc1NC(=O)c1ccccc1C(C)(C)C)CCCCC2] | 351.5 | 3.2 | >30 |
| 44 | 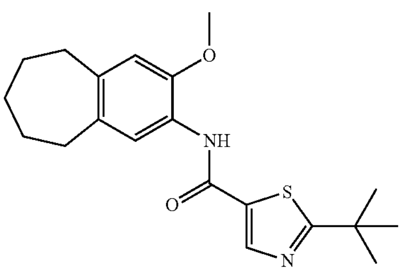 [SMILES: COc1cc2c(cc1NC(=O)c1cnc(C(C)(C)C)s1)CCCCC2] | 358.5 | 1.2 | >30 |
| 45 | 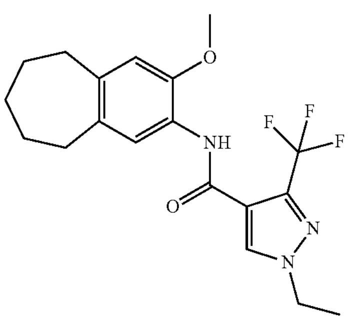 [SMILES: CCn1cc(C(=O)Nc2cc3c(cc2OC)CCCCC3)c(C(F)(F)F)n1] | 381.4 | 2.95 | 34.5 |
| 46 | 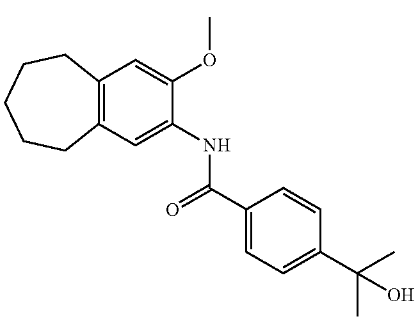 [SMILES: COc1cc2c(cc1NC(=O)c1ccc(C(C)(C)O)cc1)CCCCC2] | 353.5 | 2.45 | 79.2 |

TABLE 1-continued

| No. | Structure | MW | EC₉₀ (μM) CHIKV | CC₅₀ (μM) CHIKV |
|---|---|---|---|---|
| 47 | 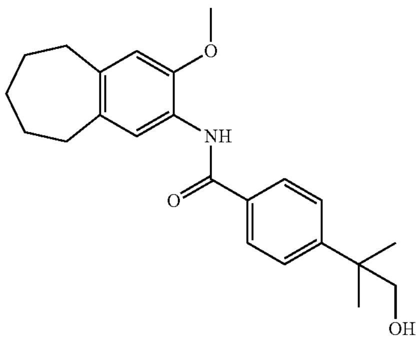 [SMILES: COc1cc2c(cc1NC(=O)c1ccc(C(C)(C)CO)cc1)CCCCC2] | 367.5 | 7.1 | 96.3 |
| 48 | 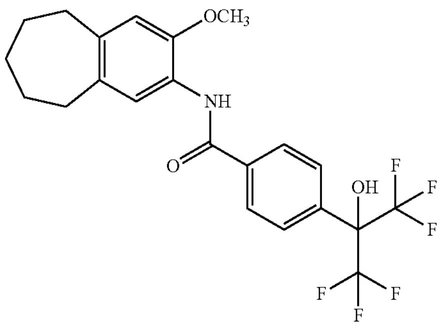 [SMILES: COc1cc2c(cc1NC(=O)c1ccc(C(O)(C(F)(F)F)C(F)(F)F)cc1)CCCCC2] | 461.4 | 2.8 | 28.9 |
| 49 | 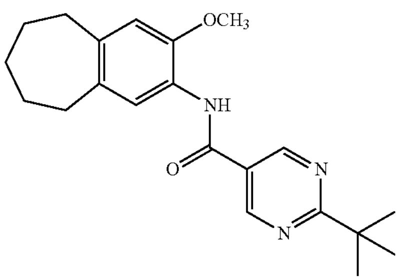 [SMILES: COc1cc2c(cc1NC(=O)c1cnc(C(C)(C)C)nc1)CCCCC2] | 353.5 | 2.99 | 37.6 |
| 50 | 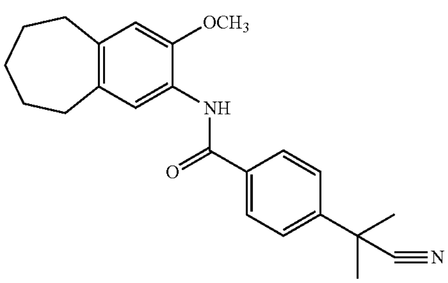 [SMILES: COc1cc2c(cc1NC(=O)c1ccc(C(C)(C)C#N)cc1)CCCCC2] | 362.5 | 1.16 | 3.57 |
| 51 | 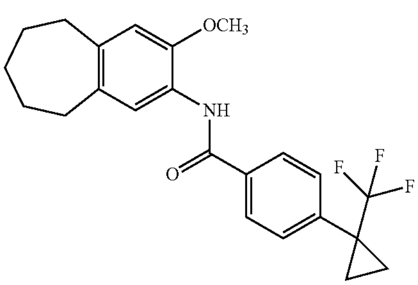 [SMILES: COc1cc2c(cc1NC(=O)c1ccc(C3(C(F)(F)F)CC3)cc1)CCCCC2] | 403.5 | 1.3 | >30 |

TABLE 1-continued

| No. | Structure | MW | EC$_{90}$ (μM) CHIKV | CC$_{50}$ (μM) CHIKV |
|---|---|---|---|---|
| 52 | 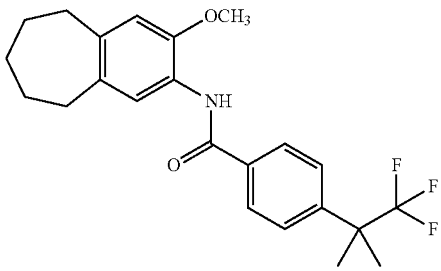 [SMILES: COc1cc2c(cc1NC(=O)c1ccc(C(C)(C)C(F)(F)F)cc1)CCCCC2] | 405.5 | 3.47 | 19.08 |
| 53 | 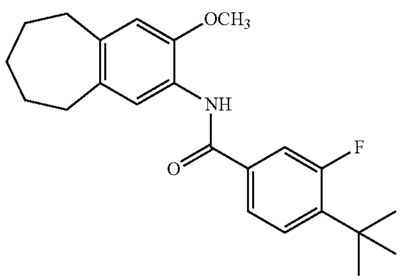 [SMILES: COc1cc2c(cc1NC(=O)c1ccc(C(C)(C)C)c(F)c1)CCCCC2] | 369.5 | 2.24 | >30 |
| 54 | 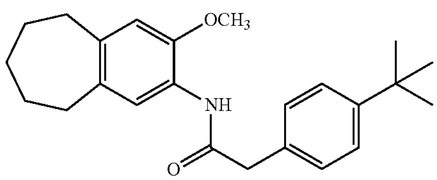 [SMILES: COc1cc2c(cc1NC(=O)Cc1ccc(C(C)(C)C)cc1)CCCCC2] | 365.5 | 42.93 | >30 |
| 55 | 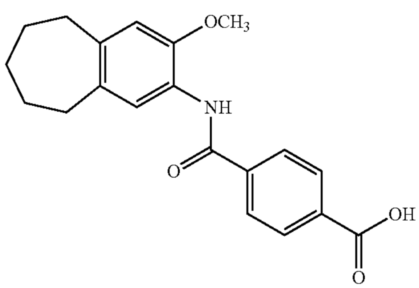 [SMILES: COc1cc2c(cc1NC(=O)c1ccc(C(=O)O)cc1)CCCCC2] | 339.4 | >10 | >30 |
| 56 | 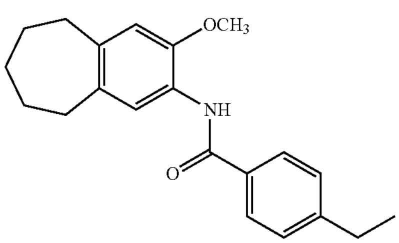 [SMILES: CCc1ccc(C(=O)Nc2cc3c(cc2OC)CCCCC3)cc1] | 323.4 | >10 | >30 |
| 57 | 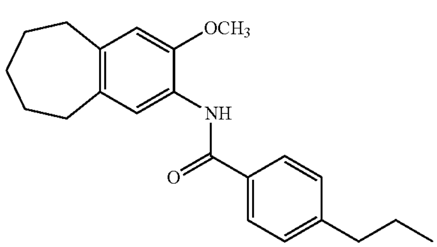 [SMILES: CCCc1ccc(C(=O)Nc2cc3c(cc2OC)CCCCC3)cc1] | 337.5 | >10 | >30 |

TABLE 1-continued

| No. | Structure | MW | EC$_{90}$ (μM) CHIKV | CC$_{50}$ (μM) CHIKV |
| --- | --- | --- | --- | --- |
| 58 | 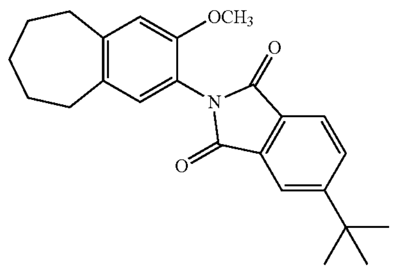 [SMILES: COc1cc2c(cc1N1C(=O)c3ccc(C(C)(C)C)cc3C1=O)CCCCC2] | 377.5 | | |
| 59 | 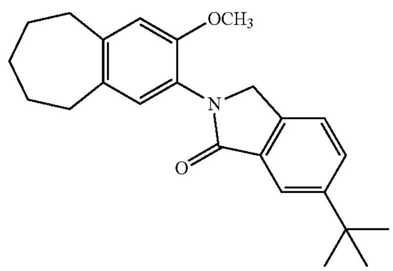 [SMILES: COc1cc2c(cc1N1Cc3ccc(C(C)(C)C)cc3C1=O)CCCCC2] | 363.5 | >10 | >30 |
| 60 | 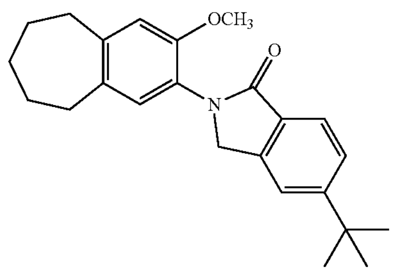 [SMILES: COc1cc2c(cc1N1Cc3cc(C(C)(C)C)ccc3C1=O)CCCCC2] | 363.5 | >10 | >30 |
| 61 | 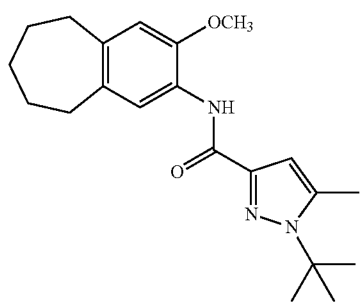 [SMILES: COc1cc2c(cc1NC(=O)c1cc(C)n(C(C)(C)C)n1)CCCCC2] | 355.5 | 5.64 | >30 |
| 62 | 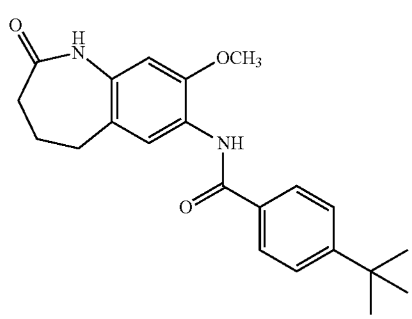 [SMILES: COc1cc2c(cc1NC(=O)c1ccc(C(C)(C)C)cc1)CCCC(=O)N2] | 366.5 | >30 | >30 |

TABLE 1-continued

| No. | Structure | MW | EC$_{90}$ (μM) CHIKV | CC$_{50}$ (μM) CHIKV |
|---|---|---|---|---|
| 63 | 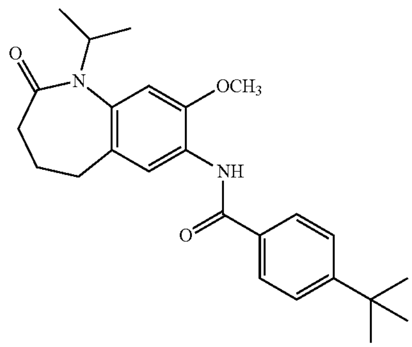 [SMILES: COc1cc2c(cc1NC(=O)c1ccc(C(C)(C)C)cc1)CCCC(=O)N2C(C)C] | 408.5 | >30 | >30 |
| 64 | 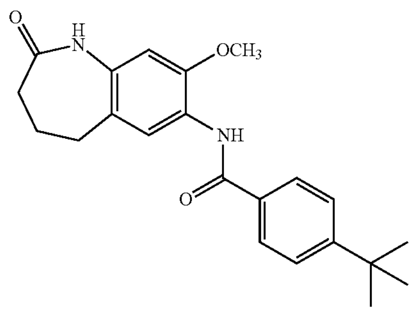 [SMILES: COc1cc2c(cc1NC(=O)c1ccc(C(C)(C)C)cc1)CCCC(=O)N2] | 352.5 | 3.3 | >30 |
| 65 | 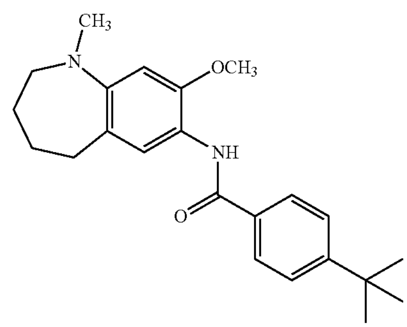 [SMILES: COc1cc2c(cc1NC(=O)c1ccc(C(C)(C)C)cc1)CCCCN2C] | 366.5 | >30 | >30 |
| 66 | 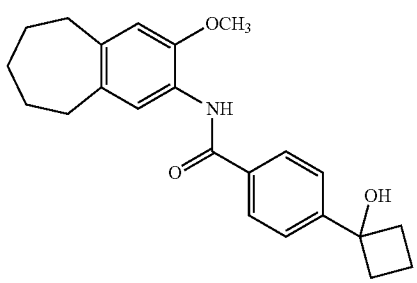 [SMILES: COc1cc2c(cc1NC(=O)c1ccc(C3(O)CCC3)cc1)CCCCC2] | 365.5 | >10 | >30 |
| 67 | 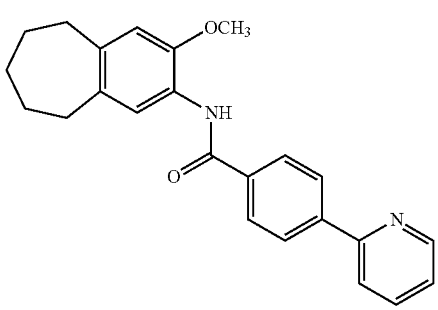 [SMILES: COc1cc2c(cc1NC(=O)c1ccc(-c3ccccn3)cc1)CCCCC2] | 372.5 | >10 | >30 |

TABLE 1-continued

| No. | Structure | MW | EC$_{90}$ (μM) CHIKV | CC$_{50}$ (μM) CHIKV |
|---|---|---|---|---|
| 68 | 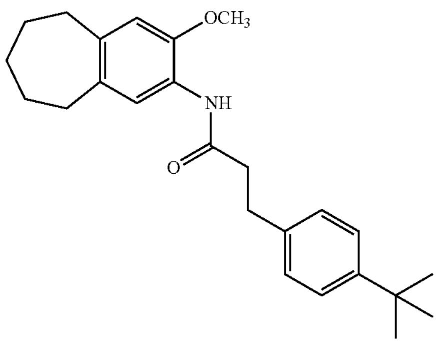 [SMILES: COc1cc2c(cc1NC(=O)CCc1ccc(C(C)(C)C)cc1)CCCCC2] | 379.5 | >10 | >30 |
| 69 | 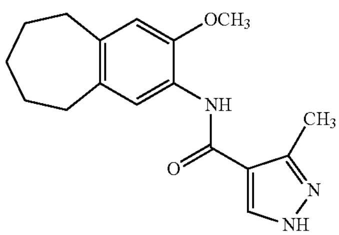 [SMILES: COc1cc2c(cc1NC(=O)c1c[nH]nc1C)CCCCC2] | 299.4 | 3.1 | >30 |
| 70 | 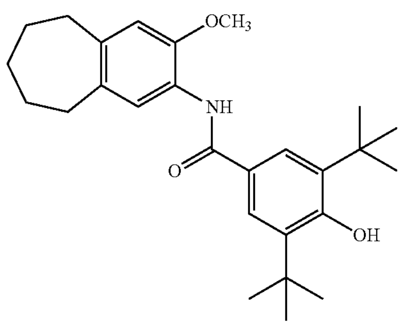 [SMILES: COc1cc2c(cc1NC(=O)c1cc(C(C)(C)C)c(O)c(C(C)(C)C)c1)CCCCC2] | 423.6 | 44.8 | >30 |
| 71 | 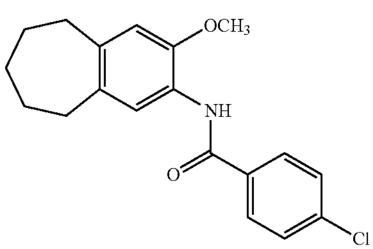 [SMILES: COc1cc2c(cc1NC(=O)c1ccc(Cl)cc1)CCCCC2] | 329.8 | 6.4 | >30 |
| 72 | 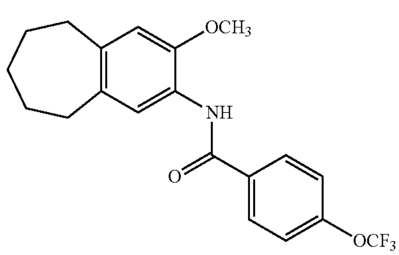 [SMILES: COc1cc2c(cc1NC(=O)c1ccc(OC(F)(F)F)cc1)CCCCC2] | 379.4 | 3.3 | >30 |

TABLE 1-continued

| No. | Structure | MW | EC$_{90}$ (μM) CHIKV | CC$_{50}$ (μM) CHIKV |
|---|---|---|---|---|
| 73 | 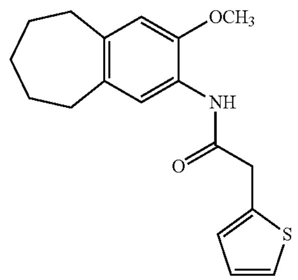 [SMILES: COc1cc2c(cc1NC(=O)Cc1cccs1)CCCCC2] | 315.4 | 18.7 | >30 |
| 74 | 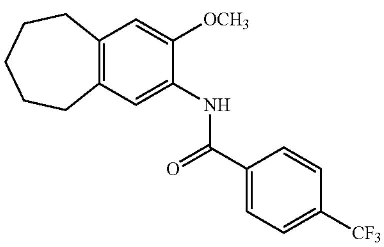 [SMILES: COc1cc2c(cc1NC(=O)c1ccc(C(F)(F)F)cc1)CCCCC2] | 363.4 | 7.4 | >30 |
| 75 | 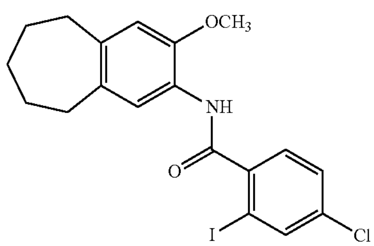 [SMILES: COc1cc2c(cc1NC(=O)c1ccc(Cl)cc1I)CCCCC2] | 455.7 | 6.1 | >30 |
| 76 | 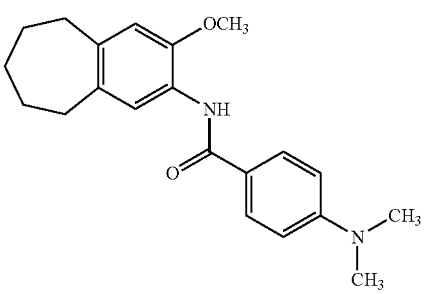 [SMILES: COc1cc2c(cc1NC(=O)c1ccc(N(C)C)cc1)CCCCC2] | 338.5 | >10 | >30 |
| 77 | 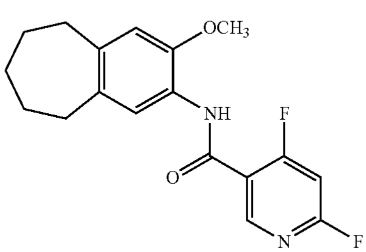 [SMILES: COc1cc2c(cc1NC(=O)c1cnc(F)cc1F)CCCCC2] | 332.4 | 2.9 | >30 |
| 78 | 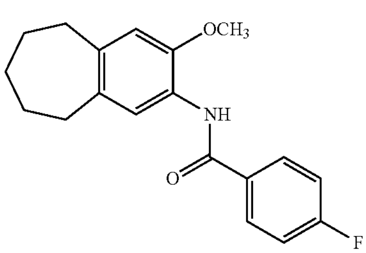 [SMILES: COc1cc2c(cc1NC(=O)c1ccc(F)cc1)CCCCC2] | 313.4 | >10 | >30 |

TABLE 1-continued
| No. | Structure | MW | EC$_{90}$ (μM) CHIKV | CC$_{50}$ (μM) CHIKV |
|-----|-----------|------|------|------|
| 79 | 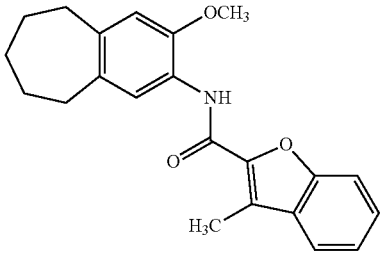 [SMILES: COc1cc2c(cc1NC(=O)c1oc3ccccc3c1C)CCCCC2] | 349.4 | >10 | >30 |
| 80 | 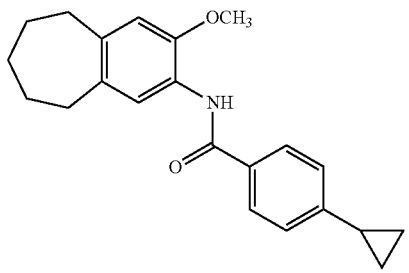 [SMILES: COc1cc2c(cc1NC(=O)c1ccc(C3CC3)cc1)CCCCC2] | 335.5 | 12.3 | >30 |
| 81 | 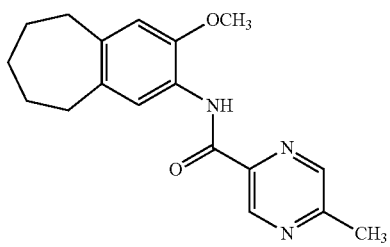 [SMILES: COc1cc2c(cc1NC(=O)c1cnc(C)cn1)CCCCC2] | 311.4 | >10 | >30 |
| 82 | 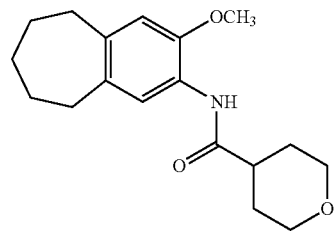 [SMILES: COc1cc2c(cc1NC(=O)C1CCOCC1)CCCCC2] | 303.4 | >10 | >30 |
| 83 | 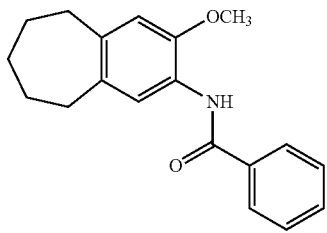 [SMILES: COc1cc2c(cc1NC(=O)c1ccccc1)CCCCC2] | 295.4 | >10 | >30 |
| 84 | 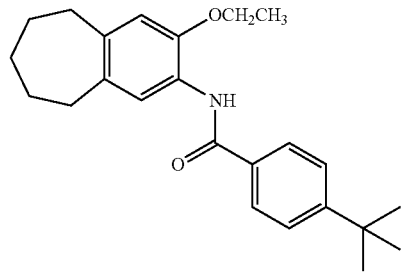 [SMILES: CCOc1cc2c(cc1NC(=O)c1ccc(C(C)(C)C)cc1)CCCCC2] | 365.5 | 5.19 | 10 |

TABLE 1-continued
| No. | Structure | MW | EC$_{90}$ (μM) CHIKV | CC$_{50}$ (μM) CHIKV |
|---|---|---|---|---|
| 85 | 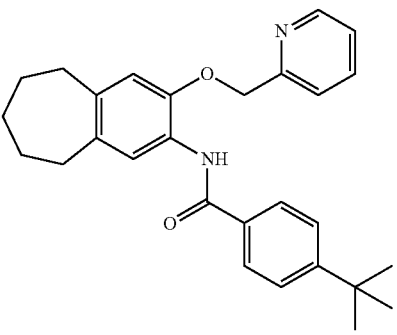 [SMILES: CC(C)(C)c1ccc(C(=O)Nc2cc3c(cc2OCc2ccccn2)CCCCC3)cc1] | 428.6 | >10 | 9.4 |
| 86 | 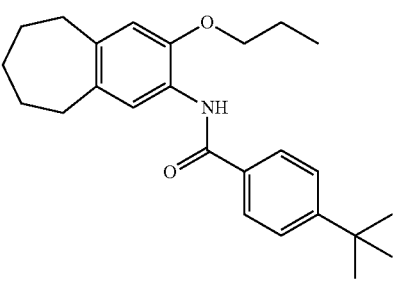 [SMILES: CCCOc1cc2c(cc1NC(=O)c1ccc(C(C)(C)C)cc1)CCCCC2] | 379.5 | 7.0 | >30 |
| 87 | 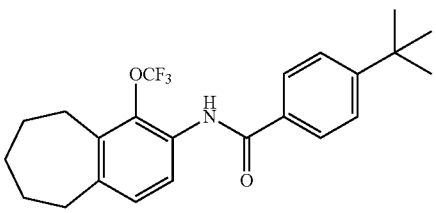 [SMILES: CC(C)(C)c1ccc(C(=O)Nc2ccc3c(c2OC(F)(F)F)CCCCC3)cc1] | 405.5 | 19.5 | >30 |
| 88 | 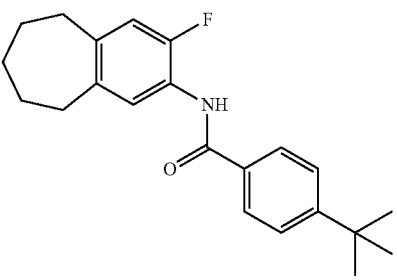 [SMILES: CC(C)(C)c1ccc(C(=O)Nc2cc3c(cc2F)CCCCC3)cc1] | 339.5 | | |
| 90 | 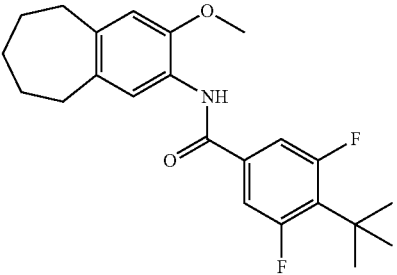 [SMILES: COc1cc2c(cc1NC(=O)c1cc(F)c(C(C)(C)C)c(F)c1)CCCCC2] | 387.5 | 3.3 | >30 |

TABLE 1-continued

| No. | Structure | MW | EC$_{90}$ (μM) CHIKV | CC$_{50}$ (μM) CHIKV |
|-----|-----------|------|----------------------|----------------------|
| 91  | 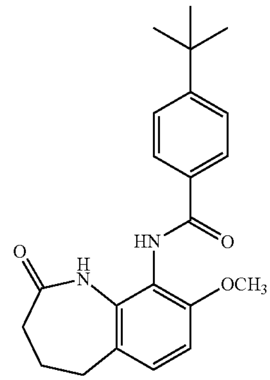          | 366.5 |                     | 91                   |
| 92  | 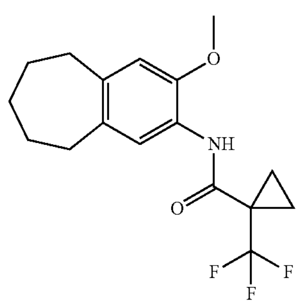 [SMILES: COc1cc2c(cc1NC(=O)C1(C(F)(F)F)CC1)CCCCC2]          | 327.34 |                    |                      |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula selected from:

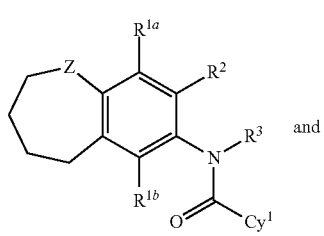

wherein each of $Q^1$ and $Q^2$ is independently selected from $CH_2$, CH(OH), and C(O), provided that at least one of $Q^1$ and $Q^2$ is C(O);

wherein Z is selected from $CH_2$ and NH;

wherein each of $R^{1a}$ and $R^{1b}$ is independently selected from hydrogen and —F;

wherein $R^2$ is selected from hydrogen, halogen, —CN, —(CH$_2$)$_n$OR$^{20}$, and —OC(O)R$^{21}$;

wherein n is selected from 0, 1, 2, 3, and 4;

wherein $R^{20}$, when present, is selected from hydrogen, C1-C4 alkyl, C1-C4 haloalkyl, Ar$^1$, and —(C1-C4 alkyl)Ar$^1$;

wherein Ar$^1$, when present, is selected from phenyl and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy;

wherein $R^{21}$, when present, is selected from hydrogen, C1-C4 alkyl, C1-C4 haloalkyl, and $Ar^1$;

wherein $R^3$ is selected from hydrogen and C1-C4 alkyl; and wherein each of $R^{4a}$, $R^{4b}$, $R^{4c}$, $R^{4d}$ is independently selected from hydrogen, halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$;

wherein $Cy^2$, when present, is selected from C3-C5 cycloalkyl, 3-8 membered heterocycle, partially or fully saturated, having 1-3 heteroatoms selected from nitrogen, oxygen, sulfur, and phosphorous, phenyl, and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy; and wherein $Cy^1$ is selected from C3-C10 cycloalkyl, phenyl, and 5-6 membered heteroaryl having 1-3 heteroatoms selected from nitrogen, oxygen, sulfur, and phosphorous, and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$, provided that when $Cy^1$ is unsubstituted phenyl, then at least one of $R^{1a}$, $R^{1b}$, and $R^2$ is not hydrogen, or a pharmaceutically acceptable salt thereof.

2. The compound of claim 1, wherein Z is CH$_2$.

3. The compound of claim 1, wherein each of $R^{1a}$ and $R^{1b}$ is hydrogen.

4. The compound of claim 1, wherein $R^2$ is —OR$^{20}$.

5. The compound of claim 1, wherein $Cy^1$ is selected from phenyl and 5-6 membered heteroaryl having 1-3 heteroatoms selected from nitrogen, oxygen, sulfur, and phosphorous, and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$.

6. The compound of claim 1, wherein $Cy^1$ is phenyl substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino and $Cy^2$.

7. The compound of claim 1, wherein $Cy^1$ is phenyl substituted with a tert-butyl group.

8. The compound of claim 1, wherein $Cy^1$ is 5-6 membered heteroaryl having 1-3 heteroatoms selected from nitrogen, oxygen, sulfur, and phosphorous, substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, $Cy^1$, and $Ar^3$.

9. The compound of claim 1, wherein $Cy^1$ is selected from thiazole, pyrazole, imidazole, furan, thiophene, isoxazole, pyrimidine, and pyridine and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, $Cy^1$, and $Ar^3$.

10. The compound of claim 1, wherein $Cy^1$ is C3-C10 cycloalkyl and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and $Cy^2$.

11. The compound of claim 1, wherein $Cy^1$ is unsubstituted adamantine.

12. The compound of claim 1, wherein the compound has a structure represented by a formula:

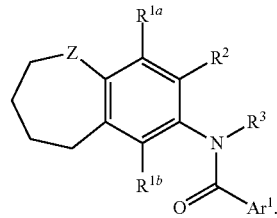

13. The compound of claim 1, wherein the compound has a structure represented by a formula:

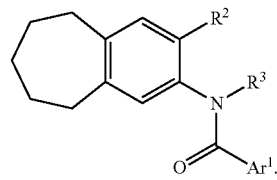

14. The compound of claim 1, wherein the compound has a structure represented by a formula:

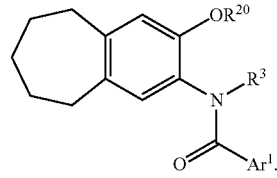

15. The compound of claim 1, wherein the compound has a structure represented by a formula:

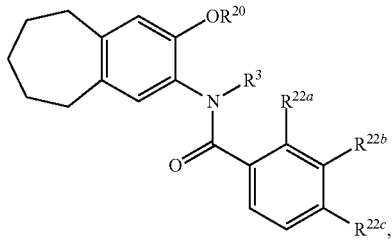

wherein each of $R^{22a}$, $R^{22b}$, and $R^{22}c$ is independently selected from hydrogen, halogen, —CO$_2$H, —CN, —OH, —NH$_2$, C1-C8 alkyl, C1-C8 haloalkyl, C1-C8 C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, Cy$^1$, and Ar$^3$.

16. A pharmaceutical composition comprising a therapeutically effective amount of at least one compound having a structure represented by a formula selected from:

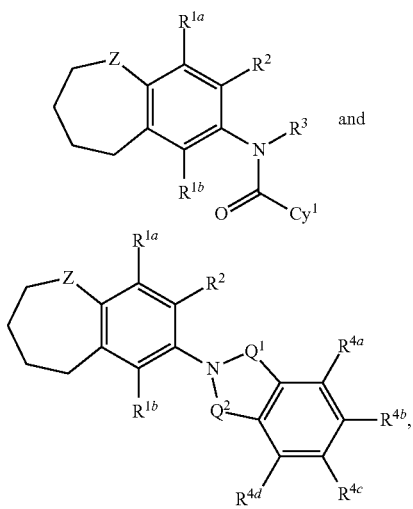

wherein each of Q$^1$ and Q$^2$ is independently selected from CH$_2$, CH(OH), and C(O), provided that at least one of Q$^1$ and Q$^2$ is C(O);
wherein Z is selected from CH$_2$ and NH;
wherein each of $R^{1a}$ and $R^{1b}$ is independently selected from hydrogen and —F;
wherein $R^2$ is selected from hydrogen, halogen, —CN, —(CH$_2$)$_n$OR$^{20}$, and —OC(O)R$^{21}$;
wherein n is selected from 0, 1, 2, 3, and 4;
wherein R$^{20}$, when present, is selected from hydrogen, C1-C4 alkyl, C1-C4 haloalkyl, Ar$^1$, and —(C1-C4 alkyl)Ar$^1$;
wherein $^1$, when present, is selected from phenyl and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy;
wherein R$^{21}$, when present, is selected from hydrogen, C1-C4 alkyl, C1-C4 haloalkyl, and Ar$^1$;
wherein R$^3$ is selected from hydrogen and C1-C4 alkyl; and
wherein each of $R^{4a}$, $R^{4b}$, $R^{4c}$, and $R^{4d}$ is independently selected from hydrogen, halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$;
wherein Cy$^2$, when present, is selected from C3-C5 cycloalkyl, 3-8 membered heterocycle, partially or fully saturated, having 1-3 heteroatoms selected from nitrogen, oxygen, sulfur, and phosphorous, phenyl, and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy; and
wherein Cy$^1$ is selected from C3-C10 cycloalkyl, phenyl, and 5-6 membered heteroaryl having 1-3 heteroatoms selected from nitrogen, oxygen, sulfur, and phosphorous, and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$,
or a pharmaceutically acceptable salt thereof, and a pharmaceutically acceptable carrier.

17. A method for the treatment of chikungunya in a subject, the method comprising the step of administering to the subject an effective amount of at least one compound having a structure represented by a formula selected from:

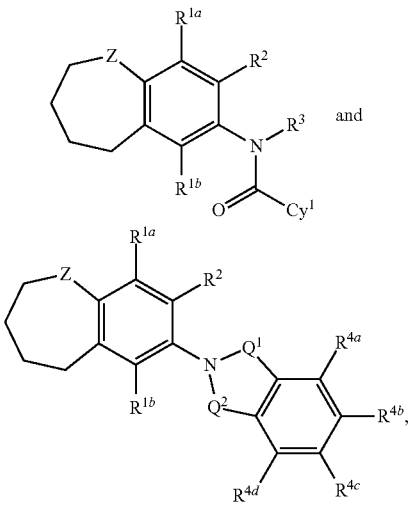

wherein each of Q$^1$ and Q$^2$ is independently selected from CH$_2$, CH(OH), and C(O), provided that at least one of Q$^1$ and Q$^2$ is C(O);
wherein Z is selected from CH$_2$ and NH;
wherein each of $R^{1a}$ and $R^{1b}$ is independently selected from hydrogen and —F;
wherein $R^2$ is selected from hydrogen, halogen, —CN, —(CH$_2$)$_n$OR$^{20}$, and —OC(O)R$^{21}$;
wherein n is selected from 0, 1, 2, 3, and 4;
wherein R$^{20}$, when present, is selected from hydrogen, C1-C4 alkyl, C1-C4 haloalkyl, Ar$^1$, and —(C1-C4 alkyl)Ar$^1$;

wherein Ar$^1$, when present, is selected from phenyl and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy;

wherein R$^{21}$, when present, is selected from hydrogen, C1-C4 alkyl, C1-C4 haloalkyl, and Ar$^1$;

wherein R$^3$ is selected from hydrogen and C1-C4 alkyl; and wherein each of R$^{4a}$, R$^{4b}$, R$^{4c}$, and R$^{4d}$ is independently selected from hydrogen, halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$;

wherein Cy$^2$, when present, is selected from C3-C5 cycloalkyl, 3-8 membered heterocycle, partially or fully saturated, having 1-3 heteroatoms selected from nitrogen, oxygen, sulfur, and phosphorous, phenyl, and 5-6 membered heteroaryl having 1-3 heteroatoms selected from nitrogen, oxygen, sulfur, and phosphorous, and substituted with 0, 1, 2, or 3 groups independently selected from halogen, C1-C4 alkyl, C1-C4 haloalkyl, C1-C4 hydroxyalkyl, and C1-C4 alkoxy; and wherein Cy$^1$ is selected from C3-C10 cycloalkyl, phenyl, and 5-6 membered heteroaryl having 1-3 heteroatoms selected from nitrogen, oxygen, sulfur, and phosphorous, and substituted with 0, 1, or 2 groups independently selected from halogen, —CO$_2$H, —CN, —OH, —NH$_2$, C1-C8 alkyl, C1-C8 haloalkyl, C1-C8 alkylnitrile, C1-C8 hydroxyalkyl, C1-C8 alkoxy, C1-C8 halohydroxyalkyl, C1-C8 aminoalkyl, C1-C8 alkylamino, (C1-C8)(C1-C8) dialkylamino, and Cy$^2$, or a pharmaceutically acceptable salt thereof.

18. The method of claim 17, wherein the subject has been diagnosed with a need for treatment of chikungunya prior to the administering step.

19. The compound of claim 1, wherein the compound has a structure represented by a formula:

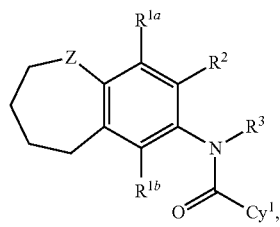

wherein Z is CH$_2$;
wherein R$^{1a}$ is selected from hydrogen and —F;
wherein R$^{1b}$ is hydrogen; and
wherein R$^3$ is hydrogen.

* * * * *

UNITED STATES PATENT AND TRADEMARK OFFICE
CERTIFICATE OF CORRECTION

PATENT NO. : 10,450,263 B2
APPLICATION NO. : 15/892302
DATED : October 22, 2019
INVENTOR(S) : Ashish Kumar Pathak et al.

It is certified that error appears in the above-identified patent and that said Letters Patent is hereby corrected as shown below:

In the Specification

Column 1, please replace Lines 14-17 after the heading "FEDERALLY SPONSORED RESEARCH AND DEVELOPMENT" with the following:
-- "This invention was made with government support under AI142759 and U19 AI109680 awarded by the National Institutes of Health. The government has certain rights in the invention." --

Signed and Sealed this
Twenty-sixth Day of August, 2025

Coke Morgan Stewart
*Acting Director of the United States Patent and Trademark Office*